United States Patent [19]

Pasteris et al.

[11] Patent Number: 4,741,765

[45] Date of Patent: May 3, 1988

[54] HERBICIDAL SULFONAMIDES

[75] Inventors: Robert J. Pasteris; Ramaurthi Muthukrishnan, both of Wilmington, Del.

[73] Assignee: E. I. Du Pont de Nemours and Company, Wilmington, Del.

[21] Appl. No.: 34,138

[22] Filed: Apr. 3, 1987

Related U.S. Application Data

[60] Division of Ser. No. 822,643, Jan. 30, 1986, Pat. No. 4,678,499, which is a continuation-in-part of Ser. No. 710,458, Mar. 11, 1985, abandoned.

[51] Int. Cl.$^4$ .................... A01N 43/90; A01N 43/66; A01N 43/72; C07D 401/12; C07D 401/14; C07D 417/12; C07D 413/12; C07D 403/12

[52] U.S. Cl. .......................................... 71/93; 71/90; 71/91; 544/212; 544/198; 544/207; 544/209; 544/211; 544/197; 544/183; 544/103; 544/100; 544/80; 544/72; 544/65; 544/34; 544/9; 544/3; 544/179; 544/208; 544/187; 544/180; 544/102; 544/89; 544/79; 544/67; 544/63; 544/33; 544/7; 544/2; 544/206; 544/184; 544/104; 544/101; 544/83; 544/73; 544/66; 544/35; 544/32; 544/5; 544/113; 540/586; 540/587; 540/590

[58] Field of Search ............... 71/93, 90, 91; 544/212, 544/198, 207, 209, 211, 197, 183, 103, 100, 80, 72, 65, 34, 9, 3, 179, 208, 206, 187, 184, 180, 104, 102, 101, 89, 83, 79, 73, 67, 66, 63, 35, 33, 32, 7, 5, 2, 113; 540/586, 587, 590

[56] References Cited

U.S. PATENT DOCUMENTS

| | | | |
|---|---|---|---|
| 4,465,505 | 8/1984 | Wolf | 71/92 |
| 4,465,506 | 8/1984 | Welch | 71/92 |
| 4,534,790 | 8/1985 | Wolf | 71/93 |
| 4,589,909 | 5/1986 | Rorer | 71/90 |
| 4,602,940 | 7/1986 | Wolf | 71/92 |
| 4,634,465 | 1/1987 | Ehrenfreund et al. | 71/91 |

FOREIGN PATENT DOCUMENTS

| | | |
|---|---|---|
| 79683 | 5/1983 | European Pat. Off. |
| 0085476 | 8/1983 | European Pat. Off. |
| 107979 | 5/1984 | European Pat. Off. |
| 838416 | 5/1984 | South Africa |

Primary Examiner—John M. Ford

[57] ABSTRACT

Benzenesulfonamide compounds such as N-[(4,6-dimethoxy-1,3,5-triazin-2-yl)aminocarbonyl]-1,4-dihydro-3-methyl-4-oxo-1-phenyl-indeno[1,2-C]pyrazole-5-sulfonamide and N-[(4-methoxy-6-methyl-pyrimidin-2-yl)aminocarbonyl]-1,4-dihydro-3-methyl-4-oxo-1-phenyl-indeno[1,2-C]pyrazole-5-sulfonamide, agricultural compositions containing them, and their herbicidal utility are disclosed.

26 Claims, No Drawings

HERBICIDAL SULFONAMIDES

RELATED APPLICATION

This application is a divisional of U.S. Ser. No. 822,643 filed Jan. 30, 1986 (now U.S. Pat. No. 4,678,499) which in turn is a continuation-in-part of Ser. No. 710,458 filed Mar. 11, 1985 (now abandoned).

BACKGROUND OF THE INVENTION

The invention relates to novel benzenesulfonamide compounds, agriculturally suitable compositions containing them, and their method-of-use as general and selective preemergent and postemergent herbicides.

European Patent Application (EP-A) No. 83,975 (published July 20, 1983) discloses herbicidal benzenesulfonamides of formula

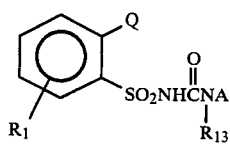

wherein Q is selected from various five or six-membered aromatic or partially unsaturated heterocyclic rings containing 2 or 3 heteroatoms selected from O, S or NR.

EP-A-85,476 (published Aug. 10, 1983) discloses herbicidal benzenesulfonamides of formulae

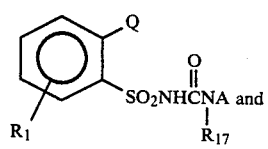

wherein
Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and
$Q^1$ is a 6-membered aromatic heterocycle containing one to three N atoms.

South African Patent Application No. 83/8416 (published May 12, 1984) discloses herbicidal benzenesulfonamides of formula

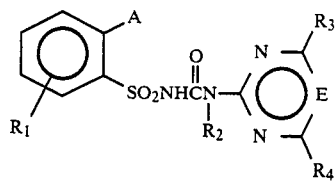

wherein A is an unsaturated or only partially saturated 5- or 6-membered heterocyclic ring system which is bonded through a carbon atom and contains 1, 2 or 3 heteroatoms.

EP-A-79,683 (published May 25, 1983) discloses herbicidal benzenesulfonamides including those of general Formulae I and II:

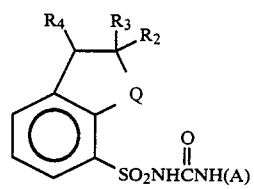

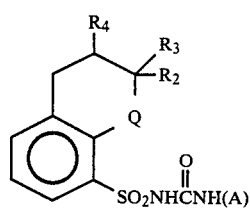

wherein
Q is O, S or $SO_2$;
$R_2$ is H or $C_1$–$C_3$ alkyl;
$R_3$ is H or $CH_3$;
$R_4$ is H or $CH_3$; and
A is a pyrimidinyl or triazinyl heterocyclic ring.

EP-A-107,979 (published May 9, 1984) teaches herbicidal sulfonamides of formula

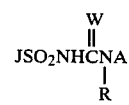

where J is, among other values,

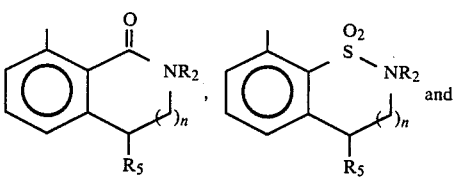

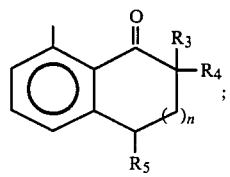

wherein n is 0, 1 or 2.

EP-A-82,681 (published June 29, 1983) discloses herbicidal indane, 1,3-benzodioxole and 1,4-benzodioxanesulfonylureas.

South African Patent Application No. 83/5165 (published Jan. 16, 1984) discloses herbicidal sulfonylureas of the general structure shown below:

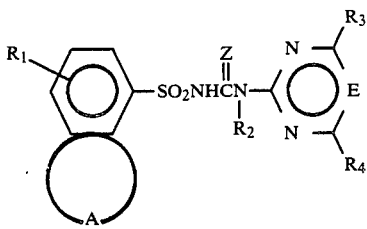

wherein A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or SO$_2$— group.

SUMMARY OF THE INVENTION

This invention pertains to novel compounds of Formula I, agriculturally suitable compositions containing them and their method of use as general and/or selective preemergent and/or postemergent herbicides or plant growth regulants.

$$\text{QSO}_2\text{NHCNA} \atop {\scriptstyle\| \atop R}^{\text{W}} \quad\quad \text{I}$$

wherein
W is O or S;
Q is

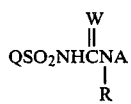

Q$_1$

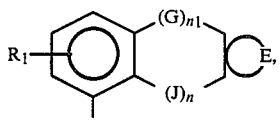

Q$_2$

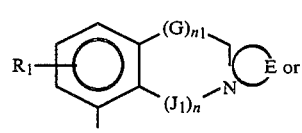

Q$_3$

G is CH$_2$, CH$_2$CH$_2$, O, S, NH, NCH$_3$ or CH=CH;
G$_1$ is CH$_2$, CH$_2$CH$_2$ or CH=CH;
J is CH$_2$, C=O, S(O)$_m$, O, NH, NCH$_3$, CHOH, CHOCH$_3$, CH(CH$_3$) or C(CH$_3$)OH;
J$_1$ is CH$_2$, C=O or SO$_2$;
n and n$_1$ are independently 0 or 1;
m is 0, 1 or 2;
E is a bridge of 3 or 4 atoms containing 0 to 2 heteroatoms selected from the group consisting of oxygen, sulfur or nitrogen, wherein 1 atom of sulfur may take the form of SO or SO$_2$, said bridge also containing 1 to 4 atoms of carbon wherein 1 atom of carbon may take the form of C=O, said bridge together with two attachment sites forming a non-aromatic heterocyclic or carbocyclic ring optionally substituted by 1 to 3 substituent groups selected from the group L, or E is a bridge of 3 or 4 atoms containing 0–1 heteroatoms of oxygen or sulfur and 0–3 heteroatoms of nigrogen, said bridge also containing 0–4 atoms of carbon, said bridge together with two attachment sites forming an aromatic heterocyclic or carbocyclic ring optionally substituted by 1 to 3 substituents selected from the group L, with the proviso that when E contains two oxygen atoms or two sulfur atoms said atoms must be separated by at least one atom of carbon and that oxygen and sulfur are only linked to each other if the sulfur is in the form of SO or SO$_2$;
L is C$_1$-C$_4$ alkyl, C$_1$-C$_4$ haloalkyl, C$_1$-C$_4$ alkoxy, C$_1$-C$_4$ haloalkoxy, C$_2$-C$_8$ alkoxyalkoxy, halogen, N(CH$_3$)$_2$, cyano, nitro, phenyl or phenyl substituted with C$_1$-C$_3$ alkyl, C$_1$-C$_3$ haloalkyl, halogen, NO$_2$, C$_1$-C$_3$ alkoxy, C$_1$-C$_3$ alkylthio, C$_1$-C$_3$ alkylsulfinyl or C$_1$-C$_3$ alkylsulfonyl;
R is H or CH$_3$;
R$_1$ is H, C$_1$-C$_3$ alkyl, C$_1$-C$_3$ haloalkyl, halogen, nitro, C$_1$-C$_3$ alkoxy, SO$_2$NR$^I$R$^{II}$, C$_1$-C$_3$ alkylthio, C$_1$-C$_3$ alkylsulfinyl, C$_1$-C$_3$ alkylsulfonyl, CO$_2$R$^{III}$ or NR$_a$R$_b$;
R$^I$ is H, C$_1$-C$_4$ alkyl, C$_2$-C$_3$ cyanoalkyl, methoxy or ethoxy;
R$^{II}$ is H, C$_1$-C$_4$ alkyl or C$_3$-C$_4$ alkenyl; or
R$^I$ and R$^{II}$ may be taken together as —(CH$_2$)$_3$—, —(CH$_2$)$_4$—, —(CH$_2$)$_5$— or —CH$_2$CH$_2$OCH$_2$CH$_2$—;
R$^{III}$ is C$_1$-C$_4$ alkyl, C$_3$-C$_4$ alkenyl, C$_3$-C$_4$ alkynyl, C$_2$-C$_4$ haloalkyl, C$_1$-C$_3$ cyanoalkyl, C$_5$-C$_6$ cycloalkyl, C$_4$-C$_7$ cycloalkylalkyl or C$_2$-C$_4$ alkoxyalkyl;
R$_a$ and R$_b$ are independently H or C$_1$-C$_2$ alkyl;
A is

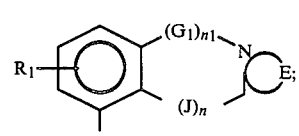

A-1   A-2   A-3

A-4   A-5

-continued

A-6: CH₂ group attached to a pyrimidine ring bearing OCH₃, N, N, X₃

A-7: pyridine/pyrazine ring bearing NC, X₄, Z, Y₄, N

X is H, C₁–C₄ alkyl, C₁–C₄ alkoxy, C₁–C₄ haloalkoxy, C₁–C₄ haloalkyl, C₁–C₄ haloalkylthio, C₁–C₄ alkylthio, halogen, C₂–C₅ alkoxyalkyl, C₂–C₅ alkoxyalkoxy, amino, C₁–C₃ alkylamino or di(C₁–C₃ alkyl)amino;

Y is H, C₁–C₄ alkyl, C₁–C₄ alkoxy, C₁–C₄ haloalkoxy, haloalkylthio, C₁–C₄ alkylthio, C₂–C₅ alkoxyalkyl, C₂–C₅ alkoxyalkoxy, amino, C₁–C₃ alkylamino, di(C₁–C₃ alkyl)amino, C₃–C₄ alkenyloxy, C₃–C₄ alkynyloxy, C₂–C₅ alkylthioalkyl, C₁–C₄ haloalkyl, C₃–C₅ cycloalkyl, C₂–C₄ alkynyl, N(OCH₃)CH₃, $$CR_4 \underset{R_4}{\overset{O}{\underset{\|}{C}}} \underset{L_2R_3}{\overset{L_1R_2}{C}}, \quad \underset{R_4}{\overset{L_1}{C}} \underset{L_2}{\overset{}{(CH_2)_p}} \text{ or } -CR_4 \underset{L_2}{\overset{L_1}{\underset{}{CH_3}}}$$ ;

p is 2 or 3;
L₁ and L₂ are independently O or S;
R₂ and R₃ are independently C₁–C₂ alkyl;
R₄ is H or CH₃;
Z is CH or N;
Y₁ is O or CH₂;
X₁ is CH₃, OCH₃, OC₂H₅ or OCF₂H;
Y₂ is H or CH₃;
X₂ is CH₃, OCH₃ or SCH₃;
Y₃ is CH₃, CH₂CH₃ or CH₂CF₃;
X₃ is CH₃ or OCH₃;
X₄ is CH₃, OCH₃, OC₂H₅, CH₂OCH₃ or Cl; and
Y₄ is CH₃, OCH₃, OC₂H₅ or Cl;

and their agriculturally suitable salts; provided that
(a) when X is Cl, F, Br or I, then Z is CH and Y is OCH₃, OC₂H₅, N(OCH₃)CH₃, NHCH₃, N(CH₃)₂ or OCF₂H;
(b) when X or Y is OCF₂H, then Z is CH;
(c) n and n₁ cannot simultaneously be 0;
(d) when G or G₁ is CH₂CH₂ or CH=CH, then n is 0;
(e) when Q is Q₁ and n is 1, then E must contain at least one heteroatom selected from oxygen, sulfur or nitrogen; and
(f) when W is S, then A is A-1, R is H, and Y is CH₃, OCH₃, OC₂H₅, CH₂OCH₃, C₂H₅, CF₃, SCH₃, OCH₂CH=CH₂, OCH₂C≡CH, OCH₂CH₂OCH₃, CH(OCH₃)₂ or $$\overset{O}{\underset{O}{CH}}\bigg]$$ .

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butyl isomers.

Alkenyl denotes straight chain or branched alkenes, e.g., vinyl, 1-propenyl, 2-propenyl, 3-propenyl or the different butenyl isomers.

Alkynyl denotes straight chain or branched alkynes, e.g., ethynyl, 1-propynyl, 2-propynyl and the different butynyl isomers.

Alkylsulfonyl denotes methylsulfonyl, ethylsulfonyl or the different propylsulfonyl isomers.

Alkylthio, alkylsulfinyl, alkylamino, etc. are defined in an analogous manner.

Cycloalkyl means cyclopropyl, cyclobutyl, cyclopentyl and cyclohexyl.

The term "halogen", either alone or in compound words such as "haloalkyl", denotes fluorine, chlorine, bromine or iodine.

The total number of carbon atoms in a substituent group is indicated by the $C_i$–$C_j$ prefix where i and j are numbers from 1 to 7. For example, $C_1$–$C_3$ alkylsulfonyl would designate methylsulfonyl through propylsulfonyl, $C_2$ alkoxyalkoxy would designate OCH₂OCH₃, $C_2$ cyanoalkyl would designate CH₂CN and $C_3$ cyanoalkyl would designate CH₂CH₂CN and CH(CN)CH₃. The term $C_4$–$C_7$ cycloalkylalkyl is meant to define cyclopropylmethyl through cyclohexylmethyl or cyclopropylbutyl and the various structural isomers embraced therein.

Preferred for reasons of increased ease of synthesis and/or greater herbicidal efficacy are:
(1) Compounds of Formula I where W is O; G and G₁ are CH₂, CH₂CH₂ or CH=CH; J is CO, SO₂ or CH₂; R is H; X is CH₃, OCH₃, OCH₂CH₃, Cl, F, Br, I, OCF₂H, CH₂F, OCH₂CH₂F, OCH₂CHF₂, OCH₂CF₃, CF₃, CH₂Cl or CH₂Br; Y is H, CH₃, OCH₃, OC₂H₅, CH₂OCH₃, NHCH₃, N(OCH₃)CH₃, N(CH₃)₂, CH₂CH₃, CF₃, SCH₃, OCH₂CH=CH₂, OCH₂C≡CH, CH₂OCH₂CH₃, OCH₂CH₂OCH₃, CH₂SCH₃, $$R_4 \underset{R_4}{\overset{O}{\underset{\|}{C}}} \underset{L_2R_3}{\overset{L_1R_2}{C}}, \quad -\underset{R_4}{\overset{L_1}{C}} \underset{L_2}{\overset{}{(CH_2)_p}}, \quad CR_4 \underset{L_2}{\overset{L_1}{\underset{}{CH_3}}},$$

OCF₂H, SCF₂H, cyclopropyl, C≡CH or C≡CCH₃;

(2) Compounds of Preferred 1 where R₁ is H, CH₃, halogen, OCH₃, SCH₃ or SO₂CH₃; A is A-1; and L is halogen, CH₃, OCH₃ or phenyl.

(3) Compounds of Preferred 2 where Q is

Q₁-1: phenyl ring bearing R₁, (G)ₙ₁, (J)ₙ, connected to C=N-O-R₅ group

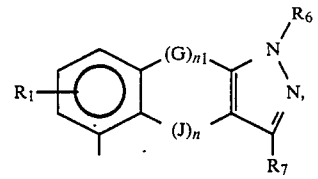 Q₁-2
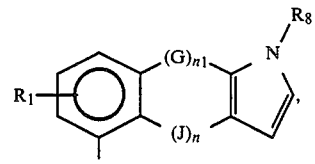 Q₁-3
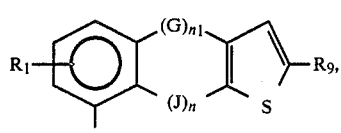 Q₁-4
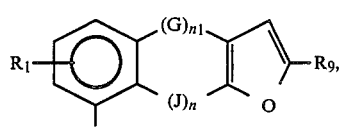 Q₁-5
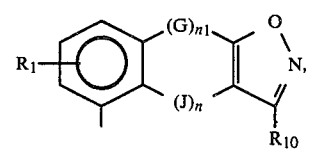 Q₁-6
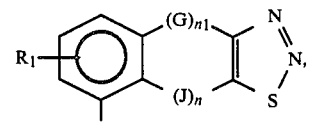 Q₁-7
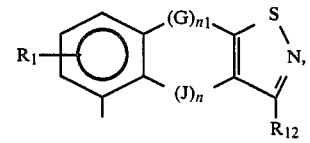 Q₁-8
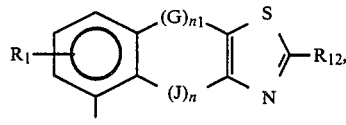 Q₁-9
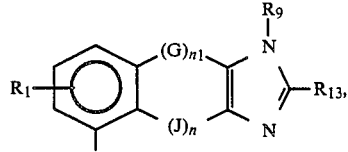 Q₁-10
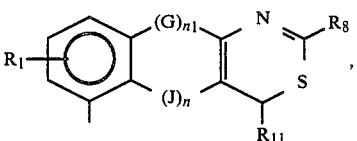 Q₁-11
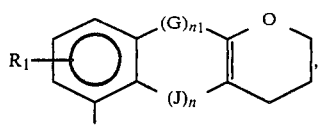 Q₁-12
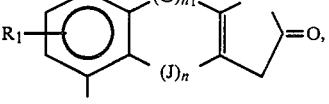 Q₁-13
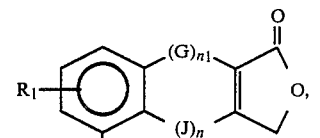 Q₁-14
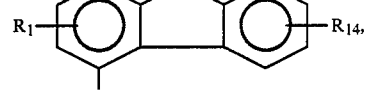 Q₁-15
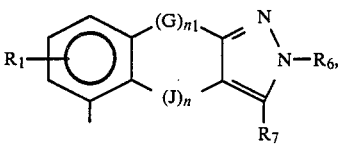 Q₁-16
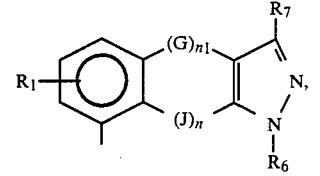 Q₁-17
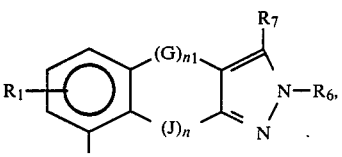 Q₁-18
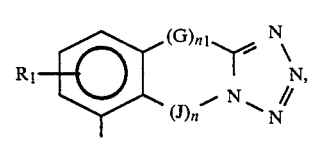 Q₂-1
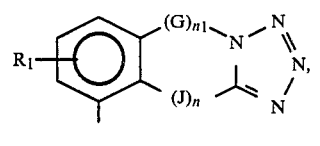 Q₃-1
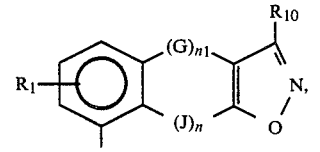 Q₁-19

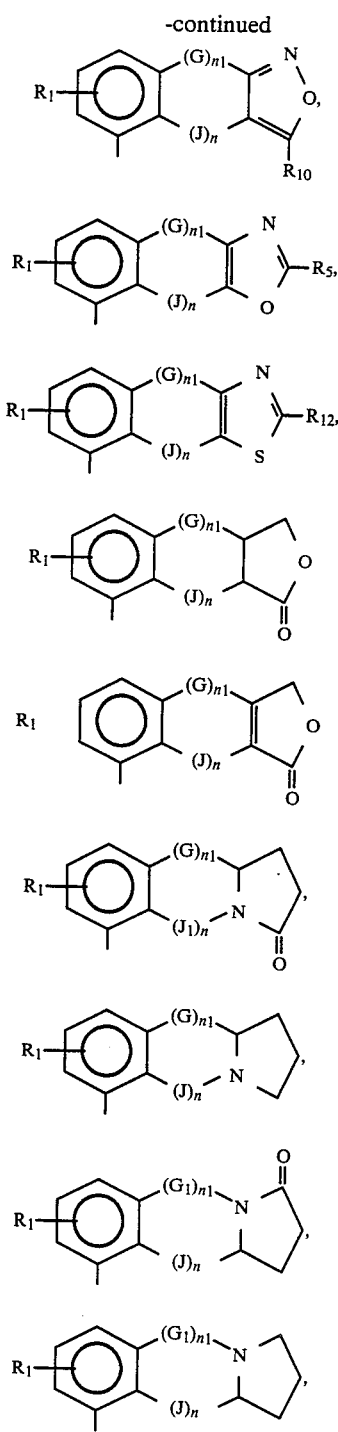

$R_5$ is H or $CH_3$;
$R_6$ is H, $CH_3$ or phenyl;
$R_7$ is H or $CH_3$;
$R_8$ is H or $CH_3$;
$R_9$ is H, $CH_3$ or phenyl;
$R_{10}$ is H or $CH_3$;
$R_{11}$ is $SCH_3$, $OCH_3$, $N(CH_3)_2$ or $CH_3$;
$R_{12}$ is H or $CH_3$;
$R_{13}$ is H, $CH_3$, $OCH_3$ or $SCH_3$; and
$R_{14}$ is H, Cl, Br, F, $CH_3$, $OCH_3$ or $NO_2$.

(4) Compounds of Preferred 3 where X is $CH_3$, $OCH_3$, $OCH_2CH_3$, Cl, $OCF_2H$ or $OCH_2CF_3$; and Y is $CH_3$, $OCH_3$, $CH_2CH_3$, $CH_2OCH_3$, $NHCH_3$ or $CH(OCH_3)_2$.

(5) Compounds of Preferred 4 where n is 0.

(6) Compounds of Preferred 4 where $n_1$ is 0.

(7) Compounds of Preferred 5 where Q is $Q_1$-4, $Q_1$-6, $Q_1$-17, $Q_1$-18, $Q_1$-19, $Q_1$-21, $Q_1$-22, $Q_1$-23, $Q_2$-1 or $Q_3$-1.

(8) Compounds of Preferred 6 where Q is $Q_1$-2, $Q_1$-3 or $Q_1$-14.

Specifically preferred for reasons of greatest ease of synthesis and/or greatest herbicidal efficacy are:

N-[(4,6-dimethoxypyrimidin-2-yl)aminocarbonyl]-1-phenyl-1H-[1]benzothieno[3,2-C]pyrazole-5-sulfonamide, 4,4-dioxide, m.p. 243°–248° C.

4,5-dihydro-N-[(4,6-dimethoxypyrimidin-2-yl)aminocarbonyl]naphth[2,1-D]isoxazole-9-sulfonamide, m.p. 189°–192° C.(d).

4,5-dihydro-N-[(4-methoxy-6-methylpyrimidin-2-yl)aminocarbonyl]naphth[2,1-D]isoxazole-9-sulfonamide, m.p. 186°–189° C.

4,5-dihydro-N-[(4,6-dimethoxy-1,3,5-triazin-2-yl)aminocarbonyl]naphth[2,1-D]isoxazole-9-sulfonamide, m.p. 147°–150° C.

DETAILED DESCRIPTION OF THE INVENTION

Synthesis

The compounds of Formula 1 can be prepared by one or more of the methods described below in Equations 1, 2, 3 and 4.

As shown in Equation 1, compounds of Formula 1 can be prepared by reacting a sulfonyl isocyanate or sulfonyl isothiocyanate of Formula 2 with an appropriate heterocyclic amine of Formula 3.

Equation 1

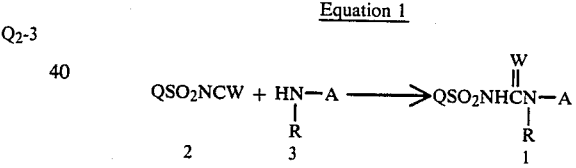

The reaction is carried out at 25° to 100° C. in an inert aprotic solvent such as methylene chloride or xylene for 0.5 to 24 hours as taught in U.S. Pat. No. 4,127,405.

Compounds of Formula 1 can also be prepared by reacting the sulfonamides of Formula 4 with a phenylcarbamate or phenylthiocarbamate of Formula 5 in the presence of DBU and in solvents such as methylene chloride or acetonitrile as taught in European Patent Application No. 70,804.

Equation 2

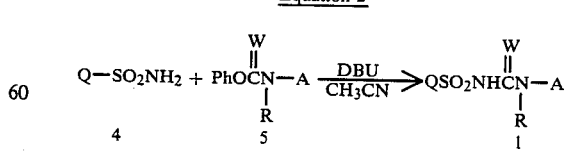

Alternatively, compounds of Formula 1 where W is O can be prepared by reacting sulfonamides of Formula 4 with a methyl carbamate of Formula 6 in the presence of an equimolar quantity of trimethylaluminum as shown in Equation 3.

Equation 3

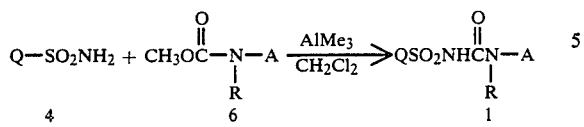

The reaction is carried out at 25°–40° C. in a solvent such as methylene chloride, for 10–96 hours, under an inert atmosphere as taught in EP-A-83,975. The required carbamates (5) are prepared by reacting the corresponding amines (3) with dimethyl carbonate or methyl chloroformate in the presence of a strong base.

Compounds of Formula 1 can also be prepared by reacting a sulfonyl carbamate or thiocarbamate of Formula 7 with an appropriate amine of Formula 3 as shown in Equation 4.

Equation 4

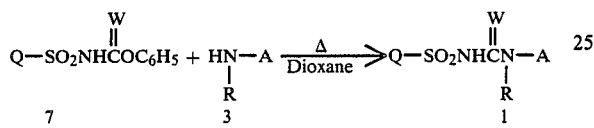

The reaction is carried out at 50°–100° C. in a solvent such as dioxane for 0.5 to 24 hours as taught in EP-A-44,807. The required carbamates and thiocarbamates (7) can be prepared by methods, or modifications thereof known to those skilled in the art, described in South African Patent Application No. 82/5671 and South African Patent Application No. 82/5045.

As shown in Equation 5, many of the sulfonyl isocyanates of Formula 2 can be prepared by the reaction of sulfonamides of Formula 4 with phosgene, in the presence of n-butylisocyanate and a tertiary amine catalyst, such as 1,4-diazabicyclo[2.2.2]-octane (DABCO), at reflux, in a solvent such as xylene by the method of U.S. Pat. No. 4,238,621.

Equation 5

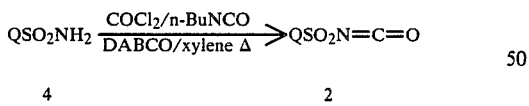

Many of the sulfonyl isocyanates can be prepared from the sulfonamides by a two-step procedure involving (a) reacting the sulfonamides with n-butylisocyanate in the presence of a base such as $K_2CO_3$ at reflux in an inert solvent such as 2-butanone forming an n-butylsulfonylurea; and (b) reacting this compound with phosgene and a tertiary amine catalyst at reflux in xylene solvent. The method is similar to a procedure taught by Ulrich and Sayigh, Newer Methods of Preparative Organic Chemistry, Vol. VI, p. 223–241, Academic Press, New York and London, W. Foerst, Ed.

Alternatively, many of the sulfonyl isocyanates of Formula 2 can be prepared by reacting the corresponding sulfonyl chlorides (8) with cyanic acid salt.

Equation 6

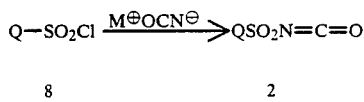

The reaction is carried out at 25°–100° in an inert aprotic solvent such as acetonitrile for 0.5–24 hours in the presence of phosphorous pentoxide and an alkali metal salt such as lithium iodide according to the teachings of Japanese Patent No. 76/26,816 (Chem. Abst. 85:77892e (1976)).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in Arch. Pharm. 299, 174 (1966).

The sulfonamides of Formula 4 of Equations 2, 3, 4, 5 and 7 are important intermediates for the preparation of compounds of this invention. As shown in Equation 7, many of the sulfonamides of Formula 4 can be prepared from the corresponding sulfonyl chlorides of Formula 8 by contacting with either anhydrous or aqueous ammonia.

Equation 7

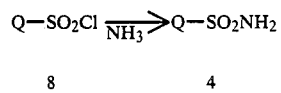

Preparation of sulfonamides from sulfonyl chlorides is widely reported in the literature, for reviews see F. Hawking and J. S. Lawrence "The Sulfonamides", H. K. Lewis and Co., London, 1950, and E. H. Northey "The Sulfonamides and Allied Compounds", Reinhold Publishing Corp., New York, 1948.

Many of the sulfonyl chlorides of Formula 8 of Equations 6 and 7 can be prepared from the corresponding amines of Formula 9 by the method shown in Equation 8.

Equation 8

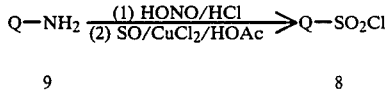

The reaction involves diazotization of the amine 9 with sodium nitrite/HCl followed by reaction of the diazonium salt with sulfur dioxide and cupric chloride in acetic acid analogous to the teachings of Yale and Sowinski, J. Org. Chem., 25, 1824 (1960).

Alternatively, many of the sulfonyl chlorides of Formula 8 can be prepared by a modification of the above procedure whereby the diazotization reaction is carried out in dilute sulfuric acid and the resulting diazonium salt is reacted with sulfur dioxide, HCl and cupric chloride in a co-solvent mixture consisting of acetic acid-water (1:1) and an immiscible inert solvent such as 1-chlorobutane or methylene chloride at 0°–40° C. for 1–24 hours.

Some of the amines of the Formula 9 in Equation 8 can be prepared from the corresponding nitro compounds (10). The reduction reaction of Equation 9 can be run by methods known in the literature.

Equation 9

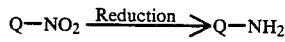

10          9

For example, the reduction can be carried out with stannous chloride or tin and hydrochloric acid either neat or in an inert solvent such as methanol at about 25° to 80° C. for 0.5 to 10 hours. For details, refer to similar procedures described in G. Corsi et al., *Bull. Chim. Farm.*, 103, 115 (1964), A. Quilico et al, *Gass. Chim. Ital.*, 76, 87 (1946) and M. Kahn and J. Polya, *J. Chem. Soc.*, 85 (1970).

Many of the sulfonyl chlorides of Formula 8 can be prepared from the bromo compounds of Formula 11 as shown in Equation 10.

Equation 10

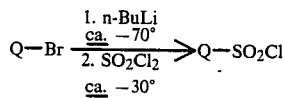

11          8

According to Equation 10 a lithium salt, prepared by reaction of the bromide of Formula 11 with butyl lithium in ether at about −70° C., is added to sulfuryl chloride in hexane at −30° to −20° C. and stirred for 0.5 to 10 hours to yield the sulfonyl chloride 8 according to the teachings of S. N. Battacharya et al., *J. Chem. Soc. C.* 1265 (1968).

Many of the sulfonyl chlorides of Formula 8 can be prepared from the chloro compounds of Formula 12 by the two-step sequence shown in Equation 11.

Equation 11

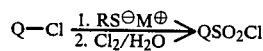

12          8 wherein $RS^{\ominus}M^{\oplus}$ represents an alkyl or benzyl mercaptide salt.

The first step involves nucleophilic displacement of the chlorine atom with an alkyl or benzyl mercaptide to give an intermediate sulfide. The reaction can be carried out at 25° to 80° C. in a polar solvent such as DMF for 0.5 to 24 hours. The sulfide is then oxidatively chlorinated to the desired sulfonyl chloride 8 by the addition of molecular chlorine or a chlorine equivalent to the sulfide in the presence of water at 15° to 80° C. in an aliphatic carboxylic acid solvent such as acetic acid or an inert organic solvent such as dichloroethane for 1 to 24 hours.

The tricyclic intermediates of Formulae 9, 10, 11 and 12 are known or can be prepared by one skilled in the art.

The synthesis of heterocyclic amines such as those represented by Formula 3 has been reviewed in "The Chemistry of Heterocyclic Compounds," a series published by Interscience Publ., New York and London. Aminopyrimidines are described by D. J. Brown in "The Pyrimidines", Vol. XVI of the series, mentioned above which is herein incorporated by reference. The 2-amino-1,3,5-triazines of Formula 3, where A is A-1 and Z is N, can be prepared according to methods described by E. M. Smolin and L. Rapaport in "s-Triazines and Derivatives," Vol. XIII.

Pyrimidines of Formula 3, where A is A-1 and Y is an acetal or thioacetal substituent, can be prepared by methods taught in European Patent Application No. 84,224 (published July 27, 1983).

Pyrimidines of Formula 3, where A is A-1 and Y is cyclopropyl or $OCF_2H$, can be synthesized according to the methods taught in South African Patent Application No. 83/7434 and South African Publication No. 82/5045, respectively.

Compounds of Formula 3, where A is A-2 or A-3, can be prepared by procedures disclosed in U.S. Pat. No. 4,339,267.

Compounds of Formula 3, where A is A-5, can be prepared by methods taught in U.S. Pat. No. 4,421,550.

Compounds of Formula 3, where A is A-6, can be prepared by methods taught in European Patent Application No. 94,260 (published Nov. 16, 1983).

Agriculturally suitable salts of compounds of Formula 1 are also useful herbicides and can be prepared in a number of ways known to the art. For example, metal salts can be made by treating compounds of Formula 1 with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405.

The preparation of the compounds of this invention is further illustrated by the following examples.

EXAMPLES

Example 1

2-Acetyl-4-nitro 1,3-indanedione

To a solution of 100 g of 3-nitrophthalic acid in 100 mL of pyridine was added 0.8 mL of piperdine followed by 500 g of 2,4-pentanedione at room temperature. The mixture was stirred at 35°–40° C. for 6 hours and then diluted with 100 mL ether. The pyridine salt was filtered off, washed with 100 ml of ether, dried, suspended in water, and acidified with 400 mL of 6N HCl. The title compound was filtered off, dried, and recrystallized from ethanol to yield 84 g of yellow crystals, m.p. 148°–150°.

200 MHz NMR($CDCL_3$)$\delta$7.8–8.08 (m.3H aromatic), $\delta$2.6 (S, $CH_3$).

IR(nujol) 3460, 3360, 1690 $cm^{-1}$.

Example 2

2-Acetyl-4-amino 1,3 indanedione

To a suspension of 20.0 g of 4-nitro-1,3-indanedione in 100 mL tetrahydrofuran and 20 mL of ethanol, 1.0 g of 10% Pd/C catalyst was added and the mixture hydrogenated at 50 psi until three molar equivalents of hydrogen were taken up. The catalyst was filtered off and solvent was removed from the filtrate under reduced pressure. Recrystallization from ethanol afforded 14.8 g of the title compound, m.p. 126°–128°.

IR(nujol) 3460, 3340, 1690 cm$^{-1}$,

Example 3

1-phenyl-5-aminoindenopyrazol-4-one

To a solution of 4.7 g of 4-amino-1,3-indanedione in 500 mL ethanol was added 2 mL of phenylhydrazine at room temperature and the mixture was heated at reflux for 2 hours. The mixture was then cooled to room temperature and 4 mL concentrated hydrochloric acid was added. The mixture was then refluxed for an additional 2 hours. The mixture was then concentrated in vacuo and the crystals that separated were filtered off and dried, to yield 3.4 g of the title compound, m.p. 200°–202° C.

200 MHz NMR (CDCl$_3$)δ6.5–6.58 (m, Aromatic 2H), 7.06–7.1 (m, Aromatic 1H), 7.51–7.65 (m, Aromatic 5H), 2.26 (s, CH$_3$), 4.2 (br, NH$_2$).

IR(nujol) 3420 and 3310. 1665 cm$^{-1}$.

Example 4

1-phenylindenopyrazol-4-one-5-sulfonylchloride

A suspension of 36 g of aminopyrazolone of Example 3 in 130 mL concentrated hydrochloric acid and 250 mL of glacial acetic acid was cooled to 0°–5° C. and 10 g of sodium nitrite was added in portions while maintaining the temperature at 0°–5°. After stirring for 30 minutes, the suspension was added in portions to a preformed mixture containing 200 mL acetic acid, 15 g of cuprous chloride, and 150 mL concentrated hydrochloric acid at 10° C. The mixture was stirred at 10° for 30 minutes and then at 40°–50° for 3 hours. The suspension was added to 1000 mL ice water, stirred and extracted with 250 mL of methylene chloride. The methylene chloride layer was washed with water, dilute bircarbonate solution and water and then dried. The solvent was removed under reduced pressure to yield 25 g of the crude sulfonyl chloride.

IR(nujol) 1700, 1380, 1165 cm$^{-1}$.

Example 5

1-phenylindenopyrazolone-4-one-5-sulfonamide

A solution of 10 g of the sulfonyl chloride prepared in Example 4 in 75 mL of tetrahydrofuran was cooled in an ice bath and treated cautiously with 40 mL of concentrated ammonium hydroxide, while maintaining the temperature at 0°–5° C. The resulting suspension was stirred at room temperature for 8 hours. The solvent was then removed under reduced pressure. The residue was stirred in 500 mL water and filtered. The solids obtained were recrystallized from a mixture of acetonitrile and water to give 6.9 g of the title compound as yellow crystals, m.p. 247°–249°.

200 MHz NMR (CDCl$_3$)δ6.5–6.58 (m, Aromatic, 2H), 7.06–7.1 (m, Aromatic, 1H), 7.51–7.65 (m, Aromatic, 5H), 2.26 (s, CH$_3$), 4.2 (s, NH$_2$).

IR(nujol) 3310, 3420, 1665 cm$^{-1}$.

Example 6

N[(4,6,Dimethyl-1,3,5-triazin-2-yl)aminocarbonyl]-1-phenylindenopyrazol-4-one-5-sulfonamide To a suspension 0.27 g of of N-phenoxycarbonyl-4,6-dimethoxy-2-aminotriazine in 20 mL of acetonitrile was added 0.327 g of the sulfonamide described in Example 5 followed by 0.2 mL of 1,8-diazabicyclo-[5.4.0]-undec-7-ene. The mixture was then stirred at room temperature for 2 hours. The mixture was added to 50 mL water containing 2 mL conc. hydrochloric acid and extracted with methylene chloride. The methylene chloride extract was dried and stripped of solvent under reduced pressure to furnish a yellow solid which was triturated with chlorobutane and filtered to give 0.12 g of yellow crystals, m.p. 152°–155°.

NMR 200 MHz (CDCl$_3$) δ 13.2 (broad s, 1H, NH), 8.06 (s, 1H, NH), 7.2–7.6 (m, 8H, Aromatic), 4.23 (s, 3H, OCH$_3$), 2.38 (s, 3H, CH$_3$).

IR(nujol) 1725, 1710, 1360, 1170 cm$^{-1}$.

Example 7

5-amino-1-methylindenopyrazol-4-one

To a solution 25 g of 4-amino-1,3-indanedione, described in Example 2, in 200 mL ethanol was added 5.5 mL of methyl hydrazine at room temperature and then heated to reflux for 2 hours. The mixture was treated with 4 mL concentrated hydrochloric acid and again heated at reflux for 2 hours. The mixture was then cooled and the solvent was removed. The residue was triturated with water, filtered and dried. Recrystallization from ethanol and water yielded 18.9 g of yellow crystals. m.p. 225°–227°.

NMR 200 MHz (CDCl$_3$) δ (m, 7.02–7.10, 1H, Aromatic), (m, 6.5–6.6, 2H, Aromatic), (br s, 5.32, 2H, NH$_2$), (s, 3.89, 3H, NCH$_3$), (s, 2.31, 3H, CH$_3$).

IR(nujol) 3420, 3310, 1665 cm$^{-1}$.

Example 8

1-Methyl-indenopyrazol-4-one 5-sulfonylchloride

A suspension of 12.5 g of the aminopyrazolone of Example 7 in 65 mL of concentrated hydrochloric acid and 125 mL of glacial acetic acid was cooled to 0° to 5° and then 5 g of sodium nitrite was added in portions while maintaining the temperature at 0°–5°. After 30 minutes, the suspension was added to a preformed mixture of 100 mL glacial acetic acid, 7.5 g of cuprous chloride, and 75 mL of concentrated hydrochloric acid at 0°–5°. The mixture was stirred at that temperature for 30 minutes and then was heated at 40° to 50° for 3 hours. The suspension was poured into 5000 mL ice water and extracted with 250 mL methylene chloride. The methylene chloride extract was washed with water and then dried. The solvent was stripped under reduced pressure to afford the crude sulfonyl chloride as a yellow solid.

IR(nujol) 1700, 1380, 1165 cm$^{-1}$.

Example 9
1-Methyl-indenopyrazol-4-one-5-sulfonamide

A solution of 5 g of the sulfonyl chloride of Example 8 in 40 mL tetrahydrofuran was cooled in an ice water bath and treated cautiously with 20 mL of concentrated ammonium hydroxide, added slowly maintaining the temperature at 0° to 5° C. The resulting suspension was stirred at room temperature for 8 hours and then stripped of the solvent under reduced pressure. The residue was stirred in 200 mL water, filtered, washed with hot ethanol and dried to afford 1.8 g of yellow crystals, m.p. 260°–265°

NMR 200 MHz δ 7.7–7.82 (m, 3H, aromatic), 3.95 (s, 3H, NCH$_3$), 2.2 (s, 3H, CH$_3$).

IR(nujol) 3350, 3260, 1700, 1370, 1160 cm$^{-1}$.

Example 10
N-[(4,6-Dimethoxypyrimidin-2-yl)aminocarbonyl]methylindenopyrazol-4-one-5-sulfonamide To a suspension of 0.2 g of N-phenoxycarbonyl4,6-dimethoxyaminopyrimidine in 15 mL of acetonitrile was added 0.2 g of methylindenopyrazolone-5-sulfonamide, followed by the addition of 0.2 mL of 1,8-diazabicyclo[5.4.0]undec-7-ene and the mixture was stirred at room temperature for 2 hours. The mixture was added to 50 mL water containing 2 mL concentrated hydrochloric acid and extracted with 50 mL methylene chloride. The methylene chloride extract was dried and the solvent was removed. The residue was triturated with chlorobutane, filtered and dried to give 0.21 g of the title compound, m.p. 224°–230°.

NMR 200 MHz(CDCl$_3$) δ (s, 12.75, 1H, NH), (s, 8.12, 1H, NH), (m, 7.4–7.6 3H, Aromatic), (s, 5.83, 1H, CH), (s, 4.17, 3H, CH$_3$), (s, 3.98, 3H, NCH$_3$), (s, 2.27, 3H, CH$_3$).

IR(nujol) 1700, 1370, 1160 cm$^{-1}$.

Example 11
N-(1,1-Dimethylethyl)-5,6,7,8-tetrahydro-8-hydroxy-1-naphthalenesulfonamide To a solution of 25.2 g (93.5 mmol) of a 1:1 mixture of N-(1,1-dimethylethyl)-5,6,7,8-tetrahydro-1-naphthalenesulfonamide and N-(1,1-dimethylethyl)-5,6,7,8-tetrahydro-2-naphthalenesulfonamide in 450 mL of tetrahydrofuran at −10° C., was added dropwise 75 mL (187 mmol) of a 2.5M solution of n-butyllithium in hexanes. After 90 minutes at this temperature the reaction mixture had turned red. The reaction mixture was cooled to −78° C. and oxygen was bubbled through for 15 minutes until the red color disappeared. After an additional 15 minutes, 200 mL of 5% NaHSO$_3$ was added. The reaction mixture was extracted with ethyl acetate, dried (Na$_2$SO$_4$) and the solvent was removed with a rotary evaporator. The residue was purified by flash chromatography to give 6.0 g of the title compound as a sticky solid; m.p. 100°–111° C.

$^1$H NMR (CDCl$_3$) δ 1.24 (s, 9H), 1.8 (m, 2H), 2.0 (m, 2H), 2.8 (m, 2H), 3.5 (d, 1H), 5.2 (br, 1H), 5.55 (m, 1H), 7.3 (m, 2H), 7.99 (d, 1H).

Example 12
N-(1,1-Dimethylethyl)-5,6,7,8-tetrahydro-8-oxo-1-naphthalenesulfonamide To a solution of 5.49 g (19.4 mmol) of material prepared in Example 11 in 250 mL of methylene chloride was added 8.35 g (39 mmol) of pyridiniumchlorochromate. After 3 hours the reaction mixture was diluted with ether and passed through a plug of fluorosil to give 5.3 g of the title compound as a colorless oil.

$^1$H NMR (CDCl$_3$) δ 1.27 (s, 9H), 2.1 (m, 2H), 2.26 (dd, 2H), 3.00 (dd, 2H), 6.77 (br, 1H), 7.54 (m, 2H), 8.13 (dd, 1H).

Example 13
N-(1,1-Dimethylethyl)-5,6,7,8-tetrahydro-7-(hydroxymethylene)-8-oxo-1-naphthanesulfonamide 1.0 g (43.5 g-atom) of sodium was added to 25 mL of ethanol. When all of the sodium had reacted the ethanol was removed with a rotary evaporator. 25 mL of benzene was added. The reaction mixture was cooled in an ice bath and 2.5 mL of ethyl formate was added. 4.82 g (17.1 mmol) of material prepared in Example 12 was added in 25 mL of benzene. The reaction mixture was allowed to stand at room temperature for 16 hours. The reaction mixture was extracted with 100 mL of water. This aqueous layer was acidified with 5% HCl and was extracted with ethyl acetate. The organic layer was dried (Na$_2$SO$_4$) and the solvent was removed with a rotary evaporator to give 4.30 g of the title compound as a yellow solid.

$^1$H NMR (CDCl$_3$) δ 1.30 (s, 9H), 2.49 (t, 2H), 2.95 (t, 2H), 6.79 (br, 1H), 7.54 (m, 3H), 8.16 (d, 1H).

Example 14
N-(1,1-Dimethylethyl)-3,4-dihydronaphth((2,1-D))isoxazole-9-sulfonamide A mixture of 0.7 g (2.85 mmol) of material prepared in Example 13 and 0.4 g (5.8 mmol) of hydroxylamine hydrochloride was dissolved in 20 mL of acetic acid. The reaction mixture was placed in an oil bath at 125° C. for 15 minutes. After cooling, water and 1-chlorobutane were added. After extraction with 1-chlorobutane, the organic layer was washed with saturated NaHCO$_3$, dried (Na$_2$SO$_4$) and the solvent was removed with a rotary evaporator. The residue was purified by flash chromatography to give 0.26 g of an orange solid.

$^1$H NMR (CDCl$_3$) δ 1.21 (s, 9H), 2.78 (m, 2H), 3.10 (m, 2H), 5.73 (br, 1H), 7.48 (m, 2H), 8.15 (d, 1H), 8.27 (s, 1H).

Example 15
3,4-Dihydronaphth((2,1-D))isoxazole-9-sulfonamide 0.20 g of material prepared in Example 14 was dissolved in 5 mL of trifluoroacetic acid. After 1 hour the volatiles were removed with a rotary evaporator. The residue was purified by flash chromatography to give 0.09 g of a brown solid.

$^1$H NMR (d$_6$-DMSO) δ 2.71 (m, 2H), 3.03 (m, 2H), 7.36 (s, 2H), 7.52 (dd, 1H), 7.62 (d, 1H), 7.90 (d, 1H), 8.62 (s, 1H).

Example 16

N-((4,6-Dimethoxypyrimidinyl-2-yl)aminocarbonyl)-3,4-dihydronaphth((2,1-D))isoxazole-9-sulfonamide To a solution of 45 mg of material prepared in Example 15 and 50 mg phenyl 4,6-dimethoxypyrimidin-2-yl carbamate in 1 mL of acetonitrile was added 0.027 mL of 1,8-diazabicyclo[5.4.0]undec-7-ene. After 1 hour, 1 mL of water and 0.5 mL of 5% HCl were added. The brown solid which precipitated out was collected to give 45 mg of the title compound: m.p. 189–192(d).

$^1$H NMR (d$_6$-DMSO) δ 2.77 (m, 2H), 3.07 (m, 2H), 3.99 (s, 6H), 5.99 (s, 1H), 7.61 (dd, 1H), 7.79 (d, 1H), 8.05 (d, 1H), 8.60 (s, 1H), 10.6 (br, 1H), 13.1 (br, 1H).

Using the techniques described in Equations 1–12 and Examples 1–16 the following compounds of Tables 1 through 28 can be prepared.

Unless otherwise indicated, all temperatures are in °C.

General Formulas for Tables

General Formula 1a
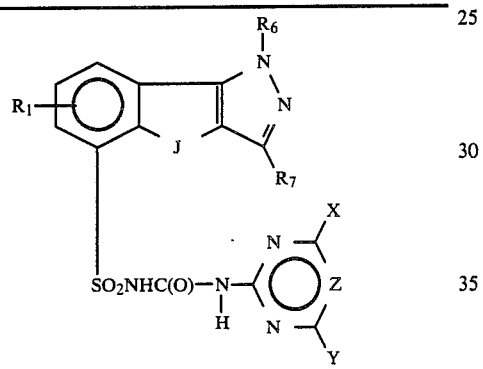

General Formula 1b
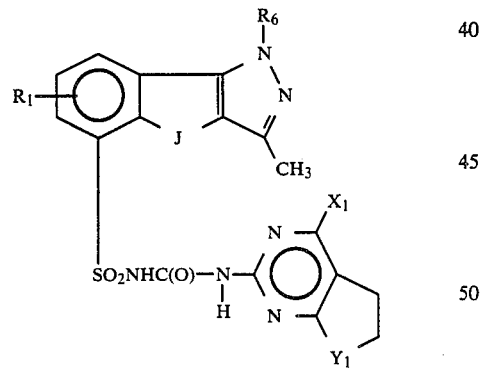

General Formula 1c
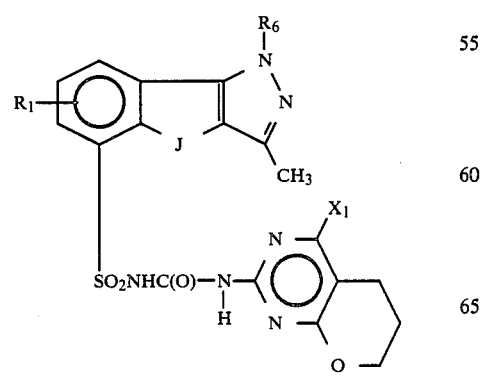

General Formulas for Tables -continued

General Formula 1d
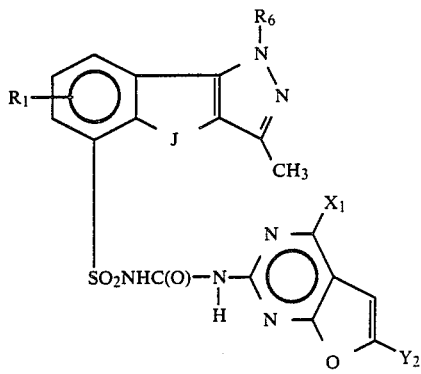

General Formula 1e
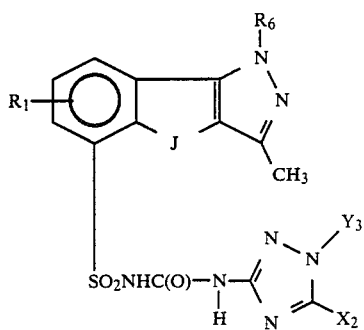

General Formula 1f
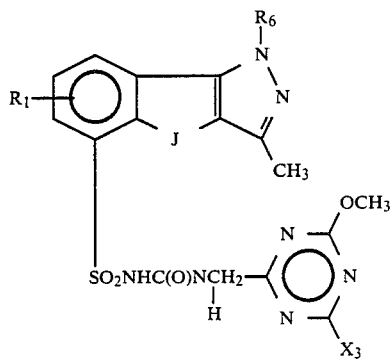

General Formula 1g
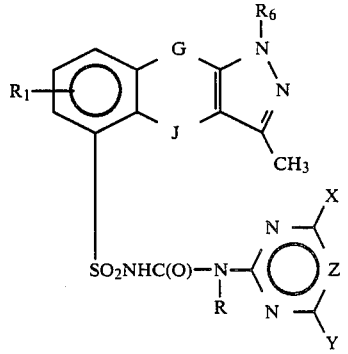

-continued
General Formulas for Tables
General Formula 1h
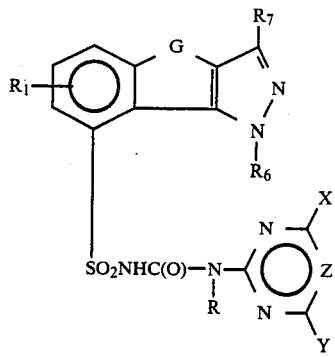
General Formula 2a
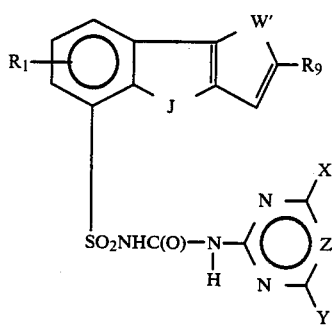
General Formula 2b
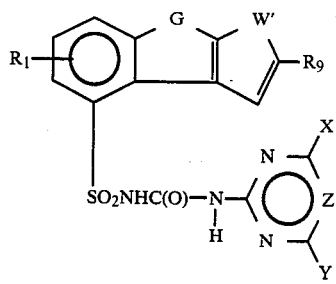
General Formula 3a
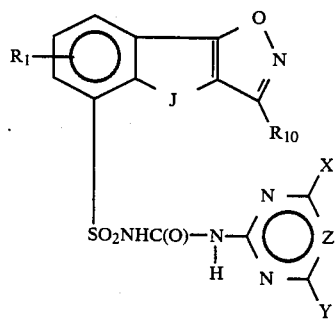
General Formula 3b
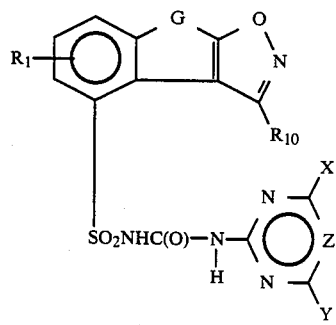
-continued
General Formulas for Tables
General Formula 4a
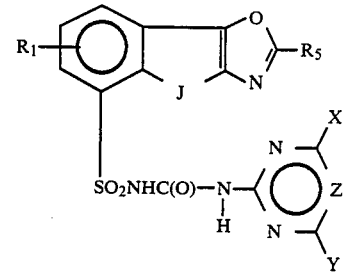
General Formula 4b
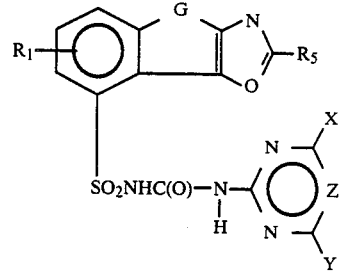
General Formula 5a
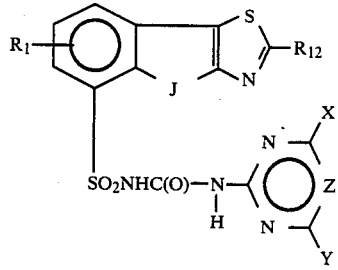
General Formula 5b
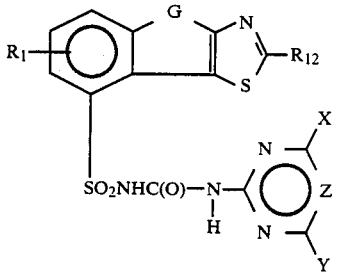
General Formula 6
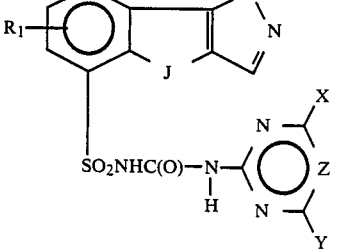

-continued
General Formulas for Tables
General Formula 7 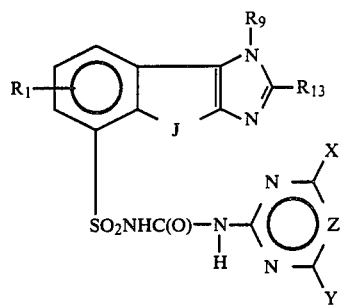
General Formula 8 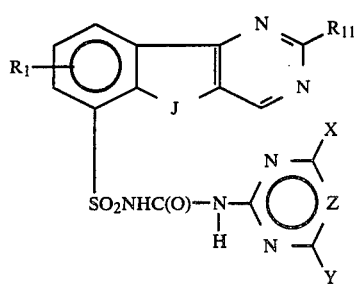
General Formula 9 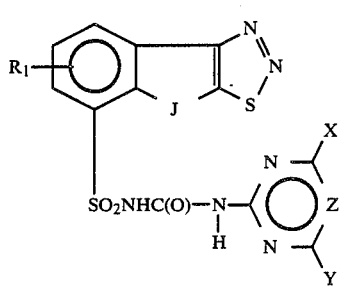
General Formula 10 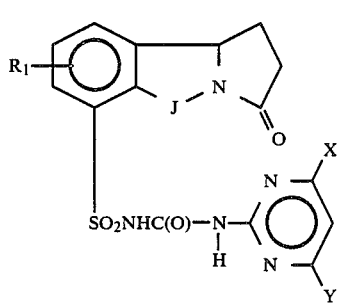
General Formula 11 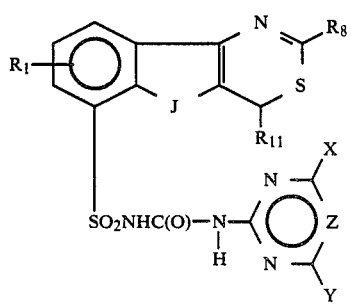
-continued
General Formulas for Tables
General Formula 12 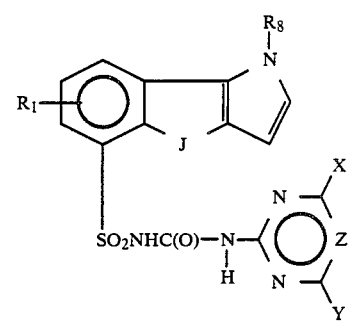
General Formula 13 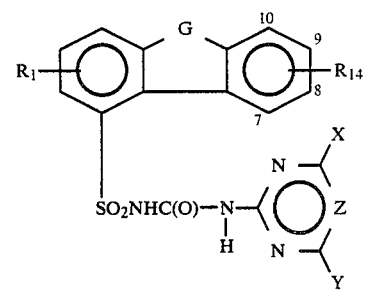
General Formula 14 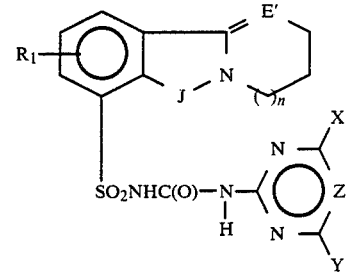
General Formula 15 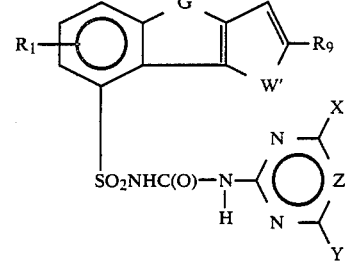
General Formula 16 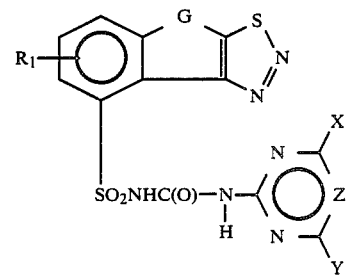

-continued
General Formulas for Tables
General Formula 17 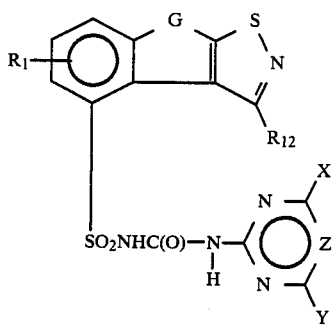
General Formula 18 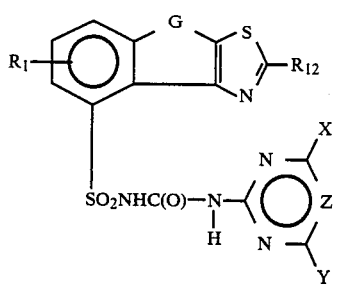
General Formula 19 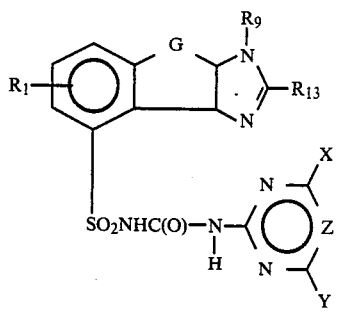
General Formula 20 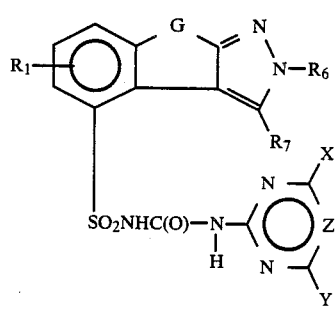
General Formula 21 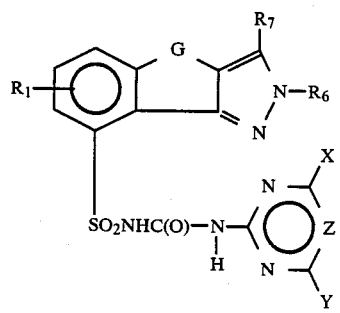
-continued
General Formulas for Tables
General Formula 22 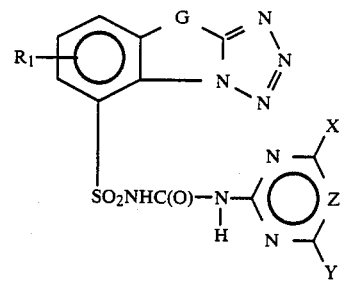
General Formula 23 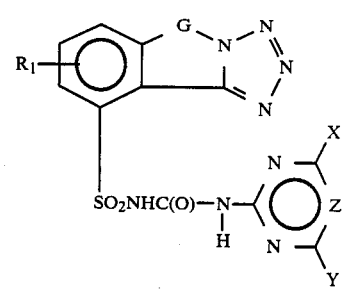
General Formula 24 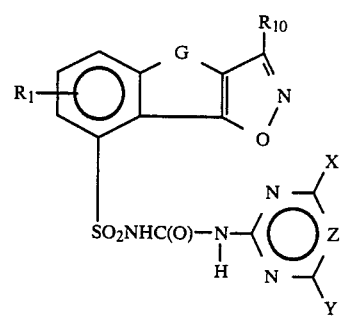
General Formula 25 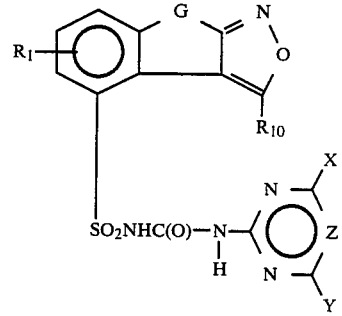
General Formula 26 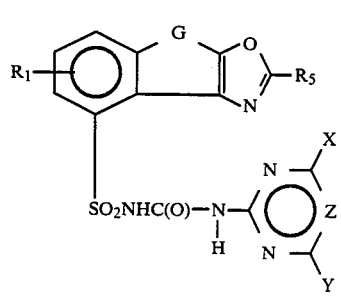

-continued
General Formulas for Tables

General Formula 27

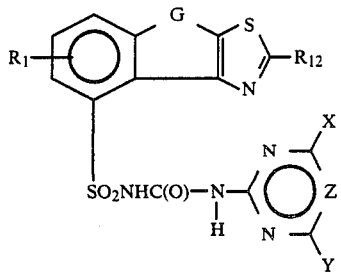

General Formula 28

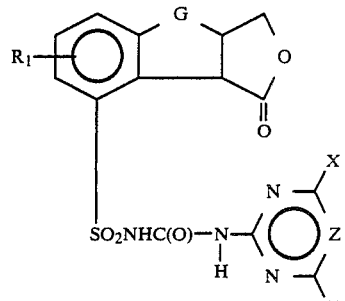

In general Formulas 1–28, the position of the substituent $R_1$ is designated as follows:

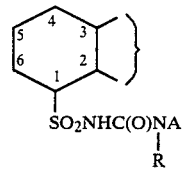

TABLE Ia

General Formula Ia

| $R_1$ | J | $R_6$ | $R_7$ | X | Y | Z | m.p. (°C.) |
|---|---|---|---|---|---|---|---|
| H | C=O | H | $CH_3$ | $CH_3$ | $CH_3$ | CH | 226–230 |
| H | C=O | H | $CH_3$ | $CH_3$ | $OCH_3$ | CH | 248–250 |
| H | C=O | H | $CH_3$ | $OCH_3$ | $OCH_3$ | CH | 242–246 |
| H | C=O | H | $CH_3$ | Cl | $OCH_3$ | CH | 245–251 |
| H | C=O | H | $CH_3$ | $CH_3$ | $OCH_3$ | N | 218–221 |
| H | C=O | H | $CH_3$ | $OCH_3$ | $OCH_3$ | N | 222–227 |
| H | C=O | $CH_3$ | $CH_3$ | $CH_3$ | $CH_3$ | CH | 238–240 |
| H | C=O | $CH_3$ | $CH_3$ | $CH_3$ | $OCH_3$ | CH | 238–240 |
| H | C=O | $CH_3$ | $CH_3$ | $OCH_3$ | $OCH_3$ | CH | 224–230 |
| H | C=O | $CH_3$ | $CH_3$ | Cl | $OCH_3$ | CH | 250–255 |
| H | C=O | $CH_3$ | $CH_3$ | $CH_3$ | $OCH_3$ | N | 232–234 |
| H | C=O | $CH_3$ | $CH_3$ | $OCH_3$ | $OCH_3$ | N | 232–235 |
| H | C=O | $CH_3$ | $CH_3$ | $CH_3$ | $CH_3$ | N | |
| H | C=O | $C_6H_5$ | $CH_3$ | $CH_3$ | $CH_3$ | CH | 212–214 |
| H | C=O | $C_6H_5$ | $CH_3$ | $OCH_3$ | $CH_3$ | CH | 185–189 |
| H | C=O | $C_6H_5$ | $CH_3$ | $OCH_3$ | $OCH_3$ | CH | 215–217 |
| H | C=O | $C_6H_5$ | $CH_3$ | Cl | $OCH_3$ | CH | 202–204 |
| H | C=O | $C_6H_5$ | $CH_3$ | $CH_3$ | $OCH_3$ | N | 168–171 |
| H | C=O | $C_6H_5$ | $CH_3$ | $OCH_3$ | $OCH_3$ | N | 152–155 |
| H | C=O | $C_6H_5$ | $CH_3$ | $CH_3$ | $CH_3$ | N | 205–208 |
| H | C=O | $C_6H_5$ | H | $CH_3$ | $CH_3$ | CH | |
| H | C=O | $C_6H_5$ | H | $CH_3$ | $OCH_3$ | CH | |
| H | C=O | $C_6H_5$ | H | $OCH_3$ | $OCH_3$ | CH | |
| H | C=O | $C_6H_5$ | H | Cl | $OCH_3$ | CH | |
| H | C=O | $C_6H_5$ | H | $CH_3$ | $OCH_3$ | N | |
| H | C=O | $C_6H_5$ | H | $OCH_3$ | $OCH_3$ | N | |
| H | C=O | $C_6H_5$ | H | $CH_3$ | $CH_3$ | N | |
| H | C=O | 4-Cl—$C_6H_5$ | $CH_3$ | $CH_3$ | $CH_3$ | CH | 227–231 |
| H | C=O | 4-Cl—$C_6H_5$ | $CH_3$ | $CH_3$ | $OCH_3$ | CH | 236–238 |
| H | C=O | 4-Cl—$C_6H_5$ | $CH_3$ | $OCH_3$ | $OCH_3$ | CH | 248–250 |
| H | C=O | 4-Cl—$C_6H_5$ | $CH_3$ | Cl | $OCH_3$ | CH | 229–232 |
| H | C=O | 4-Cl—$C_6H_5$ | $CH_3$ | $CH_3$ | $OCH_3$ | N | |
| H | C=O | 4-Cl—$C_6H_5$ | $CH_3$ | $OCH_3$ | $OCH_3$ | N | 206–210 |
| H | C=O | 4-Cl—$C_6H_5$ | $CH_3$ | $CH_3$ | $CH_3$ | N | |
| H | C=O | 4-$OCH_3$—$C_6H_5$ | $CH_3$ | $CH_3$ | $CH_3$ | CH | |
| H | C=O | 4-$OCH_3$—$C_6H_5$ | $CH_3$ | $CH_3$ | $OCH_3$ | CH | |
| H | C=O | 4-$OCH_3$—$C_6H_5$ | $CH_3$ | $OCH_3$ | $OCH_3$ | CH | 228–230 |
| H | C=O | 4-$OCH_3$—$C_6H_5$ | $CH_3$ | Cl | $OCH_3$ | CH | |
| H | C=O | 4-$OCH_3$—$C_6H_5$ | $CH_3$ | $CH_3$ | $OCH_3$ | N | |
| H | C=O | 4-$OCH_3$—$C_6H_5$ | $CH_3$ | $OCH_3$ | $OCH_3$ | N | |
| H | C=O | 4-$OCH_3$—$C_6H_5$ | $CH_3$ | $CH_3$ | $CH_3$ | N | |
| H | C=O | 4-$SO_2CH_3$—$C_6H_5$ | $CH_3$ | $CH_3$ | $CH_3$ | CH | 172–176 |
| H | C=O | 4-$SO_2CH_3$—$C_6H_5$ | $CH_3$ | $CH_3$ | $OCH_3$ | CH | 166–169 |
| H | C=O | 4-$SO_2CH_3$—$C_6H_5$ | $CH_3$ | $OCH_3$ | $OCH_3$ | CH | 204–208 |
| H | C=O | 4-$SO_2CH_3$—$C_6H_5$ | $CH_3$ | Cl | $OCH_3$ | CH | |

TABLE Ia-continued

General Formula Ia

| R₁ | J | R₆ | R₇ | X | Y | Z | m.p. (°C.) |
|---|---|---|---|---|---|---|---|
| H | C=O | 4-SO₂CH₃—C₆H₅ | CH₃ | CH₃ | OCH₃ | N | |
| H | C=O | 4-SO₂CH₃—C₆H₅ | CH₃ | OCH₃ | OCH₃ | N | 104–109 |
| H | C=O | 4-SO₂CH₃—C₆H₅ | CH₃ | CH₃ | CH₃ | N | |
| H | C=O | 4-NO₂—C₆H₅ | CH₃ | CH₃ | CH₃ | CH | |
| H | C=O | 4-NO₂—C₆H₅ | CH₃ | CH₃ | OCH₃ | CH | |
| H | C=O | 4-NO₂—C₆H₅ | CH₃ | OCH₃ | OCH₃ | CH | |
| H | C=O | 4-NO₂—C₆H₅ | CH₃ | Cl | OCH₃ | CH | |
| H | C=O | 4-NO₂—C₆H₅ | CH₃ | OCH₃ | CH₃ | N | |
| H | C=O | 4-NO₂—C₆H₅ | CH₃ | OCH₃ | OCH₃ | N | |
| H | C=O | 4-NO₂—C₆H₅ | CH₃ | CH₃ | CH₃ | N | |
| H | C=O | 4-CH₃—C₆H₅ | CH₃ | CH₃ | CH₃ | CH | |
| H | C=O | 4-CH₃—C₆H₅ | CH₃ | CH₃ | OCH₃ | CH | |
| H | C=O | 4-CH₃—C₆H₅ | CH₃ | OCH₃ | OCH₃ | CH | |
| H | C=O | 4-CH₃—C₆H₅ | CH₃ | Cl | OCH₃ | CH | |
| H | C=O | 4-CH₃—C₆H₅ | CH₃ | OCH₃ | CH₃ | N | |
| H | C=O | 4-CH₃—C₆H₅ | CH₃ | OCH₃ | OCH₃ | N | |
| H | C=O | 4-CH₃—C₆H₅ | CH₃ | OH₃ | CH₃ | N | |
| H | C=O | 2-pyridyl | H | CH₃ | CH₃ | CH | 158–160 |
| H | C=O | 2-pyridyl | H | CH₃ | OCH₃ | CH | 160–164 |
| H | C=O | 2-pyridyl | H | OCH₃ | OCH₃ | CH | 203–207 |
| H | C=O | 2-pyridyl | H | Cl | OCH₃ | CH | 145–151 |
| H | C=O | 2-pyridyl | H | CH₃ | OCH₃ | N | 135–141 |
| H | C=O | 2-pyridyl | H | OCH₃ | OCH₃ | N | 148–153 |
| H | C=O | 2-pyridyl | H | CH₃ | CH₃ | N | |
| H | C=O | 2-pyridyl | CH₃ | CH₃ | CH₃ | CH | |
| H | C=O | 2-pyridyl | CH₃ | CH₃ | OCH₃ | CH | |
| H | C=O | 2-pyridyl | CH₃ | OCH₃ | OCH₃ | CH | |
| H | C=O | 2-pyridyl | CH₃ | Cl | OCH₃ | CH | |
| H | C=O | 2-pyridyl | CH₃ | CH₃ | OCH₃ | N | |
| H | C=O | 2-pyridyl | CH₃ | OCH₃ | OCH₃ | N | |
| H | C=O | 2-pyridyl | CH₃ | CH₃ | CH₃ | N | |
| H | SO₂ | 2-pyridyl | CH₃ | CH | CH₃ | CH | |
| H | SO₂ | 2-pyridyl | CH₃ | CH₃ | OCH₃ | CH | |
| H | SO₂ | 2-pyridyl | CH₃ | OCH₃ | OCH₃ | CH | |
| H | SO₂ | 2-pyridyl | CH₃ | Cl | OCH₃ | CH | |
| H | SO₂ | 2-pyridyl | CH₃ | CH₃ | OCH₃ | N | |
| H | SO₂ | 2-pyridyl | CH₃ | OCH₃ | OCH₃ | N | |
| H | SO₂ | 2-pyridyl | CH₃ | CH₃ | CH₃ | N | |
| H | C=O | CH₃ | CH₃ | CH₃ | OCH₂CH₃ | CH | |
| H | C=O | CH₃ | CH₃ | CH₃ | NH₂ | CH | |
| H | C=O | CH₃ | CH₃ | CH₃ | NHCH₃ | CH | |
| H | C=O | CH₃ | CH₃ | CH₃ | N(CH₃)₂ | CH | |
| H | C=O | CH₃ | CH₃ | CH₃ | CH₂CH₃ | CH | |
| H | C=O | CH₃ | CH₃ | CH₃ | CH₂CH₃ | CH | |
| H | C=O | CH₃ | CH₃ | CH₃ | CF₃ | CH | |
| H | C=O | CH₃ | CH₃ | CH₃ | SCH₃ | CH | |
| H | C=O | CH₃ | CH₃ | CH₃ | OCH₂CH=CH₂ | CH | |
| H | C=O | CH₃ | CH₃ | CH₃ | OCH₂CH=CH₂ | CH | |
| H | C=O | CH₃ | CH₃ | CH₃ | OCH₂C≡CH | CH | |
| H | C=O | CH₃ | CH₃ | CH₃ | OCH₂CF₃ | CH | |
| H | C=O | CH₃ | CH₃ | CH₃ | OCH₂CH₂OCH₃ | CH | |
| H | C=O | CH₃ | CH₃ | CH₃ | CH(OCH₃)₂ | CH | |
| H | C=O | CH₃ | CH₃ | CH₃ | 1,3-dioxolan-2-yl | CH | |
| H | C=O | CH₃ | CH₂ | CH₃ | CH₂OCH₃ | CH | |
| H | C=O | CH₃ | CH₃ | F | OCH₃ | CH | |
| H | C=O | CH₃ | CH₃ | Br | OCH₃ | CH | |
| H | C=O | CH₃ | CH₃ | OCH₂F | OCH₃ | CH | |
| H | C=O | CH₃ | CH₃ | OCF₃ | OCH₃ | CH | |
| H | C=O | CH₃ | CH₃ | CF₃ | OCH₃ | CH | |
| H | C=O | CH₃ | CH₃ | CH₃ | 4-methyl-1,3-dioxolan-2-yl | CH | |
| H | C=O | CH₃ | CH₃ | CH₃ | OCH₂F | CH | |
| H | C=O | CH₃ | CH₃ | CH₃ | CN | CH | |
| H | C=O | CH₃ | CH₃ | CH₃ | CH(OCH₂CH₃)₂ | CH | |
| H | C=O | CH₃ | CH₃ | CH₃ | OCF₂CHClF | CH | |
| H | C=O | CH₃ | CH₃ | CH₃ | SCH₂F | CH | |
| H | C=O | CH₃ | CH₃ | CH₃ | OCF₂CHBrF | CH | |
| H | C=O | CH₃ | CH₃ | CH₃ | OCF₂CHFCF₃ | CH | |
| H | C=O | C₆H₅ | CH₃ | CH₃ | OCH₂CH₃ | CH | |
| H | C=O | C₆H₅ | CH₃ | CH₃ | NHCH₃ | CH | |
| H | C=O | C₆H₅ | CH₃ | CH₃ | N(CH₃)₂ | CH | |
| H | C=O | C₆H₅ | CH₃ | CH₃ | CH₂CH₃ | CH | |
| H | C=O | C₆H₅ | CH₃ | CH₃ | SCH₃ | CH | |
| H | C=O | C₆H₅ | CH₃ | CH₃ | OCH₂C≡CH | CH | |
| H | C=O | C₆H₅ | CH₃ | CH₃ | OCH₂CH₂OCH₃ | CH | |
| H | C=O | C₆H₅ | CH₃ | CH₃ | CH(OCH₃)₂ | CH | |
| H | C=O | C₆H₅ | CH₃ | CH₃ | SCH₂F | CH | |
| H | C=O | C₆H₅ | CH₃ | CH₃ | 1,3-dioxolan-2-yl | CH | |
| H | C=O | C₆H₅ | CH₃ | CH₃ | OCF₂CHClF | CH | |
| H | C=O | C₆H₅ | CH₃ | CH₃ | CN | CH | |

TABLE Ia-continued

General Formula Ia

| R₁ | J | R₆ | R₇ | X | Y | Z | m.p. (°C.) |
|---|---|---|---|---|---|---|---|
| H | SO₂ | H | H | CH₃ | CH₃ | CH | |
| H | SO₂ | H | H | CH₃ | OCH₃ | CH | |
| H | SO₂ | H | H | OCH₃ | OCH₃ | CH | |
| H | SO₂ | H | H | Cl | OCH₃ | CH | |
| H | SO₂ | H | H | CH₃ | OCH₃ | N | |
| H | SO₂ | H | H | OCH₃ | OCH₃ | N | |
| H | SO₂ | H | H | CH₃ | CH₃ | N | |
| H | SO₂ | CH₃ | H | CH₃ | CH₃ | CH | 262–266 |
| H | SO₂ | CH₃ | H | CH₃ | OCH₃ | CH | 238–242 |
| H | SO₂ | CH₃ | H | OCH₃ | OCH₃ | CH | 232–235 |
| H | SO₂ | CH₃ | H | Cl | OCH₃ | CH | 245–247 |
| H | SO₂ | CH₃ | H | CH₃ | OCH₃ | N | 227–230 |
| H | SO₂ | CH₃ | H | OCH₃ | OCH₃ | N | 228–231 |
| H | SO₂ | CH₃ | H | CH₃ | CH₃ | N | |
| H | SO₂ | C₆H₅ | H | CH₃ | CH₃ | CH | 244–247 |
| H | SO₂ | C₆H₅ | H | CH₃ | OCH₃ | CH | 250–253 |
| H | SO₂ | C₆H₅ | H | OCH₃ | OCH₃ | CH | 243–248 |
| H | SO₂ | C₆H₅ | H | Cl | OCH₃ | CH | 236–240 |
| H | SO₂ | C₆H₅ | H | CH₃ | OCH₃ | N | 215–226 |
| H | SO₂ | C₆H₅ | H | OCH₃ | OCH₃ | N | 212–213 |
| H | SO₂ | C₆H₅ | H | CH₃ | CH₃ | N | |
| H | SO₂ | H | CH₃ | CH₃ | CH₃ | CH | |
| H | SO₂ | H | CH₃ | CH₃ | OCH₃ | CH | |
| H | SO₂ | H | CH₃ | OCH₃ | OCH₃ | CH | |
| H | SO₂ | H | CH₃ | Cl | OCH₃ | CH | |
| H | SO₂ | H | CH₃ | CH₃ | OCH₃ | N | |
| H | SO₂ | H | CH₃ | OCH₃ | OCH₃ | N | |
| H | SO₂ | H | CH₃ | CH₃ | CH₃ | N | |
| H | SO₂ | CH₃ | CH₃ | CH₃ | CH₃ | CH | |
| H | SO₂ | CH₃ | CH₃ | CH₃ | OCH₃ | CH | 245–247 |
| H | SO₂ | CH₃ | CH₃ | OCH₃ | OCH₃ | CH | 259–262 |
| H | SO₂ | CH₃ | CH₃ | Cl | OCH₃ | CH | |
| H | SO₂ | CH₃ | CH₃ | CH₃ | OCH₃ | N | 220–224 |
| H | SO₂ | CH₃ | CH₃ | OCH₃ | OCH₃ | N | 240–243 |
| H | SO₂ | C₆H₅ | CH₃ | CH₃ | CH₃ | CH | 255–258 |
| H | SO₂ | C₆H₅ | CH₃ | CH₃ | OCH₃ | CH | 264–266 |
| H | SO₂ | C₆H₅ | CH₃ | OCH₃ | OCH₃ | CH | 260–264 |
| H | SO₂ | C₆H₅ | CH₃ | Cl | OCH₃ | CH | 262–266 |
| H | SO₂ | C₆H₅ | CH₃ | OCH₃ | OCH₃ | N | 217–219 |
| H | SO₂ | C₆H₅ | CH₃ | CH₃ | OCH₃ | N | 214–218 |
| H | SO₂ | C₆H₅ | CH₃ | CH₃ | CH₃ | N | |
| H | NH | H | CH₃ | CH₃ | CH₃ | CH | |
| H | NH | H | CH₃ | CH₃ | OCH₃ | CH | |
| H | NH | H | CH₃ | OCH₃ | OCH₃ | CH | |
| H | NH | H | CH₃ | Cl | OCH₃ | CH | |
| H | NH | H | CH₃ | CH₃ | OCH₃ | N | |
| H | NH | H | CH₃ | OCH₃ | OCH₃ | N | |
| H | NH | H | CH₃ | CH₃ | CH₃ | N | |
| H | NH | CH₃ | CH₃ | CH₃ | CH₃ | CH | |
| H | NH | CH₃ | CH₃ | CH₃ | OCH₃ | CH | |
| H | NH | CH₃ | CH₃ | OCH₃ | OCH₃ | CH | |
| H | NH | CH₃ | CH₃ | Cl | OCH₃ | CH | |
| H | NH | CH₃ | CH₃ | CH₃ | OCH₃ | N | |
| H | NH | CH₃ | CH₃ | OCH₃ | OCH₃ | N | |
| H | NH | CH₃ | CH₃ | CH₃ | CH₃ | N | |
| H | NH | C₆H₅ | CH₃ | CH₃ | CH₃ | CH | |
| H | NH | C₆H₅ | CH₃ | CH₃ | OCH₃ | CH | |
| H | NH | C₆H₅ | CH₃ | OCH₃ | OCH₃ | CH | |
| H | NH | C₆H₅ | CH₃ | Cl | OCH₃ | CH | |
| H | NH | C₆H₅ | CH₃ | CH₃ | OCH₃ | N | |
| H | NH | C₆H₅ | CH₃ | OCH₃ | OCH₃ | N | |
| H | NH | C₆H₅ | CH₃ | CH₃ | CH₃ | N | |
| H | SO₂ | C₆H₅ | CH₃ | CH₃ | OCH₂CH₃ | CH | |
| H | SO₂ | C₆H₅ | CH₃ | CH₃ | NH₂ | CH | |
| H | SO₂ | C₆H₅ | CH₃ | CH₃ | NHCH₃ | CH | |
| H | SO₂ | C₆H₅ | CH₃ | CH₃ | N(CH₃)₂ | CH | |
| H | SO₂ | C₆H₅ | CH₃ | CH₃ | CH₂CH₃ | CH | |
| H | SO₂ | C₆H₅ | CH₃ | CH₃ | CF₃ | CH | |
| H | SO₂ | C₆H₅ | CH₃ | CH₃ | SCH₃ | CH | |
| H | SO₂ | C₆H₅ | CH₃ | CH₃ | OCH₂CH=CH₂ | CH | |
| H | SO₂ | C₆H₅ | CH₃ | CH₃ | OCH₂CH≡CH | CH | |
| H | SO₂ | C₆H₅ | CH₃ | CH₃ | OCH₂CF₃ | CH | |
| H | SO₂C₆H₅CH₃ | | CH₃ | OCH₂CH₂OCH₃ | | CH | |
| H | SO₂ | C₆H₅ | CH₃ | CH₃ | CH(OCH₃)₂ | CH | |
| H | SO₂ | C₆H₅ | CH₃ | CH₃ | 1,3-dioxolan-2-yl | CH | |
| H | SO₂ | C₆H₅ | CH₃ | CH₂OCH₃ | N(CH₃)₂ | CH | |
| H | SO₂ | C₆H₅ | CH₃ | OCH₃ | N(CH₃)₂ | CH | |
| H | SO₂ | C₆H₅ | CH₃ | Br | OCH₃ | CH | |
| H | SO₂ | C₆H₅ | CH₃ | OCH₂F | OCH₃ | CH | |

TABLE Ia-continued

General Formula Ia

| $R_1$ | J | $R_6$ | $R_7$ | X | Y | Z | m.p. (°C.) |
|---|---|---|---|---|---|---|---|
| H | $SO_2$ | $C_6H_5$ | $CH_3$ | $CF_3$ | $OCH_3$ | CH | |
| H | $SO_2$ | $C_6H_5$ | $CH_3$ | $CH_3$ | $OCH_2F$ | CH | |
| H | $SO_2$ | $C_6H_5$ | $CH_3$ | $CH_3$ | CN | CH | |
| H | $SO_2$ | $C_6H_5$ | $CH_3$ | $CH_3$ | $CH(OCH_2CH_3)_2$ | CH | |
| H | $SO_2$ | $C_6H_5$ | $CH_3$ | $CH_3$ | $SCH_2F$ | CH | |
| H | $SO_2$ | $C_6H_5$ | $CH_3$ | $CH_3$ | $OCH_2CFBrF$ | CH | |
| H | $SO_2$ | $C_6H_5$ | $CH_3$ | $CH_3$ | $OCH_2CHFCF_3$ | CH | |
| H | S | $CH_3$ | $CH_3$ | $CH_3$ | $OCH_2CH_3$ | CH | |
| H | S | $CH_3$ | $CH_3$ | $CH_3$ | $NH_2$ | CH | |
| H | S | $CH_3$ | $CH_3$ | $CH_3$ | $NHCH_3$ | CH | |
| H | S | $CH_3$ | $CH_3$ | $CH_3$ | $N(CH_3)_2$ | CH | |
| H | S | $CH_3$ | $CH_3$ | $CH_3$ | $CH_2CH_3$ | CH | |
| H | S | $CH_3$ | $CH_3$ | $CH_3$ | $CF_3$ | CH | |
| H | S | $CH_3$ | $CH_3$ | $CH_3$ | $SCH_3$ | CH | |
| H | S | $CH_3$ | $CH_3$ | $CH_3$ | $OCH_2CH=CH_2$ | CH | |
| H | S | $CH_3$ | $CH_3$ | $CH_3$ | $OCH_2C\equiv CH$ | CH | |
| H | S | $CH_3$ | $CH_3$ | $CH_3$ | $OCH_2CF_3$ | CH | |
| H | S | $CH_3$ | $CH_3$ | $CH_3$ | $OCH_2CH_2OCH_3$ | CH | |
| H | S | $CH_3$ | $CH_3$ | $CH_3$ | $CH(OCH_3)_2$ | CH | |
| H | S | $CH_3$ | $CH_3$ | $CH_3$ | 1,3-dioxolan-2-yl | CH | |
| H | S | $CH_3$ | $CH_3$ | $CH_3$ | $CH_2OCH_3$ | CH | |
| H | S | $CH_3$ | $CH_3$ | Br | $OCH_3$ | CH | |
| H | S | $CH_3$ | $CH_3$ | $OCH_2F$ | $OCH_3$ | CH | |
| H | S | $CH_3$ | $CH_3$ | $CF_3$ | $OCH_3$ | CH | |
| H | S | $CH_3$ | $CH_3$ | $CH_3$ | $OCH_2F$ | CH | |
| H | S | $CH_3$ | $CH_3$ | $CH_3$ | CN | CH | |
| H | S | $CH_3$ | $CH_3$ | $CH_3$ | $CH(OCH_2CH_3)_2$ | CH | |
| H | S | $CH_3$ | $CH_3$ | $CH_3$ | $OCF_2CHClF$ | CH | |
| H | S | $CH_3$ | $CH_3$ | $CH_3$ | $SCH_2F$ | CH | |
| H | S | $CH_3$ | $CH_3$ | $CH_3$ | $OCH_2CFBrF$ | CH | |
| H | S | $CH_3$ | $CH_3$ | $CH_3$ | $OCF_2CHFCF_3$ | CH | |
| H | $SO_2$ | $CH_3$ | $CH_3$ | $CH_3$ | $OCH_2CH_3$ | CH | |
| H | $SO_2$ | $CH_3$ | $CH_3$ | $CH_3$ | $NH_2$ | CH | |
| H | $SO_2$ | $CH_3$ | $CH_3$ | $CH_3$ | $NHCH_3$ | CH | |
| H | $SO_2$ | $CH_3$ | $CH_3$ | $CH_3$ | $N(CH_3)_2$ | CH | |
| H | $SO_2$ | $CH_3$ | $CH_3$ | $CH_3$ | $CH_2CH_3$ | CH | |
| H | $SO_2$ | $CH_3$ | $CH_3$ | $CH_3$ | $CF_3$ | CH | |
| H | $SO_2$ | $CH_3$ | $CH_3$ | $CH_3$ | $SCH_3$ | CH | |
| H | $SO_2$ | $CH_3$ | $CH_3$ | $CH_3$ | $OCH_2CH=CH_2$ | CH | |
| H | $SO_2$ | $CH_3$ | $CH_3$ | $CH_3$ | $OCH_2C\equiv CH$ | CH | |
| H | $SO_2$ | $CH_3$ | $CH_3$ | $CH_3$ | $OCH_2CF_3$ | CH | |
| H | $SO_2$ | $CH_3$ | $CH_3$ | $CH_3$ | $OCH_2CH_2OCH_3$ | CH | |
| H | $SO_2$ | $CH_3$ | $CH_3$ | $CH_3$ | $CH(OCH_3)_2$ | CH | |
| H | $SO_2$ | $CH_3$ | $CH_3$ | $CH_3$ | 1,3-dioxolan-2-yl | CH | |
| H | $SO_2$ | $CH_3$ | $CH_3$ | $CH_3$ | $CH_2OCH_3$ | CH | |
| H | $SO_2$ | $CH_3$ | $CH_3$ | Br | $OCH_3$ | CH | |
| H | $SO_2$ | $CH_3$ | $CH_3$ | $OCH_2F$ | $OCH_3$ | CH | |
| H | $SO_2$ | $CH_3$ | $CH_3$ | $CF_3$ | $OCH_3$ | CH | |
| H | $SO_2$ | $CH_3$ | $CH_3$ | $CH_3$ | $OCH_2F$ | CH | |
| H | $SO_2$ | $CH_3$ | $CH_3$ | $CH_3$ | CN | CH | |
| H | $SO_2$ | $CH_3$ | $CH_3$ | $CH_3$ | $CH(OCH_2CH_3)$ | CH | |
| H | $SO_2$ | $CH_3$ | $CH_3$ | $CH_3$ | $OCF_2CHClF)$ | CH | |
| H | $SO_2$ | $CH_3$ | $CH_3$ | $CH_3$ | $SCH_2F$ | CH | |
| H | $SO_2$ | $CH_3$ | $CH_3$ | $CH_3$ | $OCH_2CFBrF$ | CH | |
| H | $SO_2$ | $CH_3$ | $CH_3$ | $CH_3$ | $OCF_2CHFCF_3$ | CH | |
| H | $CH_2$ | $C_6H_5$ | $CH_3$ | $CH_3$ | $OCH_2CH_3$ | CH | |
| H | $CH_2$ | $C_6H_5$ | $CH_3$ | $CH_3$ | $NH_2$ | CH | |
| H | $CH_2$ | $C_6H_5$ | $CH_3$ | $CH_3$ | $NHCH_3$ | CH | |
| H | $CH_2$ | $C_6H_5$ | $CH_3$ | $CH_3$ | $N(CH_3)_2$ | CH | |
| H | $CH_2$ | $C_6H_5$ | $CH_3$ | $CH_3$ | $CH_2CH_3$ | CH | |
| H | $CH_2$ | $C_6H_5$ | $CH_3$ | $CH_3$ | $CF_3$ | CH | |
| H | $CH_2$ | $C_6H_5$ | $CH_3$ | $CH_3$ | $SCH_3$ | CH | |
| H | $CH_2$ | $C_6H_5$ | $CH_3$ | $CH_3$ | $OCH_2CH=CH_2$ | CH | |
| H | $CH_2$ | $C_6H_5$ | $CH_3$ | $CH_3$ | $OCH_2C\equiv CH$ | CH | |
| H | $CH_2$ | $C_6H_5$ | $CH_3$ | $CH_3$ | $OCH_2CF_3$ | CH | |
| H | $CH_2$ | $C_6H_5$ | $CH_3$ | $CH_3$ | $OCH_2CH_2OCH_3$ | CH | |
| H | $CH_2$ | $C_6H_5$ | $CH_3$ | $CH_3$ | $CH(OCH_3)_2$ | CH | |
| H | $CH_2$ | $C_6H_5$ | $CH_3$ | $CH_3$ | 1,3-dioxolan-2-yl | CH | |
| H | $CH_2$ | $C_6H_5$ | $CH_3$ | $CH_3$ | $CH_2OCH_3$ | CH | |
| H | $CH_2$ | $C_6H_5$ | $CH_3$ | Br | $OCH_3$ | CH | |
| H | $CH_2$ | $C_6H_5$ | $CH_3$ | $OCH_2F$ | $OCH_3$ | CH | |
| H | $CH_2$ | $C_6H_5$ | $CH_3$ | $CF_3$ | $OCH_3$ | CH | |
| H | $CH_2$ | $C_6H_5$ | $CH_3$ | $CH_3$ | $OCH_2F$ | CH | |
| H | $CH_2$ | $C_6H_5$ | $CH_3$ | $CH_3$ | CN | CH | |
| H | $CH_2$ | $C_6H_5$ | $CH_3$ | $CH_3$ | $CH(OCH_2CH_3)_2$ | CH | |
| H | $CH_2$ | $C_6H_5$ | $CH_3$ | $CH_3$ | $SCH_2F$ | CH | |
| H | $CH_2$ | $C_6H_5$ | $CH_3$ | $CH_3$ | $OCH_2CFBrF$ | CH | |
| H | $CH_2$ | $C_6H_5$ | $CH_3$ | $CH_3$ | $OCF_2CHFCF_3$ | CH | |
| H | $CH_2$ | $CH_3$ | $CH_3$ | $CH_3$ | $OCH_2CH_3$ | CH | |
| H | $CH_2$ | $CH_3$ | $CH_3$ | $CH_3$ | $NH_2$ | CH | |

TABLE Ia-continued

General Formula Ia

| R₁ | J | R₆ | R₇ | X | Y | Z | m.p. (°C.) |
|---|---|---|---|---|---|---|---|
| H | CH₂ | CH₃ | CH₃ | CH₃ | NHCH₃ | CH | |
| H | CH₂ | CH₃ | CH₃ | CH₃ | N(CH₃)₂ | CH | |
| H | CH₂ | CH₃ | CH₃ | CH₃ | CH₂CH₃ | CH | |
| H | CH₂ | CH₃ | CH₃ | CH₃ | CF₃ | CH | |
| H | CH₂ | CH₃ | CH₃ | CH₃ | SCH₃ | CH | |
| H | CH₂ | CH₃ | CH₃ | CH₃ | OCH₂CH=CH₂ | CH | |
| H | CH₂ | CH₃ | CH₃ | CH₃ | OCH₂C≡CH | CH | |
| H | CH₂ | CH₃ | CH₃ | CH₃ | OCH₂CF₃ | CH | |
| H | CH₂ | CH₃ | CH₃ | CH₃ | OCH₂CH₂OCH₃ | CH | |
| H | CH₂ | CH₃ | CH₃ | CH₃ | CH(OCH₃)₂ | CH | |
| H | CH₂ | CH₃ | CH₃ | CH₃ | 1,3-dioxolan-2-yl | CH | |
| H | CH₂ | CH₃ | CH₃ | CH₃ | CH₂OCH₃ | CH | |
| H | CH₂ | CH₃ | CH₃ | Br | OCH₃ | CH | |
| H | CH₂ | CH₃ | CH₃ | OCH₂F | OCH₃ | CH | |
| H | CH₂ | CH₃ | CH₃ | CF₃ | OCH₃ | CH | |
| H | CH₂ | CH₃ | CH₃ | CH₃ | OCH₂F | CH | |
| H | CH₂ | CH₃ | CH₃ | CH₃ | CN | CH | |
| H | CH₂ | CH₃ | CH₃ | CH₃ | CH(OCH₂CH₃)₂ | CH | |
| H | CH₂ | CH₃ | CH₃ | CH₃ | OCF₂CHClF | CH | |
| H | CH₂ | CH₃ | CH₃ | CH₃ | SCH₂F | CH | |
| H | CH₂ | CH₃ | CH₃ | CH₃ | OCH₂CFBrF | CH | |
| H | CH₂ | CH₃ | CH₃ | CH₃ | OCF₂CHFCF₃ | CH | |
| 6-CH₃ | C=O | H | CH₃ | CH₃ | CH₃ | CH | |
| 6-CH₃ | C=O | H | CH₃ | CH₃ | OCH₃ | CH | |
| 6-CH₃ | C=O | H | CH₃ | OCH₃ | OCH₃ | CH | |
| 6-CH₃ | C=O | H | CH₃ | Cl | OCH₃ | CH | |
| 6-CH₃ | C=O | H | CH₃ | CH₃ | OCH₃ | N | |
| 6-CH₃ | C=O | H | CH₃ | OCH₃ | OCH₃ | N | |
| 6-CH₃ | C=O | H | CH₃ | CH₃ | CH₃ | N | |
| 6-CH₃ | C=O | C₆H₅ | CH₃ | CH₃ | CH₃ | CH | |
| 6-CH₃ | C=O | C₆H₅ | CH₃ | CH₃ | OCH₃ | CH | |
| 6-CH₃ | C=O | C₆H₅ | CH₃ | OCH₃ | OCH₃ | CH | |
| 6-CH₃ | C=O | C₆H₅ | CH₃ | Cl | OCH₃ | CH | |
| 6-CH₃ | C=O | C₆H₅ | CH₃ | CH₃ | OCH₃ | N | |
| 6-CH₃ | C=O | C₆H₅ | CH₃ | OCH₃ | OCH₃ | N | |
| 6-CH₃ | C=O | C₆H₅ | CH₃ | CH₃ | CH₃ | N | |
| 6-CH₃ | C=O | C₆H₅ | H | CH₃ | CH₃ | N | |
| 6-CH₃ | C=O | C₆H₅ | H | CH₃ | OCH₃ | CH | |
| 6-CH₃ | C=O | C₆H₅ | H | OCH₃ | OCH₃ | CH | |
| 6-CH₃ | C=O | C₆H₅ | H | Cl | OCH₃ | CH | |
| 6-CH₃ | C=O | C₆H₅ | H | CH₃ | OCH₃ | N | |
| 6-CH₃ | C=O | C₆H₅ | H | OCH₃ | OCH₃ | N | |
| 6-CH₃ | C=O | C₆H₅ | H | CH₃ | CH₃ | N | |
| 6-CH₃ | C=O | H | CH₃ | CH₃ | CH₃ | CH | |
| 6-CH₃ | C=O | H | CH₃ | CH₃ | OCH₃ | CH | |
| 6-CH₃ | C=O | H | CH₃ | OCH₃ | OCH₃ | CH | |
| 6-CH₃ | C=O | H | CH₃ | Cl | OCH₃ | CH | |
| 6-CH₃ | C=O | H | CH₃ | CH₃ | OCH₃ | N | |
| 6-CH₃ | C=O | H | CH₃ | OCH₃ | OCH₃ | N | |
| 6-CH₃ | C=O | H | CH₃ | CH₃ | CH₃ | N | |
| 6-CH₃ | C=O | CH₃ | CH₃ | CH₃ | CH₃ | CH | |
| 6-CH₃ | C=O | CH₃ | CH₃ | CH₃ | OCH₃ | CH | |
| 6-CH₃ | C=O | CH₃ | CH₃ | OCH₃ | OCH₃ | CH | |
| 6-CH₃ | C=O | CH₃ | CH₃ | Cl | OCH₃ | CH | |
| 6-CH₃ | C=O | CH₃ | CH₃ | CH₃ | OCH₃ | N | |
| 6-CH₃ | C=O | CH₃ | CH₃ | OCH₃ | OCH₃ | N | |
| 6-CH₃ | C=O | CH₃ | CH₃ | CH₃ | | N | |
| 6-CH₃ | C=O | CH₃ | H | CH₃ | CH₃ | CH | |
| 6-CH₃ | C=O | CH₃ | H | CH₃ | OCH₃ | CH | |
| 6-CH₃ | C=O | CH₃ | H | OCH₃ | OCH₃ | CH | |
| 6-CH₃ | C=O | CH₃ | H | Cl | OCH₃ | CH | |
| 6-CH₃ | C=O | CH₃ | H | CH₃ | OCH₃ | N | |
| 6-CH₃ | C=O | CH₃ | H | OCH₃ | OCH₃ | N | |
| 6-CH₃ | C=O | CH₃ | H | CH₃ | CH₃ | N | |
| 6-CH₃ | C=O | H | H | CH₃ | OCH₃ | CH | |
| 6-CH₃ | C=O | H | H | OCH₃ | OCH₃ | CH | |
| 6-CH₃ | C=O | H | H | Cl | OCH₃ | CH | |
| 6-CH₃ | C=O | H | H | CH₃ | OCH₃ | N | |
| 6-CH₃ | C=O | H | H | OCH₃ | OCH₃ | N | |
| 6-CH₃ | C=O | H | H | CH₃ | CH₃ | N | |
| 6-CH₃ | C=O | 2-pyridyl | CH₃ | CH₃ | CH₃ | CH | |
| 6-CH₃ | C=O | 2-pyridyl | CH₃ | CH₃ | OCH₃ | CH | |
| 6-CH₃ | C=O | 2-pyridyl | CH₃ | OCH₃ | OCH₃ | CH | |
| 6-CH₃ | C=O | 2-pyridyl | CH₃ | Cl | OCH₃ | CH | |
| 6-CH₃ | C=O | 2-pyridyl | CH₃ | CH₃ | OCH₃ | N | |
| 6-CH₃ | C=O | 2-pyridyl | CH₃ | OCH₃ | OCH₃ | N | |
| 6-CH₃ | C=O | 2-pyridyl | CH₃ | CH₃ | CH₃ | N | |
| 6-CH₃ | C=O | 4-Cl—C₆H₅ | CH₃ | CH₃ | CH₃ | CH | |
| 6-CH₃ | C=O | 4-Cl—C₆H₅ | CH₃ | CH₃ | OCH₃ | CH | |
| 6-CH₃ | C=O | 4-Cl—C₆H₅ | CH₃ | OCH₃ | OCH₃ | CH | |

TABLE Ia-continued

General Formula Ia

| $R_1$ | J | $R_6$ | $R_7$ | X | Y | Z | m.p. (°C.) |
|---|---|---|---|---|---|---|---|
| 6-$CH_3$ | C=O | 4-Cl—$C_6H_5$ | $CH_3$ | Cl | $OCH_3$ | CH | |
| 6-$CH_3$ | C=O | 4-Cl—$C_6H_5$ | $CH_3$ | $CH_3$ | $OCH_3$ | N | |
| 6-$CH_3$ | C=O | 4-Cl—$C_6H_5$ | $CH_3$ | $OCH_3$ | $OCH_3$ | N | |
| 6-$CH_3$ | C=O | 4-Cl—$C_6H_5$ | $CH_3$ | $CH_3$ | $CH_3$ | N | |
| 6-$CH_3$ | C=O | 4-Cl—$C_6H_5$ | H | $CH_3$ | $CH_3$ | CH | |
| 6-$CH_3$ | C=O | 2-pyridyl | H | $CH_3$ | $OCH_3$ | CH | |
| 6-$CH_3$ | C=O | 2-pyridyl | H | $OCH_3$ | $OCH_3$ | CH | |
| 6-$CH_3$ | C=O | 2-pyridyl | H | Cl | $OCH_3$ | CH | |
| 6-$CH_3$ | C=O | 2-pyridyl | H | $CH_3$ | $OCH_3$ | N | |
| 6-$CH_3$ | C=O | 2-pyridyl | H | $OCH_3$ | $OCH_3$ | N | |
| 6-$CH_3$ | C=O | 2-pyridyl | H | $CH_3$ | $CH_3$ | N | |
| 6-Cl | C=O | H | $CH_3$ | $CH_3$ | $CH_3$ | CH | |
| 6-Cl | C=O | H | $CH_3$ | $CH_3$ | $OCH_3$ | CH | |
| 6-Cl | C=O | H | $CH_3$ | $OCH_3$ | $OCH_3$ | CH | |
| 6-Cl | C=O | H | $CH_3$ | Cl | $OCH_3$ | CH | |
| 6-Cl | C=O | H | $CH_3$ | $CH_3$ | $OCH_3$ | N | |
| 6-Cl | C=O | H | $CH_3$ | $OCH_3$ | $OCH_3$ | N | |
| 6-Cl | C=O | H | $CH_3$ | $CH_3$ | $CH_3$ | N | |
| 6-Cl | C=O | $C_6H_5$ | $CH_3$ | $CH_3$ | $CH_3$ | CH | |
| 6-Cl | C=O | $C_6H_5$ | $CH_3$ | $CH_3$ | $OCH_3$ | CH | |
| 6-Cl | C=O | $C_6H_5$ | $CH_3$ | $OCH_3$ | $OCH_3$ | CH | |
| 6-Cl | C=O | $C_6H_5$ | $CH_3$ | Cl | $OCH_3$ | CH | |
| 6-Cl | C=O | $C_6H_5$ | $CH_3$ | $CH_3$ | $OCH_3$ | N | |
| 6-Cl | C=O | $C_6H_5$ | $CH_3$ | $OCH_3$ | $OCH_3$ | N | |
| 6-Cl | C=O | $C_6H_5$ | $CH_3$ | $CH_3$ | $CH_3$ | N | |
| 6-Cl | C=O | $C_6H_5$ | H | $CH_3$ | $CH_3$ | CH | |
| 6-Cl | C=O | $C_6H_5$ | H | $CH_3$ | $OCH_3$ | CH | |
| 6-Cl | C=O | $C_6H_5$ | H | $OCH_3$ | $OCH_3$ | CH | |
| 6-Cl | C=O | $C_6H_5$ | H | Cl | $OCH_3$ | CH | |
| 6-Cl | C=O | $C_6H_5$ | H | $CH_3$ | $OCH_3$ | N | |
| 6-Cl | C=O | $C_6H_5$ | H | $OCH_3$ | $OCH_3$ | N | |
| 6-Cl | C=O | $C_6H_5$ | H | $CH_3$ | $CH_3$ | N | |
| 6-Cl | C=O | $CH_3$ | $CH_3$ | $CH_3$ | $CH_3$ | CH | |
| 6-Cl | C=O | $CH_3$ | $CH_3$ | $CH_3$ | $OCH_3$ | CH | |
| 6-Cl | C=O | H | $CH_3$ | $OCH_3$ | $OCH_3$ | CH | |
| 6-Cl | C=O | H | $CH_3$ | Cl | $OCH_3$ | CH | |
| 6-Cl | C=O | H | $CH_3$ | $CH_3$ | $OCH_3$ | N | |
| 6-Cl | C=O | H | $CH_3$ | $OCH_3$ | $OCH_3$ | N | |
| 6-Cl | C=O | H | $CH_3$ | $CH_3$ | $CH_3$ | N | |
| 6-Cl | C=O | $CH_3$ | H | $CH_3$ | $CH_3$ | CH | |
| 6-Cl | C=O | $CH_3$ | H | $CH_3$ | $OCH_3$ | CH | |
| 6-Cl | C=O | $CH_3$ | H | $OCH_3$ | $OCH_3$ | CH | |
| 6-Cl | C=O | $CH_3$ | $CH_3$ | Cl | $OCH_3$ | CH | |
| 6-Cl | C=O | $CH_3$ | $CH_3$ | $CH_3$ | $OCH_3$ | N | |
| 6-Cl | C=O | $CH_3$ | $CH_3$ | $OCH_3$ | $OCH_3$ | N | |
| 6-Cl | C=O | $CH_3$ | $CH_3$ | $CH_3$ | $CH_3$ | N | |
| 6-Cl | C=O | H | H | $CH_3$ | $CH_3$ | CH | |
| 6-Cl | C=O | H | H | $CH_3$ | $OCH_3$ | CH | |
| 6-Cl | C=O | H | H | $OCH_3$ | $OCH_3$ | CH | |
| 6-Cl | C=O | H | H | Cl | $OCH_3$ | CH | |
| 6-Cl | C=O | H | H | $CH_3$ | $OCH_3$ | N | |
| 6-Cl | C=O | H | H | $OCH_3$ | $OCH_3$ | N | |
| 6-Cl | C=O | H | H | $CH_3$ | $CH_3$ | N | |
| 6-Cl | C=O | 2-pyridyl | $CH_3$ | $CH_3$ | $CH_3$ | CH | |
| 6-Cl | C=O | 2-pyridyl | $CH_3$ | $CH_3$ | $OCH_3$ | CH | |
| 6-Cl | C=O | 2-pyridyl | $CH_3$ | $OCH_3$ | $OCH_3$ | CH | |
| 6-Cl | C=O | 2-pyridyl | $CH_3$ | Cl | $OCH_3$ | CH | |
| 6-Cl | C=O | 2-pyridyl | $CH_3$ | $CH_3$ | $OCH_3$ | N | |
| 6-Cl | C=O | 2-pyridyl | $CH_3$ | $OCH_3$ | $OCH_3$ | N | |
| 6-Cl | C=O | 2-pyridyl | $CH_3$ | $CH_3$ | $CH_3$ | N | |
| 6-Cl | C=O | 4-Cl—phenyl | $CH_3$ | $CH_3$ | $CH_3$ | CH | |
| 6-Cl | C=O | 4-Cl—phenyl | $CH_3$ | $CH_3$ | $OCH_3$ | CH | |
| 6-Cl | C=O | 4-Cl—phenyl | $CH_3$ | $OCH_3$ | $OCH_3$ | CH | |
| 6-Cl | C=O | 4-Cl—phenyl | $CH_3$ | Cl | $OCH_3$ | CH | |
| 6-Cl | C=O | 4-Cl—phenyl | $CH_3$ | $CH_3$ | $OCH_3$ | N | |
| 6-Cl | C=O | 4-Cl—phenyl | $CH_3$ | $OCH_3$ | $OCH_3$ | N | |
| 6-Cl | C=O | 4-Cl—phenyl | $CH_3$ | $CH_3$ | $CH_3$ | N | |
| 6-Cl | C=O | 2-pyridyl | H | $CH_3$ | $CH_3$ | CH | |
| 6-Cl | C=O | 2-pyridyl | H | $CH_3$ | $OCH_3$ | CH | |
| 6-Cl | C=O | 2-pyridyl | H | $OCH_3$ | $OCH_3$ | CH | |
| 6-Cl | C=O | 2-pyridyl | H | Cl | $OCH_3$ | CH | |
| 6-Cl | C=O | 2-pyridyl | H | $CH_3$ | $OCH_3$ | N | |
| 6-Cl | C=O | 2-pyridyl | H | $OCH_3$ | $OCH_3$ | N | |
| 6-Cl | C=O | 2-pyridyl | H | $CH_3$ | $CH_3$ | N | |
| 5-$NO_2$ | C=O | H | $CH_3$ | $CH_3$ | $CH_3$ | CH | |
| 5-$NO_2$ | C=O | H | $CH_3$ | $CH_3$ | $OCH_3$ | CH | |
| 5-$NO_2$ | C=O | H | $CH_3$ | $OCH_3$ | $OCH_3$ | CH | |
| 5-$NO_2$ | C=O | H | $CH_3$ | Cl | $OCH_3$ | CH | |
| 5-$NO_2$ | C=O | H | $CH_3$ | $CH_3$ | $OCH_3$ | N | |
| 5-$NO_2$ | C=O | H | $CH_3$ | $OCH_3$ | $OCH_3$ | N | |

TABLE Ia-continued

General Formula Ia

| R₁ | J | R₆ | R₇ | X | Y | Z | m.p. (°C.) |
|---|---|---|---|---|---|---|---|
| 5-NO₂ | C=O | H | CH₃ | CH₃ | CH₃ | N | |
| 5-NO₂ | C=O | C₆H₅ | CH₃ | CH₃ | CH₃ | CH | |
| 5-NO₂ | C=O | C₆H₅ | CH₃ | CH₃ | OCH₃ | CH | |
| 5-NO₂ | C=O | C₆H₅ | CH₃ | OCH₃ | OCH₃ | CH | |
| 5-NO₂ | C=O | C₆H₅ | CH₃ | Cl | OCH₃ | CH | |
| 5-NO₂ | C=O | C₆H₅ | CH₃ | CH₃ | OCH₃ | N | |
| 5-NO₂ | C=O | C₆H₅ | CH₃ | OCH₃ | OCH₃ | N | |
| 5-NO₂ | C=O | C₆H₅ | CH₃ | CH₃ | CH₃ | N | |
| 5-NO₂ | C=O | C₆H₅ | CH₃ | CH₃ | CH₃ | CH | |
| 5-NO₂ | C=O | CH₃ | CH₃ | CH₃ | OCH₃ | CH | |
| 5-NO₂ | C=O | CH₃ | CH₃ | OCH₃ | OCH₃ | CH | |
| 5-NO₂ | C=O | CH₃ | CH₃ | Cl | OCH₃ | CH | |
| 5-NO₂ | C=O | CH₃ | CH₃ | CH₃ | OCH₃ | N | |
| 5-NO₂ | C=O | CH₃ | CH₃ | OCH₃ | OCH₃ | N | |
| 5-NO₂ | C=O | CH₃ | CH₃ | CH₃ | CH₃ | N | |
| 5-SCH₃ | C=O | H | CH₃ | CH₃ | CH₃ | CH | |
| 5-SCH₃ | C=O | H | CH₃ | CH₃ | OCH₃ | CH | |
| 5-SCH₃ | C=O | H | CH₃ | OCH₃ | OCH₃ | CH | |
| 5-SCH₃ | C=O | H | CH₃ | Cl | OCH₃ | CH | |
| 5-SCH₃ | C=O | H | CH₃ | CH₃ | OCH₃ | N | |
| 5-SCH₃ | C=O | H | CH₃ | OCH₃ | OCH₃ | N | |
| 5-SCH₃ | C=O | H | CH₃ | CH₃ | CH₃ | N | |
| 5-SCH₃ | C=O | C₆H₅ | CH₃ | CH₃ | CH₃ | CH | |
| 5-SCH₃ | C=O | C₆H₅ | CH₃ | CH₃ | OCH₃ | CH | |
| 5-SCH₃ | C=O | C₆H₅ | CH₃ | OCH₃ | OCH₃ | CH | |
| 5-SCH₃ | C=O | C₆H₅ | CH₃ | Cl | OCH₃ | CH | |
| 5-SCH₃ | C=O | C₆H₅ | CH₃ | CH₃ | OCH₃ | N | |
| 5-SCH₃ | C=O | C₆H₅ | CH₃ | OCH₃ | OCH₃ | N | |
| 5-SCH₃ | C=O | C₆H₅ | CH₃ | CH₃ | CH₃ | N | |
| 5-SCH₃ | C=O | CH₃ | CH₃ | CH₃ | CH₃ | CH | |
| 5-SCH₃ | C=O | CH₃ | CH₃ | CH₃ | OCH₃ | CH | |
| 5-SCH₃ | C=O | CH₃ | CH₃ | OCH₃ | OCH₃ | CH | |
| 5-SCH₃ | C=O | CH₃ | CH₃ | Cl | OCH₃ | CH | |
| 5-SCH₃ | C=O | CH₃ | CH₃ | CH₃ | OCH₃ | N | |
| 5-SCH₃ | C=O | CH₃ | CH₃ | OCH₃ | OCH₃ | N | |
| 5-SCH₃ | C=O | CH₃ | CH₃ | CH₃ | CH₃ | N | |
| 6-F | C=O | H | CH₃ | CH₃ | CH₃ | CH | |
| 6-F | C=O | H | CH₃ | CH₃ | OCH₃ | CH | |
| 6-F | C=O | H | CH₃ | OCH₃ | OCH₃ | CH | |
| 6-F | C=O | H | CH₃ | Cl | OCH₃ | CH | |
| 6-F | C=O | H | CH₃ | CH₃ | OCH₃ | N | |
| 6-F | C=O | H | CH₃ | OCH₃ | OCH₃ | N | |
| 6-F | C=O | H | CH₃ | CH₃ | CH₃ | N | |
| 5-F | C=O | C₆H₅ | CH₃ | CH₃ | CH₃ | CH | |
| 5-F | C=O | C₆H₅ | CH₃ | CH₃ | OCH₃ | CH | |
| 5-F | C=O | C₆H₅ | CH₃ | OCH₃ | OCH₃ | CH | |
| 5-F | C=O | C₆H₅ | CH₃ | Cl | OCH₃ | CH | |
| 5-F | C=O | C₆H₅ | CH₃ | CH₃ | OCH₃ | N | |
| 5-F | C=O | C₆H₅ | CH₃ | OCH₃ | OCH₃ | N | |
| 5-F | C=O | C₆H₅ | CH₃ | CH₃ | CH₃ | N | |
| 6-F | C=O | C₆H₅ | CH₃ | CH₃ | CH₃ | CH | |
| 6-F | C=O | CH₃ | CH₃ | CH₃ | OCH₃ | CH | |
| 6-F | C=O | CH₃ | CH₃ | OCH₃ | OCH₃ | CH | |
| 6-F | C=O | CH₃ | CH₃ | Cl | OCH₃ | CH | |
| 6-F | C=O | CH₃ | CH₃ | CH₃ | OCH₃ | N | |
| 6-F | C=O | CH₃ | CH₃ | OCH₃ | OCH₃ | N | |
| 6-F | C=O | CH₃ | CH₃ | CH₃ | CH₃ | N | |
| H | SO₂ | CH₂CH₂CH₃ | H | OCH₃ | OCH₃ | CH | 244–247 |
| H | SO₂ | CH₂CH₂CH₃ | H | CH₃ | OCH₃ | CH | |
| H | SO₂ | CH₂CH₂CH₃ | H | Cl | OCH₃ | CH | 245–250 |
| H | SO₂ | CH₂CH₂CH₃ | H | OCH₃ | OCH₃ | N | 213–216 |
| H | SO₂ | CH₂CH₂CH₃ | H | CH₃ | OCH₃ | N | 210–212 |
| H | SO₂ | CH₂C₆H₅ | H | OCH₃ | OCH₃ | CH | 214–216 |
| H | SO₂ | CH₂C₆H₅ | H | CH₃ | OCH₃ | CH | 227–231 |
| H | SO₂ | CH₂C₆H₅ | H | CH₃ | CH₃ | CH | 237–243 |
| H | SO₂ | CH₂C₆H₅ | H | OCH₃ | OCH₃ | N | 221–225 |
| H | SO₂ | CH₂C₆H₅ | H | CH₃ | OCH₃ | N | 237–243 |
| H | SO₂ | 3-F—C₆H₅ | H | OCH₃ | OCH₃ | CH | 208–210 |
| H | SO₂ | 3-F—C₆H₅ | H | CH₃ | OCH₃ | CH | 215–220 |
| H | SO₂ | CH₂C₆H₅ | H | Cl | OCH₃ | CH | 202–205 |

TABLE Ib

General Formula Ib

| R₁ | J | R₆ | X₁ | Y₁ | m.p.(°C.) |
|---|---|---|---|---|---|
| H | C=O | H | CH₃ | O | |
| H | C=O | H | OCH₃ | O | |
| H | C=O | H | OC₂H₅ | O | |
| H | C=O | H | OCF₂H | O | |
| H | C=O | CH₃ | CH₃ | O | |
| H | C=O | CH₃ | OCH₃ | O | |

TABLE Ib-continued

General Formula Ib

| R₁ | J | R₆ | X₁ | Y₁ | m.p.(°C.) |
|---|---|---|---|---|---|
| H | C=O | CH₃ | OC₂H₅ | O | |
| H | C=O | CH₃ | OCF₂H | O | |
| H | C=O | C₆H₅ | CH₃ | O | |
| H | C=O | C₆H₅ | OCH₃ | O | |
| H | C=O | C₆H₅ | OC₂H₅ | O | |
| H | C=O | C₆H₅ | OCF₂H | O | |
| H | C=O | CH₃ | CH₃ | CH₂ | |
| H | C=O | CH₃ | OCH₃ | CH₂ | |
| H | C=O | CH₃ | OC₂H₅ | CH₂ | |
| H | C=O | CH₃ | OCF₂H | CH₂ | |
| H | C=O | C₆H₅ | CH₃ | CH₂ | |
| H | C=O | C₆H₅ | OCH₃ | CH₂ | |
| H | C=O | C₆H₅ | OC₂H₅ | CH₂ | |
| H | C=O | C₆H₅ | OCF₂H | CH₂ | |
| H | SO₂ | H | CH₃ | O | |
| H | SO₂ | H | OCH₃ | O | |
| H | SO₂ | H | OC₂H₅ | O | |
| H | SO₂ | H | OCF₂H | O | |
| H | SO₂ | CH₃ | CH₃ | O | |
| H | SO₂ | CH₃ | OCH₃ | O | |
| H | SO₂ | CH₃ | OC₂H₅ | O | |
| H | SO₂ | CH₃ | OCF₂H | O | |
| H | SO₂ | C₆H₅ | CH₃ | O | |
| H | SO₂ | C₆H₅ | OCH₃ | O | |
| H | SO₂ | C₆H₅ | OC₂H₅ | O | |
| H | SO₂ | C₆H₅ | OCF₂H | O | |
| H | SO₂ | CH₃ | CH₃ | CH₂ | |
| H | SO₂ | CH₃ | OCH₃ | CH₂ | |
| H | SO₂ | CH₃ | OC₂H₅ | CH₂ | |
| H | SO₂ | CH₃ | OCF₂H | CH₂ | |
| H | SO₂ | C₆H₅ | CH₃ | CH₂ | |
| H | SO₂ | C₆H₅ | OCH₃ | CH₂ | |
| H | SO₂ | C₆H₅ | OC₂H₅ | CH₂ | |
| H | SO₂ | C₆H₅ | OCF₂H | CH₂ | |

TABLE Ic

General Formula Ic

| R₁ | J | R₆ | X₁ | m.p.(°C.) |
|---|---|---|---|---|
| H | C=O | H | CH₃ | |
| H | C=O | H | OCH₃ | |
| H | C=O | H | OC₂H₅ | |
| H | C=O | H | OCF₂H | |
| H | C=O | CH₃ | CH₃ | |
| H | C=O | CH₃ | OCH₃ | |
| H | C=O | CH₃ | OC₂H₅ | |
| H | C=O | CH₃ | OCF₂H | |
| H | C=O | C₆H₅ | CH₃ | |
| H | C=O | C₆H₅ | OCH₃ | |
| H | C=O | C₆H₅ | OC₂H₅ | |
| H | C=O | C₆H₅ | OCF₂H | |
| H | SO₂ | CH₃ | CH₃ | |
| H | SO₂ | CH₃ | OCH₃ | |
| H | SO₂ | CH₃ | OC₂H₅ | |
| H | SO₂ | CH₃ | OCF₂H | |
| H | SO₂ | C₆H₅ | CH₃ | |
| H | SO₂ | C₆H₅ | OCH₃ | |
| H | SO₂ | C₆H₅ | OC₂H₅ | |
| H | SO₂ | C₆H₅ | OCF₂H | |

TABLE Id

General Formula Id

| R₁ | J | R₆ | X₁ | Y₂ | m.p.(°C.) |
|---|---|---|---|---|---|
| H | C=O | H | CH₃ | CH₃ | |
| H | C=O | H | OCH₃ | CH₃ | |
| H | C=O | H | OC₂H₅ | CH₃ | |
| H | C=O | H | OCF₂H | CH₃ | |
| H | C=O | CH₃ | CH₃ | H | |
| H | C=O | CH₃ | OCH₃ | H | |
| H | C=O | CH₃ | OC₂H₅ | H | |
| H | C=O | CH₃ | OCF₂H | H | |
| H | C=O | C₆H₅ | CH₃ | H | |
| H | C=O | C₆H₅ | OCH₃ | H | |
| H | C=O | C₆H₅ | OC₂H₅ | H | |
| H | C=O | C₆H₅ | OCF₂H | H | |

TABLE Id-continued

General Formula Id

| R₁ | J | R₆ | X₁ | Y₂ | m.p.(°C.) |
|---|---|---|---|---|---|
| H | SO₂ | CH₃ | CH₃ | CH₃ | |
| H | SO₂ | CH₃ | OCH₃ | CH₃ | |
| H | SO₂ | CH₃ | OC₂H₅ | CH₃ | |
| H | SO₂ | CH₃ | OCF₂H | CH₃ | |
| H | SO₂ | C₆H₅ | CH₃ | H | |
| H | SO₂ | C₆H₅ | OCH₃ | H | |
| H | SO₂ | C₆H₅ | OC₂H₅ | H | |
| H | SO₂ | C₆H₅ | OCF₂H | H | |

TABLE Ie

General Formula Ie

| R₁ | J | R₆ | X₂ | Y₃ | m.p.(°C.) |
|---|---|---|---|---|---|
| H | C=O | C₆H₅ | CH₃ | CH₃ | |
| H | C=O | C₆H₅ | OCH₃ | CH₃ | |
| H | C=O | C₆H₅ | SCH₃ | CH₃ | |
| H | C=O | H | CH₃ | C₂H₅ | |
| H | C=O | H | OCH₃ | C₂H₅ | |
| H | C=O | H | SCH₃ | C₂H₅ | |
| H | C=O | CH₃ | CH₃ | CH₂CF₃ | |
| H | C=O | CH₃ | OCH₃ | CH₂CF₃ | |
| H | C=O | CH₃ | SCH₃ | CH₂CF₃ | |
| H | C=O | H | CH₃ | CH₃ | |
| H | C=O | H | OCH₃ | CH₃ | |
| H | C=O | H | SCH₃ | CH₃ | |
| H | C=O | CH₃ | CH₃ | C₂H₅ | |
| H | C=O | CH₃ | OCH₃ | C₂H₅ | |
| H | C=O | CH₃ | SCH₃ | C₂H₅ | |
| H | C=O | C₆H₅ | CH₃ | CH₂CF₃ | |
| H | C=O | C₆H₅ | OCH₃ | CH₂CF₃ | |
| H | C=O | C₆H₅ | SCH₃ | CH₂CF₃ | |
| H | C=O | CH₃ | CH₃ | CH₃ | |
| H | C=O | CH₃ | OCH₃ | CH₃ | |
| H | C=O | CH₃ | SCH₃ | CH₃ | |
| H | C=O | C₆H₅ | CH₃ | C₂H₅ | |
| H | C=O | C₆H₅ | OCH₃ | C₂H₅ | |
| H | C=O | C₆H₅ | SCH₃ | C₂H₅ | |
| H | C=O | H | CH₃ | CH₂CF₃ | |
| H | C=O | H | OCH₃ | CH₂CF₃ | |
| H | C=O | H | SCH₃ | CH₂CF₃ | |
| H | SO₂ | C₆H₅ | CH₃ | CH₃ | |
| H | SO₂ | C₆H₅ | OCH₃ | CH₃ | |
| H | SO₂ | C₆H₅ | SCH₃ | CH₃ | |
| H | SO₂ | H | CH₃ | C₂H₅ | |
| H | SO₂ | H | OCH₃ | C₂H₅ | |
| H | SO₂ | H | SCH₃ | C₂H₅ | |
| H | SO₂ | CH₃ | CH₃ | CH₂CF₃ | |
| H | SO₂ | CH₃ | OCH₃ | CH₂CF₃ | |
| H | SO₂ | CH₃ | SCH₃ | CH₂CF₃ | |
| H | SO₂ | H | CH₃ | CH₃ | |
| H | SO₂ | H | OCH₃ | CH₃ | |
| H | SO₂ | H | SCH₃ | CH₃ | |
| H | SO₂ | CH₃ | CH₃ | C₂H₅ | |
| H | SO₂ | CH₃ | OCH₃ | C₂H₅ | |
| H | SO₂ | CH₃ | SCH₃ | C₂H₅ | |
| H | SO₂ | C₆H₅ | CH₃ | CH₂CF₃ | |
| H | SO₂ | C₆H₅ | OCH₃ | OH₂CF₃ | |
| H | SO₂ | C₆H₅ | SCH₃ | CH₂CF₃ | |
| H | SO₂ | CH₃ | CH₃ | CH₃ | |
| H | SO₂ | CH₃ | OCH₃ | CH₃ | |
| H | SO₂ | CH₃ | SCH₃ | CH₃ | |
| H | SO₂ | C₆H₅ | CH₃ | C₂H₅ | |
| H | SO₂ | C₆H₅ | OCH₃ | C₂H₅ | |
| H | SO₂ | C₆H₅ | SCH₃ | C₂H₅ | |

TABLE If

General Structure If

| R₁ | J | R₆ | X₃ | m.p.(°C.) |
|---|---|---|---|---|
| H | C=O | H | CH | |
| H | C=O | H | OCH₃ | |
| H | C=O | CH₃ | CH₃ | |
| H | C=O | CH₃ | OCH₃ | |
| H | C=O | C₆H₅ | CH₃ | |
| H | C=O | C₆H₅ | OCH₃ | |
| H | SO₂ | H | CH₃ | |

TABLE If-continued

General Structure If

| R₁ | J | R₆ | X₃ | m.p.(°C.) |
|---|---|---|---|---|
| H | SO₂ | H | OCH₃ | |
| H | SO₂ | CH₃ | CH₃ | |
| H | SO₂ | CH₃ | OCH₃ | |
| H | SO₂ | C₆H₅ | CH₃ | |
| H | SO₂ | C₆H₅ | OCH₃ | |

TABLE Iq

General Structure Iq

| R₁ | G | J | R₆ | X | Y | Z | m.p (°C.) |
|---|---|---|---|---|---|---|---|
| H | CH₂ | C=O | H | CH₃ | CH₃ | CH | |
| H | CH₂ | C=O | H | CH₃ | OCH₃ | CH | |
| H | CH₂ | C=O | H | OCH₃ | OCH₃ | CH | |
| H | CH₂ | C=O | H | Cl | OCH₃ | CH | |
| H | CH₂ | C=O | H | CH₃ | OCH₃ | N | |
| H | CH₂ | C=O | H | OCH₃ | OCH₃ | N | |
| H | CH₂ | C=O | H | CH₃ | CH₃ | N | |
| H | CH₂ | C=O | H | CH₃ | CH₃ | CH | |
| H | CH₂ | C=O | H | CH₃ | OCH₃ | CH | |
| H | CH₂ | C=O | H | OCH₃ | OCH₃ | CH | |
| H | CH₂ | C=O | H | Cl | OCH₃ | CH | |
| H | CH₂ | C=O | H | CH₃ | OCH₃ | N | |
| H | CH₂ | C=O | H | OCH₃ | OCH₃ | N | |
| H | CH₂ | C=O | H | CH₃ | CH₃ | N | |
| H | CH₂ | C=O | H | CH₃ | CH₃ | CH | |
| H | CH₂ | C=O | H | CH₃ | OCH₃ | CH | |
| H | CH₂ | C=O | H | OCH₃ | OCH₃ | CH | |
| H | CH₂ | C=O | H | Cl | OCH₃ | CH | |
| H | CH₂ | C=O | CH₃ | CH₃ | OCH₃ | N | |
| H | CH₂ | C=O | CH₃ | CH₃ | CH₃ | N | |
| H | CH₂ | C=O | CH₃ | OCH₃ | OCH₃ | N | |

TABLE Ih

General Structure Ih

| R₁ | G | R₆ | R₇ | X | Y | Z | m.p.(°C.) |
|---|---|---|---|---|---|---|---|
| H | CH₂ | H | CH₃ | CH₃ | CH₃ | CH | |
| H | CH₂ | H | CH₃ | CH₃ | OCH₃ | CH | |
| H | CH₂ | H | CH₃ | OCH₃ | OCH₃ | CH | |
| H | CH₂ | H | CH₃ | Cl | OCH₃ | CH | |
| H | CH₂ | H | CH₃ | CH₃ | OCH₃ | N | |
| H | CH₂ | H | CH₃ | OCH₃ | OCH₃ | N | |
| H | CH₂ | H | CH₃ | CH₃ | CH₃ | N | |
| H | CH₂ | CH₃ | CH₃ | CH₃ | CH₃ | CH | |
| H | CH₂ | CH₃ | CH₃ | CH₃ | OCH₃ | CH | |
| H | CH₂ | CH₃ | CH₃ | OCH₃ | OCH₃ | CH | |
| H | CH₂ | CH₃ | CH₃ | Cl | OCH₃ | CH | |
| H | CH₂ | CH₃ | CH₃ | CH₃ | OCH₃ | N | |
| H | CH₂ | CH₃ | CH₃ | OCH₃ | OCH₃ | N | |
| H | CH₂ | CH₃ | CH₃ | CH₃ | CH₃ | N | |
| H | CH₂ | C₆H₅ | CH₃ | CH₃ | CH₃ | CH | |
| H | CH₂ | C₆H₅ | CH₃ | CH₃ | OCH₃ | CH | |
| H | CH | C₆H₅ | CH₃ | OCH₃ | OCH₃ | CH | |
| H | CH₂ | C₆H₅ | CH₃ | Cl | OCH₃ | CH | |
| H | CH₂ | C₆H₅ | CH₃ | CH₃ | OCH₃ | N | |
| H | CH₂ | C₆H₅ | CH₃ | OCH₃ | OCH₃ | N | |
| H | CH₂ | C₆H₅ | CH₃ | CH₃ | CH₃ | N | |
| H | CH₂ | H | H | CH₃ | CH₃ | CH | |
| H | CH₂ | H | H | CH₃ | OCH₃ | CH | |
| H | CH₂ | H | H | OCH₃ | OCH₃ | CH | |
| H | CH₂ | H | H | Cl | OCH₃ | CH | |
| H | CH₂ | H | H | CH₃ | OCH₃ | N | |
| H | CH₂ | H | H | OCH₃ | OCH₃ | N | |
| H | CH₂ | H | H | CH₃ | CH₃ | N | |
| H | CH₂ | C₆H₅ | H | CH₃ | CH₃ | CH | |
| H | CH₂ | C₆H₅ | H | CH₃ | OCH₃ | CH | |
| H | CH₂ | C₆H₅ | H | OCH₃ | OCH₃ | CH | |
| H | CH₂ | C₆H₅ | H | Cl | OCH₃ | CH | |
| H | CH₂ | C₆H₅ | H | CH₃ | OCH₃ | N | |
| H | CH₂ | C₆H₅ | H | OCH₃ | OCH₃ | N | |
| H | CH₂ | C₆H₅ | H | CH₃ | CH₃ | N | |
| 6-Cl | CH₂ | CH₃ | H | CH₃ | CH₃ | CH | |
| 6-Cl | CH₂ | CH₃ | H | CH₃ | OCH₃ | CH | |
| 6-Cl | CH₂ | CH₃ | H | OCH₃ | OCH₃ | CH | |
| 6-Cl | CH₂ | CH₃ | H | Cl | OCH₃ | CH | |
| 6-Cl | CH₂ | CH₃ | H | CH₃ | OCH₃ | N | |

TABLE Ih-continued

General Structure Ih

| R₁ | G | R₆ | R₇ | X | Y | Z | m.p.(°C.) |
|---|---|---|---|---|---|---|---|
| 6-Cl | CH₂ | CH₃ | H | OCH₃ | OCH₃ | N | |
| 6-Cl | CH₂ | C₆H₅ | H | CH₃ | CH₃ | CH | |
| 6-Cl | CH₂ | C₆H₅ | H | CH₃ | OCH₃ | CH | |
| 6-Cl | CH₂ | C₆H₅ | H | OCH₃ | OCH₃ | CH | |
| 6-Cl | CH₂ | C₆H₅ | H | Cl | OCH₃ | CH | |
| 6-Cl | CH₂ | C₆H₅ | H | CH₃ | OCH₃ | N | |
| 6-Cl | CH₂ | C₆H₅ | H | OCH₃ | OCH₃ | N | |
| H | CH₂CH₂ | H | CH₃ | CH₃ | CH₃ | CH | |
| H | CH₂CH₂ | H | CH₃ | CH₃ | OCH₃ | CH | |
| H | CH₂CH₂ | H | CH₃ | OCH₃ | OCH₃ | CH | |
| H | CH₂CH₂ | H | CH₃ | Cl | OCH₃ | CH | |
| H | CH₂CH₂ | H | CH₃ | CH₃ | OCH₃ | N | |
| H | CH₂CH₂ | H | CH₃ | OCH₃ | OCH₃ | N | |
| H | CH₂CH₂ | H | CH₃ | CH₃ | CH₃ | N | |
| H | CH₂CH₂ | CH₃ | CH₃ | CH₃ | CH₃ | CH | |
| H | CH₂CH₂ | CH₃ | CH₃ | CH₃ | OCH₃ | CH | |
| H | CH₂CH₂ | CH₃ | CH₃ | OCH₃ | OCH₃ | CH | |
| H | CH₂CH₂ | CH₃ | CH₃ | Cl | OCH₃ | CH | |
| H | CH₂CH₂ | CH₃ | CH₃ | CH₃ | OCH₃ | N | |
| H | CH₂CH₂ | CH₃ | CH₃ | OCH₃ | OCH₃ | N | |
| H | CH₂CH₂ | CH₃ | CH₃ | CH₃ | CH₃ | N | |
| H | CH₂CH₂ | C₆H₅ | CH₃ | CH₃ | CH₃ | CH | |
| H | CH₂CH₂ | C₆H₅ | CH₃ | CH₃ | OCH₃ | CH | |
| H | CH₂CH₂ | C₆H₅ | CH₃ | OCH₃ | OCH₃ | CH | |
| H | CH₂CH₂ | C₆H₅ | CH₃ | Cl | OCH₃ | CH | |
| H | CH₂CH₂ | C₆H₅ | CH₃ | CH₃ | OCH₃ | N | |
| H | CH₂CH₂ | C₆H₅ | CH₃ | OCH₃ | OCH₃ | N | |
| H | CH₂CH₂ | C₆H₅ | CH₃ | CH₃ | CH₃ | N | |
| H | CH₂CH₂ | H | H | CH₃ | CH₃ | CH | |
| H | CH₂CH₂ | H | H | CH₃ | OCH₃ | CH | |
| H | CH₂CH₂ | H | H | OCH₃ | OCH₃ | CH | |
| H | CH₂CH₂ | H | H | Cl | OCH₃ | CH | |
| H | CH₂CH₂ | H | H | CH₃ | OCH₃ | N | |
| H | CH₂CH₂ | H | H | OCH₃ | OCH₃ | N | |
| H | CH₂CH₂ | H | H | CH₃ | CH₃ | N | |
| H | CH₂CH₂ | C | H | CH₃ | CH₃ | CH | |
| H | CH₂CH₂ | C₆H₅ | H | CH₃ | OCH₃ | CH | |
| H | CH₂CH₂ | C₆H₅ | H | OCH₃ | OCH₃ | CH | |
| H | CH₂CH₂ | C₆H₅ | H | Cl | OCH₃ | CH | |
| H | CH₂CH₂ | C₆H₅ | H | CH₃ | OCH₃ | N | |
| H | CH₂CH₂ | C₆H₅ | H | OCH₃ | OCH₃ | N | |
| H | CH₂CH₂ | C₆H₅ | H | CH₃ | CH₃ | N | |
| 6-Cl | CH₂CH₂ | CH₃ | H | CH₃ | CH₃ | CH | |
| 6-Cl | CH₂CH₂ | CH₃ | H | CH₃ | OCH₃ | CH | |
| 6-Cl | CH₂CH₂ | CH₃ | H | OCH₃ | OCH₃ | CH | |
| 6-Cl | CH₂CH₂ | CH₃ | H | Cl | OCH₃ | CH | |
| 6-Cl | CH₂CH₂ | CH₃ | H | CH₃ | OCH₃ | N | |
| 6-Cl | CH₂CH₂ | CH₃ | H | OCH₃ | OCH₃ | N | |
| 6-Cl | CH₂CH₂ | C₆H₅ | H | CH₃ | CH₃ | CH | |
| 6-Cl | CH₂CH₂ | C₆H₅ | H | CH₃ | OCH₃ | CH | |
| 6-Cl | CH₂CH₂ | C₆H₅ | H | OCH₃ | OCH₃ | CH | |
| 6-Cl | CH₂CH₂ | C₆H₅ | H | Cl | OCH₃ | CH | |
| 6-Cl | CH₂CH₂ | C₆H₅ | H | CH₃ | OCH₃ | N | |
| 6-Cl | CH₂CH₂ | C₆H₅ | H | OCH₃ | OCH₃ | N | |
| H | CH=CH | H | CH₃ | CH₃ | CH₃ | CH | |
| H | CH=CH | H | CH₃ | CH₃ | OCH₃ | CH | |
| H | CH=CH | H | CH₃ | OCH₃ | OCH₃ | CH | |
| H | CH=CH | H | CH₃ | Cl | OCH₃ | CH | |
| H | CH=CH | H | CH₃ | CH₃ | OCH₃ | N | |
| H | CH=CH | H | CH₃ | OCH₃ | OCH₃ | N | |
| H | CH=CH | H | CH₃ | CH₃ | CH₃ | N | |
| H | CH=CH | CH₃ | CH₃ | CH₃ | CH₃ | CH | |
| H | CH=CH | CH₃ | CH₃ | CH₃ | OCH₃ | CH | |
| H | CH=CH | CH₃ | CH₃ | OCH₃ | OCH₃ | CH | |
| H | CH=CH | CH₃ | CH₃ | Cl | OCH₃ | CH | |
| H | CH=CH | CH₃ | CH₃ | CH₃ | OCH₃ | N | |
| H | CH=CH | CH₃ | CH₃ | OCH₃ | OCH₃ | N | |
| H | CH=CH | CH₃ | CH₃ | CH₃ | CH₃ | N | |
| H | CH=CH | C₆H₅ | CH₃ | CH₃ | CH₃ | CH | |
| H | CH=CH | C₆H₅ | CH₃ | CH₃ | OCH₃ | CH | |
| H | CH=CH | C₆H₅ | CH₃ | OCH₃ | OCH₃ | CH | |
| H | CH=CH | C₆H₅ | CH₃ | Cl | OCH₃ | CH | |
| H | CH=CH | C₆H₅ | CH₃ | CH₃ | OCH₃ | N | |
| H | CH=CH | C₆H₅ | CH₃ | OCH₃ | OCH₃ | N | |
| H | CH=CH | C₆H₅ | CH₃ | CH₃ | CH₃ | N | |
| H | CH=CH | H | H | CH₃ | CH₃ | CH | |
| H | CH=CH | H | H | CH₃ | OCH₃ | CH | |
| H | CH=CH | H | H | OCH₃ | OCH₃ | CH | |

TABLE Ih-continued

General Structure Ih

| $R_1$ | G | $R_6$ | $R_7$ | X | Y | Z | m.p.(°C.) |
|---|---|---|---|---|---|---|---|
| H | CH=CH | H | H | Cl | OCH₃ | CH | |
| H | CH=CH | H | H | CH₃ | OCH₃ | N | |
| H | CH=CH | H | H | OCH₃ | OCH₃ | N | |
| H | CH=CH | H | H | CH₃ | CH₃ | N | |
| H | CH=CH | C₆H₅ | H | CH₃ | CH₃ | CH | |
| H | CH=CH | C₆H₅ | H | CH₃ | OCH₃ | CH | |
| H | CH=CH | C₆H₅ | H | OCH₃ | OCH₃ | CH | |
| H | CH=CH | C₆H₅ | H | Cl | OCH₃ | CH | |
| H | CH=CH | C₆H₅ | H | CH₃ | OCH₃ | N | |
| H | CH=CH | C₆H₅ | H | OCH₃ | OCH₃ | N | |
| H | CH=CH | C₆H₅ | H | CH₃ | CH₃ | N | |
| 6-Cl | CH=CH | CH₃ | H | CH₃ | CH₃ | CH | |
| 6-Cl | CH=CH | CH₃ | H | CH₃ | OCH₃ | CH | |
| 6-Cl | CH=CH | CH₃ | H | OCH₃ | OCH₃ | CH | |
| 6-Cl | CH=CH | CH₃ | H | Cl | OCH₃ | CH | |
| 6-Cl | CH=CH | CH₃ | H | CH₃ | OCH₃ | N | |
| 6-Cl | CH=CH | CH₃ | H | OCH₃ | OCH₃ | N | |
| 6-Cl | CH=CH | C₆H₅ | H | CH₃ | CH₃ | CH | |
| 6-Cl | CH=CH | C₆H₅ | H | CH₃ | OCH₃ | CH | |
| 6-Cl | CH=CH | C₆H₅ | H | OCH₃ | OCH₃ | CH | |
| 6-Cl | CH=CH | C₆H₅ | H | Cl | OCH₃ | CH | |
| 6-Cl | CH=CH | C₆H₅ | H | CH₃ | OCH₃ | N | |
| 6-Cl | CH=CH | C₆H₅ | H | OCH₃ | OCH₃ | N | |
| H | CH₂ | CH₃ | H | OCH₃ | OCH₃ | CH | |
| H | CH₂ | CH₃ | H | OCH₃ | CH₃ | CH | |
| H | CH₂ | CH₃ | H | CH₃ | CH₃ | CH | |
| H | CH₂ | CH₃ | H | OCH₃ | Cl₃ | CH | |
| H | CH₂ | CH₃ | H | OCH₃ | OCH₃ | N | |
| H | CH₂ | CH₃ | H | CH₃ | CH₃ | N | |
| H | CH₂CH₂ | CH₃ | H | OCH₃ | OCH₃ | CH | 221–223(d) |
| H | CH₂CH₂ | CH₃ | H | OCH₃ | CH₃ | CH | |
| H | CH₂CH₂ | CH₃ | H | CH₃ | CH₃ | CH | |
| H | CH₂CH₂ | CH₃ | H | OCH₃ | Cl₃ | CH | |
| H | CH₂CH₂ | CH₃ | H | OCH₃ | OCH₃ | N | |
| H | CH₂CH₂ | CH₃ | H | OCH₃ | OCH₃ | N | |
| H | CH=CH | CH₃ | H | OCH₃ | OCH₃ | CH | |
| H | CH=CH | CH₃ | H | OCH₃ | CH₃ | CH | |
| H | CH=CH | CH₃ | H | CH₃ | CH₃ | CH | |
| H | CH=CH | CH₃ | H | OCH₃ | Cl₃ | CH | |
| H | CH=CH | CH₃ | H | OCH₃ | OCH₃ | N | |
| H | CH=CH | CH₃ | H | OCH₃ | CH₃ | N | |

TABLE 2a

General Formula 2a

| $R_1$ | J | W' | $R_9$ | X | Y | Z | m.p.(°C.) |
|---|---|---|---|---|---|---|---|
| H | C=O | O | H | CH₃ | CH₃ | CH | |
| H | C=O | O | H | CH₃ | OCH₃ | CH | |
| H | C=O | O | H | OCH₃ | OCH₃ | CH | |
| H | C=O | O | H | Cl | OCH₃ | CH | |
| H | C=O | O | H | CH₃ | OCH₃ | N | |
| H | C=O | O | H | OCH₃ | OCH₃ | N | |
| H | C=O | O | H | CH₃ | CH₃ | N | |
| H | C=O | O | CH₃ | CH₃ | OCH₃ | CH | |
| H | C=O | O | CH₃ | OCH₃ | OCH₃ | CH | |
| H | C=O | O | CH₃ | CH₃ | CH₃ | CH | |
| H | C=O | O | CH₃ | Cl | OCH₃ | CH | |
| H | C=O | O | CH₃ | CH₃ | OCH₃ | N | |
| H | C=O | O | CH₃ | OCH₃ | OCH₃ | N | |
| H | C=O | O | CH₃ | CH₃ | CH₃ | N | |
| H | C=O | O | C₆H₅ | CH₃ | CH₃ | CH | |
| H | C=O | O | C₆H₅ | CH₃ | OCH₃ | CH | |
| H | C=O | O | C₆H₅ | OCH₃ | OCH₃ | CH | |
| H | C=O | O | C₆H₅ | Cl | OCH₃ | CH | |
| H | C=O | O | C₆H₅ | CH₃ | OCH₃ | N | |
| H | C=O | O | C₆H₅ | OCH₃ | OCH₃ | N | |
| H | C=O | O | C₆H₅ | CH₃ | CH₃ | N | |
| H | C=O | S | H | CH₃ | CH₃ | CH | |
| H | C=O | S | H | CH₃ | OCH₃ | CH | |
| H | C=O | S | H | OCH₃ | OCH₃ | CH | |
| H | C=O | S | H | Cl | OCH₃ | CH | |
| H | C=O | S | H | CH₃ | OCH₃ | N | |
| H | C=O | S | H | OCH₃ | OCH₃ | N | |
| H | C=O | S | H | CH₃ | CH₃ | N | |
| H | C=O | S | CH₃ | CH₃ | CH₃ | CH | |
| H | C=O | S | CH₃ | CH₃ | OCH₃ | CH | |
| H | C=O | S | CH₃ | CH₃ | Cl | OCH₃ | CH |

TABLE 2a-continued

General Formula 2a

| $R_1$ | J | W' | $R_9$ | X | Y | Z | m.p.(°C.) |
|---|---|---|---|---|---|---|---|
| H | C=O | S | CH₃ | CH₃ | OCH₃ | N | |
| H | C=O | S | CH₃ | OCH₃ | OCH₃ | N | |
| H | C=O | S | CH₃ | CH₃ | CH₃ | N | |
| H | C=O | S | C₆H₅ | CH₃ | CH₃ | CH | |
| H | C=O | S | C₆H₅ | CH₃ | OCH₃ | CH | |
| H | C=O | S | C₆H₅ | OCH₃ | OCH₃ | CH | |
| H | C=O | S | C₆H₅ | Cl | OCH₃ | CH | |
| H | C=O | S | C₆H₅ | CH₃ | OCH₃ | N | |
| H | C=O | S | C₆H₅ | OCH₃ | OCH₃ | N | |
| H | C=O | S | C₆H₅ | CH₃ | CH₃ | N | |
| H | CH₂ | O | CH₃ | CH₃ | CH₃ | CH | |
| H | CH₂ | O | CH₃ | CH₃ | OCH₃ | CH | |
| H | CH₂ | O | CH₃ | OCH₃ | OCH₃ | CH | |
| H | CH₂ | O | CH₃ | Cl | OCH₃ | CH | |
| H | CH₂ | O | CH₃ | CH₃ | CH₃ | N | |
| H | CH₂ | O | CH₃ | OCH₃ | OCH₃ | N | |
| H | CH₂ | O | CH₃ | CH₃ | CH₃ | N | |
| H | CH₂ | S | CH₃ | CH₃ | CH₃ | CH | |
| H | CH₂ | S | CH₃ | CH₃ | OCH₃ | CH | |
| H | CH₂ | S | CH₃ | OCH₃ | OCH₃ | CH | |
| H | CH₂ | S | CH₃ | Cl | OCH₃ | CH | |
| H | CH₂ | S | CH₃ | CH₃ | OCH₃ | N | |
| H | CH₂ | S | CH₃ | OCH₃ | OCH₃ | N | |
| H | CH₂ | S | CH₃ | CH₃ | CH₃ | N | |
| H | CH₂ | S | C₆H₅ | CH₃ | CH₃ | CH | |
| H | CH₂ | S | C₆H₅ | CH₃ | OCH₃ | CH | |
| H | CH₂ | S | C₆H₅ | OCH₃ | OCH₃ | CH | |
| H | CH₂ | S | C₆H₅ | Cl | OCH₃ | CH | |
| H | CH₂ | S | C₆H₅ | CH₃ | OCH₃ | N | |
| H | CH₂ | S | C₆H₅ | OCH₃ | OCH₃ | N | |
| H | CH₂ | S | C₆H₅ | CH₃ | CH₃ | N | |
| H | SO₂ | O | H | CH₃ | CH₃ | CH | |
| H | SO₂ | O | H | CH₃ | OCH₃ | CH | |
| H | SO₂ | O | H | OCH₃ | OCH₃ | CH | |
| H | SO₂ | O | H | Cl | OCH₃ | CH | |
| H | SO₂ | O | H | CH₃ | OCH₃ | N | |
| H | SO₂ | O | H | OCH₃ | OCH₃ | N | |
| H | SO₂ | O | H | CH₃ | CH₃ | N | |
| H | SO₂ | S | H | CH₃ | CH₃ | CH | |
| H | SO₂ | S | H | CH₃ | OCH₃ | CH | |
| H | SO₂ | S | H | OCH₃ | OCH₃ | CH | |
| H | SO₂ | S | H | Cl | OCH₃ | CH | |
| H | SO₂ | S | H | CH₃ | OCH₃ | N | |
| H | SO₂ | S | H | OCH₃ | OCH₃ | N | |
| H | SO₂ | S | H | CH₃ | CH₃ | N | |
| H | SO₂ | S | CH₃ | CH₃ | CH₃ | CH | |
| H | SO₂ | S | CH₃ | CH₃ | OCH₃ | CH | |
| H | SO₂ | S | CH₃ | OCH₃ | OCH₃ | CH | |
| H | SO₂ | S | CH₃ | Cl | OCH₃ | CH | |
| H | SO₂ | S | CH₃ | CH₃ | OCH₃ | N | |
| H | SO₂ | S | CH₃ | OCH₃ | OCH₃ | N | |
| H | SO₂ | S | CH₃ | CH₃ | CH₃ | N | |
| H | O | O | CH₃ | CH₃ | OCH₃ | CH | |
| H | O | O | CH₃ | OCH₃ | OCH₃ | CH | |
| H | O | O | CH₃ | Cl | OCH₃ | CH | |
| H | O | O | CH₃ | CH₃ | OCH₃ | N | |
| H | O | O | CH₃ | OCH₃ | OCH₃ | N | |
| H | O | O | CH₃ | CH₃ | CH₃ | N | |
| H | O | S | CH₃ | CH₃ | CH₃ | CH | |
| H | O | S | CH₃ | CH₃ | OCH₃ | CH | |
| H | O | S | CH₃ | OCH₃ | OCH₃ | CH | |
| H | O | S | CH₃ | Cl | OCH₃ | CH | |
| H | O | S | CH₃ | CH₃ | OCH₃ | N | |
| H | O | S | CH₃ | OCH₃ | OCH₃ | N | |
| H | O | S | CH₃ | CH₃ | CH₃ | N | |
| H | O | S | C₆H₅ | CH | CH₃ | CH | |
| H | O | S | C₆H₅ | CH₃ | OCH₃ | CH | |
| H | O | S | C₆H₅ | OCH₃ | OCH₃ | CH | |
| H | O | S | C₆H₅ | Cl | OCH₃ | CH | |
| H | O | S | C₆H₅ | CH₃ | OCH₃ | N | |
| H | O | S | C₆H₅ | OCH₃ | OCH₃ | N | |
| H | O | S | C₆H₅ | CH₃ | CH₃ | N | |
| 6-Cl | C=O | O | H | CH₃ | CH₃ | CH | |
| 6-Cl | C=O | O | H | CH₃ | OCH₃ | CH | |
| 6-Cl | C=O | O | H | OCH₃ | OCH₃ | CH | |
| 6-Cl | C=O | O | H | Cl | OCH₃ | CH | |
| 6-Cl | C=O | O | H | CH₃ | OCH₃ | N | |
| 6-Cl | C=O | O | H | OCH₃ | OCH₃ | N | |

TABLE 2a-continued

General Formula 2a

| R₁ | J | W' | R₉ | X | Y | Z | m.p.(°C.) |
|---|---|---|---|---|---|---|---|
| 6-Cl | C=O | O | H | CH₃ | CH₃ | N | |
| 6-CH₃ | C=O | O | CH₃ | CH₃ | OCH₃ | CH | |
| 6-CH₃ | C=O | O | CH₃ | OCH₃ | OCH₃ | CH | |
| 6-CH₃ | C=O | O | CH₃ | Cl | OCH₃ | CH | |
| 6-CH₃ | C=O | O | CH₃ | CH₃ | OCH₃ | N | |
| 6-CH₃ | C=O | O | CH₃ | OCH₃ | OCH₃ | N | |
| 6-CH₃ | C=O | O | CH₃ | CH₃ | CH₃ | N | |
| 6-CH₃ | C=O | O | C₆H₅ | CH₃ | CH₃ | CH | |
| 6-CH₃ | C=O | O | C₆H₅ | CH₃ | OCH₃ | CH | |
| 6-CH₃ | C=O | O | C₆H₅ | OCH₃ | OCH₃ | CH | |
| 6-CH₃ | C=O | O | C₆H₅ | Cl | OCH₃ | CH | |
| 6-CH₃ | C=O | O | C₆H₅ | CH₃ | OCH₃ | N | |
| 6-CH₃ | C=O | O | C₆H₅ | OCH₃ | OCH₃ | N | |
| 6-CH₃ | C=O | O | C₆H₅ | CH₃ | CH₃ | N | |
| 5-NO₂ | C=O | S | H | CH₃ | CH₃ | CH | |
| 5-NO₂ | C=O | S | H | CH₃ | OCH₃ | CH | |
| 5-NO₂ | C=O | S | H | OCH₃ | OCH₃ | CH | |
| 5-NO₂ | C=O | S | H | Cl | OCH₃ | CH | |
| 5-NO₂ | C=O | S | H | CH₃ | OCH₃ | N | |
| 5-NO₂ | C=O | S | H | OCH₃ | OCH₃ | N | |
| 5-NO₂ | C=O | S | H | CH₃ | CH₃ | N | |
| 5-SCH₃ | C=O | S | CH₃ | CH₃ | CH₃ | CH | |
| 5-SCH₃ | C=O | S | CH₃ | CH₃ | OCH₃ | CH | |
| 5-SCH₃ | C=O | S | CH₃ | OCH | OCH₃ | CH | |
| 5-SCH₃ | C=O | S | CH₃ | Cl | OCH₃ | CH | |
| 5-SCH₃ | C=O | S | CH₃ | CH₃ | OCH₃ | N | |
| 5-SCH₃ | C=O | S | CH₃ | OCH₃ | OCH₃ | N | |
| 5-SCH₃ | C=O | S | CH₃ | CH₃ | CH₃ | N | |
| 5-NO₂ | C=O | S | C₆H₅ | CH₃ | CH₃ | CH | |
| 5-NO₂ | C=O | S | C₆H₅ | CH₃ | OCH₃ | CH | |
| 5-NO₂ | C=O | S | C₆H₅ | OCH₃ | OCH₃ | CH | |
| 5-NO₂ | C=O | S | C₆H₅ | Cl | OCH₃ | CH | |
| 5-NO₂ | C=O | S | C₆H₅ | CH₃ | OCH₃ | N | |
| 5-NO₂ | C=O | S | C₆H₅ | OCH₃ | OCH₃ | N | |
| 5-NO₂ | C=O | S | C₆H₅ | CH₃ | CH₃ | N | |
| 6-Cl | CH₂ | O | CH₃ | CH₃ | CH₃ | CH | |
| 6-Cl | CH₂ | O | CH₃ | CH₃ | OCH₃ | CH | |
| 6-Cl | CH₂ | O | CH₃ | OCH₃ | OCH₃ | CH | |
| 6-Cl | CH₂ | O | CH₃ | Cl | OCH₃ | CH | |
| 6-Cl | CH₂ | O | CH₃ | CH₃ | OCH₃ | N | |
| 6-Cl | CH₂ | O | CH₃ | OCH₃ | OCH₃ | N | |
| 6-Cl | CH₂ | O | CH₃ | CH₃ | CH₃ | N | |
| 6-Cl | CH₂ | S | CH₃ | CH₃ | CH₃ | CH | |
| 6-Cl | CH₂ | S | CH₃ | CH₃ | OCH₃ | CH | |
| 6-Cl | CH₂ | S | CH₃ | OCH₃ | OCH₃ | CH | |
| 6-Cl | CH₂ | S | CH₃ | Cl | OCH₃ | CH | |
| 6-Cl | CH₂ | S | CH₃ | CH₃ | OCH₃ | N | |
| 6-Cl | CH₂ | S | CH₃ | OCH₃ | OCH₃ | N | |
| 6-Cl | CH₂ | S | CH₃ | CH₃ | CH₃ | N | |
| 6-Cl | CH₂ | S | C₆H₅ | CH | CH₃ | CH | |
| 6-Cl | CH₂ | S | C₆H₅ | CH₃ | OCH₃ | CH | |
| 6-Cl | CH₂ | S | C₆H₅ | OCH₃ | OCH₃ | CH | |
| 6-Cl | CH₂ | S | C₆H₅ | Cl | OCH₃ | CH | |
| 6-Cl | CH₂ | S | C₆H₅ | CH₃ | OCH₃ | N | |
| 6-Cl | CH₂ | S | C₆H₅ | OCH₃ | OCH₃ | N | |
| 6-Cl | CH₂ | S | C₆H₅ | CH₃ | CH₃ | N | |
| 6-CH₃ | SO₂ | O | H | CH₃ | CH₃ | CH | |
| 6-CH₃ | SO₂ | O | H | CH₃ | OCH₃ | CH | |
| 6-CH₃ | SO₂ | O | H | OCH₃ | OCH₃ | CH | |
| 6-CH₃ | SO₂ | O | H | Cl | OCH₃ | CH | |
| 6-CH₃ | SO₂ | O | H | CH₃ | OCH₃ | N | |
| 6-CH₃ | SO₂ | O | H | OCH₃ | OCH₃ | N | |
| 6-CH₃ | SO₂ | O | H | CH₃ | CH₃ | N | |
| 6-CH₃ | SO₂ | S | H | CH₃ | CH₃ | CH | |
| 6-CH₃ | SO₂ | S | H | CH₃ | OCH₃ | CH | |
| 6-CH₃ | SO₂ | S | H | OCH₃ | OCH₃ | CH | |
| 6-CH₃ | SO₂ | S | H | Cl | OCH₃ | CH | |
| 6-CH₃ | SO₂ | S | H | CH₃ | OCH₃ | N | |
| 6-CH₃ | SO₂ | S | H | OCH₃ | OCH₃ | N | |
| 6-CH₃ | SO₂ | S | H | CH₃ | CH₃ | N | |
| 5-NO₂ | SO₂ | S | CH₃ | CH₃ | CH₃ | CH | |
| 5-NO₂ | SO₂ | S | CH₃ | CH₃ | OCH₃ | CH | |
| 5-NO₂ | SO₂ | S | CH₃ | OCH₃ | OCH₃ | CH | |
| 5-NO₂ | SO₂ | S | CH₃ | Cl | OCH₃ | CH | |
| 5-NO₂ | SO₂ | S | CH₃ | CH₃ | OCH₃ | N | |
| 5-NO₂ | SO₂ | S | CH₃ | OCH₃ | OCH₃ | N | |
| 5-NO₂ | SO₂ | S | CH₃ | CH₃ | CH₃ | N | |
| 6-CH₃ | O | O | CH₃ | CH₃ | CH₃ | CH | |
| 6-CH₃ | O | O | CH₃ | CH₃ | OCH₃ | CH | |
| 6-CH₃ | O | O | CH₃ | OCH₃ | OCH₃ | CH | |
| 6-CH₃ | O | O | CH₃ | Cl | OCH₃ | CH | |
| 6-CH₃ | O | O | CH₃ | CH₃ | OCH₃ | N | |
| 6-CH₃ | O | O | CH₃ | OCH₃ | OCH₃ | N | |
| 6-CH₃ | O | O | CH₃ | CH₃ | CH₃ | N | |
| 6-Cl | O | S | CH₃ | CH₃ | CH₃ | CH | |
| 6-Cl | O | S | CH₃ | CH₃ | OCH₃ | CH | |
| 6-Cl | O | S | CH₃ | OCH₃ | OCH₃ | CH | |
| 6-Cl | O | S | CH₃ | Cl | OCH₃ | CH | |
| 6-Cl | O | S | CH₃ | CH₃ | OCH₃ | N | |
| 6-Cl | O | S | CH₃ | OCH₃ | OCH₃ | N | |
| 6-Cl | O | S | CH₃ | CH₃ | CH₃ | N | |
| 5-NO₂ | O | S | C₆H₅ | CH₃ | CH₃ | CH | |
| 5-NO₂ | O | S | C₆H₅ | CH₃ | OCH₃ | CH | |
| 5-NO₂ | O | S | C₆H₅ | OCH₃ | OCH₃ | CH | |
| 5-NO₂ | O | S | C₆H₅ | Cl | OCH₃ | CH | |
| 5-NO₂ | O | S | C₆H₅ | CH₃ | OCH₃ | N | |
| 5-NO₂ | O | S | C₆H₅ | OCH₃ | OCH₃ | N | |
| 5-NO₂ | O | S | C₆H₅ | CH₃ | CH₃ | N | |

TABLE 2b

General Formula 2b

| R₁ | G | W' | R₉ | X | Y | Z | m.p.(°C.) |
|---|---|---|---|---|---|---|---|
| H | CH₂ | O | H | CH₃ | CH₃ | CH | |
| H | CH₂ | O | H | CH₃ | OCH₃ | CH | |
| H | CH₂ | O | H | OCH₃ | OCH₃ | CH | |
| H | CH₂ | O | H | Cl | OCH₃ | CH | |
| H | CH₂ | O | H | CH₃ | OCH₃ | N | |
| H | CH₂ | O | H | OCH₃ | OCH₃ | N | |
| H | CH₂ | O | H | CH₃ | CH₃ | N | |
| H | CH₂ | S | CH₃ | CH₃ | CH₃ | CH | |
| H | CH₂ | S | CH₃ | CH₃ | OCH₃ | CH | |
| H | CH₂ | S | CH₃ | OCH₃ | OCH₃ | CH | |
| H | CH₂ | S | CH₃ | Cl | OCH₃ | CH | |
| H | CH₂ | S | CH₃ | CH₃ | OCH₃ | N | |
| H | CH₂ | S | CH₃ | OCH₃ | OCH₃ | N | |
| H | CH₂ | S | CH₃ | CH₃ | CH₃ | N | |
| H | CH₂ | NH | H | CH₃ | CH₃ | CH | |
| H | CH₂ | NH | H | CH₃ | OCH₃ | CH | |
| H | CH₂ | NH | H | OCH₃ | OCH₃ | CH | |
| H | CH₂ | NH | H | Cl | OCH₃ | CH | |
| H | CH₂ | NH | H | CH₃ | OCH₃ | N | |
| H | CH₂ | NH | H | OCH₃ | OCH₃ | N | |
| H | CH₂ | NH | H | CH₃ | CH₃ | N | |
| 6-Cl | CH₂ | O | H | CH₃ | CH₃ | CH | |
| 6-Cl | CH₂ | O | H | CH₃ | OCH₃ | CH | |
| 6-Cl | CH₂ | O | H | OCH₃ | OCH₃ | CH | |
| 6-Cl | CH₂ | O | H | Cl | OCH₃ | CH | |
| 6-Cl | CH₂ | O | H | CH₃ | OCH₃ | N | |
| 6-Cl | CH₂ | O | H | OCH₃ | OCH₃ | N | |
| 6-Cl | CH₂ | O | H | CH₃ | CH₃ | N | |
| 6-Cl | CH₂ | S | CH₃ | CH₃ | CH₃ | CH | |
| 6-Cl | CH₂ | S | CH₃ | CH₃ | OCH₃ | CH | |
| 6-Cl | CH₂ | S | CH₃ | OCH₃ | OCH₃ | CH | |
| 6-Cl | CH₂ | S | CH₃ | Cl | OCH₃ | CH | |
| 6-Cl | CH₂ | S | CH₃ | CH₃ | OCH₃ | N | |
| 6-Cl | CH₂ | S | CH₃ | OCH₃ | OCH₃ | N | |
| 6-Cl | CH₂ | S | CH₃ | CH₃ | CH₃ | N | |
| 6-Cl | CH₂ | NH | H | CH | CH₃ | CH | |
| 6-Cl | CH₂ | NH | H | CH₃ | OCH₃ | CH | |
| 6-Cl | CH₂ | NH | H | OCH₃ | OCH₃ | CH | |
| 6-Cl | CH₂ | NH | H | Cl | OCH₃ | CH | |
| 6-Cl | CH₂ | NH | H | CH₃ | OCH₃ | N | |
| 6-Cl | CH₂ | NH | H | OCH₃ | OCH₃ | N | |
| 6-Cl | CH₂ | NH | H | CH₃ | CH₃ | N | |
| H | CH₂ | S | H | OCH₃ | OCH₃ | CH | |
| H | CH₂ | S | H | CH₃ | OCH₃ | CH | |
| H | CH₂ | S | H | CH₃ | OCH₃ | N | |
| H | CH₂ | S | H | OCH₃ | OCH₃ | N | |
| H | CH₂ | S | H | Cl | OCH₃ | CH | |
| H | CH₂ | NCH₃ | H | OCH₃ | OCH₃ | CH | |
| H | CH₂ | NCH₃ | H | CH₃ | OCH₃ | N | |
| H | CH₂CH₂ | O | H | CH₃ | CH₃ | CH | |
| H | CH₂CH₂ | O | H | CH₃ | OCH₃ | CH | |
| H | CH₂CH₂ | O | H | OCH₃ | OCH₃ | CH | |
| H | CH₂CH₂ | O | H | Cl | OCH₃ | CH | |

TABLE 2b-continued

General Formula 2b

| R$_1$ | G | W' | R$_9$ | X | Y | Z | m.p.(°C.) |
|---|---|---|---|---|---|---|---|
| H | CH$_2$CH$_2$ | O | H | CH$_3$ | OCH$_3$ | N | |
| H | CH$_2$CH$_2$ | O | H | OCH$_3$ | OCH$_3$ | N | |
| H | CH$_2$CH$_2$ | O | H | CH$_3$ | CH$_3$ | N | |
| H | CH$_2$CH$_2$ | S | CH$_3$ | CH$_3$ | CH$_3$ | CH | |
| H | CH$_2$CH$_2$ | S | CH$_3$ | CH$_3$ | OCH$_3$ | CH | |
| H | CH$_2$CH$_2$ | S | CH$_3$ | OCH$_3$ | OCH$_3$ | CH | |
| H | CH$_2$CH$_2$ | S | CH$_3$ | Cl | OCH$_3$ | CH | |
| H | CH$_2$CH$_2$ | S | CH$_3$ | CH$_3$ | OCH$_3$ | N | |
| H | CH$_2$CH$_2$ | S | CH$_3$ | OCH$_3$ | OCH$_3$ | N | |
| H | CH$_2$CH$_2$ | S | CH$_3$ | CH$_3$ | CH$_3$ | N | |
| H | CH$_2$CH$_2$ | NH | H | CH$_3$ | CH$_3$ | CH | |
| H | CH$_2$CH$_2$ | NH | H | CH$_3$ | OCH$_3$ | CH | |
| H | CH$_2$CH$_2$ | NH | H | OCH$_3$ | OCH$_3$ | CH | |
| H | CH$_2$CH$_2$ | NH | H | Cl | OCH$_3$ | CH | |
| H | CH$_2$CH$_2$ | NH | H | CH$_3$ | OCH$_3$ | N | |
| H | CH$_2$CH$_2$ | NH | H | OCH$_3$ | OCH$_3$ | N | |
| H | CH$_2$CH$_2$ | NH | H | CH$_3$ | CH$_3$ | N | |
| 6-Cl | CH$_2$CH$_2$ | O | H | CH$_3$ | CH$_3$ | CH | |
| 6-Cl | CH$_2$CH$_2$ | O | H | CH$_3$ | OCH$_3$ | CH | |
| 6-Cl | CH$_2$CH$_2$ | O | H | OCH$_3$ | OCH$_3$ | CH | |
| 6-Cl | CH$_2$CH$_2$ | O | H | Cl | OCH$_3$ | CH | |
| 6-Cl | CH$_2$CH$_2$ | O | H | CH$_3$ | OCH$_3$ | N | |
| 6-Cl | CH$_2$CH$_2$ | O | H | OCH$_3$ | OCH$_3$ | N | |
| 6-Cl | CH$_2$CH$_2$ | O | H | CH$_3$ | CH$_3$ | N | |
| 6-Cl | CH$_2$CH$_2$ | S | CH$_3$ | CH$_3$ | CH$_3$ | CH | |
| 6-Cl | CH$_2$CH$_2$ | S | CH$_3$ | CH$_3$ | OCH$_3$ | CH | |
| 6-Cl | CH$_2$CH$_2$ | S | CH$_3$ | OCH$_3$ | OCH$_3$ | CH | |
| 6-Cl | CH$_2$CH$_2$ | S | CH$_3$ | Cl | OCH$_3$ | CH | |
| 6-Cl | CH$_2$CH$_2$ | S | CH$_3$ | CH$_3$ | OCH$_3$ | N | |
| 6-Cl | CH$_2$CH$_2$ | S | CH$_3$ | OCH$_3$ | OCH$_3$ | N | |
| 6-Cl | CH$_2$CH$_2$ | S | CH$_3$ | CH$_3$ | CH$_3$ | N | |
| 6-Cl | CH$_2$CH$_2$ | NH | H | CH | CH$_3$ | CH | |
| 6-Cl | CH$_2$CH$_2$ | NH | H | CH$_3$ | OCH$_3$ | CH | |
| 6-Cl | CH$_2$CH$_2$ | NH | H | OCH$_3$ | OCH$_3$ | CH | |
| 6-Cl | CH$_2$CH$_2$ | NH | H | Cl | OCH$_3$ | CH | |
| 6-Cl | CH$_2$CH$_2$ | NH | H | CH$_3$ | OCH$_3$ | N | |
| 6-Cl | CH$_2$CH$_2$ | NH | H | OCH$_3$ | OCH$_3$ | N | |
| 6-Cl | CH$_2$CH$_2$ | NH | H | CH$_3$ | CH$_3$ | N | |
| H | CH$_2$CH$_2$ | S | H | OCH$_3$ | OCH$_3$ | CH | |
| H | CH$_2$CH$_2$ | S | H | CH$_3$ | CH$_3$ | CH | |
| H | CH$_2$CH$_2$ | S | H | CH$_3$ | CH$_3$ | CH | |
| H | CH$_2$CH$_2$ | S | H | CH$_3$ | OCH$_3$ | N | |
| H | CH$_2$CH$_2$ | S | H | OCH$_3$ | OCH$_3$ | N | |
| H | CH$_2$CH$_2$ | S | H | Cl | OCH$_3$ | CH | |
| H | CH$_2$CH$_2$ | NCH$_3$ | H | OCH$_3$ | OCH$_3$ | CH | |
| H | CH$_2$CH$_2$ | NCH$_3$ | H | CH$_3$ | CH$_3$ | N | |
| H | CH=CH | O | H | CH$_3$ | CH$_3$ | CH | |
| H | CH=CH | O | H | CH$_3$ | OCH$_3$ | CH | |
| H | CH=CH | O | H | OCH$_3$ | OCH$_3$ | CH | |
| H | CH=CH | O | H | Cl | OCH$_3$ | CH | |
| H | CH=CH | O | H | CH$_3$ | OCH$_3$ | N | |
| H | CH=CH | O | H | OCH$_3$ | OCH$_3$ | N | |
| H | CH=CH | O | H | CH$_3$ | CH$_3$ | N | |
| H | CH=CH | S | CH$_3$ | CH$_3$ | CH$_3$ | CH | |
| H | CH=CH | S | CH$_3$ | CH$_3$ | OCH$_3$ | CH | |
| H | CH=CH | S | CH$_3$ | OCH$_3$ | OCH$_3$ | CH | |
| H | CH=CH | S | CH$_3$ | Cl | OCH$_3$ | CH | |
| H | CH=CH | S | CH$_3$ | CH$_3$ | OCH$_3$ | N | |
| H | CH=CH | S | CH$_3$ | OCH$_3$ | OCH$_3$ | N | |
| H | CH=CH | S | CH$_3$ | CH$_3$ | CH$_3$ | N | |
| H | CH=CH | NH | H | CH$_3$ | CH$_3$ | CH | |
| H | CH=CH | NH | H | CH$_3$ | OCH$_3$ | CH | |
| H | CH=CH | NH | H | OCH$_3$ | OCH$_3$ | CH | |
| H | CH=CH | NH | H | Cl | OCH$_3$ | CH | |
| H | CH=CH | NH | H | CH$_3$ | OCH$_3$ | N | |
| H | CH=CH | NH | H | OCH$_3$ | OCH$_3$ | N | |
| H | CH=CH | NH | H | CH$_3$ | CH$_3$ | N | |
| 6-Cl | CH=CH | O | H | CH$_3$ | CH$_3$ | CH | |
| 6-Cl | CH=CH | O | H | CH$_3$ | OCH$_3$ | CH | |
| 6-Cl | CH=CH | O | H | OCH$_3$ | OCH$_3$ | CH | |
| 6-Cl | CH=CH | O | H | Cl | OCH$_3$ | CH | |
| 6-Cl | CH=CH | O | H | CH$_3$ | OCH$_3$ | N | |
| 6-Cl | CH=CH | O | H | OCH$_3$ | OCH$_3$ | N | |
| 6-Cl | CH=CH | O | H | CH$_3$ | CH$_3$ | N | |
| 6-Cl | CH=CH | S | CH$_3$ | CH$_3$ | CH$_3$ | CH | |
| 6-Cl | CH=CH | S | CH$_3$ | CH$_3$ | OCH$_3$ | CH | |
| 6-Cl | CH=CH | S | CH$_3$ | OCH$_3$ | OCH$_3$ | CH | |
| 6-Cl | CH=CH | S | CH$_3$ | Cl | OCH$_3$ | CH | |
| 6-Cl | CH=CH | S | CH$_3$ | CH$_3$ | OCH$_3$ | N | |
| 6-Cl | CH=CH | S | CH$_3$ | OCH$_3$ | OCH$_3$ | N | |
| 6-Cl | CH=CH | S | CH$_3$ | CH$_3$ | CH$_3$ | N | |
| 6-Cl | CH=CH | NH | H | CH | CH$_3$ | CH | |
| 6-Cl | CH=CH | NH | H | CH$_3$ | OCH$_3$ | CH | |
| 6-Cl | CH=CH | NH | H | OCH$_3$ | OCH$_3$ | CH | |
| 6-Cl | CH=CH | NH | H | Cl | OCH$_3$ | CH | |
| 6-Cl | CH=CH | NH | H | CH$_3$ | OCH$_3$ | N | |
| 6-Cl | CH=CH | NH | H | OCH$_3$ | OCH$_3$ | N | |
| 6-Cl | CH=CH | NH | H | CH$_3$ | CH$_3$ | N | |
| H | CH=CH | S | H | OCH$_3$ | OCH$_3$ | CH | |
| H | CH=CH | S | H | CH$_3$ | CH$_3$ | CH | |
| H | CH=CH | S | H | CH$_3$ | CH$_3$ | CH | |
| H | CH=CH | S | H | CH$_3$ | OCH$_3$ | N | |
| H | CH=CH | S | H | OCH$_3$ | OCH$_3$ | N | |
| H | CH=CH | S | H | Cl | OCH$_3$ | CH | |
| H | CH=CH | NCH$_3$ | H | OCH$_3$ | OCH$_3$ | CH | |
| H | CH=CH | NCH$_3$ | H | CH$_3$ | OCH$_3$ | N | |

TABLE 3a

General Formula 3a

| R$_1$ | J | R$_{10}$ | X | Y | Z | m.p. (°C.) |
|---|---|---|---|---|---|---|
| H | C=O | H | CH$_3$ | CH$_3$ | CH | |
| H | C=O | H | CH$_3$ | OCH$_3$ | CH | |
| H | C=O | H | OCH$_3$ | OCH$_3$ | CH | |
| H | C=O | H | Cl | OCH$_3$ | CH | |
| H | C=O | H | CH$_3$ | OCH$_3$ | N | |
| H | C=O | H | OCH$_3$ | OCH$_3$ | N | |
| H | C=O | H | CH$_3$ | CH$_3$ | N | |
| H | C=O | CH$_3$ | CH$_3$ | CH$_3$ | CH | |
| H | C=O | CH$_3$ | CH$_3$ | OCH$_3$ | CH | |
| H | C=O | CH$_3$ | OCH$_3$ | OCH$_3$ | CH | |
| H | C=O | CH$_3$ | Cl | OCH$_3$ | CH | |
| H | C=O | CH$_3$ | CH$_3$ | OCH$_3$ | N | |
| H | C=O | CH$_3$ | OCH$_3$ | OCH$_3$ | N | |
| H | C=O | CH$_3$ | CH$_3$ | CH$_3$ | N | |
| H | CH$_2$ | CH$_3$ | CH$_3$ | CH$_3$ | CH | |
| H | CH$_2$ | CH$_3$ | CH$_3$ | OCH$_3$ | CH | |
| H | CH$_2$ | CH$_3$ | OCH$_3$ | OCH$_3$ | CH | |
| H | CH$_2$ | CH$_3$ | Cl | OCH$_3$ | CH | |
| H | CH$_2$ | CH$_3$ | CH$_3$ | OCH$_3$ | N | |
| H | CH$_2$ | CH$_3$ | OCH$_3$ | OCH$_3$ | N | |
| H | CH$_2$ | CH$_3$ | CH$_3$ | CH$_3$ | N | |
| H | S | H | CH$_3$ | CH$_3$ | CH | |
| H | S | H | CH$_3$ | OCH$_3$ | CH | |
| H | S | H | OCH$_3$ | OCH$_3$ | CH | |
| H | S | H | Cl | OCH$_3$ | CH | |
| H | S | H | CH$_3$ | OCH$_3$ | N | |
| H | S | H | OCH$_3$ | OCH$_3$ | N | |
| H | S | H | CH$_3$ | CH$_3$ | N | |
| H | SO$_2$ | H | CH$_3$ | CH$_3$ | CH | |
| H | SO$_2$ | H | CH$_3$ | OCH$_3$ | CH | |
| H | SO$_2$ | H | OCH$_3$ | OCH$_3$ | CH | |
| H | SO$_2$ | H | Cl | OCH$_3$ | CH | |
| H | SO$_2$ | H | CH$_3$ | OCH$_3$ | N | |
| H | SO$_2$ | H | OCH$_3$ | OCH$_3$ | N | |
| H | SO$_2$ | H | CH$_3$ | CH$_3$ | N | |
| H | O | CH$_3$ | CH$_3$ | CH$_3$ | CH | |
| H | O | CH$_3$ | CH$_3$ | OCH$_3$ | CH | |
| H | O | CH$_3$ | OCH$_3$ | OCH$_3$ | CH | |
| H | O | CH$_3$ | Cl | OCH$_3$ | CH | |
| H | O | CH$_3$ | CH$_3$ | OCH$_3$ | N | |
| H | O | CH$_3$ | OCH$_3$ | OCH$_3$ | N | |
| H | O | CH$_3$ | CH$_3$ | CH$_3$ | N | |
| 6-CH$_3$ | C=O | H | CH$_3$ | CH$_3$ | CH | |
| 6-CH$_3$ | C=O | H | CH$_3$ | OCH$_3$ | CH | |
| 6-CH$_3$ | C=O | H | OCH$_3$ | OCH$_3$ | CH | |
| 6-CH$_3$ | C=O | H | Cl | OCH$_3$ | CH | |
| 6-CH$_3$ | C=O | H | CH$_3$ | OCH$_3$ | N | |
| 6-CH$_3$ | C=O | H | OCH$_3$ | OCH$_3$ | N | |
| 6-CH$_3$ | C=O | H | CH$_3$ | CH$_3$ | N | |
| 6-CH$_3$ | C=O | CH$_3$ | CH$_3$ | CH$_3$ | CH | |
| 6-CH$_3$ | C=O | CH$_3$ | CH$_3$ | OCH$_3$ | CH | |
| 6-CH$_3$ | C=O | CH$_3$ | OCH$_3$ | OCH$_3$ | CH | |
| 6-CH$_3$ | C=O | CH$_3$ | Cl | OCH$_3$ | CH | |
| 6-CH$_3$ | C=O | CH$_3$ | CH$_3$ | CH$_3$ | N | |
| 6-CH$_3$ | C=O | CH$_3$ | OCH$_3$ | OCH$_3$ | N | |

TABLE 3a-continued

General Formula 3a

| R₁ | J | R₁₀ | X | Y | Z | m.p. (°C.) |
|---|---|---|---|---|---|---|
| 6-CH₃ | C=O | CH₃ | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | S | H | CH₃ | CH₃ | CH | |
| 6-CH₃ | S | H | CH₃ | OCH₃ | CH | |
| 6-CH₃ | S | H | OCH₃ | OCH₃ | CH | |
| 6-CH₃ | S | H | Cl | OCH₃ | CH | |
| 6-CH₃ | S | H | CH₃ | OCH₃ | N | |
| 6-CH₃ | S | H | OCH₃ | OCH₃ | N | |
| 6-CH₃ | S | H | CH₃ | CH₃ | N | |
| 6-CH₃ | SO₂ | H | CH₃ | CH₃ | CH | |
| 6-CH₃ | SO₂ | H | CH₃ | OCH₃ | CH | |
| 6-CH₃ | SO₂ | H | OCH₃ | OCH₃ | CH | |
| 6-CH₃ | SO₂ | H | Cl | OCH₃ | CH | |
| 6-CH₃ | SO₂ | H | CH₃ | OCH₃ | N | |
| 6-CH₃ | SO₂ | H | OCH₃ | OCH₃ | N | |
| 6-CH₃ | SO₂ | H | CH₃ | CH₃ | N | |
| 6-CH₃ | O | CH₃ | CH₃ | CH₃ | CH | |
| 6-CH₃ | O | CH₃ | CH₃ | OCH₃ | CH | |
| 6-CH₃ | O | CH₃ | OCH₃ | OCH₃ | CH | |
| 6-CH₃ | O | CH₃ | Cl | OCH₃ | CH | |
| 6-CH₃ | O | CH₃ | CH₃ | OCH₃ | N | |
| 6-CH₃ | O | CH₃ | OCH₃ | OCH₃ | N | |
| 6-CH₃ | O | CH₃ | CH₃ | CH₃ | N | |
| 6-Cl | C=O | H | CH₃ | CH₃ | CH | |
| 6-Cl | C=O | H | CH₃ | OCH₃ | CH | |
| 6-Cl | C=O | H | OCH₃ | OCH₃ | CH | |
| 6-Cl | C=O | H | Cl | OCH₃ | CH | |
| 6-Cl | C=O | H | CH₃ | OCH₃ | N | |
| 6-Cl | C=O | H | OCH₃ | OCH₃ | N | |
| 6-Cl | C=O | H | CH₃ | CH₃ | N | |
| 6-Cl | C=O | CH₃ | CH₃ | CH₃ | CH | |
| 6-Cl | C=O | CH₃ | CH₃ | OCH₃ | CH | |
| 6-Cl | C=O | CH₃ | OCH₃ | OCH₃ | CH | |
| 6-Cl | C=O | CH₃ | Cl | OCH₃ | CH | |
| 6-Cl | C=O | CH₃ | CH₃ | OCH₃ | N | |
| 6-Cl | C=O | CH₃ | OCH₃ | OCH₃ | N | |
| 6-Cl | C=O | CH₃ | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | S | H | CH₃ | CH₃ | CH | |
| 6-Cl | S | H | CH₃ | OCH₃ | CH | |
| 6-Cl | S | H | OCH₃ | OCH₃ | CH | |
| 6-Cl | S | H | Cl | OCH₃ | CH | |
| 6-Cl | S | H | CH₃ | OCH₃ | N | |
| 6-Cl | S | H | OCH₃ | OCH₃ | N | |
| 6-Cl | S | H | CH₃ | CH₃ | N | |
| 6-Cl | SO₂ | H | CH₃ | CH₃ | CH | |
| 6-Cl | SO₂ | H | CH₃ | OCH₃ | CH | |
| 6-Cl | SO₂ | H | OCH₃ | OCH₃ | CH | |
| 6-Cl | SO₂ | H | Cl | OCH₃ | CH | |
| 6-Cl | SO₂ | H | CH₃ | OCH₃ | N | |
| 6-Cl | SO₂ | H | OCH₃ | OCH₃ | N | |
| 6-Cl | SO₂ | H | CH₃ | CH₃ | N | |
| 6-Cl | O | CH₃ | CH₃ | CH₃ | CH | |
| 6-Cl | O | CH₃ | CH₃ | OCH₃ | CH | |
| 6-Cl | O | CH₃ | OCH₃ | OCH₃ | CH | |
| 6-Cl | O | CH₃ | Cl | OCH₃ | CH | |
| 6-Cl | O | CH₃ | CH₃ | OCH₃ | N | |
| 6-Cl | O | CH₃ | OCH₃ | OCH₃ | N | |
| 6-Cl | O | CH₃ | CH₃ | CH₃ | N | |

TABLE 3b

General Formula 3b

| R₁ | G | R₁₀ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | CH₂ | C₆H₅ | CH₃ | CH₃ | CH | |
| H | CH₂ | C₆H₅ | CH₃ | OCH₃ | CH | |
| H | CH₂ | C₆H₅ | OCH₃ | OCH₃ | CH | |
| H | CH₂ | C₆H₅ | Cl | OCH₃ | CH | |
| H | CH₂ | C₆H₅ | CH₃ | OCH₃ | N | |
| H | CH₂ | C₆H₅ | OCH₃ | OCH₃ | N | |
| H | CH₂ | C₆H₅ | CH₃ | CH₃ | N | |
| 6-CH₃ | CH₂ | H | CH₃ | CH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | CH₂ | C₆H₅ | CH₃ | CH₃ | CH | |
| 6-CH₃ | CH₂ | C₆H₅ | CH₃ | OCH₃ | CH | |
| 6-CH₃ | CH₂ | C₆H₅ | OCH₃ | OCH₃ | CH | |
| 6-CH₃ | CH₂ | C₆H₅ | Cl | OCH₃ | CH | |
| 6-CH₃ | CH₂ | C₆H₅ | CH₃ | OCH₃ | N | |
| 6-CH₃ | CH₂ | C₆H₅ | OCH₃ | OCH₃ | N | |
| 6-CH₃ | CH₂ | C₆H₅ | CH₃ | CH₃ | N | |
| 6-Cl | CH₂ | H | CH₃ | CH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | CH₂ | C₆H₅ | CH₃ | CH₃ | CH | |
| 6-Cl | CH₂ | C₆H₅ | CH₃ | OCH₃ | CH | |
| 6-Cl | CH₂ | C₆H₅ | OCH₃ | OCH₃ | CH | |
| 6-Cl | CH₂ | C₆H₅ | Cl | OCH₃ | CH | |
| 6-Cl | CH₂ | C₆H₅ | CH₃ | OCH₃ | N | |
| 6-Cl | CH₂ | C₆H₅ | OCH₃ | OCH₃ | N | |
| 6-Cl | CH₂ | C₆H₅ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| H | CH₂CH₂ | C₆H₅ | CH₃ | CH₃ | CH | |
| H | CH₂CH₂ | C₆H₅ | CH₃ | OCH₃ | CH | |
| H | CH₂CH₂ | C₆H₅ | OCH₃ | OCH₃ | CH | |
| H | CH₂CH₂ | C₆H₅ | Cl | OCH₃ | CH | |

TABLE 3b-continued

| R₁ | G | R₁₀ | X | Y | Z | m.p. (°C.) |
|---|---|---|---|---|---|---|
| H | CH₂CH₂ | C₆H₅ | CH₃ | OCH₃ | N | |
| H | CH₂CH₂ | C₆H₅ | OCH₃ | OCH₃ | N | |
| H | CH₂CH₂ | C₆H₅ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | OCH₃ | CH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| 6-CH₃ | CH₂CH₂ | C₆H₅ | CH₃ | CH₃ | CH | |
| 6-CH₃ | CH₂CH₂ | C₆H₅ | CH₃ | OCH₃ | CH | |
| 6-CH₃ | CH₂CH₂ | C₆H₅ | OCH₃ | OCH₃ | CH | |
| 6-CH₃ | CH₂CH₂ | C₆H₅ | Cl | OCH₃ | CH | |
| 6-CH₃ | CH₂CH₂ | C₆H₅ | CH₃ | OCH₃ | N | |
| 6-CH₃ | CH₂CH₂ | C₆H₅ | OCH₃ | OCH₃ | N | |
| 6-CH₃ | CH₂CH₂ | C₆H₅ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | OCH₃ | CH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| 6-Cl | CH₂CH₂ | C₆H₅ | CH₃ | CH₃ | CH | |
| 6-Cl | CH₂CH₂ | C₆H₅ | CH₃ | OCH₃ | CH | |
| 6-Cl | CH₂CH₂ | C₆H₅ | OCH₃ | OCH₃ | CH | |
| 6-Cl | CH₂CH₂ | C₆H₅ | Cl | OCH₃ | CH | |
| 6-Cl | CH₂CH₂ | C₆H₅ | CH₃ | OCH₃ | N | |
| 6-Cl | CH₂CH₂ | C₆H₅ | OCH₃ | OCH₃ | N | |
| 6-Cl | CH₂CH₂ | C₆H₅ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| H | CH=CH | C₆H₅ | CH₃ | CH₃ | CH | |
| H | CH=CH | C₆H₅ | CH₃ | OCH₃ | CH | |
| H | CH=CH | C₆H₅ | OCH₃ | OCH₃ | CH | |
| H | CH=CH | C₆H₅ | Cl | OCH₃ | CH | |
| H | CH=CH | C₆H₅ | CH₃ | OCH₃ | N | |
| H | CH=CH | C₆H₅ | OCH₃ | OCH₃ | N | |
| H | CH=CH | C₆H₅ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | OCH₃ | CH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |
| 6-CH₃ | CH=CH | C₆H₅ | CH₃ | CH₃ | CH | |
| 6-CH₃ | CH=CH | C₆H₅ | CH₃ | OCH₃ | CH | |
| 6-CH₃ | CH=CH | C₆H₅ | OCH₃ | OCH₃ | CH | |
| 6-CH₃ | CH=CH | C₆H₅ | Cl | OCH₃ | CH | |
| 6-CH₃ | CH=CH | C₆H₅ | CH₃ | OCH₃ | N | |
| 6-CH₃ | CH=CH | C₆H₅ | OCH₃ | OCH₃ | N | |
| 6-CH₃ | CH=CH | C₆H₅ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | CH₃ | OCH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |
| 6-Cl | CH=CH | C₆H₅ | CH₃ | CH₃ | CH | |
| 6-Cl | CH=CH | C₆H₅ | CH₃ | OCH₃ | CH | |
| 6-Cl | CH=CH | C₆H₅ | OCH₃ | OCH₃ | CH | |
| 6-Cl | CH=CH | C₆H₅ | Cl | OCH₃ | CH | |
| 6-Cl | CH=CH | C₆H₅ | CH₃ | OCH₃ | N | |
| 6-Cl | CH=CH | C₆H₅ | OCH₃ | OCH₃ | N | |
| 6-Cl | CH=CH | C₆H₅ | CH₃ | CH₃ | N | |

TABLE 4a

| R₁ | J | R₅ | X | Y | Z | m.p. (°C.) |
|---|---|---|---|---|---|---|
| H | C=O | H | CH₃ | CH₃ | CH | |
| H | C=O | H | CH₃ | OCH₃ | CH | |
| H | C=O | H | OCH₃ | OCH₃ | CH | |
| H | C=O | H | Cl | OCH₃ | CH | |
| H | C=O | H | CH₃ | OCH₃ | N | |
| H | C=O | H | OCH₃ | OCH₃ | N | |
| H | C=O | H | CH₃ | CH₃ | N | |
| H | C=O | CH₃ | CH₃ | CH₃ | CH | |
| H | C=O | CH₃ | CH₃ | OCH₃ | CH | |
| H | C=O | CH₃ | OCH₃ | OCH₃ | CH | |
| H | C=O | CH₃ | Cl | OCH₃ | CH | |
| H | C=O | CH₃ | CH₃ | OCH₃ | N | |
| H | C=O | CH₃ | OCH₃ | OCH₃ | N | |
| H | C=O | CH₃ | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | S | CH₃ | CH₃ | CH₃ | CH | |
| H | S | CH₃ | CH₃ | OCH₃ | CH | |
| H | S | CH₃ | OCH₃ | OCH₃ | CH | |
| H | S | CH₃ | Cl | OCH₃ | CH | |
| H | S | CH₃ | CH₃ | OCH₃ | N | |
| H | S | CH₃ | OCH₃ | OCH₃ | N | |
| H | S | CH₃ | CH₃ | CH₃ | N | |
| H | SO₂ | H | CH₃ | CH₃ | CH | |
| H | SO₂ | H | CH₃ | OCH₃ | CH | |
| H | SO₂ | H | OCH₃ | OCH₃ | CH | |
| H | SO₂ | H | Cl | OCH₃ | CH | |
| H | SO₂ | H | CH₃ | OCH₃ | N | |
| H | SO₂ | H | OCH₃ | OCH₃ | N | |
| H | SO₂ | H | CH₃ | CH₃ | N | |
| H | SO₂ | CH₃ | CH₃ | CH₃ | CH | |
| H | SO₂ | CH₃ | CH₃ | OCH₃ | CH | |
| H | SO₂ | CH₃ | OCH₃ | OCH₃ | CH | |
| H | SO₂ | CH₃ | Cl | OCH₃ | CH | |
| H | SO₂ | CH₃ | CH₃ | OCH₃ | N | |
| H | SO₂ | CH₃ | OCH₃ | OCH₃ | N | |
| H | SO₂ | CH₃ | CH₃ | CH₃ | N | |
| H | O | CH₃ | CH₃ | CH₃ | CH | |
| H | O | CH₃ | CH₃ | OCH₃ | CH | |

TABLE 4a-continued

General Formula 4a

| R₁ | J | R₅ | X | Y | Z | m.p. (°C.) |
|---|---|---|---|---|---|---|
| H | O | CH₃ | OCH₃ | OCH₃ | CH | |
| H | O | CH₃ | Cl | OCH₃ | CH | |
| H | O | CH₃ | CH₃ | OCH₃ | N | |
| H | O | CH₃ | OCH₃ | OCH₃ | N | |
| H | O | CH₃ | CH₃ | CH₃ | N | |
| 6-CH₃ | C=O | H | CH₃ | CH₃ | CH | |
| 6-CH₃ | C=O | H | CH₃ | OCH₃ | CH | |
| 6-CH₃ | C=O | H | OCH₃ | OCH₃ | CH | |
| 6-CH₃ | C=O | H | Cl | OCH₃ | CH | |
| 6-CH₃ | C=O | H | CH₃ | OCH₃ | N | |
| 6-CH₃ | C=O | H | OCH₃ | OCH₃ | N | |
| 6-CH₃ | C=O | H | CH₃ | CH₃ | N | |
| 6-CH₃ | C=O | CH₃ | CH₃ | CH₃ | CH | |
| 6-CH₃ | C=O | CH₃ | CH₃ | OCH₃ | CH | |
| 6-CH₃ | C=O | CH₃ | OCH₃ | OCH₃ | CH | |
| 6-CH₃ | C=O | CH₃ | Cl | OCH₃ | CH | |
| 6-CH₃ | C=O | CH₃ | CH₃ | OCH₃ | N | |
| 6-CH₃ | C=O | CH₃ | OCH₃ | OCH₃ | N | |
| 6-CH₃ | C=O | CH₃ | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | S | CH₃ | CH₃ | CH₃ | CH | |
| 6-CH₃ | S | CH₃ | CH₃ | OCH₃ | CH | |
| 6-CH₃ | S | CH₃ | OCH₃ | OCH₃ | CH | |
| 6-CH₃ | S | CH₃ | Cl | OCH₃ | CH | |
| 6-CH₃ | S | CH₃ | CH₃ | OCH₃ | N | |
| 6-CH₃ | S | CH₃ | OCH₃ | OCH₃ | N | |
| 6-CH₃ | S | CH₃ | CH₃ | CH₃ | N | |
| 5-NO₂ | C=O | H | CH₃ | CH₃ | CH | |
| 5-NO₂ | C=O | H | CH₃ | OCH₃ | CH | |
| 5-NO₂ | C=O | H | OCH₃ | OCH₃ | CH | |
| 5-NO₂ | C=O | H | Cl | OCH₃ | CH | |
| 5-NO₂ | C=O | H | CH₃ | OCH₃ | N | |
| 5-NO₂ | C=O | H | OCH₃ | OCH₃ | N | |
| 5-NO₂ | C=O | H | CH₃ | CH₃ | N | |
| 5-NO₂ | C=O | CH₃ | CH₃ | CH₃ | CH | |
| 5-NO₂ | C=O | CH₃ | CH₃ | OCH₃ | CH | |
| 5-NO₂ | C=O | CH₃ | OCH₃ | OCH₃ | CH | |
| 5-NO₂ | C=O | CH₃ | Cl | OCH₃ | CH | |
| 5-NO₂ | C=O | CH₃ | CH₃ | OCH₃ | N | |
| 5-NO₂ | C=O | CH₃ | OCH₃ | OCH₃ | N | |
| 5-NO₂ | C=O | CH₃ | CH₃ | CH₃ | N | |
| 5-NO₂ | CH₂ | CH₃ | CH₃ | CH₃ | CH | |
| 5-NO₂ | CH₂ | CH₃ | CH₃ | OCH₃ | CH | |
| 5-NO₂ | CH₂ | CH₃ | OCH₃ | OCH₃ | CH | |
| 5-NO₂ | CH₂ | CH₃ | Cl | OCH₃ | CH | |
| 5-NO₂ | CH₂ | CH₃ | CH₃ | OCH₃ | N | |
| 5-NO₂ | CH₂ | CH₃ | OCH₃ | OCH₃ | N | |
| 5-NO₂ | CH₂ | CH₃ | CH₃ | CH₃ | N | |
| 5-NO₂ | S | CH₃ | CH₃ | CH₃ | CH | |
| 5-NO₂ | S | CH₃ | CH₃ | OCH₃ | CH | |
| 5-NO₂ | S | CH₃ | OCH₃ | OCH₃ | CH | |
| 5-NO₂ | S | CH₃ | Cl | OCH₃ | CH | |
| 5-NO₂ | S | CH₃ | CH₃ | OCH₃ | N | |
| 5-NO₂ | S | CH₃ | OCH₃ | OCH₃ | N | |
| 5-NO₂ | S | CH₃ | CH₃ | CH₃ | N | |
| 6-CH₃ | SO₂ | H | CH₃ | CH₃ | CH | |
| 6-CH₃ | SO₂ | H | CH₃ | OCH₃ | CH | |
| 6-CH₃ | SO₂ | H | OCH₃ | OCH₃ | CH | |
| 6-CH₃ | SO₂ | H | Cl | OCH₃ | CH | |
| 6-CH₃ | SO₂ | H | CH₃ | OCH₃ | N | |
| 6-CH₃ | SO₂ | H | OCH₃ | OCH₃ | N | |
| 6-CH₃ | SO₂ | H | CH₃ | CH₃ | N | |
| 6-CH₃ | SO₂ | CH₃ | CH₃ | CH₃ | CH | |
| 6-CH₃ | SO₂ | CH₃ | CH₃ | OCH₃ | CH | |
| 6-CH₃ | SO₂ | CH₃ | OCH₃ | OCH₃ | CH | |
| 6-CH₃ | SO₂ | CH₃ | Cl | OCH₃ | CH | |
| 6-CH₃ | SO₂ | CH₃ | CH₃ | OCH₃ | N | |
| 6-CH₃ | SO₂ | CH₃ | OCH₃ | OCH₃ | N | |
| 6-CH₃ | SO₂ | CH₃ | CH₃ | CH₃ | N | |
| 6-CH₃ | O | CH₃ | CH₃ | CH₃ | CH | |
| 6-CH₃ | O | CH₃ | CH₃ | OCH₃ | CH | |
| 6-CH₃ | O | CH₃ | OCH₃ | OCH₃ | CH | |
| 6-CH₃ | O | CH₃ | Cl | OCH₃ | CH | |
| 6-CH₃ | O | CH₃ | CH₃ | OCH₃ | N | |
| 6-CH₃ | O | CH₃ | OCH₃ | OCH₃ | N | |
| 6-CH₃ | O | CH₃ | CH₃ | CH₃ | N | |

TABLE 4b

General Formula 4b

| R₁ | G | R₅ | X | Y | Z | m. p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | CH₃ | OCH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |

TABLE 4b-continued

General Formula 4b

| R₁ | G | R₅ | X | Y | Z | m. p. (°C.) |
|---|---|---|---|---|---|---|
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | CH₃ | OCH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |

TABLE 5a

General Formula 5a

| R₁ | J | R₁₂ | X | Y | Z | m. p. (°C.) |
|---|---|---|---|---|---|---|
| H | C=O | H | CH₃ | CH₃ | CH | |
| H | C=O | H | CH₃ | OCH₃ | CH | |
| H | C=O | H | OCH₃ | OCH₃ | CH | |
| H | C=O | H | Cl | OCH₃ | CH | |
| H | C=O | H | CH₃ | OCH₃ | N | |
| H | C=O | H | OCH₃ | OCH₃ | N | |
| H | C=O | H | CH₃ | CH₃ | N | |
| H | C=O | CH₃ | CH₃ | CH₃ | CH | |
| H | C=O | CH₃ | CH₃ | OCH₃ | CH | |
| H | C=O | CH₃ | OCH₃ | OCH₃ | CH | |
| H | C=O | CH₃ | Cl | OCH₃ | CH | |
| H | C=O | CH₃ | CH₃ | OCH₃ | N | |
| H | C=O | CH₃ | OCH₃ | OCH₃ | N | |
| H | C=O | CH₃ | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | S | CH₃ | CH₃ | CH₃ | CH | |
| H | S | CH₃ | CH₃ | OCH₃ | CH | |
| H | S | CH₃ | OCH₃ | OCH₃ | CH | |
| H | S | CH₃ | Cl | OCH₃ | CH | |
| H | S | CH₃ | CH₃ | OCH₃ | N | |
| H | S | CH₃ | OCH₃ | OCH₃ | N | |
| H | S | CH₃ | CH₃ | CH₃ | N | |
| H | SO₂ | CH₃ | CH₃ | CH₃ | CH | |
| H | SO₂ | CH₃ | CH₃ | OCH₃ | CH | |
| H | SO₂ | CH₃ | OCH₃ | OCH₃ | CH | |
| H | SO₂ | CH₃ | Cl | OCH₃ | CH | |
| H | SO₂ | CH₃ | CH₃ | OCH₃ | N | |
| H | SO₂ | CH₃ | OCH₃ | OCH₃ | N | |
| H | SO₂ | CH₃ | CH₃ | CH₃ | N | |
| H | NH | CH₃ | CH₃ | CH₃ | CH | |
| H | NH | CH₃ | CH₃ | OCH₃ | CH | |
| H | NH | CH₃ | OCH₃ | OCH₃ | CH | |
| H | NH | CH₃ | Cl | OCH₃ | CH | |
| H | NH | CH₃ | CH₃ | OCH₃ | N | |
| H | NH | CH₃ | OCH₃ | OCH₃ | N | |
| H | NH | CH₃ | CH₃ | CH₃ | N | |
| H | O | CH₃ | CH₃ | CH₃ | CH | |
| H | O | CH₃ | CH₃ | OCH₃ | CH | |
| H | O | CH₃ | OCH₃ | OCH₃ | CH | |
| H | O | CH₃ | Cl | OCH₃ | CH | |
| H | O | CH₃ | CH₃ | OCH₃ | N | |
| H | O | CH₃ | OCH₃ | OCH₃ | N | |
| H | O | CH₃ | CH₃ | CH₃ | N | |
| 6-Cl | C=O | H | CH₃ | CH₃ | CH | |
| 6-Cl | C=O | H | CH₃ | OCH₃ | CH | |
| 6-Cl | C=O | H | OCH₃ | OCH₃ | CH | |
| 6-Cl | C=O | H | Cl | OCH₃ | CH | |
| 6-Cl | C=O | H | CH₃ | OCH₃ | N | |
| 6-Cl | C=O | H | OCH₃ | OCH₃ | N | |
| 6-Cl | C=O | H | CH₃ | CH₃ | N | |
| 6-Cl | C=O | CH₃ | CH₃ | CH₃ | CH | |
| 6-Cl | C=O | CH₃ | CH₃ | OCH₃ | CH | |
| 6-Cl | C=O | CH₃ | OCH₃ | OCH₃ | CH | |
| 6-Cl | C=O | CH₃ | Cl | OCH₃ | CH | |
| 6-Cl | C=O | CH₃ | CH₃ | OCH₃ | N | |
| 6-Cl | C=O | CH₃ | OCH₃ | OCH₃ | N | |
| 6-Cl | C=O | CH₃ | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | S | CH₃ | CH₃ | CH₃ | CH | |
| 6-Cl | S | CH₃ | CH₃ | OCH₃ | CH | |
| 6-Cl | S | CH₃ | Cl | OCH₃ | CH | |
| 6-Cl | S | CH₃ | CH₃ | OCH₃ | N | |
| 6-Cl | S | CH₃ | OCH₃ | OCH₃ | N | |
| 6-Cl | S | CH₃ | CH₃ | CH₃ | N | |
| 6-Cl | SO₂ | CH₃ | CH₃ | CH₃ | CH | |
| 6-Cl | SO₂ | CH₃ | CH₃ | OCH₃ | CH | |
| 6-Cl | SO₂ | CH₃ | OCH₃ | OCH₃ | CH | |
| 6-Cl | SO₂ | CH₃ | Cl | OCH₃ | CH | |
| 6-Cl | SO₂ | CH₃ | CH₃ | OCH₃ | N | |
| 6-Cl | SO₂ | CH | OCH₃ | OCH₃ | N | |
| 6-Cl | SO₂ | CH₃ | CH₃ | CH₃ | N | |
| 6-Cl | NH | CH₃ | CH | CH₃ | CH | |
| 6-Cl | NH | CH₃ | CH₃ | OCH₃ | CH | |
| 6-Cl | NH | CH₃ | OCH₃ | OCH₃ | CH | |
| 6-Cl | NH | CH₃ | Cl | OCH₃ | CH | |
| 6-Cl | NH | CH₃ | CH₃ | OCH₃ | N | |
| 6-Cl | NH | CH₃ | OCH₃ | OCH₃ | N | |
| 6-Cl | NH | CH₃ | CH₃ | CH₃ | N | |
| 6-Cl | O | CH₃ | CH₃ | CH₃ | CH | |
| 6-Cl | O | CH₃ | CH₃ | OCH₃ | CH | |
| 6-Cl | O | CH₃ | Cl | OCH₃ | CH | |
| 6-Cl | O | CH₃ | CH₃ | OCH₃ | N | |
| 6-Cl | O | CH₃ | OCH₃ | OCH₃ | N | |
| 6-Cl | O | CH₃ | CH₃ | CH₃ | N | |

TABLE 5b

General Formula 5b

| R₁ | G | R₁₂ | X | Y | Z | m. p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |

TABLE 5b-continued

General Formula 5b

| R₁ | G | R₁₂ | X | Y | Z | m. p. (°C.) |
|---|---|---|---|---|---|---|
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | CH₃ | OCH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | CH₃ | OCH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |

TABLE 6

General Formula 6

| R₁ | J | X | Y | Z | m. p. (°C.) |
|---|---|---|---|---|---|
| H | C=O | CH₃ | CH₃ | CH | |
| H | C=O | CH₃ | OCH₃ | CH | |
| H | C=O | OCH₃ | OCH₃ | CH | |
| H | C=O | Cl | OCH₃ | CH | |
| H | C=O | CH₃ | OCH₃ | N | |
| H | C=O | OCH₃ | OCH₃ | N | |
| H | C=O | CH₃ | CH₃ | N | |
| H | SO₂ | CH₃ | CH₃ | CH | |
| H | SO₂ | CH₃ | OCH₃ | CH | |
| H | SO₂ | OCH₃ | OCH₃ | CH | |
| H | SO₂ | Cl | OCH₃ | CH | |
| H | SO₂ | CH₃ | OCH₃ | N | |
| H | SO₂ | OCH₃ | OCH₃ | N | |
| H | SO₂ | CH₃ | CH₃ | N | |
| H | NH | CH | CH₃ | CH | |
| H | NH | CH₃ | OCH₃ | CH | |
| H | NH | OCH₃ | OCH₃ | CH | |
| H | NH | Cl | OCH₃ | CH | |
| H | NH | CH₃ | OCH₃ | N | |
| H | NH | OCH₃ | OCH₃ | N | |
| H | NH | CH₃ | CH₃ | N | |
| H | O | CH₃ | CH₃ | CH | |
| H | O | CH₃ | OCH₃ | CH | |
| H | O | OCH₃ | OCH₃ | CH | |
| H | O | Cl | OCH₃ | CH | |
| H | O | CH₃ | OCH₃ | N | |
| H | O | OCH₃ | OCH₃ | N | |
| H | O | CH₃ | CH₃ | N | |
| 6-Cl | C=O | CH₃ | CH₃ | CH | |
| 6-Cl | C=O | CH₃ | OCH₃ | CH | |
| 6-Cl | C=O | OCH₃ | OCH₃ | CH | |
| 6-Cl | C=O | Cl | OCH₃ | CH | |
| 6-Cl | C=O | CH₃ | OCH₃ | N | |
| 6-Cl | C=O | OCH₃ | OCH₃ | N | |
| 6-Cl | C=O | CH₃ | CH₃ | N | |
| 6-Cl | SO₂ | CH₃ | CH₃ | CH | |
| 6-Cl | SO₂ | CH₃ | OCH₃ | CH | |
| 6-Cl | SO₂ | OCH₃ | OCH₃ | CH | |
| 6-Cl | SO₂ | Cl | OCH₃ | CH | |
| 6-Cl | SO₂ | CH₃ | OCH₃ | N | |
| 6-Cl | SO₂ | OCH₃ | OCH₃ | N | |
| 6-Cl | SO₂ | CH₃ | CH₃ | N | |
| 6-Cl | NH | CH | CH₃ | CH | |
| 6-Cl | NH | CH₃ | OCH₃ | CH | |
| 6-Cl | NH | OCH₃ | OCH₃ | CH | |
| 6-Cl | NH | Cl | OCH₃ | CH | |
| 6-Cl | NH | CH₃ | OCH₃ | N | |
| 6-Cl | NH | OCH₃ | OCH₃ | N | |
| 6-Cl | NH | CH₃ | CH₃ | N | |
| 6-Cl | O | CH₃ | CH₃ | CH | |
| 6-Cl | O | CH₃ | OCH₃ | CH | |
| 6-Cl | O | Cl | OCH₃ | CH | |
| 6-Cl | O | CH₃ | OCH₃ | N | |
| 6-Cl | O | OCH₃ | OCH₃ | N | |
| 6-Cl | O | CH₃ | CH₃ | N | |
| 5-SCH₃ | C=O | CH₃ | CH₃ | CH | |
| 5-SCH₃ | C=O | CH₃ | OCH₃ | CH | |
| 5-SCH₃ | C=O | OCH₃ | OCH₃ | CH | |
| 5-SCH₃ | C=O | Cl | OCH₃ | CH | |
| 5-SCH₃ | C=O | CH₃ | OCH₃ | N | |
| 5-SCH₃ | C=O | OCH₃ | OCH₃ | N | |
| 5-SCH₃ | C=O | CH₃ | CH₃ | N | |
| 5-SCH₃ | SO₂ | CH₃ | CH₃ | CH | |
| 5-SCH₃ | SO₂ | CH₃ | OCH₃ | CH | |
| 5-SCH₃ | SO₂ | OCH₃ | OCH₃ | CH | |
| 5-SCH₃ | SO₂ | Cl | OCH₃ | CH | |
| 5-SCH₃ | SO₂ | CH₃ | OCH₃ | N | |
| 5-SCH₃ | SO₂ | OCH₃ | OCH₃ | N | |
| 5-SCH₃ | SO₂ | CH₃ | CH₃ | N | |
| 5-SCH₃ | NH | CH | CH₃ | CH | |
| 5-SCH₃ | NH | CH₃ | OCH₃ | CH | |
| 5-SCH₃ | NH | OCH₃ | OCH₃ | CH | |
| 5-SCH₃ | NH | Cl | OCH₃ | CH | |
| 5-SCH₃ | NH | CH₃ | OCH₃ | N | |
| 5-SCH₃ | NH | OCH₃ | OCH₃ | N | |
| 5-SCH₃ | NH | CH₃ | CH₃ | N | |
| 5-SCH₃ | O | CH₃ | CH₃ | CH | |
| 5-SCH₃ | O | CH₃ | OCH₃ | CH | |
| 5-SCH₃ | O | OCH₃ | OCH₃ | CH | |
| 5-SCH₃ | O | Cl | OCH₃ | CH | |
| 5-SCH₃ | O | CH₃ | OCH₃ | N | |
| 5-SCH₃ | O | OCH₃ | OCH₃ | N | |
| 5-SCH₃ | O | CH₃ | CH₃ | N | |

TABLE 7

General Formula 7

| R₁ | J | R₉ | R₁₃ | X | Y | Z | m.p. (°C.) |
|---|---|---|---|---|---|---|---|
| H | C=O | H | OCH₃ | CH₃ | CH₃ | CH | |
| H | C=O | H | OCH₃ | CH₃ | OCH₃ | CH | |
| H | C=O | H | OCH₃ | OCH₃ | OCH₃ | CH | |
| H | C=O | H | OCH₃ | Cl | OCH₃ | CH | |
| H | C=O | H | OCH₃ | CH₃ | OCH₃ | N | |
| H | C=O | H | OCH₃ | OCH₃ | OCH₃ | N | |
| H | C=O | H | OCH₃ | CH₃ | CH₃ | N | |
| H | C=O | CH₃ | SCH₃ | CH₃ | CH₃ | CH | |
| H | C=O | CH₃ | SCH₃ | CH₃ | OCH₃ | CH | |
| H | C=O | CH₃ | SCH₃ | OCH₃ | OCH₃ | CH | |
| H | C=O | CH₃ | SCH₃ | Cl | OCH₃ | CH | |

TABLE 7-continued

General Formula 7

| $R_1$ | J | $R_9$ | $R_{13}$ | X | Y | Z | m.p. (°C.) |
|---|---|---|---|---|---|---|---|
| H | C=O | $CH_3$ | $SCH_3$ | $CH_3$ | $OCH_3$ | N | |
| H | C=O | $CH_3$ | $SCH_3$ | $OCH_3$ | $OCH_3$ | N | |
| H | C=O | $CH_3$ | $SCH_3$ | $CH_3$ | $CH_3$ | N | |
| H | $SO_2$ | $CH_3$ | $OCH_3$ | $CH_3$ | $CH_3$ | CH | |
| H | $SO_2$ | $CH_3$ | $OCH_3$ | $CH_3$ | $OCH_3$ | CH | |
| H | $SO_2$ | $CH_3$ | $OCH_3$ | $OCH_3$ | $OCH_3$ | CH | |
| H | $SO_2$ | $CH_3$ | $OCH_3$ | Cl | $OCH_3$ | CH | |
| H | $SO_2$ | $CH_3$ | $OCH_3$ | $CH_3$ | $OCH_3$ | N | |
| H | $SO_2$ | $CH_3$ | $OCH_3$ | $OCH_3$ | $OCH_3$ | N | |
| H | $SO_2$ | $CH_3$ | $OCH_3$ | $CH_3$ | $CH_3$ | N | |
| H | C=O | H | $CH_3$ | $CH_3$ | $CH_3$ | CH | |
| H | C=O | H | $CH_3$ | $CH_3$ | $OCH_3$ | CH | |
| H | C=O | H | $CH_3$ | $OCH_3$ | $OCH_3$ | CH | |
| H | C=O | H | $CH_3$ | Cl | $OCH_3$ | CH | |
| H | C=O | H | $CH_3$ | $CH_3$ | $OCH_3$ | N | |
| H | C=O | H | $CH_3$ | $OCH_3$ | $OCH_3$ | N | |
| H | C=O | H | $CH_3$ | $CH_3$ | $CH_3$ | N | |
| H | $SO_2$ | H | $CH_3$ | $CH_3$ | $CH_3$ | CH | |
| H | $SO_2$ | H | $CH_3$ | $CH_3$ | $OCH_3$ | CH | |
| H | $SO_2$ | H | $CH_3$ | $OCH_3$ | $OCH_3$ | CH | |
| H | $SO_2$ | H | $CH_3$ | Cl | $OCH_3$ | CH | |
| H | $SO_2$ | H | $CH_3$ | $CH_3$ | $OCH_3$ | N | |
| H | $SO_2$ | H | $CH_3$ | $OCH_3$ | $OCH_3$ | N | |
| H | $SO_2$ | H | $CH_3$ | $CH_3$ | $CH_3$ | N | |
| H | $CH_2$ | H | $OCH_3$ | $CH_3$ | $CH_3$ | CH | |
| H | $CH_2$ | H | $OCH_3$ | $CH_3$ | $OCH_3$ | CH | |
| H | $CH_2$ | H | $OCH_3$ | $OCH_3$ | $OCH_3$ | CH | |
| H | $CH_2$ | H | $OCH_3$ | Cl | $OCH_3$ | CH | |
| H | $CH_2$ | H | $OCH_3$ | $CH_3$ | $OCH_3$ | N | |
| H | $CH_2$ | H | $OCH_3$ | $OCH_3$ | $OCH_3$ | N | |
| H | $CH_2$ | H | $OCH_3$ | $CH_3$ | $CH_3$ | N | |
| H | $CH_2$ | $CH_3$ | $SCH_3$ | $CH_3$ | $CH_3$ | CH | |
| H | $CH_2$ | $CH_3$ | $SCH_3$ | $CH_3$ | $OCH_3$ | CH | |
| H | $CH_2$ | $CH_3$ | $SCH_3$ | $OCH_3$ | $OCH_3$ | CH | |
| H | $CH_2$ | $CH_3$ | $SCH_3$ | Cl | $OCH_3$ | CH | |
| H | $CH_2$ | $CH_3$ | $SCH_3$ | $CH_3$ | $OCH_3$ | N | |
| H | $CH_2$ | $CH_3$ | $SCH_3$ | $OCH_3$ | $OCH_3$ | N | |
| H | $CH_2$ | $CH_3$ | $SCH_3$ | $CH_3$ | $CH_3$ | N | |
| H | $CH_2$ | $CH_3$ | $CH_3$ | $CH_3$ | $CH_3$ | CH | |
| H | $CH_2$ | $CH_3$ | $CH_3$ | $CH_3$ | $OCH_3$ | CH | |
| H | $CH_2$ | $CH_3$ | $CH_3$ | $OCH_3$ | $OCH_3$ | CH | |
| H | $CH_2$ | $CH_3$ | $CH_3$ | $OCH_3$ | Cl | CH | |
| H | $CH_2$ | $CH_3$ | $CH_3$ | $CH_3$ | $OCH_3$ | N | |
| H | $CH_2$ | $CH_3$ | $CH_3$ | $OCH_3$ | $OCH_3$ | N | |
| H | $CH_2$ | $CH_3$ | $CH_3$ | $CH_3$ | $CH_3$ | N | |
| H | O | H | $CH_3$ | $CH_3$ | $CH_3$ | CH | |
| H | O | H | $CH_3$ | $CH_3$ | $OCH_3$ | CH | |
| H | O | H | $CH_3$ | $OCH_3$ | $OCH_3$ | CH | |
| H | O | H | $CH_3$ | Cl | $OCH_3$ | CH | |
| H | O | H | $CH_3$ | $CH_3$ | $OCH_3$ | N | |
| H | O | H | $CH_3$ | $OCH_3$ | $OCH_3$ | N | |
| H | O | H | $CH_3$ | $CH_3$ | $CH_3$ | N | |
| H | O | H | $OCH_3$ | $CH_3$ | $CH_3$ | CH | |
| H | O | H | $OCH_3$ | $CH_3$ | $OCH_3$ | CH | |
| H | O | H | $OCH_3$ | $OCH_3$ | $OCH_3$ | CH | |
| H | O | H | $OCH_3$ | Cl | $OCH_3$ | CH | |
| H | O | H | $OCH_3$ | $CH_3$ | $OCH_3$ | N | |
| H | O | H | $OCH_3$ | $OCH_3$ | $OCH_3$ | N | |
| H | O | H | $OCH_3$ | $CH_3$ | $CH_3$ | N | |
| 6-$CH_3$ | C=O | H | $OCH_3$ | $CH_3$ | $CH_3$ | CH | |
| 6-$CH_3$ | C=O | H | $OCH_3$ | $CH_3$ | $OCH_3$ | CH | |
| 6-$CH_3$ | C=O | H | $OCH_3$ | $OCH_3$ | $OCH_3$ | CH | |
| 6-$CH_3$ | C=O | H | $OCH_3$ | Cl | $OCH_3$ | CH | |
| 6-$CH_3$ | C=O | H | $OCH_3$ | $CH_3$ | $OCH_3$ | N | |
| 6-$CH_3$ | C=O | H | $OCH_3$ | $OCH_3$ | $OCH_3$ | N | |
| 6-$CH_3$ | C=O | H | $OCH_3$ | $CH_3$ | $CH_3$ | N | |
| 6-$CH_3$ | C=O | $CH_3$ | $SCH_3$ | $CH_3$ | $CH_3$ | CH | |
| 6-$CH_3$ | C=O | $CH_3$ | $SCH_3$ | $CH_3$ | $OCH_3$ | CH | |
| 6-$CH_3$ | C=O | $CH_3$ | $SCH_3$ | $OCH_3$ | $OCH_3$ | CH | |
| 6-$CH_3$ | C=O | $CH_3$ | $SCH_3$ | Cl | $OCH_3$ | CH | |
| 6-$CH_3$ | C=O | $CH_3$ | $SCH_3$ | $CH_3$ | $OCH_3$ | N | |
| 6-$CH_3$ | C=O | $CH_3$ | $SCH_3$ | $OCH_3$ | $OCH_3$ | N | |
| 6-$CH_3$ | C=O | $CH_3$ | $SCH_3$ | $CH_3$ | $CH_3$ | N | |
| 6-$CH_3$ | $SO_2$ | $CH_3$ | $OCH_3$ | $CH_3$ | $CH_3$ | CH | |
| 6-$CH_3$ | $SO_2$ | $CH_3$ | $OCH_3$ | $CH_3$ | $OCH_3$ | CH | |
| 6-$CH_3$ | $SO_2$ | $CH_3$ | $OCH_3$ | $OCH_3$ | $OCH_3$ | CH | |
| 6-$CH_3$ | $SO_2$ | $CH_3$ | $OCH_3$ | Cl | $OCH_3$ | CH | |
| 6-$CH_3$ | $SO_2$ | $CH_3$ | $OCH_3$ | $CH_3$ | $OCH_3$ | N | |
| 6-$CH_3$ | $SO_2$ | $CH_3$ | $OCH_3$ | $OCH_3$ | $OCH_3$ | N | |
| 6-$CH_3$ | $SO_2$ | $CH_3$ | $OCH_3$ | $CH_3$ | $CH_3$ | N | |
| 6-$CH_3$ | C=O | H | $CH_3$ | $CH_3$ | $CH_3$ | CH | |
| 6-$CH_3$ | C=O | H | $CH_3$ | $CH_3$ | $OCH_3$ | CH | |
| 6-$CH_3$ | C=O | H | $CH_3$ | $OCH_3$ | $OCH_3$ | CH | |
| 6-$CH_3$ | C=O | H | $CH_3$ | Cl | $OCH_3$ | CH | |
| 6-$CH_3$ | C=O | H | $CH_3$ | $CH_3$ | $OCH_3$ | N | |
| 6-$CH_3$ | C=O | H | $CH_3$ | $OCH_3$ | $OCH_3$ | N | |
| 6-$CH_3$ | C=O | H | $CH_3$ | $CH_3$ | $CH_3$ | N | |
| 6-$CH_3$ | $SO_2$ | H | $CH_3$ | $CH_3$ | $CH_3$ | CH | |
| 6-$CH_3$ | $SO_2$ | H | $CH_3$ | $CH_3$ | $OCH_3$ | CH | |
| 6-$CH_3$ | $SO_2$ | H | $CH_3$ | $OCH_3$ | $OCH_3$ | CH | |
| 6-$CH_3$ | $SO_2$ | H | $CH_3$ | Cl | $OCH_3$ | CH | |
| 6-$CH_3$ | $SO_2$ | H | $CH_3$ | $CH_3$ | $OCH_3$ | N | |
| 6-$CH_3$ | $SO_2$ | H | $CH_3$ | $OCH_3$ | $OCH_3$ | N | |
| 6-$CH_3$ | $SO_2$ | H | $CH_3$ | $CH_3$ | $CH_3$ | N | |
| 6-$CH_3$ | $CH_2$ | H | $OCH_3$ | $CH_3$ | $CH_3$ | CH | |
| 6-$CH_3$ | $CH_2$ | H | $OCH_3$ | $CH_3$ | $OCH_3$ | CH | |
| 6-$CH_3$ | $CH_2$ | H | $OCH_3$ | $OCH_3$ | $OCH_3$ | CH | |
| 6-$CH_3$ | $CH_2$ | H | $OCH_3$ | Cl | $OCH_3$ | CH | |
| 6-$CH_3$ | $CH_2$ | H | $OCH_3$ | $CH_3$ | $OCH_3$ | N | |
| 6-$CH_3$ | $CH_2$ | H | $OCH_3$ | $OCH_3$ | $OCH_3$ | N | |
| 6-$CH_3$ | $CH_2$ | H | $OCH_3$ | $CH_3$ | $CH_3$ | N | |
| 6-$CH_3$ | $CH_2$ | $CH_3$ | $SCH_3$ | $CH_3$ | $CH_3$ | CH | |
| 6-$CH_3$ | $CH_2$ | $CH_3$ | $SCH_3$ | $CH_3$ | $OCH_3$ | CH | |
| 6-$CH_3$ | $CH_2$ | $CH_3$ | $SCH_3$ | $OCH_3$ | $OCH_3$ | CH | |
| 6-$CH_3$ | $CH_2$ | $CH_3$ | $SCH_3$ | Cl | $OCH_3$ | CH | |
| 6-$CH_3$ | $CH_2$ | $CH_3$ | $SCH_3$ | $CH_3$ | $OCH_3$ | N | |
| 6-$CH_3$ | $CH_2$ | $CH_3$ | $SCH_3$ | $OCH_3$ | $OCH_3$ | N | |
| 6-$CH_3$ | $CH_2$ | $CH_3$ | $SCH_3$ | $CH_3$ | $CH_3$ | N | |
| 6-$CH_3$ | $CH_2$ | $CH_3$ | $CH_3$ | $CH_3$ | $CH_3$ | CH | |
| 6-$CH_3$ | $CH_2$ | $CH_3$ | $CH_3$ | $CH_3$ | $OCH_3$ | CH | |
| 6-$CH_3$ | $CH_2$ | $CH_3$ | $CH_3$ | $OCH_3$ | $OCH_3$ | CH | |
| 6-$CH_3$ | $CH_2$ | $CH_3$ | $CH_3$ | $OCH_3$ | Cl | CH | |
| 6-$CH_3$ | $CH_2$ | $CH_3$ | $CH_3$ | $CH_3$ | $OCH_3$ | N | |
| 6-$CH_3$ | $CH_2$ | $CH_3$ | $CH_3$ | $OCH_3$ | $OCH_3$ | N | |
| 6-$CH_3$ | $CH_2$ | $CH_3$ | $CH_3$ | $CH_3$ | $CH_3$ | N | |
| 6-$CH_3$ | O | H | $CH_3$ | $CH_3$ | $CH_3$ | CH | |
| 6-$CH_3$ | O | H | $CH_3$ | $CH_3$ | $OCH_3$ | CH | |
| 6-$CH_3$ | O | H | $CH_3$ | $OCH_3$ | $OCH_3$ | CH | |
| 6-$CH_3$ | O | H | $CH_3$ | Cl | $OCH_3$ | CH | |
| 6-$CH_3$ | O | H | $CH_3$ | $CH_3$ | $OCH_3$ | N | |
| 6-$CH_3$ | O | H | $CH_3$ | $OCH_3$ | $OCH_3$ | N | |
| 6-$CH_3$ | O | H | $CH_3$ | $CH_3$ | $CH_3$ | N | |
| 6-$CH_3$ | O | H | $OCH_3$ | $CH_3$ | $CH_3$ | CH | |
| 6-$CH_3$ | O | H | $OCH_3$ | $CH_3$ | $OCH_3$ | CH | |
| 6-$CH_3$ | O | H | $OCH_3$ | $OCH_3$ | $OCH_3$ | CH | |
| 6-$CH_3$ | O | H | $OCH_3$ | Cl | $OCH_3$ | CH | |
| 6-$CH_3$ | O | H | $OCH_3$ | $CH_3$ | $OCH_3$ | N | |
| 6-$CH_3$ | O | H | $OCH_3$ | $OCH_3$ | $OCH_3$ | N | |
| 6-$CH_3$ | O | H | $OCH_3$ | $CH_3$ | $CH_3$ | N | |
| 5-$OCH_3$ | C=O | H | $OCH_3$ | $CH_3$ | $CH_3$ | CH | |
| 5-$OCH_3$ | C=O | H | $OCH_3$ | $CH_3$ | $OCH_3$ | CH | |
| 5-$OCH_3$ | C=O | H | $OCH_3$ | $OCH_3$ | $OCH_3$ | CH | |
| 5-$OCH_3$ | C=O | H | $OCH_3$ | Cl | $OCH_3$ | CH | |
| 5-$OCH_3$ | C=O | H | $OCH_3$ | $CH_3$ | $OCH_3$ | N | |
| 5-$OCH_3$ | C=O | H | $OCH_3$ | $OCH_3$ | $OCH_3$ | N | |
| 5-$OCH_3$ | C=O | H | $OCH_3$ | $CH_3$ | $CH_3$ | N | |
| 5-$OCH_3$ | C=O | $CH_3$ | $SCH_3$ | $CH_3$ | $CH_3$ | CH | |
| 5-$OCH_3$ | C=O | $CH_3$ | $SCH_3$ | $CH_3$ | $OCH_3$ | CH | |
| 5-$OCH_3$ | C=O | $CH_3$ | $SCH_3$ | $OCH_3$ | $OCH_3$ | CH | |
| 5-$OCH_3$ | C=O | $CH_3$ | $SCH_3$ | Cl | $OCH_3$ | CH | |
| 5-$OCH_3$ | C=O | $CH_3$ | $SCH_3$ | $CH_3$ | $OCH_3$ | N | |
| 5-$OCH_3$ | C=O | $CH_3$ | $SCH_3$ | $OCH_3$ | $OCH_3$ | N | |
| 5-$OCH_3$ | C=O | $CH_3$ | $SCH_3$ | $CH_3$ | $CH_3$ | N | |
| 5-$OCH_3$ | $SO_2$ | $CH_3$ | $OCH_3$ | $CH_3$ | $CH_3$ | CH | |
| 5-$OCH_3$ | $SO_2$ | $CH_3$ | $OCH_3$ | $CH_3$ | $OCH_3$ | CH | |
| 5-$OCH_3$ | $SO_2$ | $CH_3$ | $OCH_3$ | $OCH_3$ | $OCH_3$ | CH | |
| 5-$OCH_3$ | $SO_2$ | $CH_3$ | $OCH_3$ | Cl | $OCH_3$ | CH | |
| 5-$OCH_3$ | $SO_2$ | $CH_3$ | $OCH_3$ | $CH_3$ | $OCH_3$ | N | |
| 5-$OCH_3$ | $SO_2$ | $CH_3$ | $OCH_3$ | $OCH_3$ | $OCH_3$ | N | |
| 5-$OCH_3$ | $SO_2$ | $CH_3$ | $OCH_3$ | $CH_3$ | $CH_3$ | N | |
| 5-$OCH_3$ | C=O | H | $CH_3$ | $CH_3$ | $CH_3$ | CH | |
| 5-$OCH_3$ | C=O | H | $CH_3$ | $CH_3$ | $OCH_3$ | CH | |
| 5-$OCH_3$ | C=O | H | $CH_3$ | Cl | $OCH_3$ | CH | |
| 5-$OCH_3$ | C=O | H | $CH_3$ | $CH_3$ | $OCH_3$ | N | |
| 5-$OCH_3$ | C=O | H | $CH_3$ | $OCH_3$ | $OCH_3$ | N | |

TABLE 7-continued

General Formula 7

| R₁ | J | R₉ | R₁₃ | X | Y | Z | m.p. (°C.) |
|---|---|---|---|---|---|---|---|
| 5-OCH₃ | C=O | H | CH₃ | CH₃ | CH₃ | N | |
| 5-OCH₃ | SO₂ | H | CH₃ | CH₃ | CH₃ | CH | |
| 5-OCH₃ | SO₂ | H | CH₃ | CH₃ | OCH₃ | CH | |
| 5-OCH₃ | SO₂ | H | CH₃ | OCH₃ | OCH₃ | CH | |
| 5-OCH₃ | SO₂ | H | CH₃ | Cl | OCH₃ | CH | |
| 5-OCH₃ | SO₂ | H | CH₃ | CH₃ | OCH₃ | N | |
| 5-OCH₃ | SO₂ | H | CH₃ | OCH₃ | OCH₃ | N | |
| 5-OCH₃ | SO₂ | H | CH₃ | CH₃ | CH₃ | N | |
| 5-OCH₃ | CH₂ | H | OCH₃ | CH₃ | CH₃ | CH | |
| 5-OCH₃ | CH₂ | H | OCH₃ | OCH₃ | OCH₃ | CH | |
| 5-OCH₃ | CH₂ | H | OCH₃ | Cl | OCH₃ | CH | |
| 5-OCH₃ | CH₂ | H | OCH₃ | CH₃ | OCH₃ | N | |
| 5-OCH₃ | CH₂ | H | OCH₃ | OCH₃ | OCH₃ | N | |
| 5-OCH₃ | CH₂ | H | OCH₃ | CH₃ | CH₃ | N | |
| 5-OCH₃ | CH₂ | CH₃ | SCH₃ | CH₃ | CH₃ | CH | |
| 5-OCH₃ | CH₂ | CH₃ | SCH₃ | CH₃ | OCH₃ | CH | |
| 5-OCH₃ | CH₂ | CH₃ | SCH₃ | OCH₃ | OCH₃ | CH | |
| 5-OCH₃ | CH₂ | CH₃ | SCH₃ | Cl | OCH₃ | CH | |
| 5-OCH₃ | CH₂ | CH₃ | SCH₃ | CH₃ | OCH₃ | N | |
| 5-OCH₃ | CH₂ | CH₃ | SCH₃ | OCH₃ | OCH₃ | N | |
| 5-OCH₃ | CH₂ | CH₃ | SCH₃ | CH₃ | CH₃ | N | |
| 5-OCH₃ | CH₂ | CH₃ | CH₃ | CH₃ | CH₃ | CH | |
| 5-OCH₃ | CH₂ | CH₃ | CH₃ | CH₃ | OCH₃ | CH | |
| 5-OCH₃ | CH₂ | CH₃ | CH₃ | OCH₃ | OCH₃ | CH | |
| 5-OCH₃ | CH₂ | CH₃ | CH₃ | OCH₃ | Cl | CH | |
| 5-OCH₃ | CH₂ | CH₃ | CH₃ | CH₃ | OCH₃ | N | |
| 5-OCH₃ | CH₂ | CH₃ | CH₃ | OCH₃ | OCH₃ | N | |
| 5-OCH₃ | CH₂ | CH₃ | CH₃ | CH₃ | CH₃ | N | |
| 5-OCH₃ | O | H | CH₃ | CH₃ | CH₃ | CH | |
| 5-OCH₃ | O | H | CH₃ | CH₃ | OCH₃ | CH | |
| 5-OCH₃ | O | H | CH₃ | OCH₃ | OCH₃ | CH | |
| 5-OCH₃ | O | H | CH₃ | Cl | OCH₃ | CH | |
| 5-OCH₃ | O | H | CH₃ | CH₃ | OCH₃ | N | |
| 5-OCH₃ | O | H | CH₃ | OCH₃ | OCH₃ | N | |
| 5-OCH₃ | O | H | CH₃ | CH₃ | CH₃ | N | |
| 5-OCH₃ | O | H | OCH₃ | CH₃ | CH₃ | CH | |
| 5-OCH₃ | O | H | OCH₃ | CH₃ | OCH₃ | CH | |
| 5-OCH₃ | O | H | OCH₃ | OCH₃ | OCH₃ | CH | |
| 5-OCH₃ | O | H | OCH₃ | Cl | OCH₃ | CH | |
| 5-OCH₃ | O | H | OCH₃ | CH₃ | OCH₃ | N | |
| 5-OCH₃ | O | H | OCH₃ | OCH₃ | OCH₃ | N | |
| 5-OCH₃ | O | H | OCH₃ | CH₃ | CH₃ | N | |

TABLE 8

General Formula 8

| R₁ | J | R₈ | R₁₁ | X | Y | Z | m.p. (°C.) |
|---|---|---|---|---|---|---|---|
| H | C=O | H | CH₃ | CH₃ | CH₃ | CH | |
| H | C=O | H | CH₃ | CH₃ | OCH₃ | CH | |
| H | C=O | H | CH₃ | OCH₃ | OCH₃ | CH | |
| H | C=O | H | CH₃ | Cl | OCH₃ | CH | |
| H | C=O | H | CH₃ | CH₃ | OCH₃ | N | |
| H | C=O | H | CH₃ | OCH₃ | OCH₃ | N | |
| H | C=O | H | CH₃ | CH₃ | CH₃ | N | |
| H | C=O | CH₃ | CH₃ | CH₃ | CH₃ | CH | |
| H | C=O | CH₃ | CH₃ | CH₃ | OCH₃ | CH | |
| H | C=O | CH₃ | CH₃ | OCH₃ | OCH₃ | CH | |
| H | C=O | CH₃ | CH₃ | Cl | OCH₃ | CH | |
| H | C=O | CH₃ | CH₃ | CH₃ | OCH₃ | N | |
| H | C=O | CH₃ | CH₃ | OCH₃ | OCH₃ | N | |
| H | C=O | CH₃ | CH₃ | CH₃ | CH₃ | N | |
| H | SO₂ | CH₃ | CH₃ | CH | CH₃ | CH | |
| H | SO₂ | CH₃ | CH₃ | CH₃ | OCH₃ | CH | |
| H | SO₂ | CH₃ | CH₃ | OCH₃ | OCH₃ | CH | |
| H | SO₂ | CH₃ | CH₃ | Cl | OCH₃ | CH | |
| H | SO₂ | CH₃ | CH₃ | CH₃ | OCH₃ | N | |
| H | SO₂ | CH₃ | CH₃ | OCH₃ | OCH₃ | N | |
| H | SO₂ | CH₃ | CH₃ | CH₃ | CH₃ | N | |
| H | C=O | CH₃ | N(CH₃)₂ | CH₃ | CH₃ | CH | |
| H | C=O | CH₃ | N(CH₃)₂ | CH₃ | OCH₃ | CH | |
| H | C=O | CH₃ | N(CH₃)₂ | OCH₃ | OCH₃ | CH | |
| H | C=O | CH₃ | N(CH₃)₂ | Cl | OCH₃ | CH | |
| H | C=O | CH₃ | N(CH₃)₂ | CH₃ | OCH₃ | N | |
| H | C=O | CH₃ | N(CH₃)₂ | OCH₃ | OCH₃ | N | |
| H | C=O | CH₃ | N(CH₃)₂ | CH₃ | CH₃ | N | |

TABLE 8-continued

General Formula 8

| R₁ | J | R₈ | R₁₁ | X | Y | Z | m.p. (°C.) |
|---|---|---|---|---|---|---|---|
| H | SO₂ | H | CH₃ | CH₃ | CH₃ | CH | |
| H | SO₂ | H | CH₃ | CH₃ | OCH₃ | CH | |
| H | SO₂ | H | CH₃ | OCH₃ | OCH₃ | CH | |
| H | SO₂ | H | CH₃ | Cl | OCH₃ | CH | |
| H | SO₂ | H | CH₃ | CH₃ | OCH₃ | N | |
| H | SO₂ | H | CH₃ | OCH₃ | OCH₃ | N | |
| H | SO₂ | H | CH₃ | CH₃ | CH₃ | N | |
| H | C=O | CH₃ | OCH₃ | CH₃ | CH₃ | CH | |
| H | C=O | CH₃ | OCH₃ | CH₃ | OCH₃ | CH | |
| H | C=O | CH₃ | OCH₃ | OCH₃ | OCH₃ | CH | |
| H | C=O | CH₃ | OCH₃ | Cl | OCH₃ | CH | |
| H | C=O | CH₃ | OCH₃ | CH₃ | OCH₃ | N | |
| H | C=O | CH₃ | OCH₃ | OCH₃ | OCH₃ | N | |
| H | C=O | CH₃ | OCH₃ | CH₃ | CH₃ | N | |
| H | SO₂ | CH₃ | OCH₃ | CH₃ | OCH₃ | CH | |
| H | SO₂ | CH₃ | OCH₃ | OCH₃ | OCH₃ | CH | |
| H | SO₂ | CH₃ | OCH₃ | Cl | OCH₃ | CH | |
| H | SO₂ | CH₃ | OCH₃ | CH₃ | OCH₃ | N | |
| H | SO₂ | CH₃ | OCH₃ | OCH₃ | OCH₃ | N | |
| H | SO₂ | CH₃ | OCH₃ | CH₃ | CH₃ | N | |
| H | CH₂ | H | CH₃ | CH₃ | CH₃ | CH | |
| H | CH₂ | H | CH₃ | CH₃ | OCH₃ | CH | |
| H | CH₂ | H | CH₃ | OCH₃ | OCH₃ | CH | |
| H | CH₂ | H | CH₃ | Cl | OCH₃ | CH | |
| H | CH₂ | H | CH₃ | CH₃ | OCH₃ | N | |
| H | CH₂ | H | CH₃ | OCH₃ | OCH₃ | N | |
| H | CH₂ | H | CH₃ | CH₃ | CH₃ | N | |
| H | CH₂ | CH₃ | CH₃ | CH₃ | CH₃ | CH | |
| H | CH₂ | CH₃ | CH₃ | CH₃ | OCH₃ | CH | |
| H | CH₂ | CH₃ | CH₃ | OCH₃ | OCH₃ | CH | |
| H | CH₂ | CH₃ | CH₃ | Cl | OCH₃ | CH | |
| H | CH₂ | CH₃ | CH₃ | CH₃ | OCH₃ | N | |
| H | CH₂ | CH₃ | CH₃ | CH₃ | CH₃ | N | |
| H | CH₂ | CH₃ | SCH₃ | CH₃ | CH₃ | CH | |
| H | CH₂ | CH₃ | SCH₃ | CH₃ | OCH₃ | CH | |
| H | CH₂ | CH₃ | SCH₃ | OCH₃ | OCH₃ | CH | |
| H | CH₂ | CH₃ | SCH₃ | Cl | OCH₃ | CH | |
| H | CH₂ | CH₃ | SCH₃ | CH₃ | OCH₃ | N | |
| H | CH₂ | CH₃ | SCH₃ | OCH₃ | OCH₃ | N | |
| H | CH₂ | CH₃ | SCH₃ | CH₃ | CH₃ | N | |
| H | O | H | CH₃ | CH₃ | CH₃ | CH | |
| H | O | H | CH₃ | CH₃ | OCH₃ | CH | |
| H | O | H | CH₃ | Cl | OCH₃ | CH | |
| H | O | H | CH₃ | CH₃ | OCH₃ | N | |
| H | O | H | CH₃ | OCH₃ | OCH₃ | N | |
| H | O | H | CH₃ | CH₃ | CH₃ | N | |
| H | O | H | OCH₃ | CH₃ | CH₃ | CH | |
| H | O | H | OCH₃ | CH₃ | OCH₃ | CH | |
| H | O | H | OCH₃ | OCH₃ | OCH₃ | CH | |
| H | O | H | OCH₃ | Cl | OCH₃ | CH | |
| H | O | H | OCH₃ | CH₃ | CH₃ | N | |
| H | O | H | OCH₃ | OCH₃ | OCH₃ | N | |
| H | O | H | OCH₃ | CH₃ | CH₃ | N | |
| H | O | CH₃ | CH₃ | CH₃ | CH₃ | CH | |
| H | O | CH₃ | CH₃ | CH₃ | OCH₃ | CH | |
| H | O | CH₃ | CH₃ | OCH₃ | OCH₃ | CH | |
| H | O | CH₃ | CH₃ | Cl | OCH₃ | CH | |
| H | O | CH₃ | CH₃ | CH₃ | OCH₃ | N | |
| H | O | CH₃ | CH₃ | OCH₃ | OCH₃ | N | |
| H | O | CH₃ | CH₃ | CH₃ | CH₃ | N | |
| 6-CH₃ | C=O | H | CH₃ | CH₃ | CH₃ | CH | |
| 6-CH₃ | C=O | H | CH₃ | CH₃ | OCH₃ | CH | |
| 6-CH₃ | C=O | H | CH₃ | OCH₃ | OCH₃ | CH | |
| 6-CH₃ | C=O | H | CH₃ | Cl | OCH₃ | CH | |
| 6-CH₃ | C=O | H | CH₃ | CH₃ | OCH₃ | N | |
| 6-CH₃ | C=O | H | CH₃ | OCH₃ | OCH₃ | N | |
| 6-CH₃ | C=O | H | CH₃ | CH₃ | CH₃ | N | |
| 6-CH₃ | C=O | CH₃ | CH₃ | CH₃ | CH₃ | CH | |
| 6-CH₃ | C=O | CH₃ | CH₃ | CH₃ | OCH₃ | CH | |
| 6-CH₃ | C=O | CH₃ | CH₃ | OCH₃ | OCH₃ | CH | |
| 6-CH₃ | C=O | CH₃ | CH₃ | Cl | OCH₃ | CH | |
| 6-CH₃ | C=O | CH₃ | CH₃ | CH₃ | OCH₃ | N | |
| 6-CH₃ | C=O | CH₃ | CH₃ | OCH₃ | OCH₃ | N | |
| 6-CH₃ | C=O | CH₃ | CH₃ | CH₃ | CH₃ | N | |
| 6-CH₃ | SO₂ | CH₃ | CH₃ | CH₃ | CH₃ | CH | |

TABLE 8-continued

General Formula 8

| R₁ | J | R₈ | R₁₁ | X | Y | Z | m.p. (°C.) |
|---|---|---|---|---|---|---|---|
| 6-CH₃ | SO₂ | CH₃ | CH₃ | CH₃ | OCH₃ | CH | |
| 6-CH₃ | SO₂ | CH₃ | CH₃ | OCH₃ | OCH₃ | CH | |
| 6-CH₃ | SO₂ | CH₃ | CH₃ | Cl | OCH₃ | CH | |
| 6-CH₃ | SO₂ | CH₃ | CH₃ | CH₃ | OCH₃ | N | |
| 6-CH₃ | SO₂ | CH₃ | CH₃ | OCH₃ | OCH₃ | N | |
| 6-CH₃ | SO₂ | CH₃ | CH₃ | CH₃ | CH₃ | N | |
| 6-CH₃ | C=O | CH₃ | N(CH₃)₂ | CH₃ | CH₃ | CH | |
| 6-CH₃ | C=O | CH₃ | N(CH₃)₂ | CH₃ | OCH₃ | CH | |
| 6-CH₃ | C=O | CH₃ | N(CH₃)₂ | OCH₃ | OCH₃ | CH | |
| 6-CH₃ | C=O | CH₃ | N(CH₃)₂ | Cl | OCH₃ | CH | |
| 6-CH₃ | C=O | CH₃ | N(CH₃)₂ | CH₃ | OCH₃ | N | |
| 6-CH₃ | C=O | CH₃ | N(CH₃)₂ | OCH₃ | OCH₃ | N | |
| 6-CH₃ | C=O | CH₃ | N(CH₃)₂ | CH₃ | CH₃ | N | |
| 6-CH₃ | SO₂ | H | CH₃ | CH₃ | CH₃ | CH | |
| 6-CH₃ | SO₂ | H | CH₃ | CH₃ | OCH₃ | CH | |
| 6-CH₃ | SO₂ | H | CH₃ | OCH₃ | OCH₃ | CH | |
| 6-CH₃ | SO₂ | H | CH₃ | Cl | OCH₃ | CH | |
| 6-CH₃ | SO₂ | H | CH₃ | CH₃ | OCH₃ | N | |
| 6-CH₃ | SO₂ | H | CH₃ | OCH₃ | OCH₃ | N | |
| 6-CH₃ | SO₂ | H | CH₃ | CH₃ | OCH₃ | N | |
| 6-CH₃ | C=O | CH₃ | OCH₃ | CH₃ | CH₃ | CH | |
| 6-CH₃ | C=O | CH₃ | OCH₃ | CH₃ | OCH₃ | CH | |
| 6-CH₃ | C=O | CH₃ | OCH₃ | OCH₃ | OCH₃ | CH | |
| 6-CH₃ | C=O | CH₃ | OCH₃ | Cl | OCH₃ | CH | |
| 6-CH₃ | C=O | CH₃ | OCH₃ | CH₃ | OCH₃ | N | |
| 6-CH₃ | C=O | CH₃ | OCH₃ | OCH₃ | OCH₃ | N | |
| 6-CH₃ | C=O | CH₃ | OCH₃ | CH₃ | CH₃ | N | |
| 6-CH₃ | SO₂ | CH₃ | OCH₃ | CH₃ | CH₃ | CH | |
| 6-CH₃ | SO₂ | CH₃ | OCH₃ | CH₃ | OCH₃ | CH | |
| 6-CH₃ | SO₂ | CH₃ | OCH₃ | OCH₃ | OCH₃ | CH | |
| 6-CH₃ | SO₂ | CH₃ | OCH₃ | Cl | OCH₃ | CH | |
| 6-CH₃ | SO₂ | CH₃ | OCH₃ | CH₃ | OCH₃ | N | |
| 6-CH₃ | SO₂ | CH₃ | OCH₃ | OCH₃ | OCH₃ | N | |
| 6-CH₃ | SO₂ | CH₃ | OCH₃ | CH₃ | CH₃ | N | |
| 6-CH₃ | CH₂ | H | CH₃ | CH₃ | CH₃ | CH | |
| 6-CH₃ | CH₂ | H | CH₃ | CH₃ | OCH₃ | CH | |
| 6-CH₃ | CH₂ | H | CH₃ | OCH₃ | OCH₃ | CH | |
| 6-CH₃ | CH₂ | H | CH₃ | Cl | OCH₃ | CH | |
| 6-CH₃ | CH₂ | H | CH₃ | CH₃ | OCH₃ | N | |
| 6-CH₃ | CH₂ | H | CH₃ | OCH₃ | OCH₃ | N | |
| 6-CH₃ | CH₂ | H | CH₃ | CH₃ | CH₃ | N | |
| 6-CH₃ | CH₂ | CH₃ | CH₃ | CH₃ | CH₃ | CH | |
| 6-CH₃ | CH₂ | CH₃ | CH₃ | CH₃ | OCH₃ | CH | |
| 6-CH₃ | CH₂ | CH₃ | CH₃ | OCH₃ | OCH₃ | CH | |
| 6-CH₃ | CH₂ | CH₃ | CH₃ | Cl | OCH₃ | CH | |
| 6-CH₃ | CH₂ | CH₃ | CH₃ | CH₃ | OCH₃ | N | |
| 6-CH₃ | CH₂ | CH₃ | CH₃ | OCH₃ | OCH₃ | N | |
| 6-CH₃ | CH₂ | CH₃ | CH₃ | CH₃ | CH₃ | N | |
| 6-CH₃ | CH₂ | CH₃ | SCH₃ | CH₃ | CH₃ | CH | |
| 6-CH₃ | CH₂ | CH₃ | SCH₃ | CH₃ | OCH₃ | CH | |
| 6-CH₃ | CH₂ | CH₃ | SCH₃ | OCH₃ | OCH₃ | CH | |
| 6-CH₃ | CH₂ | CH₃ | SCH₃ | Cl | OCH₃ | CH | |
| 6-CH₃ | CH₂ | CH₃ | SCH₃ | CH₃ | OCH₃ | N | |
| 6-CH₃ | CH₂ | CH₃ | SCH₃ | OCH₃ | OCH₃ | N | |
| 6-CH₃ | CH₂ | CH₃ | SCH₃ | CH₃ | CH₃ | N | |
| 6-CH₃ | O | H | CH₃ | CH₃ | CH₃ | CH | |
| 6-CH₃ | O | H | CH₃ | CH₃ | OCH₃ | CH | |
| 6-CH₃ | O | H | CH₃ | OCH₃ | OCH₃ | CH | |
| 6-CH₃ | O | H | CH₃ | Cl | OCH₃ | CH | |
| 6-CH₃ | O | H | CH₃ | CH₃ | OCH₃ | N | |
| 6-CH₃ | O | H | CH₃ | CH₃ | CH₃ | N | |
| 6-CH₃ | O | H | OCH₃ | CH₃ | CH₃ | CH | |
| 6-CH₃ | O | H | OCH₃ | CH₃ | OCH₃ | CH | |
| 6-CH₃ | O | H | OCH₃ | OCH₃ | OCH₃ | CH | |
| 6-CH₃ | O | H | OCH₃ | Cl | OCH₃ | CH | |
| 6-CH₃ | O | H | OCH₃ | CH₃ | OCH₃ | N | |
| 6-CH₃ | O | H | OCH₃ | CH₃ | CH₃ | N | |
| 6-CH₃ | O | CH₃ | CH₃ | CH₃ | CH₃ | CH | |
| 6-CH₃ | O | CH₃ | CH₃ | CH₃ | OCH₃ | CH | |
| 6-CH₃ | O | CH₃ | CH₃ | OCH₃ | OCH₃ | CH | |
| 6-CH₃ | O | CH₃ | CH₃ | Cl | OCH₃ | CH | |
| 6-CH₃ | O | CH₃ | CH₃ | CH₃ | OCH₃ | N | |
| 6-CH₃ | O | CH₃ | CH₃ | OCH₃ | OCH₃ | N | |
| 6-CH₃ | O | CH₃ | CH₃ | CH₃ | CH₃ | N | |

TABLE 9

General Formula 9

| R₁ | J | X | Y | Z | m.p. (°C.) |
|---|---|---|---|---|---|
| H | C=O | CH₃ | CH₃ | CH | |
| H | C=O | CH₃ | OCH₃ | CH | |
| H | C=O | OCH₃ | OCH₃ | CH | |
| H | C=O | Cl | OCH₃ | CH | |
| H | C=O | CH₃ | OCH₃ | N | |
| H | C=O | OCH₃ | OCH₃ | N | |
| H | C=O | CH₃ | CH₃ | N | |
| H | S | CH₃ | CH₃ | CH | |
| H | S | CH₃ | OCH₃ | CH | |
| H | S | OCH₃ | OCH₃ | CH | |
| H | S | Cl | OCH₃ | CH | |
| H | S | CH₃ | OCH₃ | N | |
| H | S | OCH₃ | OCH₃ | N | |
| H | S | CH₃ | CH₃ | N | |
| H | SO₂ | CH₃ | CH₃ | CH | |
| H | SO₂ | CH₃ | OCH₃ | CH | |
| H | SO₂ | OCH₃ | OCH₃ | CH | |
| H | SO₂ | Cl | OCH₃ | CH | |
| H | SO₂ | CH₃ | OCH₃ | N | |
| H | SO₂ | OCH₃ | OCH₃ | N | |
| H | SO₂ | CH₃ | CH₃ | N | |
| H | CH₂ | CH₃ | CH₃ | CH | |
| H | CH₂ | CH₃ | OCH₃ | CH | |
| H | CH₂ | OCH₃ | OCH₃ | CH | |
| H | CH₂ | Cl | OCH₃ | CH | |
| H | CH₂ | CH₃ | OCH₃ | N | |
| H | CH₂ | OCH₃ | OCH₃ | N | |
| H | CH₂ | CH₃ | CH₃ | N | |
| 6-CH₃ | C=O | CH₃ | CH₃ | CH | |
| 6-CH₃ | C=O | CH₃ | OCH₃ | CH | |
| 6-CH₃ | C=O | OCH₃ | OCH₃ | CH | |
| 6-CH₃ | C=O | Cl | OCH₃ | N | |
| 6-CH₃ | C=O | CH₃ | OCH₃ | N | |
| 6-CH₃ | C=O | OCH₃ | OCH₃ | N | |
| 6-CH₃ | C=O | CH₃ | CH₃ | N | |
| 6-CH₃ | S | CH₃ | CH₃ | CH | |
| 6-CH₃ | S | CH₃ | OCH₃ | CH | |
| 6-CH₃ | S | OCH₃ | OCH₃ | CH | |
| 6-CH₃ | S | Cl | OCH₃ | CH | |
| 6-CH₃ | S | CH₃ | OCH₃ | N | |
| 6-CH₃ | S | OCH₃ | OCH₃ | N | |
| 6-CH₃ | S | CH₃ | CH₃ | N | |
| 6-CH₃ | SO₂ | CH₃ | CH₃ | CH | |
| 6-CH₃ | SO₂ | CH₃ | OCH₃ | CH | |
| 6-CH₃ | SO₂ | OCH₃ | OCH₃ | CH | |
| 6-CH₃ | SO₂ | Cl | OCH₃ | CH | |
| 6-CH₃ | SO₂ | CH₃ | OCH₃ | N | |
| 6-CH₃ | SO₂ | OCH₃ | OCH₃ | N | |
| 6-CH₃ | SO₂ | CH₃ | CH₃ | N | |
| 6-CH₃ | CH₂ | CH₃ | CH₃ | CH | |
| 6-CH₃ | CH₂ | CH₃ | OCH₃ | CH | |
| 6-CH₃ | CH₂ | OCH₃ | OCH₃ | CH | |
| 6-CH₃ | CH₂ | Cl | OCH₃ | N | |
| 6-CH₃ | CH₂ | OCH₃ | OCH₃ | N | |
| 6-CH₃ | CH₂ | CH₃ | CH₃ | N | |

TABLE 10

General Formula 10

| R₁ | J | X | Y | Z | m.p. (°C.) |
|---|---|---|---|---|---|
| H | C=O | CH₃ | CH₃ | CH | |
| H | C=O | CH₃ | OCH₃ | CH | |
| H | C=O | OCH₃ | OCH₃ | CH | |
| H | C=O | Cl | OCH₃ | CH | |
| H | C=O | CH₃ | OCH₃ | N | |
| H | C=O | OCH₃ | OCH₃ | N | |
| H | C=O | CH₃ | CH₃ | N | |
| H | SO₂ | CH₃ | CH₃ | CH | |
| H | SO₂ | CH₃ | OCH₃ | CH | |
| H | SO₂ | OCH₃ | OCH₃ | CH | |
| H | SO₂ | Cl | OCH₃ | CH | |
| H | SO₂ | CH₃ | OCH₃ | N | |
| H | SO₂ | OCH₃ | OCH₃ | N | |
| H | SO₂ | CH₃ | CH₃ | N | |
| H | CH₂ | CH₃ | CH₃ | CH | |
| H | CH₂ | CH₃ | OCH₃ | CH | |
| H | CH₂ | OCH₃ | OCH₃ | CH | |

TABLE 10-continued

General Formula 10

| R₁ | J | X | Y | Z | m.p. (°C.) |
|---|---|---|---|---|---|
| H | CH₂ | Cl | OCH₃ | CH | |
| H | CH₂ | CH₃ | OCH₃ | N | |
| H | CH₂ | OCH₃ | OCH₃ | N | |
| H | CH₂ | CH₃ | CH₃ | N | |
| 6-CH₃ | C=O | CH₃ | CH₃ | CH | |
| 6-CH₃ | C=O | CH₃ | OCH₃ | CH | |
| 6-CH₃ | C=O | OCH₃ | OCH₃ | CH | |
| 6-CH₃ | C=O | Cl | OCH₃ | CH | |
| 6-CH₃ | C=O | CH₃ | OCH₃ | N | |
| 6-CH₃ | C=O | OCH₃ | OCH₃ | N | |
| 6-CH₃ | C=O | CH₃ | CH₃ | N | |
| 6-CH₃ | SO₂ | CH₃ | CH₃ | CH | |
| 6-CH₃ | SO₂ | CH₃ | OCH₃ | CH | |
| 6-CH₃ | SO₂ | OCH₃ | OCH₃ | CH | |
| 6-CH₃ | SO₂ | Cl | OCH₃ | CH | |
| 6-CH₃ | SO₂ | CH₃ | OCH₃ | N | |
| 6-CH₃ | SO₂ | OCH₃ | OCH₃ | N | |
| 6-CH₃ | SO₂ | CH₃ | CH₃ | N | |
| 6-CH₃ | CH₂ | CH₃ | CH₃ | CH | |
| 6-CH₃ | CH₂ | CH₃ | OCH₃ | CH | |
| 6-CH₃ | CH₂ | OCH₃ | OCH₃ | CH | |
| 6-CH₃ | CH₂ | Cl | OCH₃ | CH | |
| 6-CH₃ | CH₂ | CH₃ | OCH₃ | N | |
| 6-CH₃ | CH₂ | OCH₃ | OCH₃ | N | |
| 6-CH₃ | CH₂ | CH₃ | CH₃ | N | |

TABLE 11

General Formula 11

| R₁ | J | R₈ | R₁₁ | X | Y | Z | m.p. (°C.) |
|---|---|---|---|---|---|---|---|
| H | C=O | CH₃ | SCH₃ | CH₃ | CH₃ | CH | |
| H | C=O | CH₃ | SCH₃ | CH₃ | OCH₃ | CH | |
| H | C=O | CH₃ | SCH₃ | OCH₃ | OCH₃ | CH | |
| H | C=O | CH₃ | SCH₃ | Cl | OCH₃ | CH | |
| H | C=O | CH₃ | SCH₃ | CH₃ | OCH₃ | N | |
| H | C=O | CH₃ | SCH₃ | OCH₃ | OCH₃ | N | |
| H | C=O | CH₃ | SCH₃ | CH₃ | CH₃ | N | |
| H | C=O | SCH₃ | SCH₃ | CH₃ | CH₃ | CH | |
| H | C=O | SCH₃ | SCH₃ | CH₃ | OCH₃ | CH | |
| H | C=O | SCH₃ | SCH₃ | OCH₃ | OCH₃ | CH | |
| H | C=O | SCH₃ | SCH₃ | Cl | OCH₃ | CH | |
| H | C=O | SCH₃ | SCH₃ | CH₃ | OCH₃ | N | |
| H | C=O | SCH₃ | SCH₃ | OCH₃ | OCH₃ | N | |
| H | C=O | SCH₃ | SCH₃ | CH₃ | CH₃ | N | |
| H | SO₂ | CH₃ | SCH₃ | CH₃ | CH₃ | CH | |
| H | SO₂ | CH₃ | SCH₃ | CH₃ | OCH₃ | CH | |
| H | SO₂ | CH₃ | SCH₃ | OCH₃ | OCH₃ | CH | |
| H | SO₂ | CH₃ | SCH₃ | Cl | OCH₃ | CH | |
| H | SO₂ | CH₃ | SCH₃ | CH₃ | OCH₃ | N | |
| H | SO₂ | CH₃ | SCH₃ | OCH₃ | OCH₃ | N | |
| H | SO₂ | CH₃ | SCH₃ | CH₃ | CH₃ | N | |
| H | CH₂ | CH₃ | SCH₃ | CH₃ | CH₃ | CH | |
| H | CH₂ | CH₃ | SCH₃ | CH₃ | OCH₃ | CH | |
| H | CH₂ | CH₃ | SCH₃ | OCH₃ | OCH₃ | CH | |
| H | CH₂ | CH₃ | SCH₃ | Cl | OCH₃ | CH | |
| H | CH₂ | CH₃ | SCH₃ | CH₃ | OCH₃ | N | |
| H | CH₂ | CH₃ | SCH₃ | OCH₃ | OCH₃ | N | |
| H | CH₂ | CH₃ | SCH₃ | CH₃ | CH₃ | N | |
| H | CH₂ | CH₃ | OCH₃ | CH₃ | CH₃ | CH | |
| H | CH₂ | CH₃ | OCH₃ | CH₃ | OCH₃ | CH | |
| H | CH₂ | CH₃ | OCH₃ | OCH₃ | OCH₃ | CH | |
| H | CH₂ | CH₃ | OCH₃ | Cl | OCH₃ | CH | |
| H | CH₂ | CH₃ | OCH₃ | CH₃ | OCH₃ | N | |
| H | CH₂ | CH₃ | OCH₃ | OCH₃ | OCH₃ | N | |
| H | CH₂ | CH₃ | OCH₃ | CH₃ | CH₃ | N | |
| H | CH₂ | CH₃ | CH₃ | CH₃ | CH₃ | CH | |
| H | CH₂ | CH₃ | CH₃ | CH₃ | OCH₃ | CH | |
| H | CH₂ | CH₃ | CH₃ | OCH₃ | OCH₃ | CH | |
| H | CH₂ | CH₃ | CH₃ | Cl | OCH₃ | CH | |
| H | CH₂ | CH₃ | CH₃ | CH₃ | OCH₃ | N | |
| H | CH₂ | CH₃ | CH₃ | OCH₃ | OCH₃ | N | |
| H | CH₂ | CH₃ | CH₃ | CH₃ | CH₃ | N | |
| H | C=O | CH₃ | N(CH₃)₂ | CH₃ | CH₃ | CH | |
| H | C=O | CH₃ | N(CH₃)₂ | CH₃ | OCH₃ | CH | |
| H | C=O | CH₃ | N(CH₃)₂ | OCH₃ | OCH₃ | CH | |
| H | C=O | CH₃ | N(CH₃)₂ | Cl | OCH₃ | CH | |
| H | C=O | CH₃ | N(CH₃)₂ | CH₃ | OCH₃ | N | |

TABLE 11-continued

General Formula 11

| R₁ | J | R₈ | R₁₁ | X | Y | Z | m.p. (°C.) |
|---|---|---|---|---|---|---|---|
| H | C=O | CH₃ | N(CH₃)₂ | OCH₃ | OCH₃ | N | |
| H | C=O | CH₃ | N(CH₃)₂ | CH₃ | CH₃ | N | |
| H | C=O | CH₃ | OCH₃ | CH₃ | CH₃ | CH | |
| H | C=O | CH₃ | OCH₃ | CH₃ | OCH₃ | CH | |
| H | C=O | CH₃ | OCH₃ | OCH₃ | OCH₃ | CH | |
| H | C=O | CH₃ | OCH₃ | Cl | OCH₃ | CH | |
| H | C=O | CH₃ | OCH₃ | CH₃ | OCH₃ | N | |
| H | C=O | CH₃ | OCH₃ | OCH₃ | OCH₃ | N | |
| H | C=O | CH₃ | OCH₃ | CH₃ | CH₃ | N | |
| H | SO₂ | CH₃ | OCH₃ | CH₃ | CH₃ | CH | |
| H | SO₂ | CH₃ | OCH₃ | CH₃ | OCH₃ | CH | |
| H | SO₂ | CH₃ | OCH₃ | OCH₃ | OCH₃ | CH | |
| H | SO₂ | CH₃ | OCH₃ | Cl | OCH₃ | CH | |
| H | SO₂ | CH₃ | OCH₃ | CH₃ | OCH₃ | N | |
| H | SO₂ | CH₃ | OCH₃ | OCH₃ | OCH₃ | N | |
| H | SO₂ | CH₃ | OCH₃ | CH₃ | CH₃ | N | |
| 6-Cl | C=O | CH₃ | SCH₃ | CH₃ | CH₃ | CH | |
| 6-Cl | C=O | CH₃ | SCH₃ | CH₃ | OCH₃ | CH | |
| 6-Cl | C=O | CH₃ | SCH₃ | OCH₃ | OCH₃ | CH | |
| 6-Cl | C=O | CH₃ | SCH₃ | Cl | OCH₃ | CH | |
| 6-Cl | C=O | CH₃ | SCH₃ | CH₃ | OCH₃ | N | |
| 6-Cl | C=O | CH₃ | SCH₃ | OCH₃ | OCH₃ | N | |
| 6-Cl | C=O | CH₃ | SCH₃ | CH₃ | CH₃ | N | |
| 6-Cl | C=O | SCH₃ | SCH₃ | CH₃ | CH₃ | CH | |
| 6-Cl | C=O | SCH₃ | SCH₃ | CH₃ | OCH₃ | CH | |
| 6-Cl | C=O | SCH₃ | SCH₃ | OCH₃ | OCH₃ | CH | |
| 6-Cl | C=O | SCH₃ | SCH₃ | Cl | OCH₃ | CH | |
| 6-Cl | C=O | SCH₃ | SCH₃ | CH₃ | OCH₃ | N | |
| 6-Cl | C=O | SCH₃ | SCH₃ | OCH₃ | OCH₃ | N | |
| 6-Cl | C=O | SCH₃ | SCH₃ | CH₃ | CH₃ | N | |
| 6-Cl | SO₂ | CH₃ | SCH₃ | CH₃ | CH₃ | CH | |
| 6-Cl | SO₂ | CH₃ | SCH₃ | CH₃ | OCH₃ | CH | |
| 6-Cl | SO₂ | CH₃ | SCH₃ | OCH₃ | OCH₃ | CH | |
| 6-Cl | SO₂ | CH₃ | SCH₃ | Cl | OCH₃ | CH | |
| 6-Cl | SO₂ | CH₃ | SCH₃ | CH₃ | OCH₃ | N | |
| 6-Cl | SO₂ | CH₃ | SCH₃ | OCH₃ | OCH₃ | N | |
| 6-Cl | SO₂ | CH₃ | SCH₃ | CH₃ | CH₃ | N | |
| 6-Cl | CH₂ | CH₃ | SCH₃ | CH₃ | CH₃ | CH | |
| 6-Cl | CH₂ | CH₃ | SCH₃ | CH₃ | OCH₃ | CH | |
| 6-Cl | CH₂ | CH₃ | SCH₃ | OCH₃ | OCH₃ | CH | |
| 6-Cl | CH₂ | CH₃ | SCH₃ | Cl | OCH₃ | CH | |
| 6-Cl | CH₂ | CH₃ | SCH₃ | CH₃ | OCH₃ | N | |
| 6-Cl | CH₂ | CH₃ | SCH₃ | OCH₃ | OCH₃ | N | |
| 6-Cl | CH₂ | CH₃ | SCH₃ | CH₃ | CH₃ | N | |
| 5-OCH₃ | CH₂ | CH₃ | OCH₃ | CH₃ | CH₃ | CH | |
| 5-OCH₃ | CH₂ | CH₃ | OCH₃ | CH₃ | OCH₃ | CH | |
| 5-OCH₃ | CH₂ | CH₃ | OCH₃ | OCH₃ | OCH₃ | CH | |
| 5-OCH₃ | CH₂ | CH₃ | OCH₃ | Cl | OCH₃ | CH | |
| 5-OCH₃ | CH₂ | CH₃ | OCH₃ | CH₃ | OCH₃ | N | |
| 5-OCH₃ | CH₂ | CH₃ | OCH₃ | OCH₃ | OCH₃ | N | |
| 5-OCH₃ | CH₂ | CH₃ | OCH₃ | CH₃ | CH₃ | N | |
| 5-OCH₃ | CH₂ | CH₃ | CH₃ | CH₃ | CH₃ | CH | |
| 5-OCH₃ | CH₂ | CH₃ | CH₃ | CH₃ | OCH₃ | CH | |
| 5-OCH₃ | CH₂ | CH₃ | CH₃ | OCH₃ | OCH₃ | CH | |
| 5-OCH₃ | CH₂ | CH₃ | CH₃ | Cl | OCH₃ | CH | |
| 5-OCH₃ | CH₂ | CH₃ | CH₃ | CH₃ | OCH₃ | N | |
| 5-OCH₃ | CH₂ | CH₃ | CH₃ | OCH₃ | OCH₃ | N | |
| 5-OCH₃ | CH₂ | CH₃ | CH₃ | CH₃ | CH₃ | N | |
| 5-OCH₃ | C=O | CH₃ | N(CH₃)₂ | CH₃ | CH₃ | CH | |
| 5-OCH₃ | C=O | CH₃ | N(CH₃)₂ | CH₃ | OCH₃ | CH | |
| 5-OCH₃ | C=O | CH₃ | N(CH₃)₂ | OCH₃ | OCH₃ | CH | |
| 5-OCH₃ | C=O | CH₃ | N(CH₃)₂ | Cl | OCH₃ | CH | |
| 5-OCH₃ | C=O | CH₃ | N(CH₃)₂ | CH₃ | OCH₃ | N | |
| 5-OCH₃ | C=O | CH₃ | N(CH₃)₂ | OCH₃ | OCH₃ | N | |
| 5-OCH₃ | C=O | CH₃ | N(CH₃)₂ | CH₃ | CH₃ | N | |
| 5-OCH₃ | C=O | CH₃ | OCH₃ | CH₃ | CH₃ | CH | |
| 5-OCH₃ | C=O | CH₃ | OCH₃ | CH₃ | OCH₃ | CH | |
| 5-OCH₃ | C=O | CH₃ | OCH₃ | OCH₃ | OCH₃ | CH | |
| 5-OCH₃ | C=O | CH₃ | OCH₃ | Cl | OCH₃ | CH | |
| 5-OCH₃ | C=O | CH₃ | OCH₃ | CH₃ | OCH₃ | N | |
| 5-OCH₃ | C=O | CH₃ | OCH₃ | OCH₃ | OCH₃ | N | |
| 5-OCH₃ | C=O | CH₃ | OCH₃ | CH₃ | CH₃ | N | |
| 5-OCH₃ | SO₂ | CH₃ | OCH₃ | CH₃ | CH₃ | CH | |
| 5-OCH₃ | SO₂ | CH₃ | OCH₃ | CH₃ | OCH₃ | CH | |
| 5-OCH₃ | SO₂ | CH₃ | OCH₃ | Cl | OCH₃ | CH | |
| 5-OCH₃ | SO₂ | CH₃ | OCH₃ | CH₃ | OCH₃ | N | |
| 5-OCH₃ | SO₂ | CH₃ | OCH₃ | OCH₃ | OCH₃ | N | |

TABLE 11-continued

General Formula 11

| R₁ | J | R₈ | R₁₁ | X | Y | Z | m.p. (°C.) |
|---|---|---|---|---|---|---|---|
| 5-OCH₃ | SO₂ | CH₃ | OCH₃ | CH₃ | CH₃ | N | |

TABLE 12

General Formula 12

| R₁ | J | R₈ | X | Y | Z | m.p. (°C.) |
|---|---|---|---|---|---|---|
| H | C=O | H | CH₃ | CH₃ | CH | |
| H | C=O | H | CH₃ | OCH₃ | CH | |
| H | C=O | H | OCH₃ | OCH₃ | CH | |
| H | C=O | H | Cl | OCH₃ | CH | |
| H | C=O | H | CH₃ | OCH₃ | N | |
| H | C=O | H | OCH₃ | OCH₃ | N | |
| H | C=O | H | CH₃ | CH₃ | N | |
| H | C=O | CH₃ | CH₃ | CH₃ | CH | |
| H | C=O | CH₃ | CH₃ | OCH₃ | CH | |
| H | C=O | CH₃ | OCH₃ | OCH₃ | CH | |
| H | C=O | CH₃ | Cl | OCH₃ | CH | |
| H | C=O | CH₃ | CH₃ | OCH₃ | N | |
| H | C=O | CH₃ | OCH₃ | OCH₃ | N | |
| H | C=O | CH₃ | CH₃ | CH₃ | N | |
| H | SO₂ | CH₃ | CH₃ | CH₃ | CH | |
| H | SO₂ | CH₃ | CH₃ | OCH₃ | CH | |
| H | SO₂ | CH₃ | OCH₃ | OCH₃ | CH | |
| H | SO₂ | CH₃ | Cl | OCH₃ | CH | |
| H | SO₂ | CH₃ | CH₃ | OCH₃ | N | |
| H | SO₂ | CH₃ | OCH₃ | OCH₃ | N | |
| H | SO₂ | CH₃ | CH₃ | CH₃ | N | |
| H | SO₂ | H | CH₃ | CH₃ | CH | |
| H | SO₂ | H | CH₃ | OCH₃ | CH | |
| H | SO₂ | H | OCH₃ | OCH₃ | CH | |
| H | SO₂ | H | Cl | OCH₃ | CH | |
| H | SO₂ | H | CH₃ | OCH₃ | N | |
| H | SO₂ | H | OCH₃ | OCH₃ | N | |
| H | SO₂ | H | CH₃ | CH₃ | N | |
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| 5-OCH₃ | C=O | H | CH₃ | CH₃ | CH | |
| 5-OCH₃ | C=O | H | CH₃ | OCH₃ | CH | |
| 5-OCH₃ | C=O | H | OCH₃ | OCH₃ | CH | |
| 5-OCH₃ | C=O | H | Cl | OCH₃ | CH | |
| 5-OCH₃ | C=O | H | CH₃ | OCH₃ | N | |
| 5-OCH₃ | C=O | H | OCH₃ | OCH₃ | N | |
| 5-OCH₃ | C=O | H | CH₃ | CH₃ | N | |
| 5-OCH₃ | C=O | CH₃ | CH₃ | CH₃ | CH | |
| 5-OCH₃ | C=O | CH₃ | CH₃ | OCH₃ | CH | |
| 5-OCH₃ | C=O | CH₃ | OCH₃ | OCH₃ | CH | |
| 5-OCH₃ | C=O | CH₃ | Cl | OCH₃ | CH | |
| 5-OCH₃ | C=O | CH₃ | CH₃ | OCH₃ | N | |
| 5-OCH₃ | C=O | CH₃ | OCH₃ | OCH₃ | N | |
| 5-OCH₃ | C=O | CH₃ | CH₃ | CH₃ | N | |
| 5-OCH₃ | SO₂ | CH₃ | CH₃ | CH₃ | CH | |
| 5-OCH₃ | SO₂ | CH₃ | CH₃ | OCH₃ | CH | |
| 5-OCH₃ | SO₂ | CH₃ | OCH₃ | OCH₃ | CH | |
| 5-OCH₃ | SO₂ | CH₃ | Cl | OCH₃ | CH | |
| 5-OCH₃ | SO₂ | CH₃ | CH₃ | OCH₃ | N | |
| 5-OCH₃ | SO₂ | CH₃ | OCH₃ | OCH₃ | N | |
| 5-OCH₃ | SO₂ | CH₃ | CH₃ | CH₃ | N | |
| 5-OCH₃ | SO₂ | H | CH₃ | CH₃ | CH | |
| 5-OCH₃ | SO₂ | H | CH₃ | OCH₃ | CH | |
| 5-OCH₃ | SO₂ | H | OCH₃ | OCH₃ | CH | |
| 5-OCH₃ | SO₂ | H | Cl | OCH₃ | CH | |
| 5-OCH₃ | SO₂ | H | CH₃ | OCH₃ | N | |
| 5-OCH₃ | SO₂ | H | OCH₃ | OCH₃ | N | |
| 5-OCH₃ | SO₂ | H | CH₃ | CH₃ | N | |
| 5-OCH₃ | CH₂ | H | CH₃ | CH₃ | CH | |
| 5-OCH₃ | CH₂ | H | CH₃ | OCH₃ | CH | |
| 5-OCH₃ | CH₂ | H | OCH₃ | OCH₃ | CH | |
| 5-OCH₃ | CH₂ | H | Cl | OCH₃ | CH | |
| 5-OCH₃ | CH₂ | H | CH₃ | OCH₃ | N | |
| 5-OCH₃ | CH₂ | H | OCH₃ | OCH₃ | N | |
| 5-OCH₃ | CH₂ | H | CH₃ | CH₃ | N | |
| 5-OCH₃ | CH₂ | CH₃ | CH₃ | CH₃ | CH | |
| 5-OCH₃ | CH₂ | CH₃ | CH₃ | OCH₃ | CH | |
| 5-OCH₃ | CH₂ | CH₃ | OCH₃ | OCH₃ | CH | |
| 5-OCH₃ | CH₂ | CH₃ | Cl | OCH₃ | CH | |
| 5-OCH₃ | CH₂ | CH₃ | CH₃ | OCH₃ | N | |
| 5-OCH₃ | CH₂ | CH₃ | OCH₃ | OCH₃ | N | |
| 5-OCH₃ | CH₂ | CH₃ | CH₃ | CH₃ | N | |

TABLE 13

General Formula 13

| R₁ | G | R₁₄ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | 7-NO₂ | CH₃ | CH₃ | CH | |
| H | CH₂ | 7-NO₂ | CH₃ | OCH₃ | CH | |
| H | CH₂ | 7-NO₂ | OCH₃ | OCH₃ | CH | |
| H | CH₂ | 7-NO₂ | Cl | OCH₃ | CH | |
| H | CH₂ | 7-NO₂ | CH₃ | OCH₃ | N | |
| H | CH₂ | 7-NO₂ | OCH₃ | OCH₃ | N | |
| H | CH₂ | 7-NO₂ | CH₃ | CH₃ | N | |
| H | CH₂ | 8-Cl | CH₃ | CH₃ | CH | |
| H | CH₂ | 8-Cl | CH₃ | OCH₃ | CH | |
| H | CH₂ | 8-Cl | OCH₃ | OCH₃ | CH | |
| H | CH₂ | 8-Cl | Cl | OCH₃ | CH | |
| H | CH₂ | 8-Cl | CH₃ | OCH₃ | N | |
| H | CH₂ | 8-Cl | OCH₃ | OCH₃ | N | |
| H | CH₂ | 8-Cl | CH₃ | CH₃ | N | |
| H | CH₂ | 9-OCH₃ | CH₃ | CH₃ | CH | |
| H | CH₂ | 9-OCH₃ | CH₃ | OCH₃ | CH | |
| H | CH₂ | 9-OCH₃ | OCH₃ | OCH₃ | CH | |
| H | CH₂ | 9-OCH₃ | Cl | OCH₃ | CH | |
| H | CH₂ | 9-OCH₃ | H | OCH₃ | N | |
| H | CH₂ | 9-OCH₃ | OCH₃ | OCH₃ | N | |
| H | CH₂ | 9-OCH₃ | CH₃ | CH₃ | N | |
| H | CH₂ | 10-CH₃ | CH₃ | CH₃ | CH | |
| H | CH₂ | 10-CH₃ | CH₃ | OCH₃ | CH | |
| H | CH₂ | 10-CH₃ | OCH₃ | OCH₃ | CH | |
| H | CH₂ | 10-CH₃ | Cl | OCH₃ | CH | |
| H | CH₂ | 10-CH₃ | CH₃ | OCH₃ | N | |
| H | CH₂ | 10-CH₃ | OCH₃ | OCH₃ | N | |
| H | CH₂ | 10-CH₃ | CH₃ | CH₃ | N | |
| H | CH₂ | 7-F | CH₃ | CH₃ | CH | |
| H | CH₂ | 7-F | CH₃ | OCH₃ | CH | |
| H | CH₂ | 7-F | OCH₃ | OCH₃ | CH | |
| H | CH₂ | 7-F | Cl | OCH₃ | CH | |
| H | CH₂ | 7-F | CH₃ | OCH₃ | N | |
| H | CH₂ | 7-F | OCH₃ | OCH₃ | N | |
| H | CH₂ | 7-F | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | 8-NO₂ | CH₃ | CH₃ | CH | |
| 6-Cl | CH₂ | 8-NO₂ | CH₃ | OCH₃ | CH | |
| 6-Cl | CH₂ | 8-NO₂ | OCH₃ | OCH₃ | CH | |
| 6-Cl | CH₂ | 8-NO₂ | Cl | OCH₃ | CH | |
| 6-Cl | CH₂ | 8-NO₂ | CH₃ | OCH₃ | N | |
| 6-Cl | CH₂ | 8-NO₂ | OCH₃ | OCH₃ | N | |
| 6-Cl | CH₂ | 8-NO₂ | CH₃ | CH₃ | N | |
| 6-Cl | CH₂ | 9-Cl | CH₃ | CH₃ | CH | |
| 6-Cl | CH₂ | 9-Cl | CH₃ | OCH₃ | CH | |
| 6-Cl | CH₂ | 9-Cl | OCH₃ | OCH₃ | CH | |
| 6-Cl | CH₂ | 9-Cl | Cl | OCH₃ | CH | |

TABLE 13-continued

General Formula 13

| R₁ | G | R₁₄ | X | Y | Z | m.p. (°C.) |
|---|---|---|---|---|---|---|
| 6-Cl | CH₂ | 9-Cl | CH₃ | OCH₃ | N | |
| 6-Cl | CH₂ | 9-Cl | OCH₃ | OCH₃ | N | |
| 6-Cl | CH₂ | 9-Cl | CH₃ | CH₃ | N | |
| 6-CH₃ | CH₂ | 7-OCH₃ | CH₃ | CH₃ | CH | |
| 6-CH₃ | CH₂ | 7-OCH₃ | CH₃ | OCH₃ | CH | |
| 6-CH₃ | CH₂ | 7-OCH₃ | OCH₃ | OCH₃ | CH | |
| 6-CH₃ | CH₂ | 7-OCH₃ | Cl | OCH₃ | CH | |
| 6-CH₃ | CH₂ | 7-OCH₃ | H | OCH₃ | N | |
| 6-CH₃ | CH₂ | 7-OCH₃ | OCH₃ | OCH₃ | N | |
| 6-CH₃ | CH₂ | 7-OCH₃ | CH₃ | CH₃ | N | |
| 6-CH₃ | CH₂ | 10-CH₃ | CH₃ | CH₃ | CH | |
| 6-CH₃ | CH₂ | 10-CH₃ | CH₃ | OCH₃ | CH | |
| 6-CH₃ | CH₂ | 10-CH₃ | OCH₃ | OCH₃ | CH | |
| 6-CH₃ | CH₂ | 10-CH₃ | Cl | OCH₃ | CH | |
| 6-CH₃ | CH₂ | 10-CH₃ | CH₃ | OCH₃ | N | |
| 6-CH₃ | CH₂ | 10-CH₃ | OCH₃ | OCH₃ | N | |
| 6-CH₃ | CH₂ | 10-CH₃ | CH₃ | CH₃ | N | |
| 6-CH₃ | CH₂ | 9-F | CH₃ | CH₃ | CH | |
| 6-CH₃ | CH₂ | 9-F | CH₃ | OCH₃ | CH | |
| 6-CH₃ | CH₂ | 9-F | OCH₃ | OCH₃ | CH | |
| 6-CH₃ | CH₂ | 9-F | Cl | OCH₃ | CH | |
| 6-CH₃ | CH₂ | 9-F | CH₃ | OCH₃ | N | |
| 6-CH₃ | CH₂ | 9-F | OCH₃ | OCH₃ | N | |
| 6-CH₃ | CH₂ | 9-F | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | 7-NO₂ | CH₃ | CH₃ | CH | |
| H | CH₂CH₂ | 7-NO₂ | CH₃ | OCH₃ | CH | |
| H | CH₂CH₂ | 7-NO₂ | OCH₃ | OCH₃ | CH | |
| H | CH₂CH₂ | 7-NO₂ | Cl | OCH₃ | CH | |
| H | CH₂CH₂ | 7-NO₂ | CH₃ | OCH₃ | N | |
| H | CH₂CH₂ | 7-NO₂ | OCH₃ | OCH₃ | N | |
| H | CH₂CH₂ | 7-NO₂ | CH₃ | CH₃ | N | |
| H | CH₂CH₂ | 8-Cl | CH₃ | CH₃ | CH | |
| H | CH₂CH₂ | 8-Cl | CH₃ | OCH₃ | CH | |
| H | CH₂CH₂ | 8-Cl | OCH₃ | OCH₃ | CH | |
| H | CH₂CH₂ | 8-Cl | Cl | OCH₃ | CH | |
| H | CH₂CH₂ | 8-Cl | CH₃ | OCH₃ | N | |
| H | CH₂CH₂ | 8-Cl | OCH₃ | OCH₃ | N | |
| H | CH₂CH₂ | 8-Cl | CH₃ | CH₃ | N | |
| H | CH₂CH₂ | 9-OCH₃ | CH₃ | CH₃ | CH | |
| H | CH₂CH₂ | 9-OCH₃ | CH₃ | OCH₃ | CH | |
| H | CH₂CH₂ | 9-OCH₃ | OCH₃ | OCH₃ | CH | |
| H | CH₂CH₂ | 9-OCH₃ | Cl | OCH₃ | CH | |
| H | CH₂CH₂ | 9-OCH₃ | H | OCH₃ | N | |
| H | CH₂CH₂ | 9-OCH₃ | OCH₃ | OCH₃ | N | |
| H | CH₂CH₂ | 9-OCH₃ | CH₃ | CH₃ | N | |
| H | CH₂CH₂ | 10-CH₃ | CH₃ | CH₃ | CH | |
| H | CH₂CH₂ | 10-CH₃ | OCH₃ | OCH₃ | CH | |
| H | CH₂CH₂ | 10-CH₃ | Cl | OCH₃ | CH | |
| H | CH₂CH₂ | 10-CH₃ | CH₃ | OCH₃ | N | |
| H | CH₂CH₂ | 10-CH₃ | OCH₃ | OCH₃ | N | |
| H | CH₂CH₂ | 10-CH₃ | CH₃ | CH₃ | N | |
| H | CH₂CH₂ | 7-F | CH₃ | CH₃ | CH | |
| H | CH₂CH₂ | 7-F | CH₃ | OCH₃ | CH | |
| H | CH₂CH₂ | 7-F | OCH₃ | OCH₃ | CH | |
| H | CH₂CH₂ | 7-F | Cl | OCH₃ | CH | |
| H | CH₂CH₂ | 7-F | CH₃ | OCH₃ | N | |
| H | CH₂CH₂ | 7-F | OCH₃ | OCH₃ | N | |
| H | CH₂CH₂ | 7-F | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | 8-NO₂ | CH₃ | CH₃ | CH | |
| 6-Cl | CH₂CH₂ | 8-NO₂ | CH₃ | OCH₃ | CH | |
| 6-Cl | CH₂CH₂ | 8-NO₂ | OCH₃ | OCH₃ | CH | |
| 6-Cl | CH₂CH₂ | 8-NO₂ | Cl | OCH₃ | CH | |
| 6-Cl | CH₂CH₂ | 8-NO₂ | CH₃ | OCH₃ | N | |
| 6-Cl | CH₂CH₂ | 8-NO₂ | OCH₃ | OCH₃ | N | |
| 6-Cl | CH₂CH₂ | 8-NO₂ | CH₃ | CH₃ | N | |
| 6-Cl | CH₂CH₂ | 9-Cl | CH₃ | CH₃ | CH | |
| 6-Cl | CH₂CH₂ | 9-Cl | CH₃ | OCH₃ | CH | |
| 6-Cl | CH₂CH₂ | 9-Cl | OCH₃ | OCH₃ | CH | |
| 6-Cl | CH₂CH₂ | 9-Cl | Cl | OCH₃ | CH | |
| 6-Cl | CH₂CH₂ | 9-Cl | CH₃ | OCH₃ | N | |
| 6-Cl | CH₂CH₂ | 9-Cl | OCH₃ | OCH₃ | N | |
| 6-Cl | CH₂CH₂ | 9-Cl | CH₃ | CH₃ | N | |
| 6-CH₃ | CH₂CH₂ | 7-OCH₃ | CH₃ | CH₃ | CH | |
| 6-CH₃ | CH₂CH₂ | 7-OCH₃ | CH₃ | OCH₃ | CH | |
| 6-CH₃ | CH₂CH₂ | 7-OCH₃ | OCH₃ | OCH₃ | CH | |
| 6-CH₃ | CH₂CH₂ | 7-OCH₃ | Cl | OCH₃ | CH | |
| 6-CH₃ | CH₂CH₂ | 7-OCH₃ | H | OCH₃ | N | |
| 6-CH₃ | CH₂CH₂ | 7-OCH₃ | OCH₃ | OCH₃ | N | |
| 6-CH₃ | CH₂CH₂ | 7-OCH₃ | CH₃ | CH₃ | N | |
| 6-CH₃ | CH₂CH₂ | 10-CH₃ | CH₃ | CH₃ | CH | |
| 6-CH₃ | CH₂CH₂ | 10-CH₃ | CH₃ | OCH₃ | CH | |
| 6-CH₃ | CH₂CH₂ | 10-CH₃ | OCH₃ | OCH₃ | CH | |
| 6-CH₃ | CH₂CH₂ | 10-CH₃ | Cl | OCH₃ | CH | |
| 6-CH₃ | CH₂CH₂ | 10-CH₃ | CH₃ | OCH₃ | N | |
| 6-CH₃ | CH₂CH₂ | 10-CH₃ | OCH₃ | OCH₃ | N | |
| 6-CH₃ | CH₂CH₂ | 10-CH₃ | CH₃ | CH₃ | N | |
| 6-CH₃ | CH₂CH₂ | 9-F | CH₃ | CH₃ | CH | |
| 6-CH₃ | CH₂CH₂ | 9-F | CH₃ | OCH₃ | CH | |
| 6-CH₃ | CH₂CH₂ | 9-F | OCH₃ | OCH₃ | CH | |
| 6-CH₃ | CH₂CH₂ | 9-F | Cl | OCH₃ | CH | |
| 6-CH₃ | CH₂CH₂ | 9-F | CH₃ | OCH₃ | N | |
| 6-CH₃ | CH₂CH₂ | 9-F | OCH₃ | OCH₃ | N | |
| 6-CH₃ | CH₂CH₂ | 9-F | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | 7-NO₂ | CH₃ | CH₃ | CH | |
| H | CH=CH | 7-NO₂ | CH₃ | OCH₃ | CH | |
| H | CH=CH | 7-NO₂ | OCH₃ | OCH₃ | CH | |
| H | CH=CH | 7-NO₂ | Cl | OCH₃ | CH | |
| H | CH=CH | 7-NO₂ | CH₃ | OCH₃ | N | |
| H | CH=CH | 7-NO₂ | OCH₃ | OCH₃ | N | |
| H | CH=CH | 7-NO₂ | CH₃ | CH₃ | N | |
| H | CH=CH | 8-Cl | CH₃ | CH₃ | CH | |
| H | CH=CH | 8-Cl | CH₃ | OCH₃ | CH | |
| H | CH=CH | 8-Cl | OCH₃ | OCH₃ | CH | |
| H | CH=CH | 8-Cl | Cl | OCH₃ | CH | |
| H | CH=CH | 8-Cl | CH₃ | OCH₃ | N | |
| H | CH=CH | 8-Cl | OCH₃ | OCH₃ | N | |
| H | CH=CH | 8-Cl | CH₃ | CH₃ | N | |
| H | CH=CH | 9-OCH₃ | CH₃ | CH₃ | CH | |
| H | CH=CH | 9-OCH₃ | CH₃ | OCH₃ | CH | |
| H | CH=CH | 9-OCH₃ | Cl | OCH₃ | CH | |
| H | CH=CH | 9-OCH₃ | H | OCH₃ | N | |
| H | CH=CH | 9-OCH₃ | OCH₃ | OCH₃ | N | |
| H | CH=CH | 9-OCH₃ | CH₃ | CH₃ | N | |
| H | CH=CH | 10-CH₃ | CH₃ | CH₃ | CH | |
| H | CH=CH | 10-CH₃ | OCH₃ | OCH₃ | CH | |
| H | CH=CH | 10-CH₃ | Cl | OCH₃ | CH | |
| H | CH=CH | 10-CH₃ | CH₃ | OCH₃ | N | |
| H | CH=CH | 10-CH₃ | OCH₃ | OCH₃ | N | |
| H | CH=CH | 10-CH₃ | CH₃ | CH₃ | N | |
| H | CH=CH | 7-F | CH₃ | CH₃ | CH | |
| H | CH=CH | 7-F | CH₃ | OCH₃ | CH | |
| H | CH=CH | 7-F | OCH₃ | OCH₃ | CH | |
| H | CH=CH | 7-F | Cl | OCH₃ | CH | |
| H | CH=CH | 7-F | CH₃ | OCH₃ | N | |
| H | CH=CH | 7-F | OCH₃ | OCH₃ | N | |
| H | CH=CH | 7-F | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | 8-NO₂ | CH₃ | CH₃ | CH | |

TABLE 13-continued

General Formula 13

| R₁ | G | R₁₄ | X | Y | Z | m.p. (°C.) |
|---|---|---|---|---|---|---|
| 6-Cl | CH=CH | 8-NO₂ | CH₃ | OCH₃ | CH | |
| 6-Cl | CH=CH | 8-NO₂ | OCH₃ | OCH₃ | CH | |
| 6-Cl | CH=CH | 8-NO₂ | Cl | OCH₃ | CH | |
| 6-Cl | CH=CH | 8-NO₂ | CH₃ | OCH₃ | N | |
| 6-Cl | CH=CH | 8-NO₂ | OCH₃ | OCH₃ | N | |
| 6-Cl | CH=CH | 8-NO₂ | CH₃ | CH₃ | N | |
| 6-Cl | CH=CH | 9-Cl | CH₃ | CH₃ | CH | |
| 6-Cl | CH=CH | 9-Cl | CH₃ | OCH₃ | CH | |
| 6-Cl | CH=CH | 9-Cl | OCH₃ | OCH₃ | CH | |
| 6-Cl | CH=CH | 9-Cl | Cl | OCH₃ | CH | |
| 6-Cl | CH=CH | 9-Cl | CH₃ | OCH₃ | N | |
| 6-Cl | CH=CH | 9-Cl | OCH₃ | OCH₃ | N | |
| 6-Cl | CH=CH | 9-Cl | CH₃ | CH₃ | N | |
| 6-CH₃ | CH=CH | 7-OCH₃ | CH₃ | CH₃ | CH | |
| 6-CH₃ | CH=CH | 7-OCH₃ | CH₃ | OCH₃ | CH | |
| 6-CH₃ | CH=CH | 7-OCH₃ | OCH₃ | OCH₃ | CH | |
| 6-CH₃ | CH=CH | 7-OCH₃ | Cl | OCH₃ | CH | |
| 6-CH₃ | CH=CH | 7-OCH₃ | H | OCH₃ | N | |
| 6-CH₃ | CH=CH | 7-OCH₃ | OCH₃ | OCH₃ | N | |
| 6-CH₃ | CH=CH | 7-OCH₃ | CH₃ | CH₃ | N | |
| 6-CH₃ | CH=CH | 10-CH₃ | CH₃ | CH₃ | CH | |
| 6-CH₃ | CH=CH | 10-CH₃ | CH₃ | OCH₃ | CH | |
| 6-CH₃ | CH=CH | 10-CH₃ | OCH₃ | OCH₃ | CH | |
| 6-CH₃ | CH=CH | 10-CH₃ | Cl | OCH₃ | CH | |
| 6-CH₃ | CH=CH | 10-CH₃ | CH₃ | OCH₃ | N | |
| 6-CH₃ | CH=CH | 10-CH₃ | OCH₃ | OCH₃ | N | |
| 6-CH₃ | CH=CH | 10-CH₃ | CH₃ | CH₃ | N | |
| 6-CH₃ | CH=CH | 9-F | CH₃ | CH₃ | CH | |
| 6-CH₃ | CH=CH | 9-F | CH₃ | OCH₃ | CH | |
| 6-CH₃ | CH=CH | 9-F | OCH₃ | OCH₃ | CH | |
| 6-CH₃ | CH=CH | 9-F | Cl | OCH₃ | CH | |
| 6-CH₃ | CH=CH | 9-F | CH₃ | OCH₃ | N | |
| 6-CH₃ | CH=CH | 9-F | OCH₃ | OCH₃ | N | |
| 6-CH₃ | CH=CH | 9-F | CH₃ | CH₃ | N | |

TABLE 14

General Formula 14

| R | R₁ | J | E | n | X | Y | Z | m.p. (°C.) |
|---|---|---|---|---|---|---|---|---|
| H | H | CH₂ | N | 0 | CH₃ | CH₃ | CH | |
| H | H | CH₂ | N | 0 | CH₃ | OCH₃ | CH | |
| H | H | CH₂ | N | 0 | OCH₃ | OCH₃ | CH | |
| H | H | CH₂ | N | 0 | CH₃ | CH₃ | N | |
| H | H | CH₂ | N | 0 | CH₃ | OCH₃ | N | |
| H | H | CH₂ | N | 0 | OCH₃ | OCH₃ | N | |
| H | H | CH₂ | N | 1 | CH₃ | CH₃ | CH | |
| H | H | CH₂ | N | 1 | CH₃ | OCH₃ | CH | |
| H | H | CH₂ | N | 1 | OCH₃ | OCH₃ | CH | |
| H | H | CH₂ | N | 1 | CH₃ | CH₃ | N | |
| H | H | CH₂ | N | 1 | CH₃ | OCH₃ | N | |
| H | H | CH₂ | N | 1 | OCH₃ | OCH₃ | N | |
| CH₃ | H | C=O | N | 0 | OCH₃ | Cl | CH | |
| H | H | C=O | CH | 0 | CH₃ | CH₃ | CH | |
| H | H | C=O | CH | 0 | CH₃ | OCH₃ | CH | |
| H | H | C=O | CH | 0 | OCH₃ | OCH₃ | CH | |
| H | H | C=O | CH | 0 | CH₃ | CH₃ | N | |
| H | H | C=O | CH | 0 | CH₃ | OCH₃ | N | |
| H | H | C=O | CH | 0 | OCH₃ | OCH₃ | N | |
| H | H | C=O | CH | 1 | CH₃ | CH₃ | CH | |
| H | H | C=O | CH | 1 | CH₃ | OCH₃ | CH | |
| H | H | C=O | CH | 1 | OCH₃ | OCH₃ | CH | |
| H | H | C=O | CH | 1 | CH₃ | CH₃ | N | |
| H | H | C=O | CH | 1 | CH₃ | OCH₃ | N | |
| H | H | C=O | CH | 1 | OCH₃ | OCH₃ | N | |
| H | H | C=O | CH | 1 | OCH₃ | Cl | CH | |
| H | CH₃ | C=O | CH | 1 | OCH₃ | OCH₃ | CH | |
| H | 6-CH₃ | CH₂ | N | 0 | CH₃ | CH₃ | CH | |
| H | 6-CH₃ | CH₂ | N | 0 | CH₃ | OCH₃ | CH | |
| H | 6-CH₃ | CH₂ | N | 0 | OCH₃ | OCH₃ | CH | |
| H | 6-CH₃ | CH₂ | N | 0 | CH₃ | CH₃ | N | |
| H | 6-CH₃ | CH₂ | N | 0 | CH₃ | OCH₃ | N | |
| H | 6-CH₃ | CH₂ | N | 0 | OCH₃ | OCH₃ | N | |
| H | 6-CH₃ | CH₂ | N | 1 | CH₃ | CH₃ | CH | |
| H | 6-CH₃ | CH₂ | N | 1 | CH₃ | OCH₃ | CH | |
| H | 6-CH₃ | CH₂ | N | 1 | OCH₃ | OCH₃ | CH | |
| H | 6-CH₃ | CH₂ | N | 1 | CH₃ | CH₃ | N | |

TABLE 14-continued

General Formula 14

| R | R₁ | J | E | n | X | Y | Z | m.p. (°C.) |
|---|---|---|---|---|---|---|---|---|
| H | 6-CH₃ | CH₂ | N | 1 | CH₃ | OCH₃ | N | |
| H | 6-CH₃ | CH₂ | N | 1 | OCH₃ | OCH₃ | N | |
| H | 6-CH₃ | CH₂ | N | 1 | OCH₃ | Cl | CH | |
| CH₃ | 6-CH₃ | CH₂ | N | 0 | OCH₃ | OCH₃ | CH | |
| H | 6-CH₃ | C=O | CH | 0 | CH₃ | CH₃ | CH | |
| H | 6-CH₃ | C=O | CH | 0 | CH₃ | OCH₃ | CH | |
| H | 6-CH₃ | C=O | CH | 0 | OCH₃ | OCH₃ | CH | |
| H | 6-CH₃ | C=O | CH | 0 | CH₃ | CH₃ | N | |
| H | 6-CH₃ | C=O | CH | 0 | CH₃ | OCH₃ | N | |
| H | 6-CH₃ | C=O | CH | 0 | OCH₃ | OCH₃ | N | |
| H | 6-CH₃ | C=O | CH | 1 | CH₃ | CH₃ | CH | |
| H | 6-CH₃ | C=O | CH | 1 | CH₃ | OCH₃ | CH | |
| H | 6-CH₃ | C=O | CH | 1 | OCH₃ | OCH₃ | CH | |
| H | 6-CH₃ | C=O | CH | 1 | CH₃ | CH₃ | N | |
| H | 6-CH₃ | C=O | CH | 1 | CH₃ | OCH₃ | N | |
| H | 6-CH₃ | C=O | CH | 1 | OCH₃ | OCH₃ | N | |
| H | 6-CH₃ | C=O | CH | 1 | OCH₃ | Cl | CH | |
| H | 6-CH₃ | C=O | CH | 1 | OCH₃ | OCH₃ | CH | |

TABLE 15

General Formula 15

| R₁ | G | W' | R₉ | X | Y | Z | m.p. (°C.) |
|---|---|---|---|---|---|---|---|
| H | CH₂ | O | H | CH₃ | CH₃ | CH | |
| H | CH₂ | O | H | CH₃ | OCH₃ | CH | |
| H | CH₂ | O | H | OCH₃ | OCH₃ | CH | |
| H | CH₂ | O | H | Cl | OCH₃ | CH | |
| H | CH₂ | O | H | CH₃ | OCH₃ | N | |
| H | CH₂ | O | H | OCH₃ | OCH₃ | N | |
| H | CH₂ | O | H | CH₃ | CH₃ | N | |
| H | CH₂ | S | CH₃ | CH₃ | CH₃ | CH | |
| H | CH₂ | S | CH₃ | CH₃ | OCH₃ | CH | |
| H | CH₂ | S | CH₃ | Cl | OCH₃ | CH | |
| H | CH₂ | S | CH₃ | CH₃ | OCH₃ | N | |
| H | CH₂ | S | CH₃ | OCH₃ | OCH₃ | N | |
| H | CH₂ | S | CH₃ | CH₃ | CH₃ | N | |
| H | CH₂ | NH | H | CH₃ | CH₃ | CH | |
| H | CH₂ | NH | H | CH₃ | OCH₃ | CH | |
| H | CH₂ | NH | H | OCH₃ | OCH₃ | CH | |
| H | CH₂ | NH | H | Cl | OCH₃ | CH | |
| H | CH₂ | NH | H | CH₃ | OCH₃ | N | |
| H | CH₂ | NH | H | OCH₃ | OCH₃ | N | |
| H | CH₂ | NH | H | CH₃ | CH₃ | N | |
| 6-Cl | CH₂ | O | H | CH₃ | CH₃ | CH | |
| 6-Cl | CH₂ | O | H | CH₃ | OCH₃ | CH | |
| 6-Cl | CH₂ | O | H | OCH₃ | OCH₃ | CH | |
| 6-Cl | CH₂ | O | H | Cl | OCH₃ | CH | |
| 6-Cl | CH₂ | O | H | CH₃ | OCH₃ | N | |
| 6-Cl | CH₂ | O | H | OCH₃ | OCH₃ | N | |
| 6-Cl | CH₂ | O | H | CH₃ | CH₃ | N | |
| 6-Cl | CH₂ | S | CH₃ | CH₃ | CH₃ | CH | |
| 6-Cl | CH₂ | S | CH₃ | CH₃ | OCH₃ | CH | |
| 6-Cl | CH₂ | S | CH₃ | OCH₃ | OCH₃ | CH | |
| 6-Cl | CH₂ | S | CH₃ | Cl | OCH₃ | CH | |
| 6-Cl | CH₂ | S | CH₃ | CH₃ | OCH₃ | N | |
| 6-Cl | CH₂ | S | CH₃ | OCH₃ | OCH₃ | N | |
| 6-Cl | CH₂ | S | CH₃ | CH₃ | CH₃ | N | |
| 6-Cl | CH₂ | NH | H | CH | CH₃ | CH | |
| 6-Cl | CH₂ | NH | H | CH₃ | OCH₃ | CH | |
| 6-Cl | CH₂ | NH | H | OCH₃ | OCH₃ | CH | |
| 6-Cl | CH₂ | NH | H | Cl | OCH₃ | CH | |
| 6-Cl | CH₂ | NH | H | CH₃ | OCH₃ | N | |
| 6-Cl | CH₂ | NH | H | OCH₃ | OCH₃ | N | |
| 6-Cl | CH₂ | NH | H | CH₃ | CH₃ | N | |
| H | CH₂ | S | H | OCH₃ | OCH₃ | CH | |
| H | CH₂ | S | H | CH₃ | OCH₃ | CH | |
| H | CH₂ | S | H | CH₃ | CH₃ | N | |
| H | CH₂ | S | H | OCH₃ | OCH₃ | N | |
| H | CH₂ | S | H | Cl | OCH₃ | CH | |
| H | CH₂ | NCH₃ | H | OCH₃ | OCH₃ | CH | |
| H | CH₂ | NCH₃ | H | CH₃ | OCH₃ | N | |
| H | CH₂CH₂ | O | H | CH₃ | CH₃ | CH | |
| H | CH₂CH₂ | O | H | CH₃ | OCH₃ | CH | |
| H | CH₂CH₂ | O | H | OCH₃ | OCH₃ | CH | |

TABLE 15-continued

General Formula 15

| R1 | G | W' | R9 | X | Y | Z | m.p. (°C.) |
|---|---|---|---|---|---|---|---|
| H | CH2CH2 | O | H | Cl | OCH3 | CH | |
| H | CH2CH2 | O | H | CH3 | OCH3 | N | |
| H | CH2CH2 | O | H | OCH3 | OCH3 | N | |
| H | CH2CH2 | O | H | CH3 | CH3 | N | |
| H | CH2CH2 | S | CH3 | CH3 | CH3 | CH | |
| H | CH2CH2 | S | CH3 | CH3 | OCH3 | CH | |
| H | CH2CH2 | S | CH3 | OCH3 | OCH3 | CH | |
| H | CH2CH2 | S | CH3 | Cl | OCH3 | CH | |
| H | CH2CH2 | S | CH3 | CH3 | OCH3 | N | |
| H | CH2CH2 | S | CH3 | OCH3 | OCH3 | N | |
| H | CH2CH2 | S | CH3 | CH3 | CH3 | N | |
| H | CH2CH2 | NH | H | CH3 | CH3 | CH | |
| H | CH2CH2 | NH | H | CH3 | OCH3 | CH | |
| H | CH2CH2 | NH | H | OCH3 | OCH3 | CH | |
| H | CH2CH2 | NH | H | Cl | OCH3 | CH | |
| H | CH2CH2 | NH | H | CH3 | OCH3 | N | |
| H | CH2CH2 | NH | H | OCH3 | OCH3 | N | |
| H | CH2CH2 | NH | H | CH3 | CH3 | N | |
| 6-Cl | CH2CH2 | O | H | CH3 | OCH3 | CH | |
| 6-Cl | CH2CH2 | O | H | OCH3 | OCH3 | CH | |
| 6-Cl | CH2CH2 | O | H | Cl | OCH3 | CH | |
| 6-Cl | CH2CH2 | O | H | CH3 | OCH3 | N | |
| 6-Cl | CH2CH2 | O | H | OCH3 | OCH3 | N | |
| 6-Cl | CH2CH2 | O | H | CH3 | CH3 | N | |
| 6-Cl | CH2CH2 | S | CH3 | CH3 | CH3 | CH | |
| 6-Cl | CH2CH2 | S | CH3 | CH3 | OCH3 | CH | |
| 6-Cl | CH2CH2 | S | CH3 | OCH3 | OCH3 | CH | |
| 6-Cl | CH2CH2 | S | CH3 | Cl | OCH3 | CH | |
| 6-Cl | CH2CH2 | S | CH3 | CH3 | OCH3 | N | |
| 6-Cl | CH2CH2 | S | CH3 | OCH3 | OCH3 | N | |
| 6-Cl | CH2CH2 | S | CH3 | CH3 | CH3 | N | |
| 6-Cl | CH2CH2 | NH | H | CH | CH3 | CH | |
| 6-Cl | CH2CH2 | NH | H | CH3 | OCH3 | CH | |
| 6-Cl | CH2CH2 | NH | H | OCH3 | OCH3 | CH | |
| 6-Cl | CH2CH2 | NH | H | Cl | OCH3 | CH | |
| 6-Cl | CH2CH2 | NH | H | CH3 | OCH3 | N | |
| 6-Cl | CH2CH2 | NH | H | OCH3 | OCH3 | N | |
| 6-Cl | CH2CH2 | NH | H | CH3 | CH3 | N | |
| H | CH2CH2 | S | H | OCH3 | OCH3 | CH | |
| H | CH2CH2 | S | H | CH3 | OCH3 | CH | |
| H | CH2CH2 | S | H | CH3 | CH3 | CH | |
| H | CH2CH2 | S | H | CH3 | OCH3 | N | |
| H | CH2CH2 | S | H | OCH3 | OCH3 | N | |
| H | CH2CH2 | S | H | Cl | OCH3 | CH | |
| H | CH2CH2 | NCH3 | H | OCH3 | OCH3 | CH | |
| H | CH2CH2 | NCH3 | H | CH3 | OCH3 | N | |
| H | CH=CH | O | H | CH3 | CH3 | CH | |
| H | CH=CH | O | H | CH3 | OCH3 | CH | |
| H | CH=CH | O | H | OCH3 | OCH3 | CH | |
| H | CH=CH | O | H | Cl | OCH3 | CH | |
| H | CH=CH | O | H | CH3 | OCH3 | N | |
| H | CH=CH | O | H | OCH3 | OCH3 | N | |
| H | CH=CH | O | H | CH3 | CH3 | N | |
| H | CH=CH | S | CH3 | CH3 | CH3 | CH | |
| H | CH=CH | S | CH3 | CH3 | OCH3 | CH | |
| H | CH=CH | S | CH3 | OCH3 | OCH3 | CH | |
| H | CH=CH | S | CH3 | Cl | OCH3 | CH | |
| H | CH=CH | S | CH3 | CH3 | OCH3 | N | |
| H | CH=CH | S | CH3 | OCH3 | OCH3 | N | |
| H | CH=CH | S | CH3 | CH3 | CH3 | N | |
| H | CH=CH | NH | H | CH3 | CH3 | CH | |
| H | CH=CH | NH | H | CH3 | OCH3 | CH | |
| H | CH=CH | NH | H | OCH3 | OCH3 | CH | |
| H | CH=CH | NH | H | Cl | OCH3 | CH | |
| H | CH=CH | NH | H | CH3 | OCH3 | N | |
| H | CH=CH | NH | H | OCH3 | OCH3 | N | |
| H | CH=CH | NH | H | CH3 | CH3 | N | |
| 6-Cl | CH=CH | O | H | CH3 | CH3 | CH | |
| 6-Cl | CH=CH | O | H | CH3 | OCH3 | CH | |
| 6-Cl | CH=CH | O | H | OCH3 | OCH3 | CH | |
| 6-Cl | CH=CH | O | H | Cl | OCH3 | CH | |
| 6-Cl | CH=CH | O | H | CH3 | OCH3 | N | |
| 6-Cl | CH=CH | O | H | OCH3 | OCH3 | N | |
| 6-Cl | CH=CH | O | H | CH3 | CH3 | N | |
| 6-Cl | CH=CH | S | CH3 | CH3 | CH3 | CH | |
| 6-Cl | CH=CH | S | CH3 | CH3 | OCH3 | CH | |
| 6-Cl | CH=CH | S | CH3 | OCH3 | OCH3 | CH | |
| 6-Cl | CH=CH | S | CH3 | Cl | OCH3 | CH | |
| 6-Cl | CH=CH | S | CH3 | CH3 | OCH3 | N | |
| 6-Cl | CH=CH | S | CH3 | OCH3 | OCH3 | N | |
| 6-Cl | CH=CH | S | CH3 | CH3 | CH3 | N | |
| 6-Cl | CH=CH | NH | H | CH | CH3 | CH | |
| 6-Cl | CH=CH | NH | H | CH3 | OCH3 | CH | |
| 6-Cl | CH=CH | NH | H | OCH3 | OCH3 | CH | |
| 6-Cl | CH=CH | NH | H | Cl | OCH3 | CH | |
| 6-Cl | CH=CH | NH | H | CH3 | OCH3 | N | |
| 6-Cl | CH=CH | NH | H | OCH3 | OCH3 | N | |
| 6-Cl | CH=CH | NH | H | CH3 | CH3 | N | |
| H | CH=CH | S | H | OCH3 | OCH3 | CH | |
| H | CH=CH | S | H | CH3 | OCH3 | CH | |
| H | CH=CH | S | H | CH3 | CH3 | CH | |
| H | CH=CH | S | H | CH3 | OCH3 | N | |
| H | CH=CH | S | H | OCH3 | OCH3 | N | |
| H | CH=CH | S | H | Cl | OCH3 | CH | |
| H | CH=CH | NCH3 | H | OCH3 | OCH3 | CH | |
| H | CH=CH | NCH3 | H | CH3 | OCH3 | N | |

TABLE 16

General Formula 16

| R1 | G | X | Y | Z | m.p. (°C.) |
|---|---|---|---|---|---|
| H | CH2 | OCH3 | OCH3 | CH | |
| H | CH2 | CH3 | OCH3 | CH | |
| H | CH2 | Cl | OCH3 | CH | |
| H | CH2 | CH3 | CH3 | CH | |
| H | CH2 | OCH3 | OCH3 | N | |
| H | CH2 | CH3 | OCH3 | N | |
| H | CH2CH2 | OCH3 | OCH3 | CH | |
| H | CH2CH2 | CH3 | OCH3 | CH | |
| H | CH2CH2 | Cl | OCH3 | CH | |
| H | CH2CH2 | CH3 | CH3 | CH | |
| H | CH2CH2 | OCH3 | OCH3 | N | |
| H | CH2CH2 | CH3 | OCH3 | N | |
| H | CH=CH | OCH3 | OCH3 | CH | |
| H | CH=CH | CH3 | OCH3 | CH | |
| H | CH=CH | CH3 | CH3 | CH | |
| H | CH=CH | OCH3 | OCH3 | N | |
| H | CH=CH | CH3 | OCH3 | N | |
| H | CH=CH | Cl | OCH3 | N | |
| 6-CH3 | CH2 | OCH3 | OCH3 | CH | |
| 6-CH3 | CH2 | CH3 | OCH3 | CH | |
| 6-CH3 | CH2 | CH3 | CH3 | N | |
| 6-Cl | CH2 | OCH3 | OCH3 | CH | |
| 6-Cl | CH2 | OCH3 | OCH3 | N | |
| 6-Cl | CH2 | CH3 | OCH3 | CH | |
| 5-OCH3 | CH2 | OCH3 | OCH3 | CH | |
| 5-OCH3 | CH2 | CH3 | OCH3 | CH | |
| 6-CH3 | CH2CH2 | OCH3 | OCH3 | CH | |
| 6-CH3 | CH2CH2 | CH3 | OCH3 | CH | |
| 6-Cl | CH2CH2 | OCH3 | OCH3 | CH | |
| 6-Cl | CH2CH2 | CH3 | OCH3 | CH | |
| 5-OCH3 | CH2CH2 | OCH3 | OCH3 | CH | |
| 5-OCH3 | CH2CH2 | CH3 | OCH3 | CH | |
| 6-CH3 | CH=CH | OCH3 | OCH3 | CH | |
| 6-CH3 | CH=CH | CH3 | OCH3 | CH | |
| 6-Cl | CH=CH | OCH3 | OCH3 | CH | |
| 6-Cl | CH=CH | CH3 | OCH3 | CH | |

TABLE 17

General Formula 17

| R1 | G | R12 | X | Y | Z | m.p. (°C.) |
|---|---|---|---|---|---|---|
| H | CH2 | H | CH3 | CH3 | CH | |
| H | CH2 | H | CH3 | OCH3 | CH | |
| H | CH2 | H | OCH3 | OCH3 | CH | |
| H | CH2 | H | Cl | OCH3 | CH | |
| H | CH2 | H | CH3 | OCH3 | N | |
| H | CH2 | H | CH3 | CH3 | N | |
| H | CH2 | CH3 | CH3 | CH3 | CH | |
| H | CH2 | CH3 | CH3 | OCH3 | CH | |
| H | CH2 | CH3 | OCH3 | OCH3 | CH | |

TABLE 17-continued

General Formula 17

| R₁ | G | R₁₂ | X | Y | Z | m.p. (°C.) |
|---|---|---|---|---|---|---|
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | CH₂ | C₆H₅ | CH₃ | CH₃ | CH | |
| H | CH₂ | C₆H₅ | CH₃ | OCH₃ | CH | |
| H | CH₂ | C₆H₅ | OCH₃ | OCH₃ | CH | |
| H | CH₂ | C₆H₅ | Cl | OCH₃ | CH | |
| H | CH₂ | C₆H₅ | CH₃ | OCH₃ | N | |
| H | CH₂ | C₆H₅ | OCH₃ | OCH₃ | N | |
| H | CH₂ | C₆H₅ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | OCH₃ | CH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | CH₂ | C₆H₅ | CH₃ | CH₃ | CH | |
| 6-CH₃ | CH₂ | C₆H₅ | CH₃ | OCH₃ | CH | |
| 6-CH₃ | CH₂ | C₆H₅ | OCH₃ | OCH₃ | CH | |
| 6-CH₃ | CH₂ | C₆H₅ | Cl | OCH₃ | CH | |
| 6-CH₃ | CH₂ | C₆H₅ | CH₃ | OCH₃ | N | |
| 6-CH₃ | CH₂ | C₆H₅ | OCH₃ | OCH₃ | N | |
| 6-CH₃ | CH₂ | C₆H₅ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | OCH₃ | CH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | CH₂ | C₆H₅ | CH₃ | CH₃ | CH | |
| 6-Cl | CH₂ | C₆H₅ | CH₃ | OCH₃ | CH | |
| 6-Cl | CH₂ | C₆H₅ | OCH₃ | OCH₃ | CH | |
| 6-Cl | CH₂ | C₆H₅ | Cl | OCH₃ | CH | |
| 6-Cl | CH₂ | C₆H₅ | CH₃ | OCH₃ | N | |
| 6-Cl | CH₂ | C₆H₅ | OCH₃ | OCH₃ | N | |
| 6-Cl | CH₂ | C₆H₅ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| H | CH₂CH₂ | C₆H₅ | CH₃ | CH₃ | CH | |
| H | CH₂CH₂ | C₆H₅ | CH₃ | OCH₃ | CH | |
| H | CH₂CH₂ | C₆H₅ | OCH₃ | OCH₃ | CH | |
| H | CH₂CH₂ | C₆H₅ | Cl | OCH₃ | CH | |
| H | CH₂CH₂ | C₆H₅ | CH₃ | OCH₃ | N | |
| H | CH₂CH₂ | C₆H₅ | OCH₃ | OCH₃ | N | |
| H | CH₂CH₂ | C₆H₅ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | OCH₃ | CH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| 6-CH₃ | CH₂CH₂ | C₆H₅ | CH₃ | CH₃ | CH | |
| 6-CH₃ | CH₂CH₂ | C₆H₅ | CH₃ | OCH₃ | CH | |
| 6-CH₃ | CH₂CH₂ | C₆H₅ | OCH₃ | OCH₃ | CH | |
| 6-CH₃ | CH₂CH₂ | C₆H₅ | Cl | OCH₃ | CH | |
| 6-CH₃ | CH₂CH₂ | C₆H₅ | CH₃ | OCH₃ | N | |
| 6-CH₃ | CH₂CH₂ | C₆H₅ | OCH₃ | OCH₃ | N | |
| 6-CH₃ | CH₂CH₂ | C₆H₅ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | OCH₃ | CH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| 6-Cl | CH₂CH₂ | C₆H₅ | CH₃ | CH₃ | CH | |
| 6-Cl | CH₂CH₂ | C₆H₅ | CH₃ | OCH₃ | CH | |
| 6-Cl | CH₂CH₂ | C₆H₅ | OCH₃ | OCH₃ | CH | |
| 6-Cl | CH₂CH₂ | C₆H₅ | Cl | OCH₃ | CH | |
| 6-Cl | CH₂CH₂ | C₆H₅ | CH₃ | OCH₃ | N | |
| 6-Cl | CH₂CH₂ | C₆H₅ | OCH₃ | OCH₃ | N | |
| 6-Cl | CH₂CH₂ | C₆H₅ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| H | CH=CH | C₆H₅ | CH₃ | CH₃ | CH | |
| H | CH=CH | C₆H₅ | CH₃ | OCH₃ | CH | |
| H | CH=CH | C₆H₅ | OCH₃ | OCH₃ | CH | |
| H | CH=CH | C₆H₅ | Cl | OCH₃ | CH | |
| H | CH=CH | C₆H₅ | CH₃ | OCH₃ | N | |
| H | CH=CH | C₆H₅ | OCH₃ | OCH₃ | N | |
| H | CH=CH | C₆H₅ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | OCH₃ | CH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |
| 6-CH₃ | CH=CH | C₆H₅ | CH₃ | CH₃ | CH | |
| 6-CH₃ | CH=CH | C₆H₅ | CH₃ | OCH₃ | CH | |
| 6-CH₃ | CH=CH | C₆H₅ | Cl | OCH₃ | CH | |
| 6-CH₃ | CH=CH | C₆H₅ | CH₃ | OCH₃ | N | |
| 6-CH₃ | CH=CH | C₆H₅ | OCH₃ | OCH₃ | N | |
| 6-CH₃ | CH=CH | C₆H₅ | CH₃ | CH₃ | N | |

TABLE 17-continued

General Formula 17

| R₁ | G | R₁₂ | X | Y | Z | m.p. (°C.) |
|---|---|---|---|---|---|---|
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | OCH₃ | CH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |
| 6-Cl | CH=CH | C₆H₅ | CH₃ | CH₃ | CH | |
| 6-Cl | CH=CH | C₆H₅ | CH₃ | OCH₃ | CH | |
| 6-Cl | CH=CH | C₆H₅ | OCH₃ | OCH₃ | CH | |
| 6-Cl | CH=CH | C₆H₅ | Cl | OCH₃ | CH | |
| 6-Cl | CH=CH | C₆H₅ | CH₃ | OCH₃ | N | |
| 6-Cl | CH=CH | C₆H₅ | OCH₃ | OCH₃ | N | |
| 6-Cl | CH=CH | C₆H₅ | CH₃ | CH₃ | N | |

TABLE 18

General Formula 18

| R₁ | G | R₁₂ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | OCH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | CH₂ | C₆H₅ | CH₃ | CH₃ | CH | |
| H | CH₂ | C₆H₅ | CH₃ | OCH₃ | CH | |
| H | CH₂ | C₆H₅ | OCH₃ | OCH₃ | CH | |
| H | CH₂ | C₆H₅ | Cl | OCH₃ | CH | |
| H | CH₂ | C₆H₅ | CH₃ | OCH₃ | N | |
| H | CH₂ | C₆H₅ | OCH₃ | OCH₃ | N | |
| H | CH₂ | C₆H₅ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | OCH₃ | CH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | CH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | CH₂ | C₆H₅ | CH₃ | CH₃ | CH | |
| 6-CH₃ | CH₂ | C₆H₅ | CH₃ | OCH₃ | CH | |
| 6-CH₃ | CH₂ | C₆H₅ | OCH₃ | OCH₃ | CH | |
| 6-CH₃ | CH₂ | C₆H₅ | Cl | OCH₃ | CH | |
| 6-CH₃ | CH₂ | C₆H₅ | CH₃ | OCH₃ | N | |
| 6-CH₃ | CH₂ | C₆H₅ | OCH₃ | OCH₃ | N | |
| 6-CH₃ | CH₂ | C₆H₅ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | OCH₃ | CH₃ | CH | |
| 6-Cl | CH₂ | CH₃ | OCH₃ | OCH₃ | CH | |

TABLE 18-continued

General Formula 18

| R₁ | G | R₁₂ | X | Y | Z | m.p. (°C.) |
|---|---|---|---|---|---|---|
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | CH₂ | C₆H₅ | CH₃ | CH₃ | CH | |
| 6-Cl | CH₂ | C₆H₅ | CH₃ | OCH₃ | CH | |
| 6-Cl | CH₂ | C₆H₅ | OCH₃ | OCH₃ | CH | |
| 6-Cl | CH₂ | C₆H₅ | Cl | OCH₃ | CH | |
| 6-Cl | CH₂ | C₆H₅ | CH₃ | OCH₃ | N | |
| 6-Cl | CH₂ | C₆H₅ | OCH₃ | OCH₃ | N | |
| 6-Cl | CH₂ | C₆H₅ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| H | CH₂CH₂ | C₆H₅ | CH₃ | CH₃ | CH | |
| H | CH₂CH₂ | C₆H₅ | CH₃ | OCH₃ | CH | |
| H | CH₂CH₂ | C₆H₅ | OCH₃ | OCH₃ | CH | |
| H | CH₂CH₂ | C₆H₅ | Cl | OCH₃ | CH | |
| H | CH₂CH₂ | C₆H₅ | CH₃ | OCH₃ | N | |
| H | CH₂CH₂ | C₆H₅ | OCH₃ | OCH₃ | N | |
| H | CH₂CH₂ | C₆H₅ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | OCH₃ | CH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| 6-CH₃ | CH₂CH₂ | C₆H₅ | CH₃ | CH₃ | CH | |
| 6-CH₃ | CH₂CH₂ | C₆H₅ | CH₃ | OCH₃ | CH | |
| 6-CH₃ | CH₂CH₂ | C₆H₅ | OCH₃ | OCH₃ | CH | |
| 6-CH₃ | CH₂CH₂ | C₆H₅ | Cl | OCH₃ | CH | |
| 6-CH₃ | CH₂CH₂ | C₆H₅ | CH₃ | OCH₃ | N | |
| 6-CH₃ | CH₂CH₂ | C₆H₅ | OCH₃ | OCH₃ | N | |
| 6-CH₃ | CH₂CH₂ | C₆H₅ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | OCH₃ | CH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| 6-Cl | CH₂CH₂ | C₆H₅ | CH₃ | CH₃ | CH | |
| 6-Cl | CH₂CH₂ | C₆H₅ | CH₃ | OCH₃ | CH | |
| 6-Cl | CH₂CH₂ | C₆H₅ | OCH₃ | OCH₃ | CH | |
| 6-Cl | CH₂CH₂ | C₆H₅ | Cl | OCH₃ | CH | |
| 6-Cl | CH₂CH₂ | C₆H₅ | CH₃ | OCH₃ | N | |
| 6-Cl | CH₂CH₂ | C₆H₅ | OCH₃ | OCH₃ | N | |
| 6-Cl | CH₂CH₂ | C₆H₅ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |

TABLE 18-continued

General Formula 18

| R₁ | G | R₁₂ | X | Y | Z | m.p. (°C.) |
|---|---|---|---|---|---|---|
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| H | CH=CH | C₆H₅ | CH₃ | CH₃ | CH | |
| H | CH=CH | C₆H₅ | CH₃ | OCH₃ | CH | |
| H | CH=CH | C₆H₅ | OCH₃ | OCH₃ | CH | |
| H | CH=CH | C₆H₅ | Cl | OCH₃ | CH | |
| H | CH=CH | C₆H₅ | CH₃ | OCH₃ | N | |
| H | CH=CH | C₆H₅ | OCH₃ | OCH₃ | N | |
| H | CH=CH | C₆H₅ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | OCH₃ | CH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |
| 6-CH₃ | CH=CH | C₆H₅ | CH₃ | CH₃ | CH | |
| 6-CH₃ | CH=CH | C₆H₅ | CH₃ | OCH₃ | CH | |
| 6-CH₃ | CH=CH | C₆H₅ | OCH₃ | OCH₃ | CH | |
| 6-CH₃ | CH=CH | C₆H₅ | Cl | OCH₃ | CH | |
| 6-CH₃ | CH=CH | C₆H₅ | CH₃ | OCH₃ | N | |
| 6-CH₃ | CH=CH | C₆H₅ | OCH₃ | OCH₃ | N | |
| 6-CH₃ | CH=CH | C₆H₅ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | OCH₃ | CH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |
| 6-Cl | CH=CH | C₆H₅ | CH₃ | CH₃ | CH | |
| 6-Cl | CH=CH | C₆H₅ | CH₃ | OCH₃ | CH | |
| 6-Cl | CH=CH | C₆H₅ | OCH₃ | OCH₃ | CH | |
| 6-Cl | CH=CH | C₆H₅ | Cl | OCH₃ | CH | |
| 6-Cl | CH=CH | C₆H₅ | CH₃ | OCH₃ | N | |
| 6-Cl | CH=CH | C₆H₅ | OCH₃ | OCH₃ | N | |
| 6-Cl | CH=CH | C₆H₅ | CH₃ | CH₃ | N | |

TABLE 19

General Formula 19

| R₁ | G | R₉ | R₁₃ | X | Y | Z | m.p. (°C.) |
|---|---|---|---|---|---|---|---|
| H | CH₂ | H | OCH₃ | OCH₃ | OCH₃ | CH | |
| H | CH₂ | H | OCH₃ | OCH₃ | OCH₃ | N | |
| H | CH₂ | H | OCH₃ | OCH₃ | CH₃ | CH | |
| H | CH₂ | H | OCH₃ | OCH₃ | CH₃ | N | |
| H | CH₂CH₂ | H | OCH₃ | OCH₃ | OCH₃ | CH | |
| H | CH₂CH₂ | H | OCH₃ | OCH₃ | OCH₃ | N | |
| H | CH₂CH₂ | H | OCH₃ | OCH₃ | CH₃ | CH | |
| H | CH₂CH₂ | H | OCH₃ | OCH₃ | CH₃ | N | |
| H | CH=CH | H | OCH₃ | OCH₃ | OCH₃ | CH | |
| H | CH=CH | H | OCH₃ | OCH₃ | OCH₃ | N | |
| H | CH=CH | H | OCH₃ | OCH₃ | CH₃ | CH | |
| H | CH=CH | H | OCH₃ | OCH₃ | CH₃ | N | |
| H | CH₂ | CH₃ | OCH₃ | OCH₃ | OCH₃ | CH | |
| H | CH₂ | CH₃ | OCH₃ | OCH₃ | OCH₃ | N | |
| H | CH₂ | CH₃ | OCH₃ | OCH₃ | CH₃ | CH | |

TABLE 19-continued

General Formula 19

| R₁ | G | R₉ | R₁₃ | X | Y | Z | m.p. (°C.) |
|---|---|---|---|---|---|---|---|
| H | CH₂ | CH₃ | OCH₃ | CH₃ | OCH₃ | N | |
| H | CH₂CH₂ | CH₃ | OCH₃ | OCH₃ | OCH₃ | CH | |
| H | CH₂CH₂ | CH₃ | OCH₃ | OCH₃ | OCH₃ | N | |
| H | CH₂CH₂ | CH₃ | OCH₃ | CH₃ | OCH₃ | CH | |
| H | CH₂CH₂ | CH₃ | OCH₃ | CH₃ | OCH₃ | N | |
| H | CH=CH | CH₃ | OCH₃ | OCH₃ | OCH₃ | CH | |
| H | CH=CH | CH₃ | OCH₃ | OCH₃ | OCH₃ | N | |
| H | CH=CH | CH₃ | OCH₃ | CH₃ | OCH₃ | CH | |
| H | CH=CH | CH₃ | OCH₃ | CH₃ | OCH₃ | N | |
| H | CH₂ | H | CH₃ | OCH₃ | OCH₃ | CH | |
| H | CH₂ | H | CH₃ | CH₃ | OCH₃ | CH | |
| H | CH₂CH₂ | H | CH₃ | OCH₃ | OCH₃ | CH | |
| H | CH₂CH₂ | H | CH₃ | CH₃ | OCH₃ | CH | |
| H | CH=CH | H | CH₃ | OCH₃ | OCH₃ | CH | |
| H | CH=CH | H | CH₃ | OCH₃ | OCH₃ | N | |
| H | CH₂ | H | SCH₃ | OCH₃ | OCH₃ | CH | |
| H | CH₂ | H | SCH₃ | CH₃ | OCH₃ | CH | |
| H | CH₂CH₂ | H | SCH₃ | OCH₃ | OCH₃ | CH | |
| H | CH₂CH₂ | H | SCH₃ | CH₃ | OCH₃ | CH | |
| H | CH=CH | H | SCH₃ | OCH₃ | OCH₃ | CH | |
| H | CH=CH | H | SCH₃ | CH₃ | OCH₃ | CH | |

TABLE 20

General Formula 20

| R₁ | G | R₆ | R₇ | X | Y | Z | m.p. (°C.) |
|---|---|---|---|---|---|---|---|
| H | CH₂ | H | CH₃ | CH₃ | CH₃ | CH | |
| H | CH₂ | H | CH₃ | CH₃ | OCH₃ | CH | |
| H | CH₂ | H | CH₃ | OCH₃ | OCH₃ | CH | |
| H | CH₂ | H | CH₃ | Cl | OCH₃ | CH | |
| H | CH₂ | H | CH₃ | CH₃ | OCH₃ | N | |
| H | CH₂ | H | CH₃ | OCH₃ | OCH₃ | N | |
| H | CH₂ | H | CH₃ | CH₃ | CH₃ | N | |
| H | CH₂ | CH₃ | CH₃ | CH₃ | CH₃ | CH | |
| H | CH₂ | CH₃ | CH₃ | CH₃ | OCH₃ | CH | |
| H | CH₂ | CH₃ | CH₃ | OCH₃ | OCH₃ | CH | |
| H | CH₂ | CH₃ | CH₃ | Cl | OCH₃ | CH | |
| H | CH₂ | CH₃ | CH₃ | CH₃ | OCH₃ | N | |
| H | CH₂ | CH₃ | CH₃ | OCH₃ | OCH₃ | N | |
| H | CH₂ | CH₃ | CH₃ | CH₃ | CH₃ | N | |
| H | CH₂ | C₆H₅ | CH₃ | CH₃ | CH₃ | CH | |
| H | CH₂ | C₆H₅ | CH₃ | CH₃ | OCH₃ | CH | |
| H | CH₂ | C₆H₅ | CH₃ | OCH₃ | OCH₃ | CH | |
| H | CH₂ | C₆H₅ | CH₃ | Cl | OCH₃ | CH | |
| H | CH₂ | C₆H₅ | CH₃ | CH₃ | OCH₃ | N | |
| H | CH₂ | C₆H₅ | CH₃ | CH₃ | CH₃ | N | |
| H | CH₂ | H | H | CH₃ | CH₃ | CH | |
| H | CH₂ | H | H | CH₃ | OCH₃ | CH | |
| H | CH₂ | H | H | OCH₃ | OCH₃ | CH | |
| H | CH₂ | H | H | Cl | OCH₃ | CH | |
| H | CH₂ | H | H | CH₃ | OCH₃ | N | |
| H | CH₂ | H | H | OCH₃ | OCH₃ | N | |
| H | CH₂ | H | H | CH₃ | CH₃ | N | |
| H | CH₂ | C₆H₅ | H | CH₃ | CH₃ | CH | |
| H | CH₂ | C₆H₅ | H | CH₃ | OCH₃ | CH | |
| H | CH₂ | C₆H₅ | H | OCH₃ | OCH₃ | CH | |
| H | CH₂ | C₆H₅ | H | Cl | OCH₃ | CH | |
| H | CH₂ | C₆H₅ | H | CH₃ | OCH₃ | N | |
| H | CH₂ | C₆H₅ | H | OCH₃ | OCH₃ | N | |
| H | CH₂ | C₆H₅ | H | CH₃ | CH₃ | N | |
| 6-Cl | CH₂ | CH₃ | H | CH₃ | CH₃ | CH | |
| 6-Cl | CH₂ | CH₃ | H | CH₃ | OCH₃ | CH | |
| 6-Cl | CH₂ | CH₃ | H | OCH₃ | OCH₃ | CH | |
| 6-Cl | CH₂ | CH₃ | H | Cl | OCH₃ | CH | |
| 6-Cl | CH₂ | CH₃ | H | CH₃ | OCH₃ | N | |
| 6-Cl | CH₂ | CH₃ | H | OCH₃ | OCH₃ | N | |
| 6-Cl | CH₂ | C₆H₅ | H | CH₃ | CH₃ | CH | |
| 6-Cl | CH₂ | C₆H₅ | H | CH₃ | OCH₃ | CH | |
| 6-Cl | CH₂ | C₆H₅ | H | OCH₃ | OCH₃ | CH | |
| 6-Cl | CH₂ | C₆H₅ | H | Cl | OCH₃ | CH | |
| 6-Cl | CH₂ | C₆H₅ | H | CH₃ | OCH₃ | N | |
| 6-Cl | CH₂ | C₆H₅ | H | OCH₃ | OCH₃ | N | |
| H | CH₂CH₂ | H | CH₃ | CH₃ | CH₃ | CH | |
| H | CH₂CH₂ | H | CH₃ | CH₃ | OCH₃ | CH | |
| H | CH₂CH₂ | H | CH₃ | OCH₃ | OCH₃ | CH | |
| H | CH₂CH₂ | H | CH₃ | Cl | OCH₃ | CH | |
| H | CH₂CH₂ | H | CH₃ | CH₃ | OCH₃ | N | |

TABLE 20-continued

General Formula 20

| R₁ | G | R₆ | R₇ | X | Y | Z | m.p. (°C.) |
|---|---|---|---|---|---|---|---|
| H | CH₂CH₂ | H | CH₃ | OCH₃ | OCH₃ | N | |
| H | CH₂CH₂ | H | CH₃ | CH₃ | CH₃ | N | |
| H | CH₂CH₂ | CH₃ | CH₃ | CH₃ | CH₃ | CH | |
| H | CH₂CH₂ | CH₃ | CH₃ | OCH₃ | OCH₃ | CH | |
| H | CH₂CH₂ | CH₃ | CH₃ | Cl | OCH₃ | CH | |
| H | CH₂CH₂ | CH₃ | CH₃ | CH₃ | OCH₃ | N | |
| H | CH₂CH₂ | CH₃ | CH₃ | OCH₃ | OCH₃ | N | |
| H | CH₂CH₂ | CH₃ | CH₃ | CH₃ | CH₃ | N | |
| H | CH₂CH₂ | C₆H₅ | CH₃ | CH₃ | CH₃ | CH | |
| H | CH₂CH₂ | C₆H₅ | CH₃ | CH₃ | OCH₃ | CH | |
| H | CH₂CH₂ | C₆H₅ | CH₃ | OCH₃ | OCH₃ | CH | |
| H | CH₂CH₂ | C₆H₅ | CH₃ | Cl | OCH₃ | CH | |
| H | CH₂CH₂ | C₆H₅ | CH₃ | CH₃ | OCH₃ | N | |
| H | CH₂CH₂ | C₆H₅ | CH₃ | OCH₃ | OCH₃ | N | |
| H | CH₂CH₂ | C₆H₅ | CH₃ | CH₃ | CH₃ | N | |
| H | CH₂CH₂ | H | H | CH₃ | CH₃ | CH | |
| H | CH₂CH₂ | H | H | CH₃ | OCH₃ | CH | |
| H | CH₂CH₂ | H | H | OCH₃ | OCH₃ | CH | |
| H | CH₂CH₂ | H | H | Cl | OCH₃ | CH | |
| H | CH₂CH₂ | H | H | CH₃ | OCH₃ | N | |
| H | CH₂CH₂ | H | H | OCH₃ | OCH₃ | N | |
| H | CH₂CH₂ | H | H | CH₃ | CH₃ | N | |
| H | CH₂CH₂ | C₆H₅ | H | CH₃ | CH₃ | CH | |
| H | CH₂CH₂ | C₆H₅ | H | CH₃ | OCH₃ | CH | |
| H | CH₂CH₂ | C₆H₅ | H | OCH₃ | OCH₃ | CH | |
| H | CH₂CH₂ | C₆H₅ | H | Cl | OCH₃ | CH | |
| H | CH₂CH₂ | C₆H₅ | H | CH₃ | OCH₃ | N | |
| H | CH₂CH₂ | C₆H₅ | H | OCH₃ | OCH₃ | N | |
| H | CH₂CH₂ | C₆H₅ | H | CH₃ | CH₃ | N | |
| 6-Cl | CH₂CH₂ | CH₃ | H | CH₃ | CH₃ | CH | |
| 6-Cl | CH₂CH₂ | CH₃ | H | CH₃ | OCH₃ | CH | |
| 6-Cl | CH₂CH₂ | CH₃ | H | OCH₃ | OCH₃ | CH | |
| 6-Cl | CH₂CH₂ | CH₃ | H | Cl | OCH₃ | CH | |
| 6-Cl | CH₂CH₂ | CH₃ | H | CH₃ | OCH₃ | N | |
| 6-Cl | CH₂CH₂ | CH₃ | H | OCH₃ | OCH₃ | N | |
| 6-Cl | CH₂CH₂ | C₆H₅ | H | CH₃ | CH₃ | CH | |
| 6-Cl | CH₂CH₂ | C₆H₅ | H | CH₃ | OCH₃ | CH | |
| 6-Cl | CH₂CH₂ | C₆H₅ | H | OCH₃ | OCH₃ | CH | |
| 6-Cl | CH₂CH₂ | C₆H₅ | H | Cl | OCH₃ | CH | |
| 6-Cl | CH₂CH₂ | C₆H₅ | H | CH₃ | OCH₃ | N | |
| 6-Cl | CH₂CH₂ | C₆H₅ | H | OCH₃ | OCH₃ | N | |
| H | CH=CH | H | CH₃ | CH₃ | CH₃ | CH | |
| H | CH=CH | H | CH₃ | CH₃ | OCH₃ | CH | |
| H | CH=CH | H | CH₃ | OCH₃ | OCH₃ | CH | |
| H | CH=CH | H | CH₃ | Cl | OCH₃ | CH | |
| H | CH=CH | H | CH₃ | CH₃ | OCH₃ | N | |
| H | CH=CH | H | CH₃ | OCH₃ | OCH₃ | N | |
| H | CH=CH | H | CH₃ | CH₃ | CH₃ | N | |
| H | CH=CH | CH₃ | CH₃ | CH₃ | CH₃ | CH | |
| H | CH=CH | CH₃ | CH₃ | CH₃ | OCH₃ | CH | |
| H | CH=CH | CH₃ | CH₃ | OCH₃ | OCH₃ | CH | |
| H | CH=CH | CH₃ | CH₃ | Cl | OCH₃ | CH | |
| H | CH=CH | CH₃ | CH₃ | CH₃ | OCH₃ | N | |
| H | CH=CH | CH₃ | CH₃ | OCH₃ | OCH₃ | N | |
| H | CH=CH | CH₃ | CH₃ | CH₃ | CH₃ | N | |
| H | CH=CH | C₆H₅ | CH₃ | CH₃ | CH₃ | CH | |
| H | CH=CH | C₆H₅ | CH₃ | CH₃ | OCH₃ | CH | |
| H | CH=CH | C₆H₅ | CH₃ | OCH₃ | OCH₃ | CH | |
| H | CH=CH | C₆H₅ | CH₃ | Cl | OCH₃ | CH | |
| H | CH=CH | C₆H₅ | CH₃ | CH₃ | OCH₃ | N | |
| H | CH=CH | C₆H₅ | CH₃ | OCH₃ | OCH₃ | N | |
| H | CH=CH | C₆H₅ | CH₃ | CH₃ | CH₃ | N | |
| H | CH=CH | H | H | CH₃ | CH₃ | CH | |
| H | CH=CH | H | H | CH₃ | OCH₃ | CH | |
| H | CH=CH | H | H | OCH₃ | OCH₃ | CH | |
| H | CH=CH | H | H | Cl | OCH₃ | CH | |
| H | CH=CH | H | H | CH₃ | OCH₃ | N | |
| H | CH=CH | H | H | OCH₃ | OCH₃ | N | |
| H | CH=CH | H | H | CH₃ | CH₃ | N | |
| H | CH=CH | C₆H₅ | H | CH₃ | CH₃ | CH | |
| H | CH=CH | C₆H₅ | H | CH₃ | OCH₃ | CH | |
| H | CH=CH | C₆H₅ | H | OCH₃ | OCH₃ | CH | |
| H | CH=CH | C₆H₅ | H | Cl | OCH₃ | CH | |
| H | CH=CH | C₆H₅ | H | CH₃ | OCH₃ | N | |
| H | CH=CH | C₆H₅ | H | OCH₃ | OCH₃ | N | |
| H | CH=CH | C₆H₅ | H | CH₃ | CH₃ | N | |
| 6-Cl | CH=CH | CH₃ | H | CH₃ | CH₃ | CH | |
| 6-Cl | CH=CH | CH₃ | H | CH₃ | OCH₃ | CH | |
| 6-Cl | CH=CH | CH₃ | H | OCH₃ | OCH₃ | CH | |
| 6-Cl | CH=CH | CH₃ | H | Cl | OCH₃ | CH | |
| 6-Cl | CH=CH | CH₃ | H | CH₃ | OCH₃ | N | |
| 6-Cl | CH=CH | CH₃ | H | OCH₃ | OCH₃ | N | |
| 6-Cl | CH=CH | C₆H₅ | H | CH₃ | CH₃ | CH | |
| 6-Cl | CH=CH | C₆H₅ | H | CH₃ | OCH₃ | CH | |
| 6-Cl | CH=CH | C₆H₅ | H | OCH₃ | OCH₃ | CH | |
| 6-Cl | CH=CH | C₆H₅ | H | Cl | OCH₃ | CH | |
| 6-Cl | CH=CH | C₆H₅ | H | CH₃ | OCH₃ | N | |
| 6-Cl | CH=CH | C₆H₅ | H | OCH₃ | OCH₃ | N | |
| H | CH₂ | CH₃ | H | OCH₃ | OCH₃ | CH | |
| H | CH₂ | CH₃ | H | OCH₃ | CH₃ | CH | |
| H | CH₂ | CH₃ | H | CH₃ | CH₃ | CH | |
| H | CH₂ | CH₃ | H | OCH₃ | Cl₃ | CH | |
| H | CH₂ | CH₃ | H | OCH₃ | OCH₃ | N | |
| H | CH₂ | CH₃ | H | OCH₃ | CH₃ | N | |
| H | CH₂CH₂ | CH₃ | H | OCH₃ | OCH₃ | CH | |
| H | CH₂CH₂ | CH₃ | H | OCH₃ | CH₃ | CH | |
| H | CH₂CH₂ | CH₃ | H | CH₃ | CH₃ | CH | |
| H | CH₂CH₂ | CH₃ | H | OCH₃ | Cl₃ | CH | |
| H | CH₂CH₂ | CH₃ | H | OCH₃ | CH₃ | N | |
| H | CH₂CH₂ | CH₃ | H | OCH₃ | OCH₃ | N | |
| H | CH=CH | CH₃ | H | OCH₃ | OCH₃ | CH | |
| H | CH=CH | CH₃ | H | OCH₃ | CH₃ | CH | |
| H | CH=CH | CH₃ | H | CH₃ | CH₃ | CH | |
| H | CH=CH | CH₃ | H | OCH₃ | Cl₃ | CH | |
| H | CH=CH | CH₃ | H | OCH₃ | OCH₃ | N | |
| H | CH=CH | CH₃ | H | OCH₃ | CH₃ | N | |

TABLE 21

General Formula 21

| R₁ | G | R₆ | R₇ | X | Y | Z | m.p. (°C.) |
|---|---|---|---|---|---|---|---|
| H | CH₂ | H | CH₃ | CH₃ | CH₃ | CH | |
| H | CH₂ | H | CH₃ | CH₃ | OCH₃ | CH | |
| H | CH₂ | H | CH₃ | OCH₃ | OCH₃ | CH | |
| H | CH₂ | H | CH₃ | Cl | OCH₃ | CH | |
| H | CH₂ | H | CH₃ | CH₃ | OCH₃ | N | |
| H | CH₂ | H | CH₃ | OCH₃ | OCH₃ | N | |
| H | CH₂ | H | CH₃ | CH₃ | CH₃ | N | |
| H | CH₂ | CH₃ | CH₃ | CH₃ | CH₃ | CH | |
| H | CH₂ | CH₃ | CH₃ | CH₃ | OCH₃ | CH | |
| H | CH₂ | CH₃ | CH₃ | OCH₃ | OCH₃ | CH | |
| H | CH₂ | CH₃ | CH₃ | Cl | OCH₃ | CH | |
| H | CH₂ | CH₃ | CH₃ | CH₃ | OCH₃ | N | |
| H | CH₂ | CH₃ | CH₃ | OCH₃ | OCH₃ | N | |
| H | CH₂ | CH₃ | CH₃ | CH₃ | CH₃ | N | |
| H | CH₂ | C₆H₅ | CH₃ | CH₃ | CH₃ | CH | |
| H | CH₂ | C₆H₅ | CH₃ | CH₃ | OCH₃ | CH | |
| H | CH₂ | C₆H₅ | CH₃ | OCH₃ | OCH₃ | CH | |
| H | CH₂ | C₆H₅ | CH₃ | Cl | OCH₃ | CH | |
| H | CH₂ | C₆H₅ | CH₃ | CH₃ | OCH₃ | N | |
| H | CH₂ | C₆H₅ | CH₃ | OCH₃ | OCH₃ | N | |
| H | CH₂ | C₆H₅ | CH₃ | CH₃ | CH₃ | N | |
| H | CH₂ | H | H | CH₃ | CH₃ | CH | |
| H | CH₂ | H | H | CH₃ | OCH₃ | CH | |
| H | CH₂ | H | H | OCH₃ | OCH₃ | CH | |
| H | CH₂ | H | H | Cl | OCH₃ | CH | |
| H | CH₂ | H | H | CH₃ | OCH₃ | N | |
| H | CH₂ | H | H | OCH₃ | OCH₃ | N | |
| H | CH₂ | H | H | CH₃ | CH₃ | N | |
| H | CH₂ | C₆H₅ | H | CH₃ | CH₃ | CH | |
| H | CH₂ | C₆H₅ | H | CH₃ | OCH₃ | CH | |
| H | CH₂ | C₆H₅ | H | OCH₃ | OCH₃ | CH | |
| H | CH₂ | C₆H₅ | H | Cl | OCH₃ | CH | |
| H | CH₂ | C₆H₅ | H | CH₃ | OCH₃ | N | |
| H | CH₂ | C₆H₅ | H | OCH₃ | OCH₃ | N | |
| H | CH₂ | C₆H₅ | H | CH₃ | CH₃ | N | |
| 6-Cl | CH₂ | CH₃ | H | CH₃ | CH₃ | CH | |
| 6-Cl | CH₂ | CH₃ | H | CH₃ | OCH₃ | CH | |
| 6-Cl | CH₂ | CH₃ | H | OCH₃ | OCH₃ | CH | |
| 6-Cl | CH₂ | CH₃ | H | Cl | OCH₃ | CH | |
| 6-Cl | CH₂ | CH₃ | H | CH₃ | OCH₃ | N | |
| 6-Cl | CH₂ | CH₃ | H | OCH₃ | OCH₃ | N | |
| 6-Cl | CH₂ | C₆H₅ | H | CH₃ | CH₃ | CH | |
| 6-Cl | CH₂ | C₆H₅ | H | CH₃ | OCH₃ | CH | |
| 6-Cl | CH₂ | C₆H₅ | H | OCH₃ | OCH₃ | CH | |
| 6-Cl | CH₂ | C₆H₅ | H | Cl | OCH₃ | CH | |

TABLE 21-continued

General Formula 21

| R₁ | G | R₆ | R₇ | X | Y | Z | m.p. (°C.) |
|---|---|---|---|---|---|---|---|
| 6-Cl | CH₂ | C₆H₅ | H | CH₃ | OCH₃ | N | |
| 6-Cl | CH₂ | C₆H₅ | H | OCH₃ | OCH₃ | N | |
| H | CH₂CH₂ | H | CH₃ | CH₃ | CH₃ | CH | |
| H | CH₂CH₂ | H | CH₃ | CH₃ | OCH₃ | CH | |
| H | CH₂CH₂ | H | CH₃ | OCH₃ | OCH₃ | CH | |
| H | CH₂CH₂ | H | CH₃ | Cl | OCH₃ | CH | |
| H | CH₂CH₂ | H | CH₃ | CH₃ | OCH₃ | N | |
| H | CH₂CH₂ | H | CH₃ | OCH₃ | OCH₃ | N | |
| H | CH₂CH₂ | H | CH₃ | CH₃ | CH₃ | N | |
| H | CH₂CH₂ | CH₃ | CH₃ | CH₃ | CH₃ | CH | |
| H | CH₂CH₂ | CH₃ | CH₃ | CH₃ | OCH₃ | CH | |
| H | CH₂CH₂ | CH₃ | CH₃ | OCH₃ | OCH₃ | CH | |
| H | CH₂CH₂ | CH₃ | CH₃ | Cl | OCH₃ | CH | |
| H | CH₂CH₂ | CH₃ | CH₃ | CH₃ | OCH₃ | N | |
| H | CH₂CH₂ | CH₃ | CH₃ | OCH₃ | OCH₃ | N | |
| H | CH₂CH₂ | CH₃ | CH₃ | CH₃ | CH₃ | N | |
| H | CH₂CH₂ | C₆H₅ | CH₃ | CH₃ | CH₃ | CH | |
| H | CH₂CH₂ | C₆H₅ | CH₃ | CH₃ | OCH₃ | CH | |
| H | CH₂CH₂ | C₆H₅ | CH₃ | OCH₃ | OCH₃ | CH | |
| H | CH₂CH₂ | C₆H₅ | CH₃ | Cl | OCH₃ | CH | |
| H | CH₂CH₂ | C₆H₅ | CH₃ | CH₃ | OCH₃ | N | |
| H | CH₂CH₂ | C₆H₅ | CH₃ | OCH₃ | OCH₃ | N | |
| H | CH₂CH₂ | C₆H₅ | CH₃ | CH₃ | CH₃ | N | |
| H | CH₂CH₂ | H | H | CH₃ | CH₃ | CH | |
| H | CH₂CH₂ | H | H | CH₃ | OCH₃ | CH | |
| H | CH₂CH₂ | H | H | OCH₃ | OCH₃ | CH | |
| H | CH₂CH₂ | H | H | Cl | OCH₃ | CH | |
| H | CH₂CH₂ | H | H | CH₃ | OCH₃ | N | |
| H | CH₂CH₂ | H | H | OCH₃ | OCH₃ | N | |
| H | CH₂CH₂ | H | H | CH₃ | CH₃ | N | |
| H | CH₂CH₂ | C₆H₅ | H | CH₃ | CH₃ | CH | |
| H | CH₂CH₂ | C₆H₅ | H | CH₃ | OCH₃ | CH | |
| H | CH₂CH₂ | C₆H₅ | H | OCH₃ | OCH₃ | CH | |
| H | CH₂CH₂ | C₆H₅ | H | Cl | OCH₃ | CH | |
| H | CH₂CH₂ | C₆H₅ | H | CH₃ | OCH₃ | N | |
| H | CH₂CH₂ | C₆H₅ | H | OCH₃ | OCH₃ | N | |
| H | CH₂CH₂ | C₆H₅ | H | CH₃ | CH₃ | N | |
| 6-Cl | CH₂CH₂ | CH₃ | H | CH₃ | CH₃ | CH | |
| 6-Cl | CH₂CH₂ | CH₃ | H | CH₃ | OCH₃ | CH | |
| 6-Cl | CH₂CH₂ | CH₃ | H | OCH₃ | OCH₃ | CH | |
| 6-Cl | CH₂CH₂ | CH₃ | H | Cl | OCH₃ | CH | |
| 6-Cl | CH₂CH₂ | CH₃ | H | CH₃ | OCH₃ | N | |
| 6-Cl | CH₂CH₂ | CH₃ | H | OCH₃ | OCH₃ | N | |
| 6-Cl | CH₂CH₂ | C₆H₅ | H | CH₃ | CH₃ | CH | |
| 6-Cl | CH₂CH₂ | C₆H₅ | H | CH₃ | OCH₃ | CH | |
| 6-Cl | CH₂CH₂ | C₆H₅ | H | OCH₃ | OCH₃ | CH | |
| 6-Cl | CH₂CH₂ | C₆H₅ | H | Cl | OCH₃ | CH | |
| 6-Cl | CH₂CH₂ | C₆H₅ | H | CH₃ | OCH₃ | N | |
| 6-Cl | CH₂CH₂ | C₆H₅ | H | OCH₃ | OCH₃ | N | |
| H | CH=CH | H | CH₃ | CH₃ | CH₃ | CH | |
| H | CH=CH | H | CH₃ | CH₃ | OCH₃ | CH | |
| H | CH=CH | H | CH₃ | OCH₃ | OCH₃ | CH | |
| H | CH=CH | H | CH₃ | Cl | OCH₃ | CH | |
| H | CH=CH | H | CH₃ | CH₃ | OCH₃ | N | |
| H | CH=CH | H | CH₃ | OCH₃ | OCH₃ | N | |
| H | CH=CH | H | CH₃ | CH₃ | CH₃ | N | |
| H | CH=CH | CH₃ | CH₃ | CH₃ | CH₃ | CH | |
| H | CH=CH | CH₃ | CH₃ | CH₃ | OCH₃ | CH | |
| H | CH=CH | CH₃ | CH₃ | OCH₃ | OCH₃ | CH | |
| H | CH=CH | CH₃ | CH₃ | Cl | OCH₃ | CH | |
| H | CH=CH | CH₃ | CH₃ | CH₃ | OCH₃ | CH | |
| H | CH=CH | CH₃ | CH₃ | OCH₃ | OCH₃ | N | |
| H | CH=CH | CH₃ | CH₃ | CH₃ | CH₃ | N | |
| H | CH=CH | C₆H₅ | CH₃ | CH₃ | CH₃ | CH | |
| H | CH=CH | C₆H₅ | CH₃ | CH₃ | OCH₃ | CH | |
| H | CH=CH | C₆H₅ | CH₃ | OCH₃ | OCH₃ | CH | |
| H | CH=CH | C₆H₅ | CH₃ | Cl | OCH₃ | CH | |
| H | CH=CH | C₆H₅ | CH₃ | CH₃ | OCH₃ | N | |
| H | CH=CH | C₆H₅ | CH₃ | OCH₃ | OCH₃ | N | |
| H | CH=CH | C₆H₅ | CH₃ | CH₃ | CH₃ | N | |
| H | CH=CH | H | H | CH₃ | CH₃ | CH | |
| H | CH=CH | H | H | CH₃ | OCH₃ | CH | |
| H | CH=CH | H | H | OCH₃ | OCH₃ | CH | |
| H | CH=CH | H | H | Cl | OCH₃ | CH | |
| H | CH=CH | H | H | CH₃ | OCH₃ | N | |
| H | CH=CH | H | H | OCH₃ | OCH₃ | N | |
| H | CH=CH | H | H | CH₃ | CH₃ | N | |
| H | CH=CH | C₆H₅ | H | CH₃ | CH₃ | CH | |
| H | CH=CH | C₆H₅ | H | CH₃ | OCH₃ | CH | |
| H | CH=CH | C₆H₅ | H | OCH₃ | OCH₃ | CH | |
| H | CH=CH | C₆H₅ | H | Cl | OCH₃ | CH | |
| H | CH=CH | C₆H₅ | H | CH₃ | OCH₃ | N | |
| H | CH=CH | C₆H₅ | H | OCH₃ | OCH₃ | N | |
| H | CH=CH | C₆H₅ | H | CH₃ | CH₃ | N | |
| 6-Cl | CH=CH | CH₃ | H | CH₃ | CH₃ | CH | |
| 6-Cl | CH=CH | CH₃ | H | CH₃ | OCH₃ | CH | |
| 6-Cl | CH=CH | CH₃ | H | OCH₃ | OCH₃ | CH | |
| 6-Cl | CH=CH | CH₃ | H | Cl | OCH₃ | CH | |
| 6-Cl | CH=CH | CH₃ | H | CH₃ | OCH₃ | N | |
| 6-Cl | CH=CH | CH₃ | H | OCH₃ | OCH₃ | N | |
| 6-Cl | CH=CH | C₆H₅ | H | CH₃ | CH₃ | CH | |
| 6-Cl | CH=CH | C₆H₅ | H | CH₃ | OCH₃ | CH | |
| 6-Cl | CH=CH | C₆H₅ | H | OCH₃ | OCH₃ | CH | |
| 6-Cl | CH=CH | C₆H₅ | H | Cl | OCH₃ | CH | |
| 6-Cl | CH=CH | C₆H₅ | H | CH₃ | OCH₃ | N | |
| 6-Cl | CH=CH | C₆H₅ | H | OCH₃ | OCH₃ | N | |
| H | CH₂ | CH₃ | H | OCH₃ | OCH₃ | CH | |
| H | CH₂ | CH₃ | H | OCH₃ | CH₃ | CH | |
| H | CH₂ | CH₃ | H | CH₃ | CH₃ | CH | |
| H | CH₂ | CH₃ | H | OCH₃ | Cl₃ | CH | |
| H | CH₂ | CH₃ | H | OCH₃ | OCH₃ | N | |
| H | CH₂ | CH₃ | H | OCH₃ | CH₃ | N | |
| H | CH₂CH₂ | CH₃ | H | OCH₃ | OCH₃ | CH | 173–180(d) |
| H | CH₂CH₂ | CH₃ | H | OCH₃ | CH₃ | CH | |
| H | CH₂CH₂ | CH₃ | H | CH₃ | CH₃ | CH | |
| H | CH₂CH₂ | CH₃ | H | OCH₃ | Cl₃ | CH | |
| H | CH₂CH₂ | CH₃ | H | OCH₃ | CH₃ | N | |
| H | CH₂CH₂ | CH₃ | H | OCH₃ | OCH₃ | N | |
| H | CH=CH | CH₃ | H | OCH₃ | OCH₃ | CH | |
| H | CH=CH | CH₃ | H | OCH₃ | CH₃ | CH | |
| H | CH=CH | CH₃ | H | CH₃ | CH₃ | CH | |
| H | CH=CH | CH₃ | H | OCH₃ | Cl₃ | CH | |
| H | CH=CH | CH₃ | H | OCH₃ | OCH₃ | N | |
| H | CH=CH | CH₃ | H | OCH₃ | CH₃ | N | |

TABLE 22

General Formula 22

| R₁ | X | Y | Z | m.p. (°C.) |
|---|---|---|---|---|
| H | OCH₃ | OCH₃ | N | |
| H | OCH₃ | OCH₃ | CH | |
| H | CH₃ | OCH₃ | N | |
| H | CH₃ | OCH₃ | CH | |
| H | Cl | OCH₃ | CH | |
| H | CH₃ | CH₃ | CH | |
| 6-CH₃ | OCH₃ | OCH₃ | N | |
| 6-CH₃ | OCH₃ | OCH₃ | CH | |
| 6-CH₃ | CH₃ | OCH₃ | N | |
| 6-CH₃ | CH₃ | OCH₃ | CH | |
| 6-CH₃ | Cl | OCH₃ | CH | |
| 6-CH₃ | CH₃ | CH₃ | CH | |
| 6-Cl | OCH₃ | OCH₃ | N | |
| 6-Cl | OCH₃ | OCH₃ | CH | |
| 6-Cl | CH₃ | OCH₃ | N | |
| 6-Cl | CH₃ | OCH₃ | CH | |
| 6-Cl | Cl | OCH₃ | CH | |
| 6-Cl | CH₃ | CH₃ | CH | |
| 6-OCH₃ | OCH₃ | OCH₃ | N | |
| 6-OCH₃ | OCH₃ | OCH₃ | CH | |
| 6-OCH₃ | CH₃ | OCH₃ | N | |
| 6-OCH₃ | CH₃ | OCH₃ | CH | |
| 6-OCH₃ | Cl | OCH₃ | CH | |
| 6-OCH₃ | CH₃ | CH₃ | CH | |
| 5-Cl | OCH₃ | OCH₃ | N | |
| 5-Cl | OCH₃ | OCH₃ | CH | |
| 5-Cl | CH₃ | OCH₃ | N | |
| 5-Cl | CH₃ | OCH₃ | CH | |
| 5-Cl | Cl | OCH₃ | CH | |
| 5-Cl | CH₃ | CH₃ | CH | |
| 5-OCH₃ | OCH₃ | OCH₃ | N | |
| 5-OCH₃ | OCH₃ | OCH₃ | CH | |
| 5-OCH₃ | CH₃ | OCH₃ | N | |
| 5-OCH₃ | CH₃ | OCH₃ | CH | |
| 5-OCH₃ | Cl | OCH₃ | CH | |
| 5-OCH₃ | CH₃ | CH₃ | CH | |
| 5-SCH₃ | OCH₃ | OCH₃ | N | |
| 5-SCH₃ | OCH₃ | OCH₃ | CH | |

TABLE 22-continued

General Formula 22

| R₁ | X | Y | Z | m.p. (°C.) |
|---|---|---|---|---|
| 5-SCH₃ | CH₃ | OCH₃ | N | |
| 5-SCH₃ | CH₃ | OCH₃ | CH | |
| 5-SCH₃ | Cl | OCH₃ | CH | |
| 5-SCH₃ | CH₃ | CH₃ | CH | |

TABLE 23

General Formula 23

| R₁ | X | Y | Z | m.p. (°C.) |
|---|---|---|---|---|
| H | OCH₃ | OCH₃ | N | |
| H | OCH₃ | OCH₃ | CH | |
| H | CH₃ | OCH₃ | N | |
| H | CH₃ | OCH₃ | CH | |
| H | Cl | OCH₃ | CH | |
| H | CH₃ | CH₃ | CH | |
| 6-CH₃ | OCH₃ | OCH₃ | N | |
| 6-CH₃ | OCH₃ | OCH₃ | CH | |
| 6-CH₃ | CH₃ | OCH₃ | N | |
| 6-CH₃ | CH₃ | OCH₃ | CH | |
| 6-CH₃ | Cl | OCH₃ | CH | |
| 6-CH₃ | CH₃ | CH₃ | CH | |
| 6-Cl | OCH₃ | OCH₃ | N | |
| 6-Cl | OCH₃ | OCH₃ | CH | |
| 6-Cl | CH₃ | OCH₃ | N | |
| 6-Cl | CH₃ | OCH₃ | CH | |
| 6-Cl | Cl | OCH₃ | CH | |
| 6-Cl | CH₃ | CH₃ | CH | |
| 6-OCH₃ | OCH₃ | OCH₃ | N | |
| 6-OCH₃ | OCH₃ | OCH₃ | CH | |
| 6-OCH₃ | CH₃ | OCH₃ | N | |
| 6-OCH₃ | CH₃ | OCH₃ | CH | |
| 6-OCH₃ | Cl | OCH₃ | CH | |
| 6-OCH₃ | CH₃ | CH₃ | CH | |
| 5-Cl | OCH₃ | OCH₃ | N | |
| 5-Cl | OCH₃ | OCH₃ | CH | |
| 5-Cl | CH₃ | OCH₃ | N | |
| 5-Cl | CH₃ | OCH₃ | CH | |
| 5-Cl | Cl | OCH₃ | CH | |
| 5-Cl | CH₃ | CH₃ | CH | |
| 5-OCH₃ | OCH₃ | OCH₃ | N | |
| 5-OCH₃ | OCH₃ | OCH₃ | CH | |
| 5-OCH₃ | CH₃ | OCH₃ | N | |
| 5-OCH₃ | CH₃ | OCH₃ | CH | |
| 5-OCH₃ | Cl | OCH₃ | CH | |
| 5-OCH₃ | CH₃ | CH₃ | CH | |
| 5-SCH₃ | OCH₃ | OCH₃ | N | |
| 5-SCH₃ | OCH₃ | OCH₃ | CH | |
| 5-SCH₃ | CH₃ | OCH₃ | N | |
| 5-SCH₃ | CH₃ | OCH₃ | CH | |
| 5-SCH₃ | Cl | OCH₃ | CH | |
| 5-SCH₃ | CH₃ | CH₃ | CH | |

TABLE 24

General Formula 24

| R₁ | G | R₁₀ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | CH₂ | C₆H₅ | CH₃ | CH₃ | CH | |
| H | CH₂ | C₆H₅ | CH₃ | OCH₃ | CH | |
| H | CH₂ | C₆H₅ | OCH₃ | OCH₃ | CH | |
| H | CH₂ | C₆H₅ | Cl | OCH₃ | CH | |
| H | CH₂ | C₆H₅ | CH₃ | OCH₃ | N | |
| H | CH₂ | C₆H₅ | OCH₃ | OCH₃ | N | |
| H | CH₂ | C₆H₅ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | CH₂ | C₆H₅ | CH₃ | CH₃ | CH | |
| 6-CH₃ | CH₂ | C₆H₅ | CH₃ | OCH₃ | CH | |
| 6-CH₃ | CH₂ | C₆H₅ | OCH₃ | OCH₃ | CH | |
| 6-CH₃ | CH₂ | C₆H₅ | Cl | OCH₃ | CH | |
| 6-CH₃ | CH₂ | C₆H₅ | CH₃ | OCH₃ | N | |
| 6-CH₃ | CH₂ | C₆H₅ | OCH₃ | OCH₃ | N | |
| 6-CH₃ | CH₂ | C₆H₅ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | CH₂ | C₆H₅ | CH₃ | CH₃ | CH | |
| 6-Cl | CH₂ | C₆H₅ | CH₃ | OCH₃ | CH | |
| 6-Cl | CH₂ | C₆H₅ | OCH₃ | OCH₃ | CH | |
| 6-Cl | CH₂ | C₆H₅ | Cl | OCH₃ | CH | |
| 6-Cl | CH₂ | C₆H₅ | CH₃ | OCH₃ | N | |
| 6-Cl | CH₂ | C₆H₅ | OCH₃ | OCH₃ | N | |
| 6-Cl | CH₂ | C₆H₅ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | 189–192(d) |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | 147–150 |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| H | CH₂CH₂ | C₆H₅ | CH₃ | CH₃ | CH | |
| H | CH₂CH₂ | C₆H₅ | CH₃ | OCH₃ | CH | |
| H | CH₂CH₂ | C₆H₅ | OCH₃ | OCH₃ | CH | |
| H | CH₂CH₂ | C₆H₅ | Cl | OCH₃ | CH | |
| H | CH₂CH₂ | C₆H₅ | CH₃ | OCH₃ | N | |
| H | CH₂CH₂ | C₆H₅ | OCH₃ | OCH₃ | N | |
| H | CH₂CH₂ | C₆H₅ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | CH₃ | OCH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| 6-CH₃ | CH₂CH₂ | C₆H₅ | CH₃ | CH₃ | CH | |

TABLE 24-continued

General Formula 24

| R₁ | G | R₁₀ | X | Y | Z | m.p. (°C.) |
|---|---|---|---|---|---|---|
| 6-CH₃ | CH₂CH₂ | C₆H₅ | CH₃ | OCH₃ | CH | |
| 6-CH₃ | CH₂CH₂ | C₆H₅ | OCH₃ | OCH₃ | CH | |
| 6-CH₃ | CH₂CH₂ | C₆H₅ | Cl | OCH₃ | CH | |
| 6-CH₃ | CH₂CH₂ | C₆H₅ | CH₃ | OCH₃ | N | |
| 6-CH₃ | CH₂CH₂ | C₆H₅ | OCH₃ | OCH₃ | N | |
| 6-CH₃ | CH₂CH₂ | C₆H₅ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | OCH₃ | CH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| 6-Cl | CH₂CH₂ | C₆H₅ | CH₃ | CH₃ | CH | |
| 6-Cl | CH₂CH₂ | C₆H₅ | CH₃ | OCH₃ | CH | |
| 6-Cl | CH₂CH₂ | C₆H₅ | OCH₃ | OCH₃ | CH | |
| 6-Cl | CH₂CH₂ | C₆H₅ | Cl | OCH₃ | CH | |
| 6-Cl | CH₂CH₂ | C₆H₅ | CH₃ | OCH₃ | N | |
| 6-Cl | CH₂CH₂ | C₆H₅ | OCH₃ | OCH₃ | N | |
| 6-Cl | CH₂CH₂ | C₆H₅ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| H | CH=CH | C₆H₅ | CH₃ | CH₃ | CH | |
| H | CH=CH | C₆H₅ | CH₃ | OCH₃ | CH | |
| H | CH=CH | C₆H₅ | OCH₃ | OCH₃ | CH | |
| H | CH=CH | C₆H₅ | Cl | OCH₃ | CH | |
| H | CH=CH | C₆H₅ | CH₃ | OCH₃ | N | |
| H | CH=CH | C₆H₅ | OCH₃ | OCH₃ | N | |
| H | CH=CH | C₆H₅ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | OCH₃ | CH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |
| 6-CH₃ | CH=CH | C₆H₅ | CH₃ | CH₃ | CH | |
| 6-CH₃ | CH=CH | C₆H₅ | CH₃ | OCH₃ | CH | |
| 6-CH₃ | CH=CH | C₆H₅ | OCH₃ | OCH₃ | CH | |
| 6-CH₃ | CH=CH | C₆H₅ | Cl | OCH₃ | CH | |
| 6-CH₃ | CH=CH | C₆H₅ | CH₃ | OCH₃ | N | |
| 6-CH₃ | CH=CH | C₆H₅ | OCH₃ | OCH₃ | N | |
| 6-CH₃ | CH=CH | C₆H₅ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | OCH₃ | CH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |
| 6-Cl | CH=CH | C₆H₅ | CH₃ | CH₃ | CH | |
| 6-Cl | CH=CH | C₆H₅ | CH₃ | OCH₃ | CH | |
| 6-Cl | CH=CH | C₆H₅ | OCH₃ | OCH₃ | CH | |
| 6-Cl | CH=CH | C₆H₅ | Cl | OCH₃ | CH | |
| 6-Cl | CH=CH | C₆H₅ | CH₃ | OCH₃ | N | |
| 6-Cl | CH=CH | C₆H₅ | OCH₃ | OCH₃ | N | |
| 6-Cl | CH=CH | C₆H₅ | CH₃ | CH₃ | N | |

TABLE 25

General Formula 25

| R₁ | G | R₁₀ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| H | CH₂ | C₆H₅ | CH₃ | CH₃ | CH | |
| H | CH₂ | C₆H₅ | CH₃ | OCH₃ | CH | |
| H | CH₂ | C₆H₅ | OCH₃ | OCH₃ | CH | |
| H | CH₂ | C₆H₅ | Cl | OCH₃ | CH | |
| H | CH₂ | C₆H₅ | CH₃ | OCH₃ | N | |
| H | CH₂ | C₆H₅ | OCH₃ | OCH₃ | N | |
| H | CH₂ | C₆H₅ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | OCH₃ | CH₃ | CH | |
| 6-CH₃ | CH₂ | CH₃ | OCH₃ | OCH₃ | CH | |
| 6-CH₃ | CH₂ | CH₃ | Cl | OCH₃ | CH | |
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| 6-CH₃ | CH₂ | C₆H₅ | CH₃ | CH₃ | CH | |
| 6-CH₃ | CH₂ | C₆H₅ | CH₃ | OCH₃ | CH | |
| 6-CH₃ | CH₂ | C₆H₅ | OCH₃ | OCH₃ | CH | |
| 6-CH₃ | CH₂ | C₆H₅ | Cl | OCH₃ | CH | |
| 6-CH₃ | CH₂ | C₆H₅ | CH₃ | OCH₃ | N | |
| 6-CH₃ | CH₂ | C₆H₅ | OCH₃ | OCH₃ | N | |
| 6-CH₃ | CH₂ | C₆H₅ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| 6-Cl | CH₂ | C₆H₅ | CH₃ | CH₃ | CH | |
| 6-Cl | CH₂ | C₆H₅ | CH₃ | OCH₃ | CH | |
| 6-Cl | CH₂ | C₆H₅ | OCH₃ | OCH₃ | CH | |
| 6-Cl | CH₂ | C₆H₅ | Cl | OCH₃ | CH | |
| 6-Cl | CH₂ | C₆H₅ | CH₃ | OCH₃ | N | |
| 6-Cl | CH₂ | C₆H₅ | OCH₃ | OCH₃ | N | |

TABLE 25-continued

General Formula 25

| R₁ | G | R₁₀ | X | Y | Z | m.p. (°C.) |
|---|---|---|---|---|---|---|
| 6-Cl | CH₂ | C₆H₅ | CH₃ | CH₃ | N | |
| H | CH₂CH₂ | H | CH₃ | CH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| H | CH₂CH₂ | C₆H₅ | CH₃ | CH₃ | CH | |
| H | CH₂CH₂ | C₆H₅ | CH₃ | OCH₃ | CH | |
| H | CH₂CH₂ | C₆H₅ | OCH₃ | OCH₃ | CH | |
| H | CH₂CH₂ | C₆H₅ | Cl | OCH₃ | CH | |
| H | CH₂CH₂ | C₆H₅ | CH₃ | OCH₃ | N | |
| H | CH₂CH₂ | C₆H₅ | OCH₃ | OCH₃ | N | |
| H | CH₂CH₂ | C₆H₅ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | OCH₃ | CH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| 6-CH₃ | CH₂CH₂ | C₆H₅ | CH₃ | CH₃ | CH | |
| 6-CH₃ | CH₂CH₂ | C₆H₅ | CH₃ | OCH₃ | CH | |
| 6-CH₃ | CH₂CH₂ | C₆H₅ | OCH₃ | OCH₃ | CH | |
| 6-CH₃ | CH₂CH₂ | C₆H₅ | Cl | OCH₃ | CH | |
| 6-CH₃ | CH₂CH₂ | C₆H₅ | CH₃ | OCH₃ | N | |
| 6-CH₃ | CH₂CH₂ | C₆H₅ | OCH₃ | OCH₃ | N | |
| 6-CH₃ | CH₂CH₂ | C₆H₅ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | OCH₃ | CH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| 6-Cl | CH₂CH₂ | C₆H₅ | CH₃ | CH₃ | CH | |
| 6-Cl | CH₂CH₂ | C₆H₅ | CH₃ | OCH₃ | CH | |
| 6-Cl | CH₂CH₂ | C₆H₅ | OCH₃ | OCH₃ | CH | |
| 6-Cl | CH₂CH₂ | C₆H₅ | Cl | OCH₃ | CH | |
| 6-Cl | CH₂CH₂ | C₆H₅ | CH₃ | OCH₃ | N | |
| 6-Cl | CH₂CH₂ | C₆H₅ | OCH₃ | OCH₃ | N | |
| 6-Cl | CH₂CH₂ | C₆H₅ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| H | CH=CH | C₆H₅ | CH₃ | CH₃ | CH | |
| H | CH=CH | C₆H₅ | CH₃ | OCH₃ | CH | |
| H | CH=CH | C₆H₅ | OCH₃ | OCH₃ | CH | |
| H | CH=CH | C₆H₅ | Cl | OCH₃ | CH | |
| H | CH=CH | C₆H₅ | CH₃ | OCH₃ | N | |
| H | CH=CH | C₆H₅ | OCH₃ | OCH₃ | N | |
| H | CH=CH | C₆H₅ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | OCH₃ | CH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |
| 6-CH₃ | CH=CH | C₆H₅ | CH₃ | CH₃ | CH | |
| 6-CH₃ | CH=CH | C₆H₅ | CH₃ | OCH₃ | CH | |
| 6-CH₃ | CH=CH | C₆H₅ | OCH₃ | OCH₃ | CH | |
| 6-CH₃ | CH=CH | C₆H₅ | Cl | OCH₃ | CH | |
| 6-CH₃ | CH=CH | C₆H₅ | CH₃ | OCH₃ | N | |
| 6-CH₃ | CH=CH | C₆H₅ | OCH₃ | OCH₃ | N | |
| 6-CH₃ | CH=CH | C₆H₅ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | OCH₃ | CH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |
| 6-Cl | CH=CH | C₆H₅ | CH₃ | CH₃ | CH | |
| 6-Cl | CH=CH | C₆H₅ | CH₃ | OCH₃ | CH | |
| 6-Cl | CH=CH | C₆H₅ | OCH₃ | OCH₃ | CH | |
| 6-Cl | CH=CH | C₆H₅ | Cl | OCH₃ | CH | |
| 6-Cl | CH=CH | C₆H₅ | CH₃ | OCH₃ | N | |
| 6-Cl | CH=CH | C₆H₅ | OCH₃ | OCH₃ | N | |
| 6-Cl | CH=CH | C₆H₅ | CH₃ | CH₃ | N | |

TABLE 26

General Formula 26

| R₁ | G | R₅ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| 6-CH₃ | CH₂ | H | CH₃ | CH₃ | CH | |
| 6-CH₃ | CH₂ | H | CH₃ | OCH₃ | CH | |
| 6-CH₃ | CH₂ | H | OCH₃ | OCH₃ | CH | |
| 6-CH₃ | CH₂ | H | Cl | OCH₃ | CH | |
| 6-CH₃ | CH₂ | H | CH₃ | OCH₃ | N | |
| 6-CH₃ | CH₂ | H | OCH₃ | OCH₃ | N | |
| 6-CH₃ | CH₂ | H | CH₃ | CH₃ | N | |
| 6-CH₃ | CH₂ | CH₃ | CH₃ | CH₃ | CH | |
| 6-CH₃ | CH₂ | CH₃ | CH₃ | OCH₃ | CH | |
| 6-CH₃ | CH₂ | CH₃ | OCH₃ | OCH₃ | CH | |
| 6-CH₃ | CH₂ | CH₃ | Cl | OCH₃ | CH | |

TABLE 26-continued

General Formula 26

| R₁ | G | R₅ | X | Y | Z | m.p. (°C.) |
|---|---|---|---|---|---|---|
| 6-CH₃ | CH₂ | CH₃ | CH₃ | OCH₃ | N | |
| 6-CH₃ | CH₂ | CH₃ | OCH₃ | OCH₃ | N | |
| 6-CH₃ | CH₂ | CH₃ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| 6-CH₃ | CH₂CH₂ | H | CH₃ | CH₃ | CH | |
| 6-CH₃ | CH₂CH₂ | H | CH₃ | OCH₃ | CH | |
| 6-CH₃ | CH₂CH₂ | H | OCH₃ | OCH₃ | CH | |
| 6-CH₃ | CH₂CH₂ | H | Cl | OCH₃ | CH | |
| 6-CH₃ | CH₂CH₂ | H | CH₃ | OCH₃ | N | |
| 6-CH₃ | CH₂CH₂ | H | OCH₃ | OCH₃ | N | |
| 6-CH₃ | CH₂CH₂ | H | CH₃ | CH₃ | N | |
| 6-CH₃ | CH₂CH₂ | CH₃ | CH₃ | CH₃ | CH | |
| 6-CH₃ | CH₂CH₂ | CH₃ | CH₃ | OCH₃ | CH | |
| 6-CH₃ | CH₂CH₂ | CH₃ | OCH₃ | OCH₃ | CH | |
| 6-CH₃ | CH₂CH₂ | CH₃ | Cl | OCH₃ | CH | |
| 6-CH₃ | CH₂CH₂ | CH₃ | CH₃ | OCH₃ | N | |
| 6-CH₃ | CH₂CH₂ | CH₃ | OCH₃ | OCH₃ | N | |
| 6-CH₃ | CH₂CH₂ | CH₃ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| 6-CH₃ | CH=CH | H | CH₃ | CH₃ | CH | |
| 6-CH₃ | CH=CH | H | CH₃ | OCH₃ | CH | |
| 6-CH₃ | CH=CH | H | OCH₃ | OCH₃ | CH | |
| 6-CH₃ | CH=CH | H | Cl | OCH₃ | CH | |
| 6-CH₃ | CH=CH | H | CH₃ | OCH₃ | N | |
| 6-CH₃ | CH=CH | H | OCH₃ | OCH₃ | N | |
| 6-CH₃ | CH=CH | H | CH₃ | CH₃ | N | |
| 6-CH₃ | CH=CH | CH₃ | CH₃ | CH₃ | CH | |
| 6-CH₃ | CH=CH | CH₃ | CH₃ | OCH₃ | CH | |
| 6-CH₃ | CH=CH | CH₃ | OCH₃ | OCH₃ | CH | |
| 6-CH₃ | CH=CH | CH₃ | Cl | OCH₃ | CH | |
| 6-CH₃ | CH=CH | CH₃ | CH₃ | OCH₃ | N | |
| 6-CH₃ | CH=CH | CH₃ | OCH₃ | OCH₃ | N | |
| 6-CH₃ | CH=CH | CH₃ | CH₃ | CH₃ | N | |

TABLE 27

General Formula 27

| R₁ | G | R₁₂ | X | Y | Z | m.p. (°C.) |
|---|---|---|---|---|---|---|
| H | CH₂ | H | CH₃ | CH₃ | CH | |
| H | CH₂ | H | CH₃ | OCH₃ | CH | |
| H | CH₂ | H | OCH₃ | OCH₃ | CH | |
| H | CH₂ | H | Cl | OCH₃ | CH | |
| H | CH₂ | H | CH₃ | OCH₃ | N | |
| H | CH₂ | H | OCH₃ | OCH₃ | N | |
| H | CH₂ | H | CH₃ | CH₃ | N | |
| H | CH₂ | CH₃ | CH₃ | CH₃ | CH | |
| H | CH₂ | CH₃ | CH₃ | OCH₃ | CH | |
| H | CH₂ | CH₃ | OCH₃ | OCH₃ | CH | |
| H | CH₂ | CH₃ | Cl | OCH₃ | CH | |
| H | CH₂ | CH₃ | CH₃ | OCH₃ | N | |
| H | CH₂ | CH₃ | OCH₃ | OCH₃ | N | |
| H | CH₂ | CH₃ | CH₃ | CH₃ | N | |
| 6-Cl | CH₂ | H | CH₃ | CH₃ | CH | |
| 6-Cl | CH₂ | H | CH₃ | OCH₃ | CH | |
| 6-Cl | CH₂ | H | OCH₃ | OCH₃ | CH | |
| 6-Cl | CH₂ | H | Cl | OCH₃ | CH | |
| 6-Cl | CH₂ | H | CH₃ | OCH₃ | N | |
| 6-Cl | CH₂ | H | OCH₃ | OCH₃ | N | |
| 6-Cl | CH₂ | H | CH₃ | CH₃ | N | |
| 6-Cl | CH₂ | CH₃ | CH₃ | CH₃ | CH | |
| 6-Cl | CH₂ | CH₃ | CH₃ | OCH₃ | CH | |
| 6-Cl | CH₂ | CH₃ | OCH₃ | OCH₃ | CH | |
| 6-Cl | CH₂ | CH₃ | Cl | OCH₃ | CH | |
| 6-Cl | CH₂ | CH₃ | CH₃ | OCH₃ | N | |
| 6-Cl | CH₂ | CH₃ | OCH₃ | OCH₃ | N | |
| 6-Cl | CH₂ | CH₃ | CH₃ | CH₃ | N | |
| H | CH₂CH₂ | H | CH₃ | CH₃ | CH | |
| H | CH₂CH₂ | H | CH₃ | OCH₃ | CH | |
| H | CH₂CH₂ | H | OCH₃ | OCH₃ | CH | |
| H | CH₂CH₂ | H | Cl | OCH₃ | CH | |
| H | CH₂CH₂ | H | CH₃ | OCH₃ | N | |
| H | CH₂CH₂ | H | OCH₃ | OCH₃ | N | |
| H | CH₂CH₂ | H | CH₃ | CH₃ | N | |
| H | CH₂CH₂ | CH₃ | CH₃ | CH₃ | CH | |
| H | CH₂CH₂ | CH₃ | CH₃ | OCH₃ | CH | |
| H | CH₂CH₂ | CH₃ | OCH₃ | OCH₃ | CH | |
| H | CH₂CH₂ | CH₃ | Cl | OCH₃ | CH | |
| H | CH₂CH₂ | CH₃ | CH₃ | OCH₃ | N | |
| H | CH₂CH₂ | CH₃ | OCH₃ | OCH₃ | N | |
| H | CH₂CH₂ | CH₃ | CH₃ | CH₃ | N | |
| 6-Cl | CH₂CH₂ | H | CH₃ | CH₃ | CH | |
| 6-Cl | CH₂CH₂ | H | CH₃ | OCH₃ | CH | |
| 6-Cl | CH₂CH₂ | H | OCH₃ | OCH₃ | CH | |
| 6-Cl | CH₂CH₂ | H | Cl | OCH₃ | CH | |
| 6-Cl | CH₂CH₂ | H | CH₃ | OCH₃ | N | |
| 6-Cl | CH₂CH₂ | H | OCH₃ | OCH₃ | N | |
| 6-Cl | CH₂CH₂ | H | CH₃ | CH₃ | N | |
| 6-Cl | CH₂CH₂ | CH₃ | CH₃ | CH₃ | CH | |
| 6-Cl | CH₂CH₂ | CH₃ | CH₃ | OCH₃ | CH | |
| 6-Cl | CH₂CH₂ | CH₃ | OCH₃ | OCH₃ | CH | |
| 6-Cl | CH₂CH₂ | CH₃ | Cl | OCH₃ | CH | |
| 6-Cl | CH₂CH₂ | CH₃ | CH₃ | OCH₃ | N | |
| 6-Cl | CH₂CH₂ | CH₃ | OCH₃ | OCH₃ | N | |
| 6-Cl | CH₂CH₂ | CH₃ | CH₃ | CH₃ | N | |
| H | CH=CH | H | CH₃ | CH₃ | CH | |
| H | CH=CH | H | CH₃ | OCH₃ | CH | |
| H | CH=CH | H | OCH₃ | OCH₃ | CH | |
| H | CH=CH | H | Cl | OCH₃ | CH | |
| H | CH=CH | H | CH₃ | OCH₃ | N | |
| H | CH=CH | H | OCH₃ | OCH₃ | N | |
| H | CH=CH | H | CH₃ | CH₃ | N | |
| H | CH=CH | CH₃ | CH₃ | CH₃ | CH | |
| H | CH=CH | CH₃ | CH₃ | OCH₃ | CH | |
| H | CH=CH | CH₃ | OCH₃ | OCH₃ | CH | |
| H | CH=CH | CH₃ | Cl | OCH₃ | CH | |
| H | CH=CH | CH₃ | CH₃ | OCH₃ | N | |
| H | CH=CH | CH₃ | OCH₃ | OCH₃ | N | |
| H | CH=CH | CH₃ | CH₃ | CH₃ | N | |
| 6-Cl | CH=CH | H | CH₃ | CH₃ | CH | |
| 6-Cl | CH=CH | H | CH₃ | OCH₃ | CH | |
| 6-Cl | CH=CH | H | OCH₃ | OCH₃ | CH | |
| 6-Cl | CH=CH | H | Cl | OCH₃ | CH | |
| 6-Cl | CH=CH | H | CH₃ | OCH₃ | N | |
| 6-Cl | CH=CH | H | OCH₃ | OCH₃ | N | |
| 6-Cl | CH=CH | H | CH₃ | CH₃ | N | |
| 6-Cl | CH=CH | CH₃ | CH₃ | CH₃ | CH | |
| 6-Cl | CH=CH | CH₃ | CH₃ | OCH₃ | CH | |
| 6-Cl | CH=CH | CH₃ | OCH₃ | OCH₃ | CH | |
| 6-Cl | CH=CH | CH₃ | Cl | OCH₃ | CH | |
| 6-Cl | CH=CH | CH₃ | CH₃ | OCH₃ | N | |
| 6-Cl | CH=CH | CH₃ | OCH₃ | OCH₃ | N | |
| 6-Cl | CH=CH | CH₃ | CH₃ | CH₃ | N | |

TABLE 28

General Formula 28

| R₁ | X | Y | Z | m.p. (°C.) |
|---|---|---|---|---|
| H | OCH₃ | OCH₃ | N | |
| H | OCH₃ | OCH₃ | CH | |
| H | CH₃ | OCH₃ | N | |

TABLE 28-continued

General Formula 28

| R₁ | X | Y | Z | m.p. (°C.) |
|---|---|---|---|---|
| H | CH₃ | OCH₃ | CH | |
| H | Cl | OCH₃ | CH | |
| H | CH₃ | CH₃ | CH | |
| 6-CH₃ | OCH₃ | OCH₃ | N | |
| 6-CH₃ | OCH₃ | OCH₃ | CH | |
| 6-CH₃ | CH₃ | OCH₃ | N | |
| 6-CH₃ | CH₃ | OCH₃ | CH | |
| 6-CH₃ | Cl | OCH₃ | CH | |
| 6-CH₃ | CH₃ | CH₃ | CH | |
| 6-Cl | OCH₃ | OCH₃ | N | |
| 6-Cl | OCH₃ | OCH₃ | CH | |
| 6-Cl | CH₃ | OCH₃ | N | |
| 6-Cl | CH₃ | OCH₃ | CH | |
| 6-Cl | Cl | OCH₃ | CH | |
| 6-Cl | CH₃ | CH₃ | CH | |
| 6-OCH₃ | OCH₃ | OCH₃ | N | |
| 6-OCH₃ | OCH₃ | OCH₃ | CH | |
| 6-OCH₃ | CH₃ | OCH₃ | N | |
| 6-OCH₃ | CH₃ | OCH₃ | CH | |
| 6-OCH₃ | Cl | OCH₃ | CH | |
| 6-OCH₃ | CH₃ | CH₃ | CH | |
| 5-Cl | OCH₃ | OCH₃ | N | |
| 5-Cl | OCH₃ | OCH₃ | CH | |
| 5-Cl | CH₃ | OCH₃ | N | |
| 5-Cl | CH₃ | OCH₃ | CH | |
| 5-Cl | Cl | OCH₃ | CH | |
| 5-Cl | CH₃ | CH₃ | CH | |
| 5-OCH₃ | OCH₃ | OCH₃ | N | |
| 5-OCH₃ | OCH₃ | OCH₃ | CH | |
| 5-OCH₃ | CH₃ | OCH₃ | N | |
| 5-OCH₃ | CH₃ | OCH₃ | CH | |
| 5-OCH₃ | Cl | OCH₃ | CH | |
| 5-OCH₃ | CH₃ | CH₃ | CH | |
| 5-SCH₃ | OCH₃ | OCH₃ | N | |
| 5-SCH₃ | OCH₃ | OCH₃ | CH | |
| 5-SCH₃ | CH₃ | OCH₃ | N | |
| 5-SCH₃ | CH₃ | OCH₃ | CH | |
| 5-SCH₃ | Cl | OCH₃ | CH | |
| 5-SCH₃ | CH₃ | CH₃ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 29

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

In the following examples, all parts are by weight unless otherwise indicated.

Example 17

Wettable Powder

| | |
|---|---|
| N—[(4,6-dimethoxy-1,3,5-triazin-2-yl)aminocarbonyl]-1,4-dihydro-3-methyl-4-oxo-1-phenyl-indeno [1,2-C] pyrazole-5-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

Example 18

Wettable Powder

| | |
|---|---|
| N—[(4-methoxy-6-methylpyrimidin-2-yl)aminocarbonyl]-1,4-dihydro-3-methyl-4-oxo-1-phyenyl-indeno [1,2-C] | 50% |

| | |
|---|---|
| pyrazole-5-sulfonamide | |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example 19

Granule

| | |
|---|---|
| Wettable Powder of Example 18 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

Example 20

Extruded Pellet

| | |
|---|---|
| N—[(4,6-dimethoxy-1,3,5-triazin-2-yl)aminocarbonyl]-1,4-dihydro-3-methyl-4-oxo-1-phenyl-indeno[1,2-C]pyrazole-5-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example 21

Oil Suspension

| | |
|---|---|
| N—[(4-methoxy-6-methylpyrimidin-2-yl)aminocarbonyl]-1,4-dihydro-3-methyl-4-oxo-1-phenyl-indeno [1,2-C]pyrazole-5-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Example 22

Wettable Powder

| | |
|---|---|
| N—[(4-methoxy-6-methylpyrimidin-2-yl)aminocarbonyl]-1,4-dihydro-3-methyl-4-oxo-1-phenyl-indeno [1,2-C]pyrazole-5-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Example 23

Low Strength Granule

| | |
|---|---|
| N—[(4,6-dimethoxy-1,3,5-triazin-2-yl)aminocarbonyl]-1,4-dihydro-3-methyl-4-oxo-1-phenyl-indeno [1,2-C]pyrazole-5-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

Example 24

Aqueous Suspension

| | |
|---|---|
| N—[(4-methoxy-6-methylpyrimidin-2-yl)aminocarbonyl]-1,4-dihydro-3-methyl-4-oxo-1-phenyl-indeno [1,2-C]pyrazole-5-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example 25

Solution

| | |
|---|---|
| N—[(4,6-dimethoxy-1,3,5-triazin-2-yl)aminocarbonyl]-1,4-dihydro-3-methyl-4-oxo-1-phenyl-indeno [1,2-C]pyrazole-5-sulfonamide, ammonium salt | 5% |
| water | 95% |

The salt is added directly to the water with stirring to produce the solution, which may then be packaged for use.

Example 26

Low Strength Granule

| | |
|---|---|
| N—[(4,6-dimethoxy-1,3,5-triazin-2-yl)aminocarbonyl]-1,4-dihydro-3-methyl-4-oxo-1-phenyl-indeno [1,2-C]pyrazole-5-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

Example 27

Granule

| | |
|---|---|
| N—[(4-methoxy-6-methylpyrimidin-2-yl)aminocarbonyl]-1,4-dihydro-3-methyl-4-oxo-1-phenyl-indeno [1,2-C] pyrazole-5-sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

Example 28

High Strength Concentrate

| | |
|---|---|
| N—[(4-methoxy-6-methylpyrimidin-2-yl)aminocarbonyl]-1,4-dihydro-3-methyl-4-oxo-1-phenyl-indeno [1,2-C] pyrazole-5-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example 29

Wettable Powder

| | |
|---|---|
| N—[(4-methoxy-6-methylpyrimidin-2-yl)aminocarbonyl]-1,4-dihydro-3-methyl-4-oxo-1-phenyl-indeno [1,2-C] pyrazole-5-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

Example 30

Wettable Powder

| | |
|---|---|
| N—[(4,6-dimethoxy-1,3,5-triazin-2-yl)aminocarbonyl]-1,4-dihydro-3-methyl-4-oxo-1-phenyl-indeno [1,2-C] pyrazole-5-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example 31

Oil Suspension

| | |
|---|---|
| N—[(4,6-dimethoxy-1,3,5-triazin-2-yl)aminocarbonyl]-1,4-dihydro-3-methyl-4-oxo-1-phenyl-indeno [1,2-C] pyrazole-5-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Example 32

Dust

| | |
|---|---|
| N—[(4,6-dimethoxy-1,3,5-triazin-2-yl)aminocarbonyl]-1,4-dihydro-3-methyl-4-oxo-1-phenyl-indeno [1,2-C] pyrazole-5-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Example 33

Emulsifiable Concentrate

| | |
|---|---|
| N—[(4,6-dimethoxy-1,3,5-triazin-2-yl)aminocarbonyl]-1,4-dihydro-3-methyl-4-oxo-1-phenyl-indeno [1,2-C] pyrazole-5-sulfonamide | 74% |
| chlorobenzene | 74% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, soybeans and wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 20 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria spp.), barnyardgrass (Echinochloa crusqalli), wild oats (Avena fatua), cheatgrass (Bromus secalinus), velvetleaf (Abutilon theophrasti), morningglory (Ipomoea spp.), cocklebur (Xanthium pennsylvanicum), sorghum, corn, soybean, sugarbeet, cotton, rice, wheat, and purpose nutsedge (Cyperus rotundus) tubers were planted and treated preemergence with the test chemicals dissolved in a nonphytotoxic solvent. In some tests, velvetleaf and cheatgrass were not included. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axiliary stimulation
S=albinism
6Y=abscised buds or flowers.

COMPOUNDS

| Compound | $R_6$ | X | Y | Z |
|---|---|---|---|---|
| 1 | $C_6H_5$ | $OCH_3$ | $OCH_3$ | N |
| 2 | $C_6H_5$ | $OCH_3$ | $CH_3$ | CH |
| 3 | $CH_3$ | $CH_3$ | $CH_3$ | CH |
| 4 | $CH_3$ | $CH_3$ | $OCH_3$ | CH |
| 5 | $4\text{-}OCH_3\text{-}C_6H_4$ | $CH_3$ | $OCH_3$ | CH |
| 6 | $4\text{-}Cl\text{-}C_6H_4$ | $CH_3$ | $CH_3$ | CH |
| 7 | $4\text{-}Cl\text{-}C_6H_4$ | Cl | $OCH_3$ | CH |
| 8 | $4\text{-}Cl\text{-}C_6H_4$ | $OCH_3$ | $OCH_3$ | CH |
| 9 | $4\text{-}Cl\text{-}C_6H_4$ | $OCH_3$ | $OCH_3$ | N |
| 10 | $4\text{-}Cl\text{-}C_6H_4$ | $OCH_3$ | $CH_3$ | CH |
| 11 | $CH_3$ | $OCH_3$ | $CH_3$ | N |
| 12 | $CH_3$ | $OCH_3$ | $OCH_3$ | CH |
| 13 | $CH_3$ | $OCH_3$ | $OCH_3$ | N |
| 14 | $CH_3$ | Cl | $OCH_3$ | CH |
| 15 | $C_6H_5$ | $CH_3$ | $CH_3$ | N |
| 16 | $C_6H_5$ | $OCH_3$ | $OCH_3$ | CH |
| 17 | $C_6H_5$ | $OCH_3$ | Cl | CH |
| 18 | $C_6H_5$ | $OCH_3$ | $CH_3$ | N |
| 19 | $4\text{-}SO_2CH_3\text{-}C_6H_4$ | $OCH_3$ | $OCH_3$ | CH |
| 20 | $4\text{-}SO_2CH_3\text{-}C_6H_4$ | $OCH_3$ | $OCH_3$ | N |
| 21 | $4\text{-}SO_2CH_3\text{-}C_6H_4$ | $CH_3$ | $CH_3$ | CH |
| 22 | $4\text{-}SO_2CH_3\text{-}C_6H_4$ | $OCH_3$ | $CH_3$ | CH |

| Compound | X | Y | Z |
|---|---|---|---|
| 23 | $OCH_3$ | $CH_3$ | CH |
| 24 | $OCH_3$ | Cl | CH |
| 25 | $OCH_3$ | $OCH_3$ | N |

| Compound | X | Y | Z |
|---|---|---|---|
| 26 | $OCH_3$ | $OCH_3$ | CH |
| 27 | $OCH_3$ | $OCH_3$ | N |

COMPOUNDS-continued

| Compound | R<sub>6</sub> | X | Y | Z |
|---|---|---|---|---|

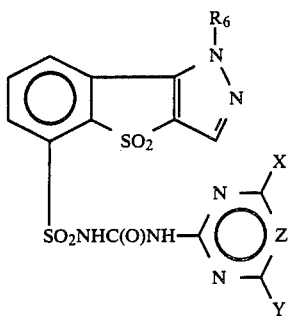

COMPOUNDS-continued

| Compound | $R_6$ | X | Y | Z |
|---|---|---|---|---|
| 28 | $CH_2CH_2CH_3$ | $OCH_3$ | $OCH_3$ | CH |
| 29 | $CH_2CH_2CH_3$ | $CH_3$ | $OCH_3$ | CH |
| 30 | $CH_2CH_2CH_3$ | Cl | $OCH_3$ | CH |
| 31 | $CH_2CH_2CH_3$ | $OCH_3$ | $OCH_3$ | N |
| 32 | $CH_2CH_2CH_3$ | $CH_3$ | $OCH_3$ | N |
| 33 | $CH_3$ | Cl | $OCH_3$ | CH |
| 34 | $CH_3$ | $CH_3$ | $CH_3$ | CH |
| 35 | $CH_3$ | $OCH_3$ | $OCH_3$ | CH |
| 36 | $CH_3$ | $CH_3$ | $OCH_3$ | CH |
| 37 | $CH_3$ | $CH_3$ | $OCH_3$ | N |
| 38 | $CH_3$ | $OCH_3$ | $OCH_3$ | N |
| 39 | $CH_2C_6H_5$ | $OCH_3$ | $OCH_3$ | CH |
| 40 | $CH_2C_6H_5$ | $CH_3$ | $OCH_3$ | CH |
| 41 | $CH_2C_6H_5$ | $CH_3$ | $CH_3$ | CH |
| 42 | $CH_2C_6H_5$ | Cl | $OCH_3$ | CH |
| 43 | $CH_2C_6H_5$ | $OCH_3$ | $OCH_3$ | N |
| 44 | $CH_2C_6H_5$ | $CH_3$ | $OCH_3$ | N |
| 45 | $3\text{-F}-C_6H_4$ | $OCH_3$ | $OCH_3$ | CH |
| 46 | $3\text{-F}-C_6H_4$ | $CH_3$ | $OCH_3$ | CH |

TABLE A

| | Compound 1 | Compound 2 | Compound 3 | Compound 4 | Compound 5 | Compound 6 | | Compound 7 | | Compound 8 | Compound 9 | Compound 10 | Compound 11 |
|---|---|---|---|---|---|---|---|---|---|---|---|---|---|
| Rate (kg/ha) | 0.4 | 0.4 | 0.4 | 0.4 | 0.4 | 0.4 | 2.0 | 0.4 | 2.0 | 2.0 | 0.4 | 0.4 | 0.4 |
| POSTEMERGENCE | | | | | | | | | | | | | |
| Morningglory | 5C,9H | 1C,4G | 0 | 1C,5G | 4G | 0 | 0 | 0 | 0 | 0 | 0 | 0 | 0 |
| Cocklebur | 10C | 5C,9H | 3C,8H | 5C,9H | 2C,5H | 0 | 0 | 0 | 0 | 0 | 3C,9H | 0 | 8G,5H |
| Velvetleaf | 4C,9H | 4C,8G | 0 | 5C,9G | 0 | 0 | 0 | 0 | 0 | 0 | 0 | 0 | 4G |
| Nutsedge | 2C,9G | 0 | 0 | 0 | 0 | 0 | 0 | 0 | 0 | 0 | 0 | 0 | 0 |
| Crabgrass | 2C,5G | 3G | 0 | 2C,5G | 2C,6H | 0 | 0 | 0 | 0 | 0 | 0 | 0 | 0 |
| Barnyardgrass | 3C,9H | 3C,8H | 0 | 3C,9H | 0 | 0 | 0 | 0 | 0 | 0 | 0 | 0 | 8G,3H |
| Cheatgrass | 8G | 3C,7G | 0 | 2C,5G | 0 | 0 | 0 | 0 | 0 | 0 | 0 | 0 | 0 |
| Wild Oats | 0 | 0 | 0 | 0 | 0 | 0 | 0 | 0 | 0 | 0 | 0 | 0 | 0 |
| Wheat | 3C,9G | 3C,9H | 0 | 3C,8G | 0 | 0 | 0 | 0 | 0 | 0 | 0 | 0 | 5G |
| Corn | 9C | 0 | 0 | 5C,9H | 0 | 0 | 0 | 0 | 0 | 0 | 0 | 0 | 0 |
| Soybean | 2G | 3C,9H | 0 | 2C,4H | 1H | 0 | 0 | 0 | 0 | 0 | 5G | 0 | 5G,3H |
| Rice | 9C | 6G | 0 | 5C,9G | 0 | 0 | 0 | 0 | 0 | 0 | 0 | 0 | 0 |
| Sorghum | 5C,9H | 3C,9H | 0 | 5C,9H | 3C,6G | 0 | 0 | 2C,3H | 0 | 0 | 0 | 2C,6G | 5G,3C |
| Sugar Beets | 5H | 4C,9H | 0 | 4C,8H | 5G | 0 | 0 | 0 | 0 | 0 | 5G | 0 | 7G,3H |
| Cotton | 3C,8H | 4C,9H | 0 | 2C,9G | 0 | 0 | 0 | 0 | 0 | 0 | 0 | 0 | 3C |
| Giant Foxtail | | | | | | | | | | | | | 6G,3H |
| PREEMERGENCE | | | | | | | | | | | | | |
| Morningglory | 2C,7H | 2H | 0 | 2C,3H | 3C,5G | 0 | 0 | 0 | 0 | 0 | 0 | 0 | 0 |
| Cocklebur | 9H | 7H | 8H | 9H | — | 0 | 0 | 0 | 0 | 0 | 2C | 0 | 5G |
| Velvetleaf | 7H | 5G | 0 | 8H | 3G | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 |
| Barnyardgrass | 3C,9H | 5C,9H | 0 | 2C,5H | 3C,9H | 0 | 0 | 2C | 0 | 0 | 0 | 0 | 5G |
| Cheatgrass | 5C,9H | 2C,8G | 0 | 3C,8G | 7G | 0 | 0 | 0 | 0 | 0 | 0 | 2C,8G | 0 |
| Wild Oats | 5G | 2C,6G | 0 | 0 | 0 | 2C,8G | 0 | 0 | 0 | 0 | 0 | 5G | 5G |
| Wheat | 5C,9H | 8G | 0 | 3C,9H | 5G | 0 | 0 | 0 | 0 | 0 | 2G | 0 | 0 |
| Corn | 3C,8G | 8H | 0 | 3C,9G | 4G | 2C,8G | 0 | 0 | 0 | 0 | 5G | 5G | 7G |
| Soybean | 0 | 0 | 0 | 0 | 2G | 0 | 0 | 0 | 0 | 0 | 3G | 0 | 3C |
| Rice | 5C,9H | 2C,7G | 0 | 5C,9H | 2C,5G | 0 | 0 | 0 | 0 | 0 | 4G | 4G | 7G |
| Sorghum | 5C,9H | 9G | 0 | 7C,9H | 0 | 0 | 0 | 0 | 0 | 0 | 0 | 0 | 5G |
| Sugar Beets | 6G | 3C,8H | 5G | 5C,9G | 4C,9G | 0 | 0 | 0 | 0 | 0 | 2G | 2C,6G | 7G |
| Cotton | 0 | 0 | 0 | 3C,4H | 8H | 0 | 0 | 0 | 0 | 0 | 0 | 5G | 9C |
| Giant Foxtail | | | | | 0 | | | | | | | 0 | 7C |
| Barley | | | | | | | | | | | | | |
| Bushbean | | | | | | | | | | | | | |
| Cassia | | | | | | | | | | | | | |

| | Compound 12 | Compound 13 | Compound 14 | Compound 15 | | Compound 16 | | Compound 17 | | Compound 18 | Compound 19 | Compound 20 | Compound 21 | Compound 22 |
|---|---|---|---|---|---|---|---|---|---|---|---|---|---|---|
| Rate (kg/ha) | 0.4 | 0.4 | 0.4 | 0.4 | 0.05 | 0.4 | 0.05 | 0.4 | 0.05 | 0.4 | 0.05 | 0.4 | 0.4 | 0.4 |
| POSTEMERGENCE | | | | | | | | | | | | | | |
| Morningglory | 5G | 3G | 5C,9H | 3C,7G | 2C,4H | 2C,4G | 1C,1H | 1H | 0 | 4C,9H | 0 | 9C | 0 | 4G | 0 |
| Cocklebur | 5C,9H | 5G | 5C,9G | 5C,9G | 4C,9G | 3C,9H | 3C,8H | 5C,9G | 3C,9H | 9C | 0 | 10C | 0 | 0 | 0 |
| Velvetleaf | 5C,9H | 3C,5H | 2C,6G | 2C,6G | 3G | 3C,8G | 2C,5G | 3G | 2G | 3C,9G | 0 | 5C,9G | 0 | 0 | 0 |
| Nutsedge | 5G | 0 | 0 | 0 | 0 | 0 | 0 | 0 | 0 | 2C,9G | 0 | 9C | 0 | 0 | 0 |
| Crabgrass | 0 | 3G | 3G | 2G | 0 | 2G | 2C,5G | 0 | 0 | 2G | 0 | 3C,6G | 0 | 0 | 0 |
| Barnyardgrass | 8H | 0 | 2H | 3C,9H | 3C,8H | 2C,8H | 2C,7H | 2C,5H | 2C,5H | 4C,9H | 0 | 9C | 0 | 0 | 0 |

TABLE A-continued

| | Compound 23 | Compound 24 | | Compound 25 | Compound 26 | | Compound 27 | | Compound 28 | | Compound 29 | Coumpound 29 | Cmpd. 30 | Cmpd. 31 | Cmpd. 32 | Compound 33 | Compound 34 |
|---|---|---|---|---|---|---|---|---|---|---|---|---|---|---|---|---|---|
| Rate (kg/ha) | 0.4 | 0.4 | 2.0 | 0.4 | 0.05 | 0.01 | 0.05 | 0.01 | 0.05 | 0.4 | 0.05 | 0.4 | 0.05 | 0.05 | 0.05 | 0.05 | 0.05 |

Cheatgrass 6G · 0 · 0 · 2C,8G · 0 · 2C,8G · 2C,7G · 0 · 0 · 4C,9G · 4C,9G · 0 · 0 · 0 · 0 · 0
Wild Oats 0 · 0 · 0 · 0 · 0 · 0 · 0 · 0 · 0 · 3G · 0 · 0 · 0 · 0 · 0 · 0
Wheat 3G · 0 · 0 · 0 · 7G · 3G · 7G · 2G · 0 · 3C,9G · 9G · 0 · 0 · 0 · 0 · 0
Corn 9H · 2U,5H · 3H · 3H · 3C,8H · 0 · 3C,9G · 0 · 2C,8H · 0 · 9C · 9C · 0 · 0 · 0 · 0 · 0
Soybean 3C,7G · 0 · 0 · 0 · 2G · 2C,6G · 2G · 3G · 0 · 2C,6G · 2C,7G · 2G · 0 · 0 · 0 · 0 · 0
Rice 4C,9G · 8G · 0 · 3G · 5C,9G · 3C,7H · 5C,9G · 7G · 4C,8H · 0 · 5C,9G · 5C,9G · 0 · 0 · 0 · 0 · 0
Sorghum 2C,6H · 1C,4G · 0 · 5G · 4C,9H · 3C,8H · 4C,9H · 1C · 1C,4G · 7G · 4C,9H · 4C,9H · 0 · 0 · 0 · 0 · 0
Sugar Beets 5H · 2H · 0 · 2H · 4C,9G · 2G · 3C,8H · 3H · 3C,6H · 1C · 9C · 10C · 0 · 0 · 0 · 0 · 0
Cotton 8H · 5H · 0 · 3G · 2C,5H · · · 2C,7H · 3H · 2C,7H · 3H · 10C · 9C · 0 · 0 · 0 · 0 ·
Giant Foxtail · · · · · · · · · · · · · · · · ·
Barley · · · · · · · · · · · · · · · · ·
Bushbean · · · · · · · · · · · · · · · · ·
Cassia · · · · · · · · · · · · · · · · ·

PREEMERGENCE

Morningglory 6G · 0 · 0 · 0 · 0 · 0 · 0 · 0 · 0 · 0 · 9G · 8G · 0 · 0 · 0 · 0 · 0
Cocklebur 8G · 5H · · 6G · 8H · 4G · 4G · · 2C,3H · · 8H · 7H · 3C,7H · · · · ·
Velvetleaf 8G · 4G · 0 · 8H · 0 · 1H · 1H · · 0 · · 2C,9G · 4G · 0 · 0 · 0 · 0 · 0
Nutsedge 4G · 0 · 0 · 4G · 0 · 0 · 0 · 0 · 0 · 0 · 0 · 0 · 0 · 0 · 0 · 0 · 0
Crabgrass 5G · 3G · 0 · 5G · 0 · 0 · 0 · 0 · 0 · 0 · 2C,5G · 2G · 0 · 0 · 0 · 0 · 0
Barnyardgrass 9H · 0 · 0 · 5G · 2H · 0 · 3C,3H · 3C,8H · 3C,7H · 2C,2H · 4C,9H · 3C,6G · 0 · 0 · 0 · 0 · 0
Cheatgrass 4C,9G · 6G · 0 · 5G · 0 · 0 · 8G · 2G · 5G · 0 · 2C,5G · 6G · 0 · 0 · 0 · 0 · 0
Wild Oats 2C,6G · 0 · 0 · 0 · 0 · 0 · 3G · 0 · 0 · 0 · 4C,9H · 1C · 0 · 0 · 0 · 0 · 0
Wheat 8G · 8G · 0 · 8G · 2H · 0 · 8H · 4H · 0 · 0 · 4C,9H · 4C,9H · 0 · 0 · 0 · 0 · 0
Corn 5G · 3C,3H · 0 · 0 · 0 · 0 · 0 · 0 · 0 · 4G · 3C,5G · 3C,7G · 0 · 0 · 0 · 0 · 0
Soybean 0 · 0 · 0 · 8G · 3G · 0 · 2C,4G · 3C,9H · 6G · 0 · 2H · 2H · 0 · 0 · 0 · 0 · 0
Rice 8G · 9H · 0 · 3G · 2G · 0 · 3C,9G · 4C,9H · 6G · 1C · 4C,9H · 2C,7G · 0 · 0 · 0 · 0 · 0
Sorghum 8G · 4C,9G · 0 · 2C,5G · 3G · 0 · 3G · 2C,9H · 2C,8H · 2C,6G · 5C,9H · 3C,9H · 0 · 0 · 0 · 0 · 0
Sugar Beets 8G · 5H · 0 · 3C,9H · 8G · 0 · 2G · 7H · 6G · 6G · 5C,9G · 5G · 2G · 0 · 0 · 0 · 0
Cotton 5G · 0 · 0 · 8H · 0 · 0 · 0 · 4C,9G · 0 · 0 · 7G · 0 · 0 · 0 · 0 · 0 · 0
Giant Foxtail · · · · · · · · · · · · · · · · ·
Barley · · · · · · · · · · · · · · · · ·
Bushbean · · · · · · · · · · · · · · · · ·
Cassia · · · · · · · · · · · · · · · · ·

POSTEMERGENCE

Morningglory 0 · 0 · 0 · 9C · 4C,8G · 3C,8H · 0 · 4C,9G · 2C · 1C · 0 · 0 · 0 · 0 · 0
Cocklebur 5G,3C · 3H · 1C,5G · 7H · 9H · 4G · · 3C,8H · 3C,7G · 4C,9H · 3C,7H · · · · · ·
Velvetleaf 6G · 0 · 0 · 10C · 10C · 4C,9G · 3C,8H · 4C,9G · 2C,4G · 2C,5G · 0 · 0 · 0 · 0 · 0 · 0
Nutsedge 0 · 0 · 0 · 2C,8G · 9G · 3C,8G · 0 · 3G · 0 · 3G · 0 · 0 · 0 · 0 · 0 · 0
Crabgrass 0 · 0 · 0 · 7G · 4G · 0 · 0 · 0 · 0 · 3H · 0 · 0 · 0 · 0 · 0 · 0
Barnyardgrass 6G,3H · 0 · 0 · 5C,9H · 10C · 4H · 0 · 0 · 0 · 5G · 0 · 0 · 0 · 0 · 0 · 0
Cheatgrass 0 · 0 · 0 · 7G · 8G · 2G · 4H · 0 · 0 · 0 · 0 · 0 · 0 · 0 · 0 · 0
Wild Oats 0 · 0 · 0 · 2G · 3C,7G · 1C · 1C · 0 · 4G · 3G · 0 · 0 · 0 · 0 · 0 · 0
Wheat 0 · 0 · 0 · 6G · 0 · 0 · 0 · 0 · 0 · 0 · 0 · 0 · 0 · 0 · 0 · 0
Corn 5G,3C · 5G',3C · 3C,3H · 5C,9G · 3C,9H · 3C,9H · 4G · 0 · 4G · 3G · 4C,9H · 4C,9H · 0 · 0 · 0 · 0 · 0
Soybean 0 · 0 · 0 · 4C,9G · 4C,9G · 4C,9H · 1C · 0 · 0 · 2C,3G · 3C,5G · 3C,7G · 0 · 0 · 0 · 0 · 0
Rice 0 · 0 · 0 · 5C,9G · 5C,9G · 4C,9H · 0 · 1C · 4G · 3G · 2H · 2C,7G · 0 · 0 · 0 · 0 · 0
Sorghum 0 · 0 · 0 · 2C,9G · 4C,9H · 2C,9H · 2C,6G · 0 · 4G · 3C,3H · 3C,5G · 3C,9H · 0 · 0 · 0 · 0 · 0
Sugar Beets 4G,3C · 0 · 0 · 5C,9G · 2C,9G · 7H · 2C,8H · 4G · 3C,4G · 3C,8G · 5G · 0 · 0 · 0 · 0 · 0
Cotton 0 · 0 · 0 · 4C,9G · 9C · 4C,9G · 6G · 3C,4G · 3C,4G · 3C,5G · 0 · 2H · 0 · 0 · 0 · 0
Giant Foxtail 0 · 0 · 0 · 9C · 3C,9G · 2C,4G · 0 · 0 · 0 · 0 · 3G · 0 · 0 · 0 · 0 · 0

TABLE A-continued

| | 2C,6G | 3G | 4G | 0 | 0 | 4G | 0 | 0 | 0 | 0 | 0 |
|---|---|---|---|---|---|---|---|---|---|---|---|
| Barley | — | | | | | | | | | | |
| Bushbean | — | | | | | | | | | | |
| Cassia | | | | | | | | | | | |

PREEMERGENCE

| | | | | | | | | | | | |
|---|---|---|---|---|---|---|---|---|---|---|---|
| Morningglory | 0 | 9G | 9H | 8G | 0 | 3C | 0 | 0 | 0 | 0 | — |
| Cocklebur | 0 | 9H | 5G | — | 8H | 7G | 3H | 0 | 0 | 0 | 5G |
| Velvetleaf | 0 | 9G | 7G | 3C,8G | 6G | 2C,5G | 0 | 2C | 0 | 0 | 0 |
| Nutsedge | 0 | 10E | 6G | 10E | 0 | 0 | 4G | 0 | 0 | 0 | 0 |
| Crabgrass | 0 | 4G | 2G | 3G | 0 | 0 | 0 | 0 | 0 | 0 | 0 |
| Barnyardgrass | 0 | 4C,9H | 9H | 9H | 5G | 2C | 0 | 0 | 0 | 0 | 0 |
| Cheatgrass | 0 | 9H | 9H | 8H | 0 | 0 | 0 | 0 | 0 | 0 | 0 |
| Wild Oats | 0 | 2C,6G | 2C | 6G | 0 | 0 | 0 | 0 | 0 | 0 | 0 |
| Wheat | 0 | 7G | 8G | 2G | 0 | 0 | 0 | 0 | 0 | 0 | 0 |
| Corn | 0 | 4C,9G | 3C,9G | 8H | 2C,7G | 0 | 0 | 0 | 0 | 0 | 0 |
| Soybean | 0 | 6H | 3H | 2C,5H | 5H | 0 | 0 | 0 | 0 | 0 | 0 |
| Rice | 0 | 10E | 3C,9H | 9H | 7H | 1C | 0 | 0 | 0 | 0 | 0 |
| Sorghum | 0 | 4C,9H | 4C,9H | 3C,9H | 3C,8H | 2G | 0 | 0 | 0 | 2G | 7G |
| Sugar Beets | 0 | 9G | 8G | 3C,9H | 8G | 5G | 4G | 0 | 0 | 0 | 5G |
| Cotton | 0 | 9G | 7G | 8G | 9G | 9G | 5G | 0 | 0 | 7G | 4G |
| Giant Foxtail | 0 | 2C,9H | 3C,6G | 3H | 0 | 2C | 0 | 0 | 0 | 0 | 0 |
| Barley | — | 9G | 5G | 8G | 7G | 0 | 0 | 0 | 0 | 0 | — |
| Bushbean | | — | | — | | | | | | | — |
| Cassia | | — | | — | | | | | | | — |

| | Compound 35 | | Compound 36 | | Compound 37 | | Compound 38 | | Cmpd. 39 | Cmpd. 40 | Cmpd. 41 | Cmpd. 42 | Cmpd. 43 | Cmpd. 44 | Cmpd. 45 | Cmpd. 46 |
|---|---|---|---|---|---|---|---|---|---|---|---|---|---|---|---|---|
| Rate kg/ha | 0.4 | 0.05 | 0.4 | 0.05 | 0.4 | 0.05 | 0.4 | 0.05 | 0.05 | 0.05 | 0.05 | 0.05 | 0.05 | 0.05 | 0.05 | 0.05 |

POSTEMERGENCE

| | | | | | | | | | | | | | | | | |
|---|---|---|---|---|---|---|---|---|---|---|---|---|---|---|---|---|
| Morningglory | 2G | 2C,2H | 1C | 1C | 0 | 0 | 0 | 0 | 0 | 0 | 0 | 0 | 0 | 0 | 4C,8H | 4C,9H |
| Cocklebur | 3C,9G | 4C,9G | 2C,3G | 2C,4G | 0 | 0 | 0 | 0 | 0 | 2H | 0 | 0 | 0 | 0 | 10C | 9C |
| Velvetleaf | 3C,7G | 2C,5G | 1C | 2C | 0 | 0 | 0 | 0 | 0 | 0 | 0 | 4G | 0 | 0 | 4C,8H | 4C,8H |
| Nutsedge | 3G | 0 | 0 | 0 | 0 | 0 | 0 | 0 | 0 | 0 | 0 | 0 | 0 | 0 | 3C,7G | 3C,7G |
| Crabgrass | 0 | 0 | 0 | 0 | 0 | 0 | 0 | 0 | 0 | 0 | 0 | 0 | 0 | 0 | 0 | 0 |
| Barnyardgrass | 0 | 2C,6G | 0 | 0 | 0 | 0 | 0 | 0 | 0 | 0 | 0 | 0 | 0 | 0 | 7G | 3C,7H |
| Cheatgrass | 0 | 0 | 0 | 0 | 0 | 0 | 0 | 0 | 0 | 0 | 0 | 0 | 0 | 0 | 3G | 3C,9G |
| Wild Oats | 0 | 0 | 0 | 0 | 0 | 0 | 0 | 0 | 0 | 0 | 0 | 0 | 0 | 0 | 5G | 2C,5G |
| Wheat | 2C,5G | 3C,8H | 0 | 0 | 0 | 0 | 0 | 0 | 0 | 0 | 0 | 0 | 0 | 0 | 1C,4G | 3G |
| Corn | 1C | 2C,2H | 0 | 0 | 0 | 0 | 0 | 0 | 0 | 0 | 0 | 0 | 0 | 0 | 0 | 3C,9H |
| Soybean | 2C,5G | 3C,8G | 0 | 0 | 0 | 0 | 0 | 0 | 0 | 0 | 0 | 0 | 0 | 0 | 9C | 2G |
| Rice | 2C,3G | 4C,9H | 0 | 0 | 0 | 0 | 0 | 0 | 0 | 0 | 0 | 0 | 0 | 0 | 4C,9H | 4C,9G |
| Sorghum | 3C,7G | 4C,9G | 0 | 3C,5H | 0 | 0 | 0 | 0 | 0 | 0 | 0 | 0 | 0 | 0 | 9C | 4C,9H |
| Sugar Beets | 3C,8H | 4C,9H | 2H | 0 | 0 | 0 | 0 | 0 | 0 | 0 | 0 | 0 | 0 | 0 | 4C,9H | 5C,9H |
| Cotton | — | — | 2C,5G | 0 | 0 | 0 | 0 | 0 | 0 | 0 | 0 | 0 | 0 | 0 | 4C,9G | 9C |
| Giant Foxtail | — | — | — | — | — | — | — | — | 0 | 0 | 0 | 0 | 0 | 0 | 2G | 3C,7G |
| Barley | | | — | — | 0 | 0 | 0 | 0 | 0 | 0 | 0 | 0 | 0 | 0 | 3C,7G | 3C,9G |

PREEMERGENCE

| | | | | | | | | | | | | | | | | |
|---|---|---|---|---|---|---|---|---|---|---|---|---|---|---|---|---|
| Morningglory | 5G | 0 | 6G | 0 | 0 | 0 | 2C,5G | 0 | 0 | 0 | 0 | 0 | 0 | 0 | 2C,4G | 2C,3G |
| Cocklebur | 8G | 7G | — | 0 | 2G | 0 | 0 | 0 | 0 | 0 | 0 | 0 | 0 | 0 | 8H | 3C,7H |
| Velvetleaf | 5G | 3G | 2C,2H | 0 | 1H | 0 | 0 | 0 | 0 | 0 | 0 | 0 | 0 | 0 | 8G | 3C,6G |
| Nutsedge | 2C,7G | 0 | 0 | 0 | 0 | 0 | 0 | 0 | 0 | 0 | 0 | 0 | 0 | 0 | 0 | 0 |
| Crabgrass | 2G | | 2C,5G | 0 | 0 | 0 | 3G | 0 | 0 | 0 | 0 | 0 | 0 | 0 | 0 | 1C |

TABLE A-continued

| | | | | | | | | | | | | |
|---|---|---|---|---|---|---|---|---|---|---|---|---|
| Barnyardgrass | 2H | 0 | 0 | 0 | 0 | 0 | 0 | 0 | 0 | 0 | 2G | 0 |
| Cheatgrass | 8G | 2C,7G | 0 | 0 | 0 | 0 | 0 | 0 | 0 | 2G | 2C,8G | 3C,8G |
| Wild Oats | 2C,5G | 0 | 0 | 0 | 0 | 0 | 0 | 0 | 0 | 0 | 0 | 3C,5G |
| Wheat | 8G | 0 | 0 | 0 | 0 | 0 | 0 | 0 | 3G | 0 | 3G | 7G |
| Corn | 2C,7G | 2C,3G | 0 | 0 | 0 | 0 | 0 | 0 | 7G | 0 | 4G | 2C,4G |
| Soybean | 3G | 0 | 0 | 0 | 0 | 0 | 0 | 0 | 0 | 0 | 0 | 0 |
| Rice | 3C,9G | 3C,7G | 3G | 0 | 0 | 0 | 0 | 0 | 5G | 0 | 2C,2H | 3C,8G |
| Sorghum | 3C,9G | 2C,4G | 0 | 2G | 0 | 0 | 0 | 0 | 6G | 0 | 6G | 3C,8H |
| Sugar Beets | 4C,8G | 5C,8G | 2G | 5G | 0 | 0 | 0 | 0 | 5G | 0 | 2C,7G | 3C,8G |
| Cotton | 6G | 2C,2G | 0 | 0 | 0 | 0 | 0 | 0 | 0 | 0 | 8G | 3G |
| Giant Foxtail | — | — | — | — | — | — | 0 | 0 | 3G | 0 | 2G | 3G |
| Barley | — | — | — | — | — | — | 0 | 0 | 5G | 0 | 2G | 3G |
| Bushbean | | | | | | | | | | | | |
| Cassia | | | | | | | | | | | 4G | 3G |

What is claimed is:
1. A compound of the formula:

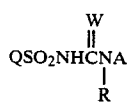

wherein
W is O or S;
Q is

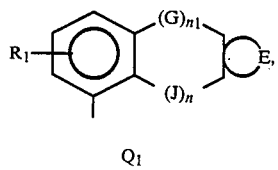

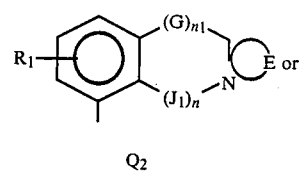

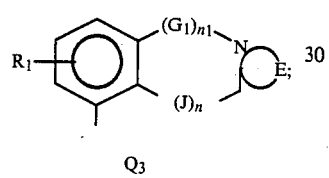

G is CH$_2$, CH$_2$CH$_2$, O, S, NH, NCH$_3$ or CH=CH;
G$_1$ is CH$_2$, CH$_2$CH$_2$ or CH=CH;
J is CH$_2$, C=O, S(O)$_m$, O, NH, NCH$_3$, CHOH, CHOCH$_3$, CH(CH$_3$) or C(CH$_3$)OH;
J$_1$ is CH$_2$, C=O or SO$_2$;
n and n$_1$ are independently 0 or 1;
m is 0, 1 or 2;
E is a bridge of 3 or 4 atoms containing 0 to 2 heteroatoms selected from the group consisting of oxygen, sulfur or nitrogen, wherein 1 atom of sulfur may take the form of SO or SO$_2$, said bridge also containing 1 to 4 atoms of carbon wherein 1 atom of carbon may take the form of C=O, said bridge together with two attachment sites forming a nonaromatic heterocyclic or carbocyclic ring optionally substituted by 1 to 3 substituent groups selected from the group L, or E is a bridge of 3 or 4 atoms containing 0-1 heteroatoms of oxygen or sulfur and 0-3 heteroatoms of nitrogen, said bridge also containing 0-4 atoms of carbon, said bridge together with two attachment sites forming an aromatic heterocyclic or carbocyclic ring optionally substituted by 1 to 3 substituents selected from the group L, with the proviso that when E contains two oxygen atoms or two sulfur atoms said atoms must be separated by at least one atom of carbon and that oxygen and sulfur are only linked to each other if the sulfur is in the form of SO or SO$_2$;
L is C$_1$-C$_4$ alkyl, C$_1$-C$_4$ haloalkyl, C$_1$-C$_4$ alkoxy, C$_1$-C$_4$ haloalkoxy, C$_2$-C$_8$ alkoxyalkoxy, halogen, N(CH$_3$)$_2$, cyano, nitro, phenyl or phenyl substituted with C$_1$-C$_3$ alkyl, C$_1$-C$_3$ haloalkyl, halogen, NO$_2$, C$_1$-C$_3$ alkoxy, C$_1$-C$_3$ alkylthio, C$_1$-C$_3$ alkylsulfinyl or C$_1$-C$_3$ alkylsulfonyl;
R is H or CH$_3$;
R$_1$ is H, C$_1$-C$_3$ alkyl, C$_1$-C$_3$ haloalkyl, halogen, nitro, C$_1$-C$_3$ alkoxy, SO$_2$NR$^I$R$^{II}$, C$_1$-C$_3$ alkylthio, C$_1$-C$_3$ alkylsulfinyl, C$_1$-C$_3$ alkylsulfonyl, CO$_2$R$^{III}$ or NR$_a$R$_b$;
R$^I$ is H, C$_1$-C$_4$ alkyl, C$_2$-C$_3$ cyanoalkyl, methoxy or ethoxy;
R$^{II}$ is H, C$_1$-C$_4$ alkyl or C$_3$-C$_4$ alkenyl; or
R$^I$ and R$^{II}$ may be taken together as —(CH$_2$)$_3$—, —(CH$_2$)$_4$—, —(CH$_2$)$_5$— or —CH$_2$CH$_2$OCH$_2$CH$_2$—;
R$^{III}$ is C$_1$-C$_4$ alkyl, C$_3$-C$_4$ alkenyl, C$_3$-C$_4$ alkynyl, C$_2$-C$_4$ haloalkyl, C$_1$-C$_3$ cyanoalkyl, C$_5$-C$_6$ cycloalkyl, C$_4$-C$_7$ cycloalkylalkyl or C$_2$-C$_4$ alkoxyalkyl;
R$_a$ and R$_b$ are independently H or C$_1$-C$_2$ alkyl;
A is

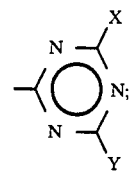

A-1

X is H, C$_1$-C$_4$ alkyl, C$_1$-C$_4$ alkoxy, C$_1$-C$_4$ haloalkoxy, C$_1$-C$_4$ haloalkoxy, C$_1$-C$_4$ haloalkylthio, C$_1$-C$_4$ alkylthio, C$_2$-C$_5$ alkylalkyl, C$_2$-C$_5$ alkoxyalkoxy, amino, C$_1$-C$_3$ alkylamino or di(C$_1$-C$_3$ alkyl)amino;
Y is H, C$_1$-C$_4$ alkyl, C$_1$-C$_4$ alkoxy, C$_1$-C$_4$ haloalkoxy, haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_1$-C$_4$ haloalkyl, C$_3$-C$_5$ cycloalkyl, C$_2$-C$_4$ alkylnyl, N(OCH$_3$)CH$_3$,

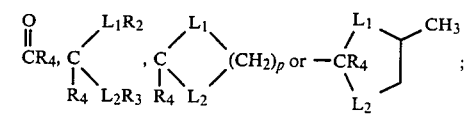

P is 2 or 3;
L$_1$ and L$_2$ are independently O or S;
R$_2$ and R$_3$ are indenpendently C$_1$-C$_2$ alkyl;
R$_4$ is H or CH$_3$;
and their agriculturally suitable salts;
provided that
  (a) X and/or Y are not C$_1$ haloalkoxy;
  (b) n and n$_1$ cannot simultaneously be O;
  (c) when G or G$_1$ is CH$_2$CH$_2$ or CH=CH, then n is O;
  (d) when Q is Q$_1$ and n is 1, then E must contain at least one heteroatom selected from oxygen, sulfur or nitrogen; and
  (e) when W is S, then R is H, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

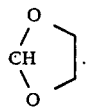

2. Compounds of claim 1 where W is O; G and $G_1$ are $CH_2$, $CH_2CH_2$ or $CH=CH$; J is CO, $SO_2$ or $CH_2$; R is H; X is $CH_3$, $OCH_3$, $OCH_2CH_3$, $CH_2F$, $OCH_2CH_2F$, $OCH_2CHF_2$, $OCH_2CF_3$, $CF_3$, $CH_2Cl$ or $CH_2Br$; Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$,

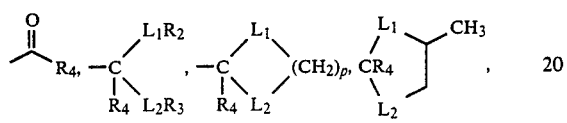

$SCF_2H$, cyclopropyl, $C\equiv CH$ or or $C\equiv CCH_3$.

3. Compounds of claim 2 where $R_1$ is H, $CH_3$, halogen, $OCH_3$, $SCH_3$ or $SO_2CH_3$; and L is halogen, $CH_3$, $OCH_3$, $SCH_3$, $NO_2$, $N(CH_3)_2$ or phenyl.

4. Compounds of claim 3 where Q is

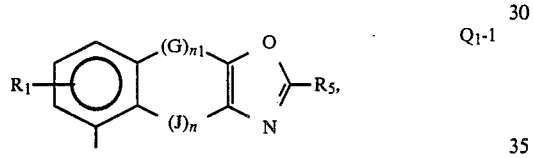

Q$_1$-1

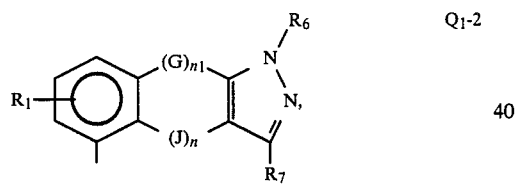

Q$_1$-2

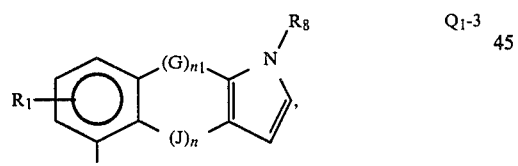

Q$_1$-3

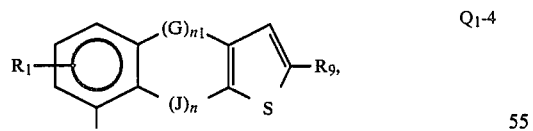

Q$_1$-4

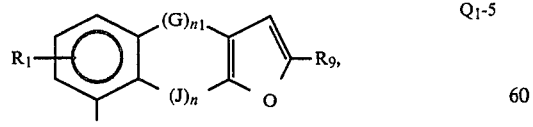

Q$_1$-5

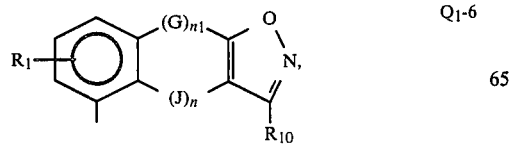

Q$_1$-6

-continued

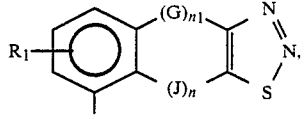

Q$_1$-7

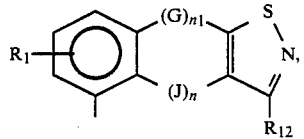

Q$_1$-8

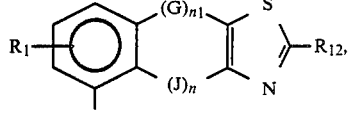

Q$_1$-9

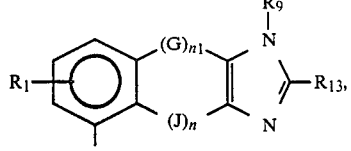

Q$_1$-10

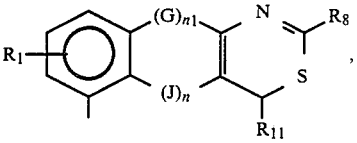

Q$_1$-11

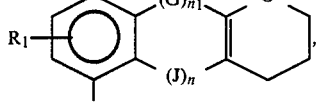

Q$_1$-12

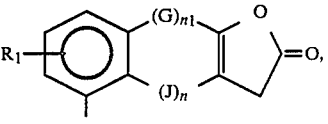

Q$_1$-13

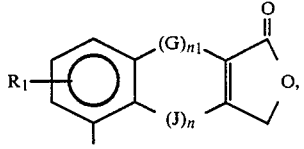

Q$_1$-14

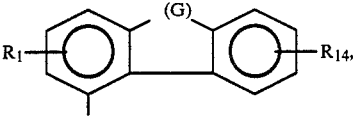

Q$_1$-15

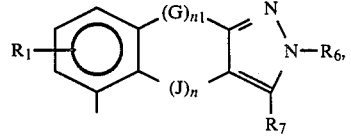

Q$_1$-16

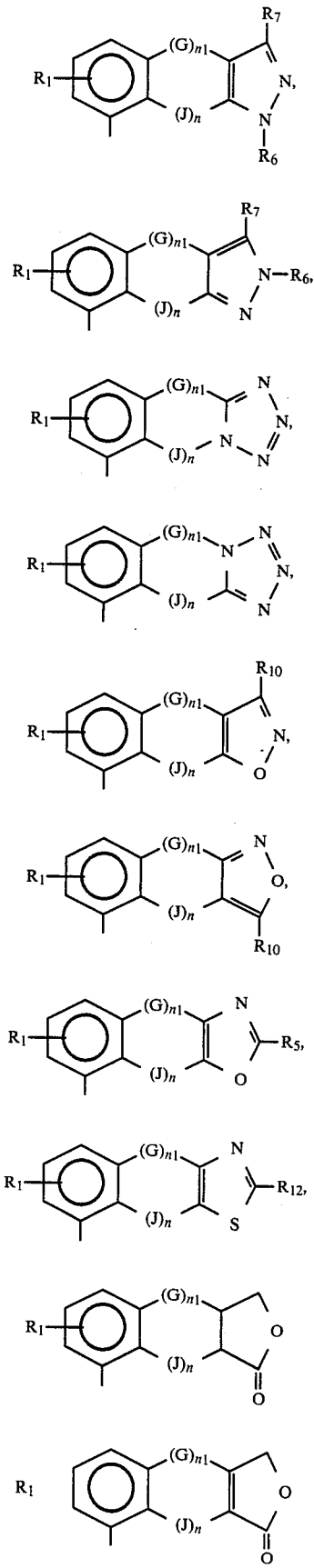
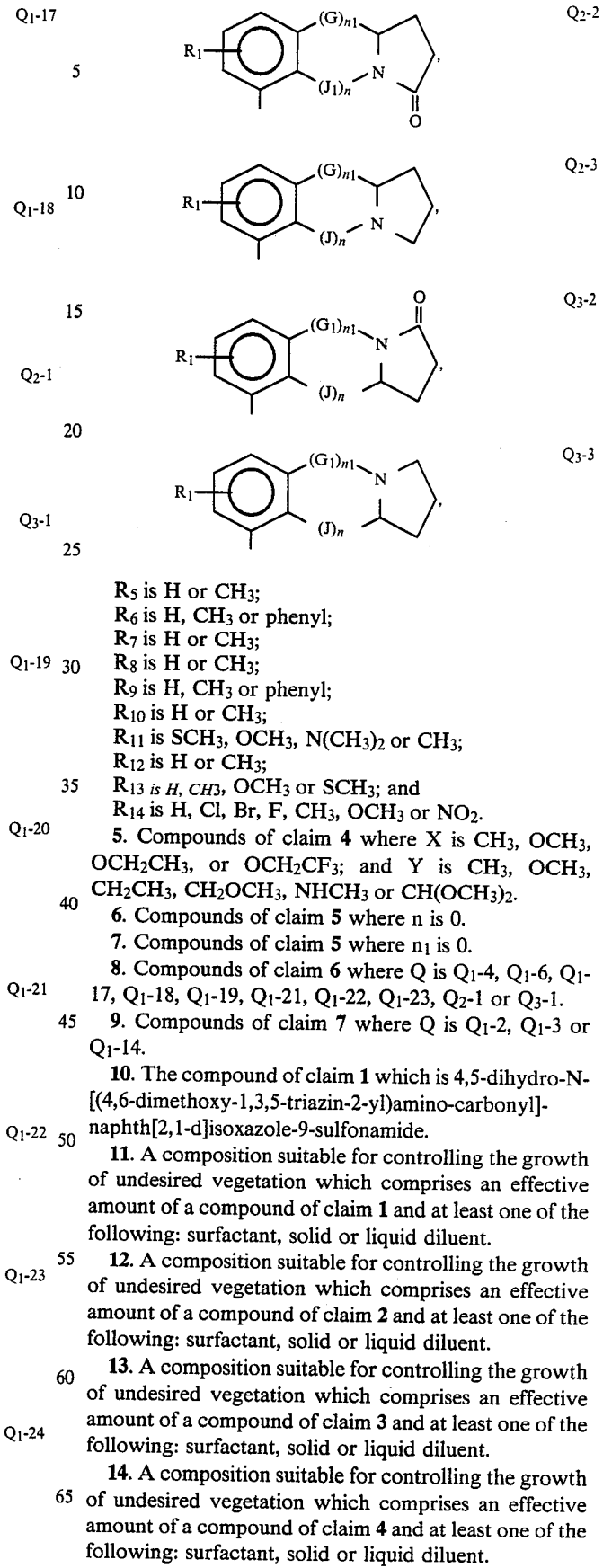

$R_5$ is H or $CH_3$;
$R_6$ is H, $CH_3$ or phenyl;
$R_7$ is H or $CH_3$;
$R_8$ is H or $CH_3$;
$R_9$ is H, $CH_3$ or phenyl;
$R_{10}$ is H or $CH_3$;
$R_{11}$ is $SCH_3$, $OCH_3$, $N(CH_3)_2$ or $CH_3$;
$R_{12}$ is H or $CH_3$;
$R_{13}$ is H, $CH_3$, $OCH_3$ or $SCH_3$; and
$R_{14}$ is H, Cl, Br, F, $CH_3$, $OCH_3$ or $NO_2$.

5. Compounds of claim 4 where X is $CH_3$, $OCH_3$, $OCH_2CH_3$, or $OCH_2CF_3$; and Y is $CH_3$, $OCH_3$, $CH_2CH_3$, $CH_2OCH_3$, $NHCH_3$ or $CH(OCH_3)_2$.

6. Compounds of claim 5 where n is 0.

7. Compounds of claim 5 where $n_1$ is 0.

8. Compounds of claim 6 where Q is $Q_1$-4, $Q_1$-6, $Q_1$-17, $Q_1$-18, $Q_1$-19, $Q_1$-21, $Q_1$-22, $Q_1$-23, $Q_2$-1 or $Q_3$-1.

9. Compounds of claim 7 where Q is $Q_1$-2, $Q_1$-3 or $Q_1$-14.

10. The compound of claim 1 which is 4,5-dihydro-N-[(4,6-dimethoxy-1,3,5-triazin-2-yl)amino-carbonyl]-naphth[2,1-d]isoxazole-9-sulfonamide.

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of a compound of claim 5 and at least one of the following: surfactant, solid or liquid diluent.

16. A composition suitable for controlling the growth of undesired vegetation which comprises an effective amount of a compound of claim 6 and at least one of the following: surfactant, solid or liquid diluent.

17. A composition suitable for controlling the growth of undesired vegetation which comprises an effective amount of a compound of claim 7 and at least one of the following: surfactant, solid or liquid diluent.

18. A composition suitable for controlling the growth of undesired vegetation which comprises an effective amount of a compound of claim 8 and at least one of the following: surfactant, solid or liquid diluent.

19. A method for controlling the growth of undesired vegetation which comprises applying to the locus to be protected an effective amount of a compound of claim 1.

20. A method for controlling the growth of undesired vegetation which comprises applying to the locus to be protected an effective amount of a compound of claim 2.

21. A method for controlling the growth of undesired vegetation which comprises applying to the locus to be protected an effective amount of a compound of claim 3.

22. A method for controlling the growth of undesired vegetation which comprises applying to the locus to be protected an effective amount of a compound of claim 4.

23. A method for controlling the growth of undesired vegetation which comprises applying to the locus to be protected an effective amount of a compound of claim 5.

24. A method for controlling the growth of undesired vegetation which comprises applying to the locus to be protected an effective amount of a compound of claim 6.

25. A method for controlling the growth of undesired vegetation which comprises applying to the locus to be protected an effective amount of a compound of claim 7.

26. A method for controlling the growth of undesired vegetation which comprises applying to the locus to be protected an effective amount of a compound of claim 8.

* * * * *

UNITED STATES PATENT AND TRADEMARK OFFICE
CERTIFICATE OF CORRECTION

PATENT NO. : 4,741,765
DATED : May 3, 1988
INVENTOR(S) : Ramaurthi Mathukrishnan and Robert J. Pasteris It is certified that error appears in the above-identified patent and that said Letters Patent is hereby corrected as shown below:

Column 114, line 33, replace "haloalkoxy" with --haloalkyl--.

Column 114, line 34, replace "alkylalkyl" with --alkoxyalkyl--.

Column 114, line 42, replace "alkylnyl" with --alkynyl--.

Column 114, line 50, replace capital letter "P" with lower case letter --p--.

Column 118, line 35, replace subscripted italicized "is H, $CH_3$" with regular tpyeface --is H, $CH_3$--.

Signed and Sealed this

Twenty-ninth Day of November, 1988

Attest:

DONALD J. QUIGG

*Attesting Officer*   *Commissioner of Patents and Trademarks*